US009012190B2

(12) United States Patent
Dauner et al.

(10) Patent No.: US 9,012,190 B2
(45) Date of Patent: Apr. 21, 2015

(54) USE OF THIAMINE AND NICOTINE ADENINE DINUCLEOTIDE FOR BUTANOL PRODUCTION

(75) Inventors: Michael Dauner, Claymont, DE (US); Mehmedalija Jahic, Wilmington, DE (US)

(73) Assignee: Butamax Advanced Biofuels LLC DE (US)

( * ) Notice: Subject to any disclaimer, the term of this patent is extended or adjusted under 35 U.S.C. 154(b) by 508 days.

(21) Appl. No.: 13/160,766

(22) Filed: Jun. 15, 2011

(65) Prior Publication Data

US 2012/0323047 A1    Dec. 20, 2012

(51) Int. Cl.
| C12P 7/20 | (2006.01) |
| C12N 9/00 | (2006.01) |
| C12N 1/20 | (2006.01) |
| C12N 15/00 | (2006.01) |
| C07H 21/04 | (2006.01) |
| C12P 7/16 | (2006.01) |
| C12N 15/52 | (2006.01) |

(52) U.S. Cl.
CPC .. *C12P 7/16* (2013.01); *Y02E 50/17* (2013.01); *Y02E 50/16* (2013.01); *C12N 15/52* (2013.01)

(58) Field of Classification Search
None
See application file for complete search history.

(56) References Cited

U.S. PATENT DOCUMENTS

| 4,683,202 | A | 7/1987 | Mullis |
| 5,795,771 | A | 8/1998 | George et al. |
| 5,916,609 | A | 6/1999 | Plomp |
| 6,750,045 | B2 | 6/2004 | Zamost |
| 7,534,597 | B2 | 5/2009 | Hause et al. |
| 7,700,332 | B1 | 4/2010 | Rajgarhia et al. |
| 2005/0059136 | A1 | 3/2005 | Van Maris et al. |
| 2005/0112737 | A1 | 5/2005 | Liu et al. |
| 2007/0031918 | A1 | 2/2007 | Dunson, Jr. et al. |
| 2007/0031950 | A1 | 2/2007 | Winkler |
| 2007/0092957 | A1 | 4/2007 | Donaldson et al. |
| 2007/0259410 | A1 | 11/2007 | Donaldson et al. |
| 2007/0292927 | A1 | 12/2007 | Donaldson et al. |
| 2008/0182308 | A1 | 7/2008 | Donaldson et al. |
| 2008/0261230 | A1 | 10/2008 | Liao et al. |
| 2009/0163376 | A1 | 6/2009 | Li et al. |
| 2009/0215137 | A1 | 8/2009 | Hawkins et al. |
| 2009/0269823 | A1 | 10/2009 | Bramucci et al. |
| 2009/0305363 | A1 | 12/2009 | Anthony et al. |
| 2010/0081154 | A1 | 4/2010 | Flint et al. |
| 2011/0244536 | A1 | 10/2011 | Nagarajan et al. |

FOREIGN PATENT DOCUMENTS

| CN | 1441053 | 9/2003 |
| CN | 1944657 | 4/2007 |
| EP | 0821057 | 1/1998 |
| JP | 04179487 | 6/1992 |
| WO | 2007050671 | 5/2007 |
| WO | 2007130521 | 11/2007 |
| WO | 2009103533 | 8/2009 |
| WO | 2010051527 | 5/2010 |
| WO | 2010075504 | 7/2010 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Aden et al., Lignocellulosic Biomass to Ethanol Process Design and Economics Utilizing Co-Current Dilute Acid Prehydrolysis and Enzymatic Hydrolysis for Corn Stover, Report NREL/TP-510-32438, National Renewable Energy Laboratory, Jun. 2002.
Alfenore et al., Improving ethanol production and viability of *Saccharomyces cerevisiae* by a vitamin feeding strategy during fed-batch process, Appl Microbiol Biotechnol, 2002, 60, 67-72.
Altschul et al., Basic Local Alignment Search Tool, Journal of Molecular Biology, 1990, 403-410, 215.
Ausubel et al., Current Protocols in Molecular Biology, 1987, vol. 1, editor Frederick M. Ausubel et al.
Begley et al., Thiamin Biosynthesis in Prokaryotes, Archives of Microbiology, 1999, 293-300, 171, Ithaca, NY.
Bellion et al., Methylamine Utilization in Yeast and Bacteria: Studies Using in vivo NMR, Microb. Growth C1 Compd., [Int. Symp.], 7th (1993), 415-32, Editor(s): Murrell, J. Collin; Kelly, Don P. Publisher: Intercept, Andover, UK.
Bianchi et al., The Petite Negative Yease *Kluyveromyces lactis* has a Single Gene Expressing Pyrruvate Decarboxylase Activity, Molecular Microbiology, 1996, 27-36, 19 (1), Blackwell Science Ltd.
Carlini et al., "Guerbet Condensation of Methanol with n-propanol to Isobutyl Alcohol over Heterogeneous Copper Chromite/Mg—Al mixed Oxides Catalysts", Journal Molecular Catalysis. A: Chem., 2004, 215-220, 220.
Casey et al., High Gravity Brewing: Effects of Nutrition on Yeast Composition, Fermentative Ability and Alcohol Production, Applied and Environmental Microbiology, 1984, 639-646, 48 (3).
Chatterjee et al., Biosynthesis of Thamin Thiazole in Eukaryotes: Conversion of NAD to an Advanced Intermediate, Journal of American Chemial Society, 2007, 2914-2922, 129.
Deshpande, "Ethanol Production from Cellulose by Coupled Saccharification/Fermentation using *Saccharomyces cerevisiae* and Cellulase Complex from *Sclerotium rolfsii* UV-8 Mutant*", Applied Biochemistry and Biotechnology, vol. 36 (1992) pp. 227-234.

(Continued)

*Primary Examiner* — Christian Fronda

(57) ABSTRACT

The invention relates generally to the field of industrial microbiology and alcohol production. More specifically, the invention relates to the use of thiamine, biosynthetic precursors of thiamine, nicotinic acid, nicotinamid, nicotinic acid riboside, nicotinamid riboside, or other biosynthetic precursors of nicotine adenine dinucleotide (NAD) to improve butanol production. Butanol production can be improved by providing sufficient amounts of thiamine, biosynthetic precursors of thiamine, nicotinic acid, nicotinamid, nicotinic acid riboside, nicotinamid riboside, or other biosynthetic precursors of nicotine adenine dinucleotide (NAD) in the production media.

9 Claims, 12 Drawing Sheets

(56) References Cited

OTHER PUBLICATIONS

Durre, "New insights and novel developments in clostridial acetone/butanol/isopropanol fermentation", Appl. Microbiol. Biotechnol. (1998) vol. 49, pp. 639-648.

Enjo et al., Isolation and Characterization of a Thiamin Transport Gene, THI10, from *Saccaromyces cerevisiae*, Journal of Biological Chemistry, 1997, 19165-19170, 272 (31).

Flikweert et al., "Pyruvate decarboxylase: an indispensable enzyme for growth of *Saccharomyces cerevisiae* on glucose", Yeast (1996) vol. 12, pp. 247-257.

Groot et al., "Technologies for butanol recovery integrated with fermentations", Process Biochemistry, vol. 27 (1992) pp. 61-75.

Hahn-Hagerdal et al., Role of Cultivation Media in the Development of Yeast Strains for Large Scale Industrial Use, Microbial Cell Factories, 2005, 4 (31), 1-16.

Hall et al., The Reacquisition of Biotin Prototrophy in *Saccharomyces cerevisiae* Involved Horizontal Gene Transfer, Gene Duplication and Gene Clustering, Genetics, 2007, 2293-2307, 177.

Henry, Growth Requirements of San Francisco Sour Dough Yeasts and Baker's Yeast, Applied and Environmental Microbiology, 1976, 395-398, 31 (3).

Higgins et al., "CLUSTAL V: improved software for multiple sequence alignment", CABIOS, 1992, vol. 8, No. 2, pp. 189-191.

Higgins et al., "Fast and sensitive multiple sequence alignments on a microcomputer", CABIOS Communications, 1989, vol. 5, No. 2, pp. 151-153.

Hohmann, Characterisation of PDC2, a Gene Necessary for High Level Expression of Pyruvate Decarboxylase Structural Genes in *Saccharomyces cerevisiae*, Molecular and General Genetics, 1993, 657-666, 241.

Hohmann et al., Thiamin Metabolism and Thiamin Diphosphate-Dependent Enzymes in the Yeast *Saccharomyces cerevisiae*: Genetic Regulation, Biochem Biophys Acta, 1998, 1385(2): 201-19.

Ichikawa et al., Thiamine Increases Expression of Yeast Gene, Bioscience, Biotechnology and Biochemistry, 1997, 1221-1224, 61(7).

Jackson et al., B Complex Vitamins in Sugar Cane and Sugar Cane Juice, Industrial and Engineering Chemistry, 1944, 261-263.

Kawasaki et al., Biosynthesis of Hydroxymethylpyrimidine Pyrophosphate in *Saccharomyces cerevisiae*, Current Genetics, 2005, 156-162, 47.

Kiers et al., Regulation of Alcoholic Fermentation in Batch and Chemostat Cultures of *Kluyveromyces lactic* CBS 2359, Yeast, 1998, 459-469, 14.

Kowalska et al., The Genes and Enzymes Involved in the Biosynthesis of Thiamin and Thiamin Diphosphate in Yeasts, Cellular & Molecular Biology Letters, 2008, 271-282, 13.

Lai et al., RNA Sensors and Riboswitches: Self-Regulating Messages, Current Biology, 2003, R285-R291, 13.

Lakaye et al., Thiamine Triphosphate, a new Signal Required for Optimal Growth of *Escherichia coli* during Amino Acid Starvation, The Journal of Biological Chemistry, 2004, 17142-17147, 279 (17).

Leonian et al., Vitamin synthesis by a Yeast Converted From a Heterotrophic to an Autotrophic Habit, Science, 1942, 658, 95 (2478).

Machado et al., Dual Role for the Yeast THI4 Gene in Thiamine Biosynthesis and DNA Damage Tolerance, Journal of Molecular Biology, 1997, 114-121, 273.

Medina-Silva et al., Heat Stress Promotes Mitochondrial Instability and Oxidative Responses in Yeast Deficient in Thiazole Biosynthesis, Research in Microbiology, 2006, 275-281, 157.

Methods in Yeast Genetics, 2005, Cold Spring Harbor Laboratory Press, Cold Spring Harbor, NY, pp. 201-202.

Mnaimneh et al., Exploration of Essential Gene Functions via Titratable Promoter Alleles, Cell, 2004, vol. 118, pp. 31-44.

Nakamura et al., Codon Usage Tabulated from International DNA Sequence Databases: status for the year 2000, Nucleic Acids Research, 2000, 292, vol. 28 (1).

Nevoigt et al., Reduced Pyruvate Decarboxylase and Increased Glycerol-3-phosphate Dehydrogenase [NAD+] Levels Enhance Glycerol Production in *Saccharomyces*, Yeast, 1996, 1331-1337, 12.

Nosaka et al., Isolation and Characterization of a Thiamin Pyrophosphokinase Gene, THI80, from *Saccharomyces cerevisiae*, Journal of Biological Chemistry, 1993, 17440-17447, 268(23).

Nosaka et al., Isolation and Characterization of the THI6 Gene Encoding a Bifunctional ThiaminPhosphate Pyrophosphorylase/Hydroxyethylthiazole Kinase from *Saccaromyces cerevisiae*, Journal of Biological Chemistry, 1994, 30510-30516, 269(41).

Nosaka et al., Recent Progress in Understanding Thiamin Biosynthesis and its Genetic Regulation in *Saccharomyces cerevisiae*, Applied Microbiology & Biotechnology, 2006, 30-40, 72.

Nosaka et al., Thiamin Dependent Transactivation Activity of PDC2 in *Saccharomyces cerevisiae*, FEBS Letters, 2008, 3991-3996, 582.

O'Connor et al., Design and Evaluation of Control Strategies for High Cell Density Fermentations, Biotechnology and Bioengineering, 1992, 293-304, 39.

Pearson, Computer Methods Genome Research, Proc. Int. Symp, 1994, Meeting Dated 1992, 111-20. Editor(s): Suhai, Sandor. Plenum: New York, NY.

Sambrook, J., Fritsch, E. F. and Maniatis, T. Molecular Cloning: A Laboratory Manual, 2nd ed., Cold Spring Harbor Laboratory: Cold Spring Harbor, NY (1989).

Shiba et al., Process Development for High Level Secretory Production of Carboxypeptidase Y by *Saccharomces cerevisiae*, Appl. Microbiology Biotechnology, 1998, 34-41, 50.

Van Hoek et al., Fermentative Capacity in High Cell Density Fed Batch Cultures of Baker's Yeast, Biotechnology Bioengineerings, 2000, 517-523, 68.

Stolz et al., Identification of the Plasma Membrane H+-Biotin Symporter of *Saccharomyces cerevisiae* by Rescue of a Fatty Acid Auxotrophic Mutant, Journal of Biological Chemistry, 1999, 18741-18746, 274 (26).

Sulter et al., Proliferation and Metabolic Significance of Peroxisomes in *Candida boidinii* during Growth on Dalanine or Oleic Acid as the Sole Carbon Source, Archves of Microbiology, 1990, 485-489, 153.

Tabor et al., A Bacteriophage T7 RNA Polymerase/Promoter System for Controlled Exclusive Expression of Specific Genes, Proceedings of the National Academy of Sciences USA, 1985, 1074-1078, 82.

Ullmann's Encyclopedia of Industrial Chemistry, 6th edition, 2003, Wiley-VCH Verlag GmbH and Co., Weinheim, Germany, vol. 5, pp. 716-719.

Alfenore et al., "Aeration strategy: a need for very high ethanol performance in *Saccharomyces cerevisiae* fed-batch process," Applied Microbiol. Biotechnol. 63(5):537-42 (2004).

Lu et al., "Assimilation of endogenous nicotinamide riboside is essential for calorie restriction-mediated life span extension in *Saccharomyces cerevisiae*," JBC 284:17110-9 (2009).

Panozzo et al., "Aerobic and anaerobic NAD+ metabolism in *Saccharomyces cerevisiae*," FEBS Lett. 517(1-3):97-102 (2002).

Akada et al., "PCR-mediated seamless gene deletion and marker recycling in *Saccharomyces cerevisiae*", Yeast (2006) 23, pp. 399-405.

Horton et al., "Engineering hybrid genes without the use of restriction enzymes: gene splicing by overlap extension", Gene, 77 (1989) pp. 61-68.

Guo et al., "Pervaporation study on the dehydration of aqueous butanol solutions: a comparison of flux vs. permeance, separation factor vs. selectivity", Journal of Membrane Science 245 (2004) pp. 199-210.

Verduyn et al., Effect of Benzoic Acid on Metabolic Fluxes in yeasts: A Continuous Culture Study on the Regulation of Respiration and Alcoholic Fermentation, Yeast, 1992, 501-517, 8.

Wach et al., New Heterologous Modules for Classical or PCR-bsed Gene Disruptions in *Saccharomyces cerevisiae*, Yeast, 1994, 1793-1808, 10.

Walker et al., Sothermal in vitro amplification of DNA by a restriction enzyme/DNA polymerase system, Proceedings of the National Academy of Sciences USA, vol. 89, Jan. 1992, pp. 392-396.

(56) References Cited

OTHER PUBLICATIONS

Wang et al., Study on the Effect of Thiamine on the Metabolism of Yeast by Intrinsic Fluorescence, Luminescence, 2005, 216-219, 20.
Wang et al., Optimization of an Ethanol Production Medium in Very High Gravity Fermentation, Biotechnology Letters, 2007, 233-236, 29.
White et al., *Saccharomyces cerevisiae* is Capagle of de Novo Pantothenic Acid Biosynthesis Involving a Novel Pathway of b-Alanine Production from Spermine, Journal of Biological Chemistry, 2001, 10794-10800, 276 (14).
Winter et al., Inhibition and Growth Factor Deficiencies in Alcoholic Fermentation by *Saccharomyces cerevisiae*, Current Microbiology, 1989, 247-252, 18.
Zeidler et al., Biosynthesis of Vitamin B1 in Yeast. Derivation of the Pyrimidine Unit from Pyridoxine and Histidine. Intermediacy of Urocanic Acid, Journal of American Chemistry, 2003, 13094-13105, 125.

* cited by examiner

SEQUENCE LISTING

```
<160> NUMBER OF SEQ ID NOS: 167

<210> SEQ ID NO 1
<211> LENGTH: 1689
<212> TYPE: DNA
<213> ORGANISM: Saccharomyces cerevisiae

<400> SEQUENCE: 1
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
```

-continued

```
gaaggtatga gatgggctgg taacgccaac gaattgaacg ctgcttacgc cgctgatggt    180
tacgctcgta tcaagggtat gtcttgtatc atcaccacct tcggtgtcgg tgaattgtct    240
gctttgaacg gtattgccgg ttcttacgct gaacacgtcg gtgttttgca cgttgttggt    300
gtcccatcca tctctgctca agctaagcaa ttgttgttgc accacacctt gggtaacggt    360
gacttcactg ttttccacag aatgtctgcc aacatttctg aaaccactgc tatgatcact    420
gacattgcta ccgccccagc tgaaattgac agatgtatca gaaccactta cgtcacccaa    480
agaccagtct acttaggttt gccagctaac ttggtcgact gaacgtccc agctaagttg    540
ttgcaaactc caattgacat gtctttgaag ccaaacgatg ctgaatccga aaaggaagtc    600
attgacacca tcttggcttt ggtcaaggat gctaagaacc cagttatctt ggctgatgct    660
tgttgttcca gacacgacgt caaggctgaa actaagaagt tgattgactt gactcaattc    720
ccagctttcg tcaccccaat gggtaagggt tccattgacg aacaacaccc aagatacggt    780
ggtgtttacg tcggtacctt gtccaagcca gaagttaagg aagccgttga atctgctgac    840
ttgattttgt ctgtcggtgc tttgttgtct gatttcaaca ccggttcttt ctcttactct    900
tacaagacca gaacattgt cgaattccac tccgaccaca tgaagatcag aaacgccact    960
ttcccaggtg tccaaatgaa attcgttttg caaaagttgt tgaccactat tgctgacgcc   1020
gctaagggtt acaagccagt tgctgtccca gctagaactc cagctaacgc tgctgtccca   1080
gcttctaccc cattgaagca agaatggatg tggaaccaat gggtaactt cttgcaagaa   1140
ggtgatgttg tcattgctga aaccggtacc tccgctttcg gtatcaacca aaccactttc   1200
ccaaacaaca cctacggtat ctctcaagtc ttatggggtt ccattggttt caccactggt   1260
gctaccttgg gtgctgcttt cgctgctgaa gaaattgatc caaagaagag agttatctta   1320
ttcattggtg acggttcttt gcaattgact gttcaagaaa tctccaccat gatcagatgg   1380
ggcttgaagc catacttgtt cgtcttgaac aacgatggtt acaccattga aaagttgatt   1440
cacggtccaa aggctcaata caacgaaatt caaggttggg accacctatc cttgttgcca   1500
actttcggtg ctaaggacta tgaaacccac agagtcgcta ccaccggtga atgggacaag   1560
ttgacccaag acaagtcttt caacgacaac tctaagatca gaatgattga atcatgttg    1620
ccagtcttcg atgctccaca aaacttggtt gaacaagcta agttgactgc tgctaccaac   1680
gctaagcaa                                                           1689
```

<210> SEQ ID NO 2
<211> LENGTH: 563
<212> TYPE: PRT
<213> ORGANISM: Saccharomyces cerevisiae

<400> SEQUENCE: 2

```
Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95
```

-continued

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
            195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
            450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 3
<211> LENGTH: 1689
<212> TYPE: DNA
<213> ORGANISM: Saccharomyces cerevisiae

<400> SEQUENCE: 3

| | | | | |
|---|---|---|---|---|
| atgtctgaaa | taaccttagg | taaatattta | tttgaaagat | tgagccaagt | caactgtaac | 60 |
| accgtcttcg | gtttgccagg | tgactttaac | ttgtctcttt | tggataagct | ttatgaagtc | 120 |
| aaaggtatga | gatgggctgg | taacgctaac | gaattgaacg | ctgcctatgc | tgctgatggt | 180 |
| tacgctcgta | tcaagggtat | gtcctgtatt | attaccacct | tcggtgttgg | tgaattgtct | 240 |
| gctttgaatg | gtattgccgg | ttcttacgct | gaacatgtcg | gtgttttgca | cgttgttggt | 300 |
| gttccatcca | tctcttctca | agctaagcaa | ttgttgttgc | atcatacctt | gggtaacggt | 360 |
| gacttcactg | ttttccacag | aatgtctgcc | aacatttctg | aaaccactgc | catgatcact | 420 |
| gatattgcta | acgctccagc | tgaaattgac | agatgtatca | gaaccaccta | cactacccaa | 480 |
| agaccagtct | acttgggttt | gccagctaac | ttggttgact | gaacgtccc | agccaagtta | 540 |
| ttggaaactc | caattgactt | gtctttgaag | ccaaacgacg | ctgaagctga | agctgaagtt | 600 |
| gttagaactg | ttgttgaatt | gatcaaggat | gctaagaacc | cagttatctt | ggctgatgct | 660 |
| tgtgcttcta | gacatgatgt | caaggctgaa | actaagaagt | tgatggactt | gactcaattc | 720 |
| ccagtttacg | tcaccccaat | gggtaagggt | gctattgacg | aacaacaccc | aagatacggt | 780 |
| ggtgtttacg | ttggtaccct | gtctagacca | gaagttaaga | aggctgtaga | atctgctgat | 840 |
| ttgatattgt | ctatcggtgc | tttgttgtct | gatttcaata | ccggttcttt | ctcttactcc | 900 |
| tacaagacca | aaaatatcgt | tgaattccac | tctgaccaca | tcaagatcag | aaacgccacc | 960 |
| ttcccaggtg | ttcaaatgaa | atttgccttg | caaaaattgt | tggatgctat | tccagaagtc | 1020 |
| gtcaaggact | acaaacctgt | tgctgtccca | gctagagttc | caattaccaa | gtctactcca | 1080 |
| gctaacactc | caatgaagca | agaatggatg | tggaaccatt | tgggtaactt | cttgagagaa | 1140 |
| ggtgatattg | ttattgctga | aaccggtact | tccgccttcg | gtattaacca | aactactttc | 1200 |
| ccaacagatg | tatacgctat | cgtccaagtc | ttgtggggtt | ccattggttt | cacagtcggc | 1260 |
| gctctattgg | gtgctactat | ggccgctgaa | gaacttgatc | aaagaagag | agttatttta | 1320 |
| ttcattggtg | acggttctct | acaattgact | gttcaagaaa | tctctaccat | gattagatgg | 1380 |
| ggtttgaagc | catacatttt | tgtcttgaat | aacaacggtt | acaccattga | aaaattgatt | 1440 |
| cacggtcctc | atgccgaata | taatgaaatt | caaggttggg | accacttggc | cttattgcca | 1500 |
| acttttggtg | ctagaaacta | cgaaacccac | agagttgcta | ccactggtga | atgggaaaag | 1560 |
| ttgactcaag | acaaggactt | ccaagacaac | tctaagatta | gaatgattga | agttatgttg | 1620 |
| ccagtctttg | atgctccaca | aaacttggtt | aaacaagctc | aattgactgc | cgctactaac | 1680 |
| gctaaacaa | | | | | 1689 |

<210> SEQ ID NO 4

-continued

```
<211> LENGTH: 563
<212> TYPE: PRT
<213> ORGANISM: Saccharomyces cerevisiae

<400> SEQUENCE: 4

Met Ser Glu Ile Thr Leu Gly Lys Tyr Leu Phe Glu Arg Leu Ser Gln
1               5                   10                  15

Val Asn Cys Asn Thr Val Phe Gly Leu Pro Gly Asp Phe Asn Leu Ser
            20                  25                  30

Leu Leu Asp Lys Leu Tyr Glu Val Lys Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Asn
    130                 135                 140

Ala Pro Ala Glu Ile Asp Arg Cys Ile Arg Thr Thr Tyr Thr Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Glu Thr Pro Ile Asp Leu Ser Leu Lys Pro Asn
            180                 185                 190

Asp Ala Glu Ala Glu Ala Glu Val Val Arg Thr Val Val Glu Leu Ile
        195                 200                 205

Lys Asp Ala Lys Asn Pro Val Ile Leu Ala Asp Ala Cys Ala Ser Arg
    210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
                245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
        275                 280                 285

Leu Ser Asp Phe Asn Thr Gly Ser Phe Ser Tyr Ser Tyr Lys Thr Lys
    290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
                325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
        355                 360                 365

Trp Met Trp Asn His Leu Gly Asn Phe Leu Arg Glu Gly Asp Ile Val
    370                 375                 380

Ile Ala Glu Thr Gly Thr Ser Ala Phe Gly Ile Asn Gln Thr Thr Phe
```

```
                385                 390                 395                 400
Pro Thr Asp Val Tyr Ala Ile Val Gln Val Leu Trp Gly Ser Ile Gly
                    405                 410                 415

Phe Thr Val Gly Ala Leu Leu Gly Ala Thr Met Ala Ala Glu Glu Leu
                    420                 425                 430

Asp Pro Lys Lys Arg Val Ile Leu Phe Ile Gly Asp Gly Ser Leu Gln
                435                 440                 445

Leu Thr Val Gln Glu Ile Ser Thr Met Ile Arg Trp Gly Leu Lys Pro
450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
                    485                 490                 495

Ala Leu Leu Pro Thr Phe Gly Ala Arg Asn Tyr Glu Thr His Arg Val
                500                 505                 510

Ala Thr Thr Gly Glu Trp Glu Lys Leu Thr Gln Asp Lys Asp Phe Gln
                515                 520                 525

Asp Asn Ser Lys Ile Arg Met Ile Glu Val Met Leu Pro Val Phe Asp
530                 535                 540

Ala Pro Gln Asn Leu Val Lys Gln Ala Gln Leu Thr Ala Ala Thr Asn
545                 550                 555                 560

Ala Lys Gln

<210> SEQ ID NO 5
<211> LENGTH: 1599
<212> TYPE: DNA
<213> ORGANISM: Saccharomyces cerevisiae

<400> SEQUENCE: 5
atgtctgaaa ttactcttgg aaaatactta tttgaaagat tgaagcaagt taatgttaac      60 accattttg  ggctaccagg cgacttcaac ttgtccctat ggacaagat  ttacgaggta     120 gatggattga gatgggctgg taatgcaaat gagctgaacg ccgcctatgc cgccgatggt     180
tacgcacgca tcaagggttt atctgtgctg gtaactactt tggcgtaggt gaattatcc      240 gccttgaatg gtattgcagg atcgtatgca gaacacgtcg gtgtactgca tgttgttggt     300
gtcccctcta tctccgctca ggctaagcaa ttgttgttgc atcatacctt gggtaacggt     360
gattttaccg ttttcacag  aatgtccgcc aatatctcag aaactacatc aatgattaca     420
gacattgcta cagccccttc agaaatcgat aggttgatca ggacaacatt tataacacaa     480
aggcctagct acttggggtt gccagcgaat ttggtagatc taaaggttcc tggttctctt     540
ttggaaaaac cgattgatct atcattaaaa cctaacgatc ccgaagctga aaaggaagtt     600
attgataccg tactagaatt gatccagaat tcgaaaaacc ctgttatact atcggatgcc     660
tgtgcttcta ggcacaacgt taaaaaagaa acccagaagt taattgattt gacgcaattc     720
ccagcttttg tgacacctct aggtaaaggg tcaatagatg aacagcatcc cagatatggc     780
ggtgtttatg tgggaacgct gtccaaacaa gacgtgaaac aggccgttga gtcggctgat     840
ttgatccttt cggtcggtgc tttgctctct gattttaaca caggttcgtt ttcctactcc     900
tacaagacta aaaatgtagt ggagtttcat tccgattacg taaggtgaa gaacgctacg     960 ttcctcggtg tacaaatgaa atttgcacta caaaacttac tgaaggttat tcccgatgtt    1020
gttaagggct acaagagcgt tcccgtacca ccaaaactc  ccgcaaacaa aggtgtacct    1080
gctagcacgc ccttgaaaca agagtggttg tggaacgaat tgtccaaatt cttgcaagaa    1140
```

```
ggtgatgtta tcatttccga gaccggcacg tctgccttcg gtatcaatca aactatcttt    1200
cctaaggacg cctacggtat ctcgcaggtg ttgtgggggt ccatcggttt tacaacagga    1260
gcaactttag gtgctgcctt tgccgctgag gagattgacc ccaacaagag agtcatctta    1320
ttcataggtg acgggtcttt gcagttaacc gtccaagaaa tctccaccat gatcagatgg    1380
gggttaaagc cgtatctttt tgtccttaac aacgacggct acactatcga aaagctgatt    1440
catgggcctc acgcagagta caacgaaatc cagacctggg atcacctcgc cctgttgccc    1500
gcatttggtg cgaaaaagta cgaaaatcac aagatcgcca ctacgggtga gtgggatgcc    1560
ttaaccactg attcagagtt ccagaaaaac tcggtgatc                           1599

<210> SEQ ID NO 6
<211> LENGTH: 533
<212> TYPE: PRT
<213> ORGANISM: Saccharomyces cerevisiae

<400> SEQUENCE: 6

Met Ser Glu Ile Thr Leu Gly Lys Tyr Leu Phe Glu Arg Leu Lys Gln
1               5                   10                  15

Val Asn Val Asn Thr Ile Phe Gly Leu Pro Gly Asp Phe Asn Leu Ser
            20                  25                  30

Leu Leu Asp Lys Ile Tyr Glu Val Asp Gly Leu Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Leu Ser Val Leu Val Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285
```

| | | | | | | | | | | | | | | |
|---|---|---|---|---|---|---|---|---|---|---|---|---|---|---|
| Leu | Ser | Asp | Phe | Asn | Thr | Gly | Ser | Phe | Ser | Tyr | Ser | Tyr | Lys | Thr | Lys |
| | 290 | | | | | 295 | | | | | 300 | | | | |

Asn Val Val Glu Phe His Ser Asp Tyr Val Lys Val Lys Asn Ala Thr
305                310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Asn Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
    450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile
    530

<210> SEQ ID NO 7
<211> LENGTH: 1692
<212> TYPE: DNA
<213> ORGANISM: Candida glabrata

<400> SEQUENCE: 7

| | | |
|---|---|---|
| atgtctgaga ttactttggg tagatacttg ttcgagagat gaaccaagt cgacgttaag | 60 |
| accatcttcg gtttgccagg tgacttcaac ttgtccctat ggacaagat ctacgaagtt | 120 |
| gaaggtatga gatgggctgg taacgctaac gaattgaacg ctgcttacgc tgctgacggt | 180 |
| tacgctagaa tcaagggtat gtcctgtatc atcaccacct tcggtgtcgg tgaattgtct | 240 |
| gccttgaacg gtattgccgg ttcttacgct gaacacgtcg gtgtcttgca cgtcgtcggt | 300 |
| gtcccatcca tctcctctca agctaagcaa ttgttgttgc accacacctt gggtaacggt | 360 |
| gacttcactg tcttccacag aatgtccgct aacatctctg agaccaccgc tatggtcact | 420 |
| gacatcgcta ccgctccagc tgagatcgac agatgtatca gaaccaccta tcacccaa | 480 |
| agaccagtct acttgggtct accagctaac ttggtcgacc taaaggtccc agccaagctt | 540 |
| ttggaaaccc caattgactt gtccttgaag ccaaacgacc agaagccga aactgaagtc | 600 |
| gttgacaccg tcttggaatt gatcaaggct gctaagaacc cagttatctt ggctgatgct | 660 |
| tgtgcttcca gacacgacgt caaggctgaa accaagaagt tgattgacgc cactcaattc | 720 |

```
ccatccttcg ttaccccaat gggtaagggt tccatcgacg aacaacaccc aagattcggt    780
ggtgtctacg tcggtacctt gtccagacca gaagttaagg aagctgttga atccgctgac    840
ttgatcttgt ctgtcggtgc tttgttgtcc gatttcaaca ctggttcttt ctcttactct    900
tacaagacca agaacatcgt cgaattccac tctgactaca tcaagatcag aaacgctacc    960
ttcccaggtg tccaaatgaa gttcgctttg caaaagttgt tgaacgccgt cccagaagct   1020
atcaagggtt acaagccagt ccctgtccca gctagagtcc cagaaaacaa gtcctgtgac   1080
ccagctaccc cattgaagca agaatggatg tggaaccaag tttccaagtt cttgcaagaa   1140
ggtgatgttg ttatcactga aaccggtacc tccgcttttg gtatcaacca accccattc    1200 ccaaacaacg cttacggtat ctcccaagtt ctatggggtt ccatcggttt caccaccggt   1260
gcttgtttgg gtgccgcttt cgctgctgaa gaaatcgacc aaagaagag agttatcttg    1320 ttcattggtg acggttcttt gcaattgact gtccaagaaa tctccaccat gatcagatgg   1380
ggcttgaagc atacttgtt cgtcttgaac aacgacggtt acaccatcga agattgatt     1440 cacggtgaaa aggctggtta caacgacatc caaaactggg accacttggc tctattgcca   1500
accttcggtg ctaaggacta cgaaaaccac agagtcgcca ccaccggtga atgggacaag   1560
ttgacccaag acaaggaatt caacaagaac tccaagatca gaatgatcga agttatgttg   1620
ccagttatgg acgctccaac ttccttgatt gaacaagcta agttgaccgc ttccatcaac   1680
gctaagcaag aa                                                       1692

<210> SEQ ID NO 8
<211> LENGTH: 564
<212> TYPE: PRT
<213> ORGANISM: Candida glabrata

<400> SEQUENCE: 8

Met Ser Glu Ile Thr Leu Gly Arg Tyr Leu Phe Glu Arg Leu Asn Gln
1               5                   10                  15

Val Asp Val Lys Thr Ile Phe Gly Leu Pro Gly Asp Phe Asn Leu Ser
                20                  25                  30

Leu Leu Asp Lys Ile Tyr Glu Val Glu Gly Met Arg Trp Ala Gly Asn
            35                  40                  45

Ala Asn Glu Leu Asn Ala Ala Tyr Ala Ala Asp Gly Tyr Ala Arg Ile
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Val Thr Asp Ile Ala Thr
130                 135                 140

Ala Pro Ala Glu Ile Asp Arg Cys Ile Arg Thr Thr Tyr Ile Thr Gln
145                 150                 155                 160

Arg Pro Val Tyr Leu Gly Leu Pro Ala Asn Leu Val Asp Leu Lys Val
                165                 170                 175

Pro Ala Lys Leu Leu Glu Thr Pro Ile Asp Leu Ser Leu Lys Pro Asn
            180                 185                 190
```

Asp Pro Glu Ala Glu Thr Glu Val Asp Thr Val Leu Glu Leu Ile
            195                 200                 205

Lys Ala Ala Lys Asn Pro Val Ile Leu Ala Asp Ala Cys Ala Ser Arg
210                 215                 220

His Asp Val Lys Ala Glu Thr Lys Lys Leu Ile Asp Ala Thr Gln Phe
225                 230                 235                 240

Pro Ser Phe Val Thr Pro Met Gly Lys Gly Ser Ile Asp Glu Gln His
            245                 250                 255

Pro Arg Phe Gly Gly Val Tyr Val Gly Thr Leu Ser Arg Pro Glu Val
            260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
290                 295                 300

Asn Ile Val Glu Phe His Ser Asp Tyr Ile Lys Ile Arg Asn Ala Thr
305                 310                 315                 320

Phe Pro Gly Val Gln Met Lys Phe Ala Leu Gln Lys Leu Leu Asn Ala
            325                 330                 335

Val Pro Glu Ala Ile Lys Gly Tyr Lys Pro Val Pro Val Pro Ala Arg
            340                 345                 350

Val Pro Glu Asn Lys Ser Cys Asp Pro Ala Thr Pro Leu Lys Gln Glu
            355                 360                 365

Trp Met Trp Asn Gln Val Ser Lys Phe Leu Gln Glu Gly Asp Val Val
            370                 375                 380

Ile Thr Glu Thr Gly Thr Ser Ala Phe Gly Ile Asn Gln Thr Pro Phe
385                 390                 395                 400

Pro Asn Asn Ala Tyr Gly Ile Ser Gln Val Leu Trp Gly Ser Ile Gly
            405                 410                 415

Phe Thr Thr Gly Ala Cys Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Arg Leu Ile
465                 470                 475                 480

His Gly Glu Lys Ala Gly Tyr Asn Asp Ile Gln Asn Trp Asp His Leu
            485                 490                 495

Ala Leu Leu Pro Thr Phe Gly Ala Lys Asp Tyr Glu Asn His Arg Val
            500                 505                 510

Ala Thr Thr Gly Glu Trp Asp Lys Leu Thr Gln Asp Lys Glu Phe Asn
            515                 520                 525

Lys Asn Ser Lys Ile Arg Met Ile Glu Val Met Leu Pro Val Met Asp
530                 535                 540

Ala Pro Thr Ser Leu Ile Glu Gln Ala Lys Leu Thr Ala Ser Ile Asn
545                 550                 555                 560

Ala Lys Gln Glu

<210> SEQ ID NO 9
<211> LENGTH: 1788
<212> TYPE: DNA
<213> ORGANISM: Pichia stipitis

<400> SEQUENCE: 9

```
atggctgaag tctcattagg aagatatctc ttcgagagat gtaccaatt gcaagtgcag      60
accatcttcg gtgtccctgg tgatttcaac ttgtcgcttt tggacaagat ctacgaagtg    120
gaagatgccc atggcaagaa ttcgtttaga tgggctggta atgccaacga attgaatgca   180
tcgtacgctg ctgacggtta ctcgagagtc aagcgtttag gtgtttggt cactaccttt    240
ggtgtcggtg aattgtctgc tttgaatggt attgccggtt cttatgccga acatgttggt    300
ttgcttcatg tcgtaggtgt tccatcgatt tcctcgcaag ctaagcaatt gttacttcac   360
cacactttgg gtaatggtga tttcactgtt ttccatagaa tgtccaacaa catttctcag   420
accacagcct ttatctccga tatcaactcg gctccagctg aaattgatag atgtatcaga   480
gaggcctacg tcaaacaaag accagtttat atcgggttac cagctaactt agttgatttg   540
aatgttccgg cctctttgct tgagtctcca atcaacttgt cgttggaaaa gaacgaccca   600
gaggctcaag atgaagtcat tgactctgtc ttagacttga tcaaaaagtc gctgaaccca   660
atcatcttgg tcgatgcctg tgcctcgaga catgactgta aggctgaagt tactcagttg   720
attgaacaaa cccaattccc agtatttgtc actccaatgg gtaaaggtac cgttgatgag   780
ggtggtgtag acggagaatt gttagaagat gatcctcatt tgattgccaa ggtcgctgct   840
aggttgtctc ctggcaagaa cgctgcctct agattcggag tgtttatgt cggaaccttg   900
tcgaagcccg aagtcaagga cgctgtagag agtgcagatt tgattttgtc tgtcggtgcc   960
cttttgtctg atttcaacac tggttcattt tcctactcct acagaaccaa gaacatcgtc  1020
gaattccatt ctgattacac taagattaga caagccactt tcccaggtgt gcagatgaag  1080
gaagccttgc aagaattgaa caagaaagtt tcatctgctg ctagtcacta tgaagtcaag  1140
cctgtgccca agatcaagtt ggccaataca ccagccacca gagaagtcaa gttaactcag  1200
gaatggttgt ggaccagagt gtcttcgtgg ttcagagaag gtgatattat tatcaccgaa  1260
accggtacat cctccttcgg tatagttcaa tccagattcc caaacaacac catcggtatc  1320
tcccaagtat tgtggggttc tattggtttc tctgttggtg ccactttggg tgctgccatg  1380
gctgcccaag aactcgaccc taacaagaga accatcttgt tgttggaga tggttctttg  1440
caattgaccg ttcaggaaat ctccaccata atcagatggg gtaccacacc ttaccttttc  1500
gtgttgaaca atgacggtta caccatcgag cgtttgatcc acggtgtaaa tgcctcatat  1560
aatgacatcc aaccatggca aaacttggaa atcttgccta ctttctcggc caagaactac  1620
gacgctgtga gaatctccaa catcggagaa gcagaagata tcttgaaaga caaggaattc  1680
ggaaagaact ccaagattag attgataaaa gtcatgttac caagattgga tgcaccatct  1740
aaccttgcca acaagctgc cattacagct gccaccaacg ccgaagct             1788
```

<210> SEQ ID NO 10
<211> LENGTH: 596
<212> TYPE: PRT
<213> ORGANISM: Pichia stipitis

<400> SEQUENCE: 10

```
Met Ala Glu Val Ser Leu Gly Arg Tyr Leu Phe Glu Arg Leu Tyr Gln
1               5                  10                  15

Leu Gln Val Gln Thr Ile Phe Gly Val Pro Gly Asp Phe Asn Leu Ser
            20                  25                  30

Leu Leu Asp Lys Ile Tyr Glu Val Glu Asp Ala His Gly Lys Asn Ser
        35                  40                  45

Phe Arg Trp Ala Gly Asn Ala Asn Glu Leu Asn Ala Ser Tyr Ala Ala
    50                  55                  60
```

-continued

```
Asp Gly Tyr Ser Arg Val Lys Arg Leu Gly Cys Leu Val Thr Thr Phe
 65                  70                  75                  80

Gly Val Gly Glu Leu Ser Ala Leu Asn Gly Ile Ala Gly Ser Tyr Ala
             85                  90                  95

Glu His Val Gly Leu Leu His Val Gly Val Pro Ser Ile Ser Ser
        100                 105                 110

Gln Ala Lys Gln Leu Leu Leu His His Thr Leu Gly Asn Gly Asp Phe
        115                 120                 125

Thr Val Phe His Arg Met Ser Asn Asn Ile Ser Gln Thr Thr Ala Phe
130                 135                 140

Ile Ser Asp Ile Asn Ser Ala Pro Ala Glu Ile Asp Arg Cys Ile Arg
145                 150                 155                 160

Glu Ala Tyr Val Lys Gln Arg Pro Val Tyr Ile Gly Leu Pro Ala Asn
                165                 170                 175

Leu Val Asp Leu Asn Val Pro Ala Ser Leu Leu Glu Ser Pro Ile Asn
            180                 185                 190

Leu Ser Leu Glu Lys Asn Asp Pro Glu Ala Gln Asp Glu Val Ile Asp
        195                 200                 205

Ser Val Leu Asp Leu Ile Lys Lys Ser Ser Asn Pro Ile Ile Leu Val
        210                 215                 220

Asp Ala Cys Ala Ser Arg His Asp Cys Lys Ala Glu Val Thr Gln Leu
225                 230                 235                 240

Ile Glu Gln Thr Gln Phe Pro Val Phe Val Thr Pro Met Gly Lys Gly
                245                 250                 255

Thr Val Asp Glu Gly Gly Val Asp Gly Glu Leu Leu Glu Asp Asp Pro
            260                 265                 270

His Leu Ile Ala Lys Val Ala Ala Arg Leu Ser Ala Gly Lys Asn Ala
        275                 280                 285

Ala Ser Arg Phe Gly Gly Val Tyr Val Gly Thr Leu Ser Lys Pro Glu
        290                 295                 300

Val Lys Asp Ala Val Glu Ser Ala Asp Leu Ile Leu Ser Val Gly Ala
305                 310                 315                 320

Leu Leu Ser Asp Phe Asn Thr Gly Ser Phe Ser Tyr Ser Tyr Arg Thr
                325                 330                 335

Lys Asn Ile Val Glu Phe His Ser Asp Tyr Thr Lys Ile Arg Gln Ala
            340                 345                 350

Thr Phe Pro Gly Val Gln Met Lys Glu Ala Leu Gln Glu Leu Asn Lys
        355                 360                 365

Lys Val Ser Ser Ala Ala Ser His Tyr Glu Val Lys Pro Val Pro Lys
        370                 375                 380

Ile Lys Leu Ala Asn Thr Pro Ala Thr Arg Glu Val Lys Leu Thr Gln
385                 390                 395                 400

Glu Trp Leu Trp Thr Arg Val Ser Ser Trp Phe Arg Glu Gly Asp Ile
                405                 410                 415

Ile Ile Thr Glu Thr Gly Thr Ser Ser Phe Gly Ile Val Gln Ser Arg
            420                 425                 430

Phe Pro Asn Asn Thr Ile Gly Ile Ser Gln Val Leu Trp Gly Ser Ile
        435                 440                 445

Gly Phe Ser Val Gly Ala Thr Leu Gly Ala Ala Met Ala Ala Gln Glu
        450                 455                 460

Leu Asp Pro Asn Lys Arg Thr Ile Leu Phe Val Gly Asp Gly Ser Leu
465                 470                 475                 480
```

```
Gln Leu Thr Val Gln Glu Ile Ser Thr Ile Ile Arg Trp Gly Thr Thr
                485                 490                 495

Pro Tyr Leu Phe Val Leu Asn Asn Asp Gly Tyr Thr Ile Glu Arg Leu
            500                 505                 510

Ile His Gly Val Asn Ala Ser Tyr Asn Asp Ile Gln Pro Trp Gln Asn
        515                 520                 525

Leu Glu Ile Leu Pro Thr Phe Ser Ala Lys Asn Tyr Asp Ala Val Arg
    530                 535                 540

Ile Ser Asn Ile Gly Glu Ala Glu Asp Ile Leu Lys Asp Lys Glu Phe
545                 550                 555                 560

Gly Lys Asn Ser Lys Ile Arg Leu Ile Glu Val Met Leu Pro Arg Leu
                565                 570                 575

Asp Ala Pro Ser Asn Leu Ala Lys Gln Ala Ala Ile Thr Ala Ala Thr
            580                 585                 590

Asn Ala Glu Ala
        595
```

<210> SEQ ID NO 11
<211> LENGTH: 1707
<212> TYPE: DNA
<213> ORGANISM: Pichia stipitis

<400> SEQUENCE: 11

| | | | | | |
|---|---|---|---|---|---|
| atggtatcaa | cctacccaga | atcagaggtt | actctaggaa | ggtacctctt | tgagcgactc | 60 |
| caccaattga | aagtggacac | cattttcggc | ttgccgggtg | acttcaacct | ttccttattg | 120 |
| gacaaagtgt | atgaagttcc | ggatatgagg | tgggctggaa | atgccaacga | attgaatgct | 180 |
| gcctatgctg | ccgatggtta | ctccagaata | aagggattgt | cttgcttggt | cacaactttt | 240 |
| ggtgttggtg | aattgtctgc | tttaaacgga | gttggtggtg | cctatgctga | acacgtagga | 300 |
| cttctacatg | tcgttggagt | tccatccata | tcgtcacagg | ctaaacagtt | gttgctccac | 360 |
| cataccttgg | gtaatggtga | cttcactgtt | tttcacagaa | tgtccaatag | catttctcaa | 420 |
| actacagcat | ttctctcaga | tatctctatt | gcaccaggtc | aaatagatag | atgcatcaga | 480 |
| gaagcatatg | ttcatcagag | accagtttat | gttggtttac | cggcaaatat | ggttgatctc | 540 |
| aaggttcctt | ctagtctctt | agaaactcca | attgatttga | aattgaaaca | aaatgatcct | 600 |
| gaagctcaag | aagttgttga | aacagtcctg | aagttggtgt | cccaagctac | aaaccccatt | 660 |
| atcttggtag | acgcttgtgc | cctcagacac | aattgcaaag | aggaagtcaa | acaattggtt | 720 |
| gatgccacta | ttttcaagt | ctttacaact | ccaatgggta | atctggtat | ctccgaatct | 780 |
| catccaagat | gggcggtgt | ctatgtcggg | acaatgtcga | gtcctcaagt | caaaaaagcc | 840 |
| gttgaaaatg | ccgatcttat | actatctgtt | ggttcgttgt | tatcggactt | caatacaggt | 900 |
| tcatttttcat | actcctacaa | gacgaagaat | gttgttgaat | ccactctga | ctatatgaaa | 960 |
| atcagacagg | ccaccttccc | aggagttcaa | atgaaagaag | ccttgcaaca | gttgataaaa | 1020 |
| agggtctctt | cttacatcaa | tccaagctac | attcctactc | gagttcctaa | aaggaaacag | 1080 |
| ccattgaaag | ctccatcaga | agctcctttg | acccaagaat | atttgtggtc | taaagtatcc | 1140 |
| ggctggttta | gagagggtga | tattatcgta | accgaaactg | gtacatctgc | tttcggaatt | 1200 |
| attcaatccc | attttcccag | caacactatc | ggtatatccc | aagtcttgtg | gggctcaatt | 1260 |
| ggtttcacag | taggtgcaac | agttggtgct | gccatggcag | cccaggaaat | cgaccctagc | 1320 |
| aggagagtaa | ttttgttcgt | cggtgatggt | tcattgcagt | tgacggttca | ggaaatctct | 1380 |
| acgttgtgta | atgggattg | taacaatact | tatctttacg | tgttgaacaa | tgatggttac | 1440 |

```
actatagaaa ggttgatcca cggcaaaagt gccagctaca acgatataca gccttggaac    1500
catttatcct tgcttcgctt attcaatgct aagaaatacc aaaatgtcag agtatcgact    1560
gctggagaat tggactcttt gttctctgat aagaaatttg cttctccaga taggataaga    1620
atgattgagg tgatgttatc gagattggat gcaccagcaa atcttgttgc tcaagcaaag    1680
ttgtctgaac gggtaaacct tgaaaat                                       1707
```

<210> SEQ ID NO 12
<211> LENGTH: 569
<212> TYPE: PRT
<213> ORGANISM: Pichia stipitis

<400> SEQUENCE: 12

```
Met Val Ser Thr Tyr Pro Glu Ser Glu Val Thr Leu Gly Arg Tyr Leu
1               5                   10                  15

Phe Glu Arg Leu His Gln Leu Lys Val Asp Thr Ile Phe Gly Leu Pro
            20                  25                  30

Gly Asp Phe Asn Leu Ser Leu Leu Asp Lys Val Tyr Glu Val Pro Asp
        35                  40                  45

Met Arg Trp Ala Gly Asn Ala Asn Glu Leu Asn Ala Ala Tyr Ala Ala
50                  55                  60

Asp Gly Tyr Ser Arg Ile Lys Gly Leu Ser Cys Leu Val Thr Thr Phe
65                  70                  75                  80

Gly Val Gly Glu Leu Ser Ala Leu Asn Gly Val Gly Gly Ala Tyr Ala
                85                  90                  95

Glu His Val Gly Leu Leu His Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Ser Ile Ser Gln Thr Thr Ala Phe
130                 135                 140

Leu Ser Asp Ile Ser Ile Ala Pro Gly Gln Ile Asp Arg Cys Ile Arg
145                 150                 155                 160

Glu Ala Tyr Val His Gln Arg Pro Val Tyr Val Gly Leu Pro Ala Asn
                165                 170                 175

Met Val Asp Leu Lys Val Pro Ser Ser Leu Leu Glu Thr Pro Ile Asp
            180                 185                 190

Leu Lys Leu Lys Gln Asn Asp Pro Glu Ala Gln Glu Val Val Glu Thr
        195                 200                 205

Val Leu Lys Leu Val Ser Gln Ala Thr Asn Pro Ile Ile Leu Val Asp
    210                 215                 220

Ala Cys Ala Leu Arg His Asn Cys Lys Glu Glu Val Lys Gln Leu Val
225                 230                 235                 240

Asp Ala Thr Asn Phe Gln Val Phe Thr Thr Pro Met Gly Lys Ser Gly
                245                 250                 255

Ile Ser Glu Ser His Pro Arg Leu Gly Gly Val Tyr Val Gly Thr Met
            260                 265                 270

Ser Ser Pro Gln Val Lys Lys Ala Val Glu Asn Ala Asp Leu Ile Leu
        275                 280                 285

Ser Val Gly Ser Leu Leu Ser Asp Phe Asn Thr Gly Ser Phe Ser Tyr
    290                 295                 300

Ser Tyr Lys Thr Lys Asn Val Val Glu Phe His Ser Asp Tyr Met Lys
305                 310                 315                 320
```

```
Ile Arg Gln Ala Thr Phe Pro Gly Val Gln Met Lys Glu Ala Leu Gln
                325                 330                 335

Gln Leu Ile Lys Arg Val Ser Ser Tyr Ile Asn Pro Ser Tyr Ile Pro
        340                 345                 350

Thr Arg Val Pro Lys Arg Lys Gln Pro Leu Lys Ala Pro Ser Glu Ala
    355                 360                 365

Pro Leu Thr Gln Glu Tyr Leu Trp Ser Lys Val Ser Gly Trp Phe Arg
370                 375                 380

Glu Gly Asp Ile Ile Val Thr Glu Thr Gly Thr Ser Ala Phe Gly Ile
385                 390                 395                 400

Ile Gln Ser His Phe Pro Ser Asn Thr Ile Gly Ile Ser Gln Val Leu
                405                 410                 415

Trp Gly Ser Ile Gly Phe Thr Val Gly Ala Thr Val Gly Ala Ala Met
            420                 425                 430

Ala Ala Gln Glu Ile Asp Pro Ser Arg Arg Val Ile Leu Phe Val Gly
        435                 440                 445

Asp Gly Ser Leu Gln Leu Thr Val Gln Glu Ile Ser Thr Leu Cys Lys
    450                 455                 460

Trp Asp Cys Asn Asn Thr Tyr Leu Tyr Val Leu Asn Asn Asp Gly Tyr
465                 470                 475                 480

Thr Ile Glu Arg Leu Ile His Gly Lys Ser Ala Ser Tyr Asn Asp Ile
                485                 490                 495

Gln Pro Trp Asn His Leu Ser Leu Leu Arg Leu Phe Asn Ala Lys Lys
            500                 505                 510

Tyr Gln Asn Val Arg Val Ser Thr Ala Gly Glu Leu Asp Ser Leu Phe
        515                 520                 525

Ser Asp Lys Lys Phe Ala Ser Pro Asp Arg Ile Arg Met Ile Glu Val
    530                 535                 540

Met Leu Ser Arg Leu Asp Ala Pro Ala Asn Leu Val Ala Gln Ala Lys
545                 550                 555                 560

Leu Ser Glu Arg Val Asn Leu Glu Asn
                565

<210> SEQ ID NO 13
<211> LENGTH: 1689
<212> TYPE: DNA
<213> ORGANISM: Kluyveromyces lactis

<400> SEQUENCE: 13
atgtctgaaa ttacattagg tcgttacttg ttcgaaagat taaagcaagt cgaagttcaa      60
accatctttg gtctaccagg tgatttcaac ttgtccctat ggacaatat ctacgaagtc      120 ccaggtatga gatgggctgg taatgccaac gaattgaacg ctgcttacgc tgctgatggt     180
tacgccagat taaagggtat gtcctgtatc atcaccacct tcggtgtcgg tgaattgtct     240
gctttgaacg gtattgccgg ttcttacgct gaacacgttg gtgtcttgca cgttgtcggt     300
gttccatccg tctcttctca agctaagcaa ttgttgttgc accacacctt gggtaacggt     360
gacttcactg ttttccacag aatgtcctcc aacatttctg aaaccactgc tatgatcacc     420
gatatcaaca ctgccccagc tgaaatcgac agatgtatca gaaccactta cgtttcccaa     480
agaccagtct acttgggttt gccagctaac ttggtcgact tgactgtccc agcttctttg     540
ttggacactc caattgattt gagcttgaag ccaaatgacc agaagccga agaagaagtc      600 atcgaaaacg tcttgcaact gatcaaggaa gctaagaacc cagttatctt ggctgatgct     660
tgttgttcca gacacgatgc caaggctgag accaagaagt tgatcgactt gactcaattc     720
```

```
ccagccttcg ttaccccaat gggtaagggt tccattgacg aaaagcaccc aagattcggt    780
ggtgtctacg tcggtaccct atcttctcca gctgtcaagg aagccgttga atctgctgac    840
ttggttctat cggtcggtgc tctattgtcc gatttcaaca ctggttcttt ctcttactct    900
tacaagacca agaacattgt cgaattccac tctgactaca ccaagatcag aagcgctacc    960
ttcccaggtg tccaaatgaa gttcgcttta caaaaattgt tgactaaggt tgccgatgct   1020
gctaagggtt acaagccagt tccagttcca tctgaaccag aacacaacga agctgtcgct   1080
gactccactc cattgaagca agaatgggtc tggactcaag tcggtgaatt cttgagagaa   1140
ggtgatgttg ttatcactga aaccggtacc tctgccttcg gtatcaacca aactcatttc   1200
ccaaacaaca catacggtat ctctcaagtt ttatggggtt ccattggttt caccactggt   1260
gctaccttgg gtgctgcctt cgctgccgaa gaaattgatc aaagaagag agttatctta    1320
```
```
ttcattggtg acggttcttt gcaattgact gttcaagaaa tctccaccat gatcagatgg   1380
ggcttgaagc atacttgtt cgtattgaac aacgacggtt acaccattga agattgatt    1440
cacggtgaaa ccgctcaata aactgtatc caaaactggc aacacttgga attattgcca    1500
actttcggtg ccaaggacta cgaagctgtc agagtttcca ccactggtga atggaacaag   1560
ttgaccactg acgaaaagtt ccaagacaac accagaatca gattgatcga agttatgttg   1620
ccaactatgg atgctccatc taacttggtt aagcaagctc aattgactgc tgctaccaac   1680
gctaagaac                                                          1689
```

<210> SEQ ID NO 14
<211> LENGTH: 563
<212> TYPE: PRT
<213> ORGANISM: Kluyveromyces lactis

<400> SEQUENCE: 14

```
Met Ser Glu Ile Thr Leu Gly Arg Tyr Leu Phe Glu Arg Leu Lys Gln
1               5                   10                  15

Val Glu Val Gln Thr Ile Phe Gly Leu Pro Gly Asp Phe Asn Leu Ser
                20                  25                  30

Leu Leu Asp Asn Ile Tyr Glu Val Pro Gly Met Arg Trp Ala Gly Asn
            35                  40                  45

Ala Asn Glu Leu Asn Ala Ala Tyr Ala Ala Asp Gly Tyr Ala Arg Leu
        50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
        115                 120                 125

Ser Ser Asn Ile Ser Glu Thr Thr Ala Met Ile Thr Asp Ile Asn Thr
130                 135                 140

Ala Pro Ala Glu Ile Asp Arg Cys Ile Arg Thr Thr Tyr Val Ser Gln
145                 150                 155                 160

Arg Pro Val Tyr Leu Gly Leu Pro Ala Asn Leu Val Asp Leu Thr Val
                165                 170                 175

Pro Ala Ser Leu Leu Asp Thr Pro Ile Asp Leu Ser Leu Lys Pro Asn
            180                 185                 190
```

Asp Pro Glu Ala Glu Glu Val Ile Glu Asn Val Leu Gln Leu Ile
            195                 200                 205

Lys Glu Ala Lys Asn Pro Val Ile Leu Ala Asp Ala Cys Cys Ser Arg
210                 215                 220

His Asp Ala Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Lys His
            245                 250                 255

Pro Arg Phe Gly Gly Val Tyr Val Gly Thr Leu Ser Ser Pro Ala Val
            260                 265                 270

Lys Glu Ala Val Glu Ser Ala Asp Leu Val Leu Ser Val Gly Ala Leu
275                 280                 285

Leu Ser Asp Phe Asn Thr Gly Ser Phe Ser Tyr Ser Tyr Lys Thr Lys
290                 295                 300

Asn Ile Val Glu Phe His Ser Asp Tyr Thr Lys Ile Arg Ser Ala Thr
305                 310                 315                 320

Phe Pro Gly Val Gln Met Lys Phe Ala Leu Gln Lys Leu Leu Thr Lys
            325                 330                 335

Val Ala Asp Ala Ala Lys Gly Tyr Lys Pro Val Pro Val Pro Ser Glu
            340                 345                 350

Pro Glu His Asn Glu Ala Val Ala Asp Ser Thr Pro Leu Lys Gln Glu
            355                 360                 365

Trp Val Trp Thr Gln Val Gly Glu Phe Leu Arg Glu Gly Asp Val Val
            370                 375                 380

Ile Thr Glu Thr Gly Thr Ser Ala Phe Gly Ile Asn Gln Thr His Phe
385                 390                 395                 400

Pro Asn Asn Thr Tyr Gly Ile Ser Gln Val Leu Trp Gly Ser Ile Gly
            405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Arg Leu Ile
465                 470                 475                 480

His Gly Glu Thr Ala Gln Tyr Asn Cys Ile Gln Asn Trp Gln His Leu
            485                 490                 495

Glu Leu Leu Pro Thr Phe Gly Ala Lys Asp Tyr Glu Ala Val Arg Val
            500                 505                 510

Ser Thr Thr Gly Glu Trp Asn Lys Leu Thr Thr Asp Glu Lys Phe Gln
            515                 520                 525

Asp Asn Thr Arg Ile Arg Leu Ile Glu Val Met Leu Pro Thr Met Asp
530                 535                 540

Ala Pro Ser Asn Leu Val Lys Gln Ala Gln Leu Thr Ala Ala Thr Asn
545                 550                 555                 560

Ala Lys Asn

<210> SEQ ID NO 15
<211> LENGTH: 1713
<212> TYPE: DNA
<213> ORGANISM: Yarrowia lipolytica

<400> SEQUENCE: 15

```
atgagcgact ccgaacccca atggtcgac ctgggcgact atctctttgc ccgattcaag     60
cagctaggcg tggactccgt ctttggagtg cccggcgact tcaacctcac cctgttggac    120
cacgtgtaca atgtcgacat gcggtgggtt gggaacacaa acgagctgaa tgccggctac    180
tcggccgacg gctactcccg ggtcaagcgg ctggcatgtc ttgtcaccac ctttggcgtg    240
ggagagctgt ctgccgtggc tgctgtggca ggctcgtacg ccgagcatgt gggcgtggtg    300
catgttgtgg gcgttccag cacctctgct gagaacaagc atctgctgct gcaccacaca    360
ctcggtaacg gcgacttccg ggtctttgcc cagatgtcca aactcatctc cgagtacacc    420
caccatattg ggaccccag cgaggctgcc gacgtaatcg acaccgccat ccgaatcgcc    480
tacacccacc agcggcccgt ttacattgct gtgccctcca acttctccga ggtcgatatt    540
gccgaccagg ctagactgga taccccctg gaccttcgc tgcagcccaa cgaccccgag    600
agccagtacg aggtgattga ggagatttgc tcgcgtatca aggccgccaa gaagcccgtg    660
attctcgtcg acgcctgcgc ttcgcgatac agatgtgtgg acgagaccaa ggagctggcc    720
aagatcacca actttgccta ctttgtcact cccatgggta agggttctgt ggacgaggat    780
actgaccggt acggaggaac atacgtcgga tcgctgactg ctcctgctac tgccgaggtg    840
gttgagacag ctgatctcat catctcccgta ggagctcttc tgtcggactt caacaccggt    900
tccttctcgt actcctactc caccaaaaac gtggtggaat tgcattcgga ccacgtcaaa    960
atcaagtccg ccacctacaa caacgtcggc atgaaaatgc tgttcccgcc cctgctcgaa   1020
gccgtcaaga aactggttgc cgagaccct gactttgcat ccaaggctct ggctgttccc   1080
gacaccactc ccaagatccc cgaggtaccc gatgatcaca ttacgaccca ggcatggctg   1140
tggcagcgtc tcagttactt tctgaggccc accgacatcg tggtcaccga accggaacc    1200
tcgtcctttg gaatcatcca gaccaagttc ccccacaacg tccgaggtat ctcgcaggtg   1260
ctgtggggct ctattggata ctcggtggga gcagcctgtg agcctccat gctgcacag    1320
gagattgacc cccagcagcg agtgattctg tttgtgggcg acggctctct tcagctgacg   1380
gtgaccgaga tctcgtgcat gatccgcaac aacgtcaagc cgtacatttt tgtgctcaac   1440
aacgacggct acaccatcga gaggctcatt acggcgaaa acgcctcgta caacgatgtg   1500
cacatgtgga agtactccaa gattctcgac acgttcaacg ccaaggccca cgagtcgatt   1560
gtggtcaaca ccaagggcga gatggacgct ctgttcgaca cgaagagtt tgccaagccc   1620
gacaagatcc ggctcattga ggtcatgtgc gacaagatgg acgcgcctgc ctcgttgatc   1680
aagcaggctg agctctctgc caagaccaac gtt                                1713
```

<210> SEQ ID NO 16
<211> LENGTH: 571
<212> TYPE: PRT
<213> ORGANISM: Yarrowia lipolytica

<400> SEQUENCE: 16

Met Ser Asp Ser Glu Pro Gln Met Val Asp Leu Gly Asp Tyr Leu Phe
1               5                   10                  15

Ala Arg Phe Lys Gln Leu Gly Val Asp Ser Val Phe Gly Val Pro Gly
            20                  25                  30

Asp Phe Asn Leu Thr Leu Leu Asp His Val Tyr Asn Val Asp Met Arg
        35                  40                  45

Trp Val Gly Asn Thr Asn Glu Leu Asn Ala Gly Tyr Ser Ala Asp Gly
    50                  55                  60

Tyr Ser Arg Val Lys Arg Leu Ala Cys Leu Val Thr Thr Phe Gly Val

```
            65                  70                  75                  80
    Gly Glu Leu Ser Ala Val Ala Val Ala Gly Ser Tyr Ala Glu His
                        85                  90                  95

Val Gly Val Val His Val Val Gly Val Pro Ser Thr Ser Ala Glu Asn
                    100                 105                 110

Lys His Leu Leu Leu His His Thr Leu Gly Asn Gly Asp Phe Arg Val
                    115                 120                 125

Phe Ala Gln Met Ser Lys Leu Ile Ser Glu Tyr Thr His His Ile Glu
                130                 135                 140

Asp Pro Ser Glu Ala Ala Asp Val Ile Asp Thr Ala Ile Arg Ile Ala
    145                 150                 155                 160

Tyr Thr His Gln Arg Pro Val Tyr Ile Ala Val Pro Ser Asn Phe Ser
                        165                 170                 175

Glu Val Asp Ile Ala Asp Gln Ala Arg Leu Asp Thr Pro Leu Asp Leu
                    180                 185                 190

Ser Leu Gln Pro Asn Asp Pro Glu Ser Gln Tyr Glu Val Ile Glu Glu
                    195                 200                 205

Ile Cys Ser Arg Ile Lys Ala Ala Lys Lys Pro Val Ile Leu Val Asp
                210                 215                 220

Ala Cys Ala Ser Arg Tyr Arg Cys Val Asp Glu Thr Lys Glu Leu Ala
    225                 230                 235                 240

Lys Ile Thr Asn Phe Ala Tyr Phe Val Thr Pro Met Gly Lys Gly Ser
                        245                 250                 255

Val Asp Glu Asp Thr Asp Arg Tyr Gly Gly Thr Tyr Val Gly Ser Leu
                    260                 265                 270

Thr Ala Pro Ala Thr Ala Glu Val Val Glu Thr Ala Asp Leu Ile Ile
                    275                 280                 285

Ser Val Gly Ala Leu Leu Ser Asp Phe Asn Thr Gly Ser Phe Ser Tyr
                290                 295                 300

Ser Tyr Ser Thr Lys Asn Val Val Glu Leu His Ser Asp His Val Lys
    305                 310                 315                 320

Ile Lys Ser Ala Thr Tyr Asn Asn Val Gly Met Lys Met Leu Phe Pro
                        325                 330                 335

Pro Leu Leu Glu Ala Val Lys Lys Leu Val Ala Glu Thr Pro Asp Phe
                    340                 345                 350

Ala Ser Lys Ala Leu Ala Val Pro Asp Thr Thr Pro Lys Ile Pro Glu
                    355                 360                 365

Val Pro Asp Asp His Ile Thr Thr Gln Ala Trp Leu Trp Gln Arg Leu
                370                 375                 380

Ser Tyr Phe Leu Arg Pro Thr Asp Ile Val Val Thr Glu Thr Gly Thr
    385                 390                 395                 400

Ser Ser Phe Gly Ile Ile Gln Thr Lys Phe Pro His Asn Val Arg Gly
                        405                 410                 415

Ile Ser Gln Val Leu Trp Gly Ser Ile Gly Tyr Ser Val Gly Ala Ala
                    420                 425                 430

Cys Gly Ala Ser Ile Ala Ala Gln Glu Ile Asp Pro Gln Gln Arg Val
                    435                 440                 445

Ile Leu Phe Val Gly Asp Gly Ser Leu Gln Leu Thr Val Thr Glu Ile
                450                 455                 460

Ser Cys Met Ile Arg Asn Asn Val Lys Pro Tyr Ile Phe Val Leu Asn
    465                 470                 475                 480

Asn Asp Gly Tyr Thr Ile Glu Arg Leu Ile His Gly Glu Asn Ala Ser
                        485                 490                 495
```

| Tyr | Asn | Asp | Val | His | Met | Trp | Lys | Tyr | Ser | Lys | Ile | Leu | Asp | Thr | Phe |
| | | | 500 | | | | 505 | | | | 510 | | | | |

| Asn | Ala | Lys | Ala | His | Glu | Ser | Ile | Val | Val | Asn | Thr | Lys | Gly | Glu | Met |
| | | 515 | | | | | 520 | | | | | 525 | | | |

| Asp | Ala | Leu | Phe | Asp | Asn | Glu | Glu | Phe | Ala | Lys | Pro | Asp | Lys | Ile | Arg |
| 530 | | | | | 535 | | | | | 540 | | | | | |

| Leu | Ile | Glu | Val | Met | Cys | Asp | Lys | Met | Asp | Ala | Pro | Ala | Ser | Leu | Ile |
| 545 | | | | | 550 | | | | | 555 | | | | | 560 |

| Lys | Gln | Ala | Glu | Leu | Ser | Ala | Lys | Thr | Asn | Val |
| | | | | 565 | | | | | 570 | |

<210> SEQ ID NO 17
<211> LENGTH: 1713
<212> TYPE: DNA
<213> ORGANISM: Schizosaccharomyces pombe

<400> SEQUENCE: 17

```
atgagtgggg atatttagt cggtgaatat ctattcaaaa ggcttgaaca attagggtc      60
aagtccattc ttggtgttcc aggagatttc aatttagctc tacttgactt aattgagaaa   120
gttggagatg agaaatttcg ttgggttggc aataccaatg agttgaatgg tgcttatgcc   180
gctgatggtt atgctcgtgt taatggtctt tcagccattg ttacaacgtt cggcgtggga   240
gagctttccg ctattaatgg agtggcaggt tcttatgcgg agcatgtccc agtagttcat   300
attgttggaa tgccttccac aaaggtgcaa gatactggag ctttgcttca tcatacttta   360
ggagatggag actttcgcac tttcatggat atgtttaaga agtttctgc ctacagtata    420
atgatcgata acggaaacga tgcagctgaa aagatcgatg aagccttgtc gatttgttat   480
aaaaaggcta ggcctgttta cattggtatt ccttctgatg ctggctactt caaagcatct   540
tcatcaaatc ttgggaaaag actaaagctc gaggaggata ctaacgatcc agcagttgag   600
caagaagtca tcaatcatat ctcggaaatg gttgtcaatg caagaaaacc agtgatttta   660
attgacgctt gtgctgtaag acatcgtgtc gttccagaag tacatgagct gattaaattg   720
acccatttcc ctacatatgt aactcccatg ggtaaatctg caattgacga aacttcgcaa   780
ttttttgacg gcgtttatgt tggttcaatt tcagatcctg aagttaaaga cagaattgaa   840
tccactgatc tgttgctatc catcggtgct ctcaaatcag actttaacac gggttccttc   900
tcttaccacc tcagccaaaa gaatgccgtt gagtttcatt cagaccacat gcgcattcga   960
tatgctcttt atccaaatgt agccatgaag tatattcttc gcaaactgtt gaaagtactt  1020
gatgcttcta tgtgtcattc caaggctgct cctaccattg gctacaacat caagcctaag  1080
catgcggaag atattcttc caacgagatt actcattgct ggttttggcc taaatttagt   1140
gaatttttga gccccgaga tgttttgatc accgagactg gaactgcaaa ctttggtgtc   1200
cttgattgca ggtttccaaa ggatgtaaca gccatttccc aggtattatg gggatctatt  1260
ggatactccg ttggtgcaat gtttggtgct gttttggccg tccacgattc taaagagccc  1320
gatcgtcgta ccattcttgt agtaggtgat ggatccttac aactgacgat tacagagatt  1380
tcaacctgca ttcgccataa cctcaaacca attattttca taattaacaa cgacggttac  1440
accattgagc gtttaattca tggtttgcat gctagctata acgaaattaa cactaaatgg  1500
ggctaccaac agattcccaa gttttcgga gctgctgaaa accacttccg cacttactgt   1560
gttaaaactc ctactgacgt tgaaaagttg tttagcgaca aggagtttgc aaatgcagat  1620
gtcattcaag tagttgagct tgtaatgcct atgttggatg cacctcgtgt cctagttgag  1680
```
caagccaagt tgacgtctaa gatcaataag caa 1713

<210> SEQ ID NO 18
<211> LENGTH: 571
<212> TYPE: PRT
<213> ORGANISM: Schizosaccharomyces pombe

<400> SEQUENCE: 18

| | | | | | | | | | | | | | | |
|---|---|---|---|---|---|---|---|---|---|---|---|---|---|---|
| Met | Ser | Gly | Asp | Ile | Leu | Val | Gly | Glu | Tyr | Leu | Phe | Lys | Arg | Leu | Glu |
| 1 | | | | 5 | | | | | 10 | | | | | 15 | |
| Gln | Leu | Gly | Val | Lys | Ser | Ile | Leu | Gly | Val | Pro | Gly | Asp | Phe | Asn | Leu |
| | | | 20 | | | | | 25 | | | | | 30 | | |
| Ala | Leu | Leu | Asp | Leu | Ile | Glu | Lys | Val | Gly | Asp | Glu | Lys | Phe | Arg | Trp |
| | | 35 | | | | | 40 | | | | | 45 | | | |
| Val | Gly | Asn | Thr | Asn | Glu | Leu | Asn | Gly | Ala | Tyr | Ala | Ala | Asp | Gly | Tyr |
| | 50 | | | | | 55 | | | | | 60 | | | | |
| Ala | Arg | Val | Asn | Gly | Leu | Ser | Ala | Ile | Val | Thr | Thr | Phe | Gly | Val | Gly |
| 65 | | | | | 70 | | | | | 75 | | | | | 80 |
| Glu | Leu | Ser | Ala | Ile | Asn | Gly | Val | Ala | Gly | Ser | Tyr | Ala | Glu | His | Val |
| | | | | 85 | | | | | 90 | | | | | 95 | |
| Pro | Val | Val | His | Ile | Val | Gly | Met | Pro | Ser | Thr | Lys | Val | Gln | Asp | Thr |
| | | | 100 | | | | | 105 | | | | | 110 | | |
| Gly | Ala | Leu | Leu | His | His | Thr | Leu | Gly | Asp | Gly | Asp | Phe | Arg | Thr | Phe |
| | | 115 | | | | | 120 | | | | | 125 | | | |
| Met | Asp | Met | Phe | Lys | Lys | Val | Ser | Ala | Tyr | Ser | Ile | Met | Ile | Asp | Asn |
| | 130 | | | | | 135 | | | | | 140 | | | | |
| Gly | Asn | Asp | Ala | Ala | Glu | Lys | Ile | Asp | Glu | Ala | Leu | Ser | Ile | Cys | Tyr |
| 145 | | | | | 150 | | | | | 155 | | | | | 160 |
| Lys | Lys | Ala | Arg | Pro | Val | Tyr | Ile | Gly | Ile | Pro | Ser | Asp | Ala | Gly | Tyr |
| | | | | 165 | | | | | 170 | | | | | 175 | |
| Phe | Lys | Ala | Ser | Ser | Ser | Asn | Leu | Gly | Lys | Arg | Leu | Lys | Leu | Glu | Glu |
| | | | 180 | | | | | 185 | | | | | 190 | | |
| Asp | Thr | Asn | Asp | Pro | Ala | Val | Glu | Gln | Glu | Val | Ile | Asn | His | Ile | Ser |
| | | 195 | | | | | 200 | | | | | 205 | | | |
| Glu | Met | Val | Val | Asn | Ala | Lys | Lys | Pro | Val | Ile | Leu | Ile | Asp | Ala | Cys |
| | 210 | | | | | 215 | | | | | 220 | | | | |
| Ala | Val | Arg | His | Arg | Val | Val | Pro | Glu | Val | His | Glu | Leu | Ile | Lys | Leu |
| 225 | | | | | 230 | | | | | 235 | | | | | 240 |
| Thr | His | Phe | Pro | Thr | Tyr | Val | Thr | Pro | Met | Gly | Lys | Ser | Ala | Ile | Asp |
| | | | | 245 | | | | | 250 | | | | | 255 | |
| Glu | Thr | Ser | Gln | Phe | Phe | Asp | Gly | Val | Tyr | Val | Gly | Ser | Ile | Ser | Asp |
| | | | 260 | | | | | 265 | | | | | 270 | | |
| Pro | Glu | Val | Lys | Asp | Arg | Ile | Glu | Ser | Thr | Asp | Leu | Leu | Leu | Ser | Ile |
| | | 275 | | | | | 280 | | | | | 285 | | | |
| Gly | Ala | Leu | Lys | Ser | Asp | Phe | Asn | Thr | Gly | Ser | Phe | Ser | Tyr | His | Leu |
| | 290 | | | | | 295 | | | | | 300 | | | | |
| Ser | Gln | Lys | Asn | Ala | Val | Glu | Phe | His | Ser | Asp | His | Met | Arg | Ile | Arg |
| 305 | | | | | 310 | | | | | 315 | | | | | 320 |
| Tyr | Ala | Leu | Tyr | Pro | Asn | Val | Ala | Met | Lys | Tyr | Ile | Leu | Arg | Lys | Leu |
| | | | | 325 | | | | | 330 | | | | | 335 | |
| Leu | Lys | Val | Leu | Asp | Ala | Ser | Met | Cys | His | Ser | Lys | Ala | Ala | Pro | Thr |
| | | | 340 | | | | | 345 | | | | | 350 | | |
| Ile | Gly | Tyr | Asn | Ile | Lys | Pro | Lys | His | Ala | Glu | Gly | Tyr | Ser | Ser | Asn |
| | | 355 | | | | | 360 | | | | | 365 | | | |

```
Glu Ile Thr His Cys Trp Phe Trp Pro Lys Phe Ser Glu Phe Leu Lys
    370                 375                 380

Pro Arg Asp Val Leu Ile Thr Glu Thr Gly Thr Ala Asn Phe Gly Val
385                 390                 395                 400

Leu Asp Cys Arg Phe Pro Lys Asp Val Thr Ala Ile Ser Gln Val Leu
                405                 410                 415

Trp Gly Ser Ile Gly Tyr Ser Val Gly Ala Met Phe Gly Ala Val Leu
                420                 425                 430

Ala Val His Asp Ser Lys Glu Pro Asp Arg Arg Thr Ile Leu Val Val
                435                 440                 445

Gly Asp Gly Ser Leu Gln Leu Thr Ile Thr Glu Ile Ser Thr Cys Ile
    450                 455                 460

Arg His Asn Leu Lys Pro Ile Ile Phe Ile Ile Asn Asn Asp Gly Tyr
465                 470                 475                 480

Thr Ile Glu Arg Leu Ile His Gly Leu His Ala Ser Tyr Asn Glu Ile
                485                 490                 495

Asn Thr Lys Trp Gly Tyr Gln Gln Ile Pro Lys Phe Phe Gly Ala Ala
                500                 505                 510

Glu Asn His Phe Arg Thr Tyr Cys Val Lys Thr Pro Thr Asp Val Glu
                515                 520                 525

Lys Leu Phe Ser Asp Lys Glu Phe Ala Asn Ala Asp Val Ile Gln Val
530                 535                 540

Val Glu Leu Val Met Pro Met Leu Asp Ala Pro Arg Val Leu Val Glu
545                 550                 555                 560

Gln Ala Lys Leu Thr Ser Lys Ile Asn Lys Gln
                565                 570

<210> SEQ ID NO 19
<211> LENGTH: 1689
<212> TYPE: DNA
<213> ORGANISM: Zygosaccharomyces rouxii

<400> SEQUENCE: 19
atgtctgaaa ttactctagg tcgttacttg ttcgaaagat taaagcaagt tgacactaac     60
accatcttcg gtgttccagg tgacttcaac ttgtccttgt tggacaaggt ctacgaagtg    120
caaggtctaa gatgggctgg taacgctaac gaattgaacg ctgcctacgc tgctgacggt    180
tacgccagag ttaagggttt ggctgctttg atcaccacct tcggtgtcgg tgaattgtct    240
gctttgaacg gtattgcagg ttcttacgct gaacacgttg gtgttttgca cattgttggt    300
gttccatctg tctcttctca agctaagcaa ttgttgttgc accacacctt gggtaacggt    360
gacttcactg ttttccacag aatgtccgcc aacatctctg aaaccaccgc tatgttgacc    420
gacatcactg ctgctccagc tgaaattgac cgttgcatca gagttgctta cgtcaaccaa    480
agaccagtct acttgggtct accagctaac ttggttgacc aaaaggtccc agcttctttg    540
ttgaacactc caattgatct atctctaaag gagaacgacc agaagctga aaccgaagtt    600 gttgacaccg tttttggaatt gatcaaggaa gctaagaacc cagttatctt ggctgatgct    660
tgctgctcca gacacgacgt caaggctgaa accaagaagt tgatcgactt gactcaattc    720
ccatctttcg ttactcctat gggtaagggt tccatcgacg aacaaaaccc aagattcggt    780
ggtgtctacg tcggtactct atccagccca gaagttaagg aagctgttga atctgctgac    840
ttggttctat ctgtcggtgc tctattgtcc gatttcaaca ctggttcttt ctcttactct    900
tacaagacca agaacgttgt tgaattccac tctgaccaca tcaagatcag aaacgctacc    960
```

-continued

```
ttcccaggtg ttcaaatgaa attcgttttg aagaaactat tgcaagctgt cccagaagct   1020
gtcaagaact acaagccagg tccagtccca gctccgccat ctccaaacgc tgaagttgct   1080
gactctacca ccttgaagca agaatggtta tggagacaag tcggtagctt cttgagagaa   1140
ggtgatgttg ttattaccga aactggtacc tctgctttcg gtatcaacca aactcacttc   1200
cctaaccaaa cttacggtat ctctcaagtc ttgtggggtt ctattggtta caccactggt   1260
tccactttgg gtgctgcctt cgctgctgaa gaaattgacc taagaagag agttatcttg   1320 ttcattggtg acggttctct acaattgacc gttcaagaaa tctccaccat gatcagatgg   1380
ggtctaaagc atacttgtt cgttttgaac aacgatggtt acaccattga agattgatt   1440 cacggtgaaa ccgctgaata caactgtatc caaccatgga agcacttgga attgttgaac   1500
accttcggtg ccaaggacta cgaaaaccac agagtctcca ctgtcggtga atggaacaag   1560
ttgactcaag atccaaaatt caacgaaaac tctagaatta gaatgatcga agttatgctt   1620
gaagtcatgg acgctccatc ttctttggtc gctcaagctc aattgaccgc tgctactaac   1680
gctaagcaa                                                           1689
```

<210> SEQ ID NO 20
<211> LENGTH: 563
<212> TYPE: PRT
<213> ORGANISM: Zygosaccharomyces rouxii

<400> SEQUENCE: 20

```
Met Ser Glu Ile Thr Leu Gly Arg Tyr Leu Phe Glu Arg Leu Lys Gln
1               5                   10                  15

Val Asp Thr Asn Thr Ile Phe Gly Val Pro Gly Asp Phe Asn Leu Ser
            20                  25                  30

Leu Leu Asp Lys Val Tyr Glu Val Gln Gly Leu Arg Trp Ala Gly Asn
        35                  40                  45

Ala Asn Glu Leu Asn Ala Ala Tyr Ala Ala Asp Gly Tyr Ala Arg Val
    50                  55                  60

Lys Gly Leu Ala Ala Leu Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Ile Val Gly Val Pro Ser Val Ser Ser Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Leu Thr Asp Ile Thr Ala
    130                 135                 140

Ala Pro Ala Glu Ile Asp Arg Cys Ile Arg Ala Tyr Val Asn Gln
145                 150                 155                 160

Arg Pro Val Tyr Leu Gly Leu Pro Ala Asn Leu Val Asp Gln Lys Val
                165                 170                 175

Pro Ala Ser Leu Leu Asn Thr Pro Ile Asp Leu Ser Leu Lys Glu Asn
            180                 185                 190

Asp Pro Glu Ala Glu Thr Glu Val Val Asp Thr Val Leu Glu Leu Ile
        195                 200                 205

Lys Glu Ala Lys Asn Pro Val Ile Leu Ala Asp Ala Cys Cys Ser Arg
    210                 215                 220

His Asp Val Lys Ala Glu Thr Lys Lys Leu Ile Asp Leu Thr Gln Phe
225                 230                 235                 240
```

-continued

Pro Ser Phe Val Thr Pro Met Gly Lys Gly Ser Ile Asp Glu Gln Asn
              245                 250                 255

Pro Arg Phe Gly Gly Val Tyr Val Gly Thr Leu Ser Ser Pro Glu Val
              260                 265                 270

Lys Glu Ala Val Glu Ser Ala Asp Leu Val Leu Ser Val Gly Ala Leu
              275                 280                 285

Leu Ser Asp Phe Asn Thr Gly Ser Phe Ser Tyr Ser Tyr Lys Thr Lys
              290                 295                 300

Asn Val Val Glu Phe His Ser Asp His Ile Lys Ile Arg Asn Ala Thr
305                 310                 315                 320

Phe Pro Gly Val Gln Met Lys Phe Val Leu Lys Lys Leu Leu Gln Ala
              325                 330                 335

Val Pro Glu Ala Val Lys Asn Tyr Lys Pro Gly Pro Val Pro Ala Pro
              340                 345                 350

Pro Ser Pro Asn Ala Glu Val Ala Asp Ser Thr Thr Leu Lys Gln Glu
              355                 360                 365

Trp Leu Trp Arg Gln Val Gly Ser Phe Leu Arg Glu Gly Asp Val Val
              370                 375                 380

Ile Thr Glu Thr Gly Thr Ser Ala Phe Gly Ile Asn Gln Thr His Phe
385                 390                 395                 400

Pro Asn Gln Thr Tyr Gly Ile Ser Gln Val Leu Trp Gly Ser Ile Gly
              405                 410                 415

Tyr Thr Thr Gly Ser Thr Leu Gly Ala Ala Phe Ala Ala Glu Glu Ile
              420                 425                 430

Asp Pro Lys Lys Arg Val Ile Leu Phe Ile Gly Asp Gly Ser Leu Gln
              435                 440                 445

Leu Thr Val Gln Glu Ile Ser Thr Met Ile Arg Trp Gly Leu Lys Pro
              450                 455                 460

Tyr Leu Phe Val Leu Asn Asn Asp Gly Tyr Thr Ile Glu Arg Leu Ile
465                 470                 475                 480

His Gly Glu Thr Ala Glu Tyr Asn Cys Ile Gln Pro Trp Lys His Leu
              485                 490                 495

Glu Leu Leu Asn Thr Phe Gly Ala Lys Asp Tyr Glu Asn His Arg Val
              500                 505                 510

Ser Thr Val Gly Glu Trp Asn Lys Leu Thr Gln Asp Pro Lys Phe Asn
              515                 520                 525

Glu Asn Ser Arg Ile Arg Met Ile Glu Val Met Leu Glu Val Met Asp
              530                 535                 540

Ala Pro Ser Ser Leu Val Ala Gln Ala Gln Leu Thr Ala Ala Thr Asn
545                 550                 555                 560

Ala Lys Gln

<210> SEQ ID NO 21
<211> LENGTH: 16387
<212> TYPE: DNA
<213> ORGANISM: Artificial sequence
<220> FEATURE:
<223> OTHER INFORMATION: Plasmid

<400> SEQUENCE: 21
gatcctctag tttctcggta ctatgcatat gatccaatat caaaggaaat gatagcattg     60
aaggatgaga ctaatccaat tgaggagtgg cagcatatag aacagctaaa gggtagtgct    120
gaaggaagca tacgataccc cgcatggaat gggataatat cacaggaggt actagactac    180

```
ctttcatcct acataaatag acgcatataa gtacgcattt aagcataaac acgcactatg    240
ccgttcttct catgtatata tatatacagg caacacgcag ataggtgc gacgtgaaca      300 gtgagctgta tgtgcgcagc tcgcgttgca ttttcggaag cgctcgtttt cggaaacgct   360
ttgaagttcc tattccgaag ttcctattct ctagaaagta taggaacttc agagcgcttt   420
tgaaaaccaa aagcgctctg aagacgcact ttcaaaaaac caaaaacgca ccggactgta   480
acgagctact aaaatattgc gaataccgct tccacaaaca ttgctcaaaa gtatctcttt   540
gctatatatc tctgtgctat atccctatat aacctaccca tccacctttc gctccttgaa   600
cttgcatcta aactcgacct ctacattttt tatgtttatc tctagtatta ctctttagac   660
aaaaaaattg tagtaagaac tattcataga gtgaatcgaa acaatacga aaatgtaaac    720 atttcctata cgtagtatat agagacaaaa tagaagaaac cgttcataat tttctgacca   780
atgaagaatc atcaacgcta tcactttctg ttcacaaagt atgcgcaatc cacatcggta   840
tagaatataa tcggggatgc ctttatcttg aaaaaatgca cccgcagctt cgctagtaat   900
cagtaaacgc gggaagtgga gtcaggcttt ttttatggaa gagaaaatag acaccaaagt   960
agccttcttc taaccttaac ggacctacag tgcaaaagt tatcaagaga ctgcattata    1020
gagcgcacaa aggagaaaaa aagtaatcta agatgctttg ttagaaaaat agcgctctcg   1080
ggatgcattt ttgtagaaca aaaagaagt atagattctt tgttggtaaa atagcgctct    1140
cgcgttgcat ttctgttctg taaaaatgca gctcagattc tttgtttgaa aaattagcgc   1200
tctcgcgttg cattttttgtt ttacaaaaat gaagcacaga ttcttcgttg gtaaaatagc  1260
gctttcgcgt tgcattttctg ttctgtaaaa atgcagctca gattctttgt ttgaaaaatt  1320
agcgctctcg cgttgcattt ttgttctaca aaatgaagca cagatgcttc gttaacaaag   1380
atatgctatt gaagtgcaag atggaaacgc agaaaaatgaa ccggggatgc gacgtgcaag   1440
attacctatg caatagatgc aatagtttct ccaggaaccg aaatacatac attgtcttcc   1500
gtaaagcgct agactatata ttattataca ggttcaaata tactatctgt ttcagggaaa   1560
actcccaggt tcggatgttc aaaattcaat gatgggtaac aagtacgatc gtaaatctgt   1620
aaaacagttt gtcggatatt aggctgtatc tcctcaaagc gtattcgaat atcattgaga   1680 agctgcatt ttttttttttt ttttttttt tttttttata tatatttcaa ggatataccca  1740 ttgtaatgtc tgcccctaag aagatcgtcg ttttgccagg tgaccacgtt ggtcaagaaa   1800
tcacagccga agccattaag gttcttaaag ctatttctga tgttcgttcc aatgtcaagt   1860
tcgatttcga aaatcattta attggtggtc tgctatcga tgctacaggt gttccacttc    1920
cagatgaggc gctggaagcc tccaagaagg ctgatgccgt tttgttaggt gctgtgggtg   1980
gtcctaaatg gggtaccggt agtgttagac ctgaacaagg tttactaaaa atccgtaaag   2040
aacttcaatt gtacgccaac ttaagaccat gtaactttgc atccgactct cttttagact   2100
tatctccaat caagccacaa tttgctaaag gtactgactt cgttgttgtt agagaattag   2160
tgggaggtat ttactttggt aagagaaagg aagacgatgg tgatggtgtc gcttgggata   2220
gtgaacaata caccgttcca gaagtgcaaa gaatcacaag aatggccgct tcatggccc    2280 tacaacatga gccaccattg cctatttggt ccttggataa agctaatgtt ttggcctctt   2340
caagattatg gagaaaaact gtggaggaaa ccatcaagaa cgaattccct acattgaaag   2400
ttcaacatca attgattgat tctgccgcca tgatcctagt taagaaccca acccacctaa   2460
atggtattat aatcaccagc aacatgtttg gtgatatcat ctccgatgaa gcctccgtta   2520
tcccaggctc cttgggtttg ttgccatctg cgtccttggc ctcttttgcca gacaagaaca   2580
```

```
ccgcatttgg tttgtacgaa ccatgccatg gttccgctcc agatttgcca aagaataagg    2640
tcaaccctat cgccactatc ttgtctgctg caatgatgtt gaaattgtca ttgaacttgc    2700
ctgaagaagg taaagccatt gaagatgcag ttaaaaaggt tttggatgca ggtatcagaa    2760
ctggtgattt aggtggttcc aacagtacca ccgaagtcgg tgatgctgtc gccgaagaag    2820
ttaagaaaat ccttgcttaa aaagattctc tttttttatg atatttgtac aaaaaaaaaa    2880
aaaaaaaaaa aaaaaaaaaa aaaaaaaaaa aaaaaaaaa aatgcagcgt cacatcggat    2940
aataatgatg gcagccattg tagaagtgcc ttttgcattt ctagtctctt tctcggtcta    3000
gctagtttta ctacatcgcg aagatagaat cttagatcac actgcctttg ctgagctgga    3060
tcaatagagt aacaaagag tggtaaggcc tcgttaaagg caaggacct gagcggaagt     3120 gtatcgtaca gtagacggag tatactagag tcgacctgca ggcatgcaag cttttcaatt    3180
catcattttt tttttattct tttttttgat ttcggtttcc ttgaaatttt tttgattcgg    3240
taatctccga acagaaggaa gaacgaagga aggagcacag acttagattg gtatatatac    3300
gcatatgtag tgttgaagaa acatgaaatt gcccagtatt cttaacccaa ctgcacagaa    3360
caaaaacctg caggaaacga agataaatca tgtcgaaagc tacatataag gaacgtgctg    3420
ctactcatcc tagtcctgtt gctgccaagc tatttaatat catgcacgaa aagcaaacaa    3480
acttgtgtgc ttcattggat gttcgtacca ccaaggaatt actggagtta gttgaagcat    3540
taggtcccaa aatttgttta ctaaaaacac atgtggatat cttgactgat ttttccatgg    3600
agggcacagt taagccgcta aaggcattat ccgccaagta caattttta ctcttcgaag    3660 acagaaaatt tgctgacatt ggtaatacag tcaaattgca gtactctgcg ggtgtataca    3720
gaatagcaga atgggcagac attacgaatg cacacggtgt ggtgggccca ggtattgtta    3780
gcggtttgaa gcaggcggca gaagaagtaa caaaggaacc tagaggcctt ttgatgttag    3840
cagaattgtc atgcaagggc tccctatcta ctggagaata tactaagggt actgttgaca    3900
ttgcgaagag cgacaaagat tttgttatcg gcttttattgc tcaaagagac atgggtggaa    3960
gagatgaagg ttacgattgg ttgattatga caccggtgt gggtttagat gacaagggag    4020
acgcattggg tcaacagtat agaaccgtgg atgatgtggt ctctacagga tctgacatta    4080
ttattgttgg aagaggacta tttgcaaagg gaagggatgc taaggtagag ggtgaacgtt    4140
acagaaaagc aggctgggaa gcatatttga aagatgcgg ccagcaaaac taaaaaactg     4200
tattataagt aaatgcatgt atactaaact cacaaattag agcttcaatt taattatatc    4260
agttattacc cgggaatctc ggtcgtaatg attttttataa tgacgaaaaa aaaaaaattg   4320
gaaagaaaaa gcttggcgta atcatggtca tagctgtttc ctgtgtgaaa ttgttatccg    4380
ctcacaattc cacacaacat acgagccgga agcataaagt gtaaagcctg gggtgcctaa    4440
tgagtgagct aactcacatt aattgcgttg cgctcactgc ccgctttcca gtcgggaaac    4500
ctgtcgtgcc agctgcatta atgaatcggc caacgcgcgg ggagaggcgg tttgcgtatt    4560
gggcgctctt ccgcttcctc gctcactgac tcgctgcgct cggtcgttcg ctgcggcga    4620 gcggtatcag ctcactcaaa ggcggtaata cggttatcca cagaatcagg ggataacgca    4680
ggaaagaaca tgtgagcaaa aggccagcaa aaggccagga accgtaaaaa ggccgcgttg    4740
ctggcgtttt tccataggct ccgccccct gacgagcatc acaaaaatcg acgctcaagt     4800
cagaggtggc gaaacccgac aggactataa agataccagg cgtttccccc tggaagctcc    4860
ctcgtgcgct ctcctgttcc gaccctgccg cttaccggat acctgtccgc ctttctccct    4920
```

```
tcgggaagcg tggcgctttc tcatagctca cgctgtaggt atctcagttc ggtgtaggtc    4980
gttcgctcca agctgggctg tgtgcacgaa ccccccgttc agcccgaccg ctgcgcctta    5040
tccggtaact atcgtcttga gtccaacccg gtaagacacg acttatcgcc actggcagca    5100
gccactggta acaggattag cagagcgagg tatgtaggcg gtgctacaga gttcttgaag    5160
tggtggccta actacggcta cactagaaga acagtatttg gtatctgcgc tctgctgaag    5220
ccagttacct tcggaaaaag agttggtagc tcttgatccg gcaaacaaac caccgctggt    5280
agcggtggtt ttttgtttg caagcagcag attacgcgca gaaaaaagg atctcaagaa     5340 gatcctttga tcttttctac ggggtctgac gctcagtgga acgaaaactc acgttaaggg    5400
attttggtca tgagattatc aaaaaggatc ttcacctaga tccttttaaa ttaaaaatga    5460
agttttaaat caatctaaag tatatatgag taaacttggt ctgacagtta ccaatgctta    5520
atcagtgagg cacctatctc agcgatctgt ctatttcgtt catccatagt tgcctgactc    5580
cccgtcgtgt agataactac gatacgggag ggcttaccat ctggccccag tgctgcaatg    5640
ataccgcgag acccacgctc accggctcca gatttatcag caataaacca gccagccgga    5700
agggccgagc gcagaagtgg tcctgcaact ttatccgcct ccatccagtc tattaattgt    5760
tgccgggaag ctagagtaag tagttcgcca gttaatagtt tgcgcaacgt tgttgccatt    5820
gctacaggca tcgtggtgtc acgctcgtcg tttggtatgg cttcattcag ctccggttcc    5880
caacgatcaa ggcgagttac atgatccccc atgttgtgca aaaaagcggt tagctccttc    5940
ggtcctccga tcgttgtcag aagtaagttg gccgcagtgt tatcactcat ggttatggca    6000
gcactgcata attctcttac tgtcatgcca tccgtaagat gcttttctgt gactggtgag    6060
tactcaacca agtcattctg agaatagtgt atgcggcgac cgagttgctc ttgcccggcg    6120
tcaatacggg ataataccgc gccacatagc agaactttaa aagtgctcat cattggaaaa    6180
cgttcttcgg ggcgaaaact ctcaaggatc ttaccgctgt tgagatccag ttcgatgtaa    6240
cccactcgtg cacccaactg atcttcagca tcttttactt tcaccagcgt ttctgggtga    6300
gcaaaaacag gaaggcaaaa tgccgcaaaa aagggaataa gggcgacacg gaaatgttga    6360
atactcatac tcttcctttt tcaatattat tgaagcattt atcagggtta ttgtctcatg    6420
agcggataca tatttgaatg tatttagaaa aataaacaaa taggggttcc gcgcacattt    6480
ccccgaaaag tgccacctga cgtctaagaa accattatta tcatgacatt aacctataaa    6540
aataggcgta tcacgaggcc ctttcgtctc gcgcgtttcg gtgatgacgg tgaaaacctc    6600
tgacacatgc agctcccgga gacggtcaca gcttgtctgt aagcggatgc cgggagcaga    6660
caagcccgtc agggcgcgtc agcgggtgtt ggcgggtgtc ggggctggct taactatgcg    6720
gcatcagagc agattgtact gagagtgcac cataaaattg taaacgttaa tattttgtta    6780
aaattcgcgt taaattttg ttaaatcagc tcatttttta accaatagac cgaaatcggc     6840
aaaatccctt ataaatcaaa agaatagccc gagatagagt tgagtgttgt tccagtttgg    6900
aacaagagtc cactattaaa gaacgtggac tccaacgtca aagggcgaaa aaccgtctat    6960
cagggcgatg gcccactacg tgaaccatca cccaaatcaa gttttttggg gtcgaggtgc    7020
cgtaaagcac taaatcggaa ccctaaaggg agcccccgat ttagagcttg acggggaaag    7080
ccggcgaacg tggcgagaaa ggaagggaag aaagcgaaag gagcgggcgc taaggcgctg    7140
gcaagtgtag cggtcacgct gcgcgtaacc accacacccg ccgcgcttaa tgcgccgcta    7200
cagggcgcgt actatggttg ctttgacgta tgcggtgtga ataccgcac agatgcgtaa      7260 ggagaaaata ccgcatcagg cgccattcgc cattcaggct gcgcaactgt tgggaagggc    7320
```

```
gatcggtgcg ggcctcttcg ctattacgcc agctggcgaa aggggatgt gctgcaaggc     7380 gattaagttg ggtaacgcca gggttttccc agtcacgacg ttgtaaaacg acggccagtg    7440
aattcgagct ccaccgcgga tagatctgaa atgaataaca atactgacag tactaaataa    7500
ttgcctactt ggcttcacat acgttgcata cgtcgtata gataataatg ataatgacag     7560
caggattatc gtaatacgta atagttgaaa atctcaaaaa tgtgtgggtc attacgtaaa    7620
taatgatagg aatgggattc ttctattttt cctttttcca ttctagcagc cgtcgggaaa    7680
acgtggcatc ctctctttcg ggctcaattg gagtcacgct gccgtgagca tcctctcttt    7740
ccatatctaa caactgagca cgtaaccaat ggaaaagcat gagcttagcg ttgctccaaa    7800
aaagtattgg atggttaata ccatttgtct gttctcttct gactttgact cctcaaaaaa    7860
aaaaaatcta caatcaacag atcgcttcaa ttacgccctc acaaaaactt ttttccttct    7920
tcttcgccca cgttaaattt tatccctcat gttgtctaac ggatttctgc acttgattta    7980
ttataaaaag acaagacat aatacttctc tatcaatttc agttattgtt cttccttgcg     8040
ttattcttct gttcttcttt ttcttttgtc atatataacc ataaccaagt aatacatatt    8100
caaatctaga gctgaggatg ttgaagcaaa tcaacttcgg tggtactgtt gaaaccgtct    8160
acgaaagagc tgactggcca agagaaaagt tgttggacta cttcaagaac gacacttttg    8220
ctttgatcgg ttacggttcc caaggttacg gtcaaggttt gaacttgaga gacaacggtt    8280
tgaacgttat cattggtgtc cgtaaagatg gtgcttcttg gaaggctgcc atcgaagacg    8340
gttgggttcc aggcaagaac ttgttcactg ttgaagatgc tatcaagaga ggtagttacg    8400
ttatgaactt gttgtccgat gccgctcaat cagaaacctg gcctgctatc aagccattgt    8460
tgaccaaggg taagactttg tacttctccc acggtttctc cccagtcttc aaggacttga    8520
ctcacgttga accaccaaag gacttagatg ttatcttggt tgctccaaag ggttccggta    8580
gaactgtcag atctttgttc aaggaaggtc gtgtgtattaa ctcttcttac gccgtctgga    8640
acgatgtcac cggtaaggct cacgaaaagg cccaagcttt ggccgttgcc attggttccg    8700
gttacgttta ccaaaccact ttcgaaagag aagtcaactc tgacttgtac ggtgaaagag    8760
gttgtttaat gggtggtatc cacggtatgt tcttggctca atacgacgtc ttgagagaaa    8820
acggtcactc cccatctgaa gctttcaacg aaaccgtcga agaagctacc caatctctat    8880
acccattgat cggtaagtac ggtatggatt acatgtacga tgcttgttcc accaccgcca    8940
gaagaggtgc tttggactgg tacccaatct tcaagaatgc tttgaagcct gttttccaag    9000
acttgtacga atctaccaag aacggtaccg aaaccaagag atctttggaa ttcaactctc    9060
aacctgacta cagagaaaag ctagaaaagg aattagacac catcagaaac atggaaatct    9120
ggaaggttgg taaggaagtc agaaagttga gaccagaaaa ccaataatta attaatcatg    9180
taattagtta tgtcacgctt acattcacgc cctccccca catccgctct aaccgaaaag    9240
gaaggagtta gacaacctga agtctaggtc cctatttatt ttttatagt tatgttagta    9300 ttaagaacgt tatttatatt tcaaattttt ctttttttc tgtacagacg cgtgtacgca    9360
tgtaacatta tactgaaaac cttgcttgag aaggttttgg gacgctcgaa ggctttaatt    9420
tgcgggcggc cgctctagag agttgttagc aaccttttgt ttcttttgag ctggttcaga    9480
cattatgtac acgtatatgt gacgagttcg agaagtattt tactatcgta ctaaatttta    9540
cctgaaaaat tatatactcg agaaagagga agccaagaat tgagaaaaaa gaaaacccg    9600 cgagtaagga aattaaatac aggtgtacac atacacgcac acatatatat atatatatat    9660
```

```
atgtatatgt gtatataqqa aqcqcqcqca tqttaqtata tacqattcqt tqqaaaqqqq    9720
ccgtccacca aacgtgactt gacgagttga caaattgacc tcaatatggc tcagtcagta    9780
atttttagtt ccgcttttatt cccgccatct ttcaggccac gagggtagct cataacgccg   9840
cgctaatgcc gctgcgtcac agcaaccagt agctcagcca aaaccgaaag agaaatcgta    9900
gctgtcccga tgaggactta tacacttgtc accatctaaa taaattattt attcgcgttt    9960
cggttcttgt tttcgattta attagattgt tcattgaatc ataataaata tgtaaaaaat   10020
atatatattt gaagctgctt cagaaaaaca gggcttccta gtgtacagat gtatgtcgga   10080
tgaaaaaaaa aaaatcttaa atgtgaaatt gggtcaattc aattgactat gacttgatgt   10140
tgcaaaaatt ccaagagaaa aagtttccag cacttgatat tattttcctc tttaattttt   10200
cgccttgtct acgatcttat tagcaccgat ccagggcatc atagacctta actgttcacc   10260
aataatttcg ataccatgtg ctgcattgtt tcttctttta gcagtcatac tcgggtaacc   10320
cgtagcgcct tcacttatga acatcttagc gtattcaccg tcctggatac gtttcaaggc   10380
atttctcatg gcttgtcttg attctgcgtt aatgacttca ggtccggtga catactcacc   10440
atattctgca ttatttgaaa tggaatagtt catattagct ataccacctt catacattaa   10500
gtctactatc aacttcaatt catgtagaca ttcgaagtat gccatttcgg gagcgtaccc   10560
tgcttcgaca agcgtctcaa agccgctttt aaccaattca acagttcctc cgcacagaac   10620
cgcttgttct ccaaataaat ctgtctcagt ctcgtcttta aaagtggttt ctattatacc   10680
cgttctcccg ccaccaactc ctgctgcgta gcttaaagct acattcttag cgtttccgct   10740
tgcgtcttgg tatatagcga tcaaatctgg aataccacca cccttaacaa attcgctcct   10800
aacagtatgc cccggagcct taggtgcaat cataataacg tccaaatctg ccctggggac   10860
tacttgattg taatgaatgg caaatccatg actgaaggcc aagtagcgc ccttcttaat    10920
gtttggttct atttcatttt tgtacaattg cgattgaaat tcatctggcg ttaaaatcat   10980
gactaaatca gcgccggcaa cagccgctgc aacatctgtg actttcaagc catgtgcttc   11040
agcctttgca acggtagcac tacctttttct cagacctact gtcacgtcga ccccagaatc   11100
tttcaagtta caggcttgtg cgtgtccttg ggaaccatat cctataatag caaccttctt   11160
tccctggatg atgctcagat cgcagtcttt atcgtaaaac accttcatgt tttattttt    11220
acttatattg ctggtagggt aaaaaaatat aactcctagg aataggttgt ctatatgttt   11280
ttgtcttgct tctataattg taacaaacaa ggaaagggaa aatactgggt gtaaaagcca   11340
ttgagtcaag ttaggtcatc cctttttatac aaaattttc aatttttttt ccaagattct   11400
tgtacgatta attatttttt ttttgcgtcc tacagcgtga tgaaaatttc cgcctgctgc   11460
aagatgagcg ggaacgggcg aaatgtgcac gcgcacaact tacgaaacgc ggatgagtca   11520
ctgacagcca ccgcagaggt tctgactcct actgagctct attggaggtg gcagaaccgg   11580
taccggagga gaccgctata accggtttga atttattgtc acagtgtcac atcagcggca   11640
actcagaagt ttgacagcaa gcaagttcat cattcgaact agccttattg ttttagttca   11700
gtgacagcga actgccgtac tcgatgcttt atttctcacg gtagagcgga agaacagata   11760
ggggcagcgt gagaagagtt agaaagtaaa tttttatcac gtctgaagta ttcttattca   11820
taggaaattt tgcaaggttt tttagctcaa taacgggcta agttatataa ggtgttcacg   11880
cgattttctt gttatgtata cctcttctct gaggaatggt actactgtcc tgatgtaggc   11940
tccttaaatt ggtgggcaag aataactat cgatattttg tatattggtc ttggagttca   12000
ccacgtaatg cctgtttaag accatcagtt aactctagta ttatttggtc ttggctactg   12060
```

```
gccgtttgct attattcaag tcttttgtgc cttcccgtcg ggtaagggag ttatttaggg    12120
atacagaatc taacgaaaac taaatctcaa tgattaactc catttaatcc ttttttgaaa    12180
ggcaaaagag gtcccttgtt cacttacaac gttcttagcc aaattcgctt atcacttact    12240
acttcacgat atacagaagt aaaaacatat aaaaagatgt ctgtttgttt agccatcaca    12300
aaaggtatcg cagtttcttc tataggcctc tactctggtc ttttggcttc cgcttcattg    12360
attacatcta ctactccact agaggtttta acaggatctc taaaaacatc gatatcgtct    12420
ctgcgttcca atcctacggt gaatatattt ccaagcaatt cactgaagaa gaaagagaag    12480
atgttgtgga acatgcatgc ccaggtcctg gttcttgtgg tggtatgtat actgccaaca    12540
caatggcttc tgccgctgaa gtgctaggtt tgaccattcc aaactcctct tccttcccag    12600
ccgtttccaa ggagaagtta gctgagtgtg acaacattgg tgaatacatc aagaagacaa    12660
tggaattggg tattttacct cgtgatatcc tcacaaaaga ggcttttgaa acgccatta    12720 cttatgtcgt tgcaaccggt gggtccacta atgctgtttt gcatttggtg gctgttgctc    12780
actctgcggg tgtcaagttg tcaccagatg atttccaaag aatcagtgat actacaccat    12840
tgatcggtga cttcaaacct tctggtaaat acgtcatggc cgatttgatt aacgttggtg    12900
gtacccaatc tgtgattaag tatctatatg aaaacaacat gttgcacggt aacacaatga    12960
ctgttaccgg tgacactttg gcagaacgtg caaagaaagc accaagccta cctgaaggac    13020
aagagattat taagccactc tcccacccaa tcaaggccaa cggtcacttg caaattctgt    13080
acggttcatt ggcaccaggt ggagctgtgg gtaaaattac cggtaaggaa ggtacttact    13140
tcaagggtag agcacgtgtg ttcgaagagg aaggtgcctt tattgaagcc ttggaaagag    13200
gtgaaatcaa gaagggtgaa aaaccgttg ttgttatcag atatgaaggt ccaagaggtg    13260
caccaggtat gcctgaaatg ctaaagcctt cctctgctct gatgggttac ggtttgggta    13320
aagatgttgc attgttgact gatggtagat tctctggtgg ttctcacggg ttcttaatcg    13380
gccacattgt tcccgaagcc gctgaaggtg gtcctatcgg gttggtcaga gacggcgatg    13440
agattatcat tgatgctgat aataacaaga ttgacctatt agtctctgat aaggaaatgg    13500
ctcaacgtaa acaaagttgg gttgcacctc cacctcgtta cacaagaggt actctatcca    13560
agtatgctaa gttggtttcc aacgcttcca acggttgtgt tttagatgct tgattaatta    13620
agagtaagcg aatttcttat gatttatgat ttttattatt aaataagtta taaaaaaaat    13680
aagtgtatac aaattttaaa gtgactctta ggttttaaaa cgaaaattct tattcttgag    13740
taactctttc ctgtaggtca ggttgctttc tcaggtatag catgaggtcg ctcttattga    13800
ccacacctct accggcatgc cgagcaaatg cctgcaaatc gctccccatt tcacccaatt    13860
gtagatatgc taactccagc aatgagttga tgaatctcgg tgtgtatttt atgtcctcag    13920
aggacaacac ctgtggtact agttctagag cggccgcccg caaattaaag ccttcgagcg    13980
tcccaaaacc ttctcaagca aggttttcag tataatgtta catgcgtaca cgcgtctgta    14040
cagaaaaaaa agaaaaattt gaaatataaa taacgttctt aatactaaca taactataaa    14100
aaaataaata gggacctaga cttcaggttg tctaactcct tccttttcgg ttagagcgga    14160 tgtggggga gggcgtgaat gtaagcgtga cataactaat tacatgatta attaactaga    14220
gagctttcgt tttcatgagt tccccgaatt cttttcggaag cttgtcactt gctaaattaa    14280
tgttatcact gtagtcaacc gggacatcga tgatgacagg accttcagcg ttcatgcctt    14340
gacgcagaac atctgccagc tggtctggtg attctacgcg caagccagtt gctccgaagc    14400
```

```
tttccgcata tttcacgata tcgatatttc cgaaatcgac cgcagatgta cggttatatt    14460
ttttcaattg ctggaatgca accatgtcat atgtgctgtc gttccataca atgtgtacaa    14520
ttggtgcttt tagtcgaact gctgtctcta attccattgc tgagaataag aaaccgccgt    14580
caccagagac agaaaccact ttttctcccg gtttcaccaa tgaagcgccg attgcccaag    14640
gaagcgcaac gccgagtgtt tgcataccgt tactgatcat taatgttaac ggctcgtagc    14700
tgcggaaata acgtgacatc caaatggcgt gcgaaccgat atcgcaagtt actgtaacat    14760
gatcatcgac tgcattacgc aactcttaa cgatttcaag agggtgcgct ctgtctgatt     14820
tccaatctgc aggcacctgc tcaccttcat gcatatattg ttttaaatca gaaaggattt    14880
tctgctcacg ctctgcaaat tccactttca cagcatcgtg ttcgatatga ttgatcgtgg    14940
acggaatgtc accgatcaat tcaagatcag gctggtaagc atgatcaatg tcagcgataa    15000
tctcgtctaa atggataatt gtccggtctc cattgatatt ccagaatttc ggatcatatt    15060
caatcgggtc atagccgatc gtcagaacaa catctgcctg ctctagcagt aaatcgccag    15120
gctggttgcg gaacaaaccg atacggccaa aatattgatc ctctaaatct ctagaaaggg    15180
taccggcagc ttgatatgtt tcaacaaatg gaagctgaac cttttcaaa agcttgcgaa     15240 ccgctttaat tgcttccggt cttccgcctt tcatgccgac caaaacgaca ggaagttttg    15300
ctgtttggat ttttgctatg ccgcactga ttgcatcatc tgctgcagga ccgagttttg     15360
gcgctgcaac agcacgcacg ttttcgtat ttgtgacttc attcacaaca tcttgcggaa     15420
agctcacaaa agcggcccca gcctgccctg ctgacgctat cctaaatgca tttgtaacag    15480
cttccggtat atttttaca tcttgaactt ctacactgta ttttgtaatc ggctggaata    15540
gcgccgcatt atccaaagat tgatgtgtcc gttttaaacg atctgcacgg atcacgtttc    15600
cagcaagcgc aacgacaggg tctccttcag tgttcgctgt cagcaggcct gttgccaagt    15660
tagaggcacc cggtcctgat gtgactaaca cgactcccgg ttttccagtt aaacggccga    15720
ctgcttgggc catgaatgct gcgttttgtt cgtgccgggc aacgataatt tcaggtcctt    15780
tatcttgtaa agcgtcaaat accgcatcaa ttttttgcacc tggaatgcca atacatgtg     15840 tgacaccttg ctccactaag caatcaacaa caagctccgc ccctctgttt ttcacaaggg    15900
atttttgttc ttttgttgct tttgtcaaca tcctcagcga tgattgattg attgattgta    15960
cagtttgttt ttcttaatat ctatttcgat gacttctata tgatattgca ctaacaagaa    16020
gatattataa tgcaattgat acaagacaag gagttatttg cttctctttt atatgattct    16080
gacaatccat attgcgttgg tagtctttt tgctggaacg gttcagcgga aaagacgcat     16140
cgctcttttt gcttctagaa gaaatgccag caaaagaatc tcttgacagt gactgacagc    16200
aaaaatgtct ttttctaact agtaacaagg ctaagatatc agcctgaaat aaagggtggt    16260
gaagtaataa ttaaatcatc cgtataaacc tatacacata tatgaggaaa aataatacaa    16320
aagtgtttta aatacagata catacatgaa catatgcacg tatagcgccc aaatgtcggt    16380
aatggga                                                               16387

<210> SEQ ID NO 22
<211> LENGTH: 1188
<212> TYPE: DNA
<213> ORGANISM: Saccharomyces cerevisiae

<400> SEQUENCE: 22
atgttgagaa ctcaagccgc cagattgatc tgcaactccc gtgtcatcac tgctaagaga      60
acctttgctt tggccacccg tgctgctgct tacagcagac cagctgcccg tttcgttaag     120
```

```
ccaatgatca ctacccgtgg tttgaagcaa atcaacttcg gtggtactgt tgaaaccgtc    180
tacgaaagag ctgactggcc aagagaaaag ttgttggact acttcaagaa cgacactttt    240
gctttgatcg gttacggttc ccaaggttac ggtcaaggtt tgaacttgag agacaacggt    300
ttgaacgtta tcattggtgt ccgtaaagat ggtgcttctt ggaaggctgc catcgaagac    360
ggttgggttc caggcaagaa cttgttcact gttgaagatg ctatcaagag aggtagttac    420
gttatgaact tgttgtccga tgccgctcaa tcagaaacct ggcctgctat caagccattg    480
ttgaccaagg gtaagacttt gtacttctcc cacggtttct ccccagtctt caaggacttg    540
actcacgtta aaccaccaaa ggacttagat gttatcttgg ttgctccaaa gggttccggt    600
agaactgtca gatctttgtt caaggaaggt cgtggtatta actcttctta cgccgtctgg    660
aacgatgtca ccggtaaggc tcacgaaaag gcccaagctt tggccgttgc cattggttcc    720
ggttacgttt accaaaccac tttcgaaaga gaagtcaact ctgacttgta cggtgaaaga    780
ggttgtttaa tgggtggtat ccacggtatg ttcttggctc aatacgacgt cttgagagaa    840
aacggtcact ccccatctga agctttcaac gaaaccgtcg aagaagctac ccaatctcta    900
tacccattga tcgtaagta cggtatggat tacatgtacg atgcttgttc caccaccgcc    960
agaagaggtg ctttggactg gtacccaatc ttcaagaatg ctttgaagcc tgttttccaa   1020
gacttgtacg aatctaccaa gaacggtacc gaaaccaaga gatctttgga attcaactct   1080
caacctgact acagagaaaa gctagaaaag gaattagaca ccatcagaaa catggaaatc   1140
tggaaggttg gtaaggaagt cagaaagttg agaccagaaa accaataa               1188

<210> SEQ ID NO 23
<211> LENGTH: 1014
<212> TYPE: DNA
<213> ORGANISM: Pseudomonas fluorescens

<400> SEQUENCE: 23
atgaaagttt tctacgataa agactgcgac ctgtcgatca tccaaggtaa gaaagttgcc     60
atcatcggct acggttccca gggccacgct caagcatgca acctgaagga ttccggcgta    120
gacgtgactg ttggcctgcg taaaggctcg gctaccgttg ccaaggctga gcccacggc     180 ttgaaagtga ccgacgttgc tgcagccgtt gccggtgccg acttggtcat gatcctgacc    240
ccggacgagt tccagtccca gctgtacaag aacgaaatcg agccgaacat caagaagggc    300
gccactctgg ccttctccca cggcttcgcg atccactaca accaggttgt gcctcgtgcc    360
gacctcgacg tgatcatgat cgcgccgaag gctccaggcc acaccgtacg ttccgagttc    420
gtcaagggcg gtggtattcc tgacctgatc gcgatctacc aggacgcttc cggcaacgcc    480
aagaacgttg ccctgtccta cgccgcaggc gtgggcggcg ccgtaccgg catcatcgaa    540 accaccttca aggacgagac tgaaaccgac ctgttcggtg agcaggctgt tctgtgtggc    600
ggtaccgtcg agctggtcaa agccggtttc gaaaccctgg ttgaagctgg ctacgctcca    660
gaaatggcct acttcgagtg cctgcacgaa ctgaagctga tcgttgacct catgtacgaa    720
ggcggtatcg ccaacatgaa ctactcgatc tccaacaacg ctgaatacgg cgagtacgtg    780
actggtccag aagtcatcaa cgccgaatcc cgtcaggcca tgcgcaatgc tctgaagcgc    840
atccaggacg gcgaatacgc gaagatgttc atcagcgaag cgctaccgg ctacccatcg    900 atgaccgcca agcgtcgtaa caacgctgct cacggtatcg aaatcatcgg cgagcaactg    960
cgctcgatga tgccttggat cggtgccaac aaaatcgtcg acaaagccaa gaac        1014
```

<210> SEQ ID NO 24
<211> LENGTH: 448
<212> TYPE: DNA
<213> ORGANISM: Saccharomyces cerevisiae

<400> SEQUENCE: 24

| | | | | | | |
|---|---|---|---|---|---|---|
| cccattaccg | acatttgggc | gctatacgtg | catatgttca | tgtatgtatc | tgtatttaaa | 60 |
| acacttttgt | attattttc | ctcatatatg | tgtataggtt | tatacggatg | atttaattat | 120 |
| tacttcacca | cccttattt | caggctgata | tcttagcctt | gttactagtt | agaaaaagac | 180 |
| atttttgctg | tcagtcactg | tcaagagatt | cttttgctgg | catttcttct | agaagcaaaa | 240 |
| agagcgatgc | gtcttttccg | ctgaaccgtt | ccagcaaaaa | agactaccaa | cgcaatatgg | 300 |
| attgtcagaa | tcatataaaa | gagaagcaaa | taactccttg | tcttgtatca | attgcattat | 360 |
| aatatcttct | tgttagtgca | atatcatata | gaagtcatcg | aaatagatat | taagaaaaac | 420 |
| aaactgtaca | atcaatcaat | caatcatc | | | | 448 |

<210> SEQ ID NO 25
<211> LENGTH: 250
<212> TYPE: DNA
<213> ORGANISM: Saccharomyces cerevisiae

<400> SEQUENCE: 25

| | | | | | | |
|---|---|---|---|---|---|---|
| ccgcaaatta | aagccttcga | gcgtcccaaa | accttctcaa | gcaaggtttt | cagtataatg | 60 |
| ttacatgcgt | acacgcgtct | gtacagaaaa | aaagaaaaa | tttgaaatat | aaataacgtt | 120 |
| cttaatacta | acataactat | aaaaaaataa | atagggacct | agacttcagg | ttgtctaact | 180 |
| ccttccttt | cggttagagc | ggatgtgggg | ggagggcgtg | aatgtaagcg | tgacataact | 240 |
| aattacatga | | | | | | 250 |

<210> SEQ ID NO 26
<211> LENGTH: 1181
<212> TYPE: DNA
<213> ORGANISM: Saccharomyces cerevisiae

<400> SEQUENCE: 26

| | | | | | | |
|---|---|---|---|---|---|---|
| taaaacctct | agtggagtag | tagatgtaat | caatgaagcg | gaagccaaaa | gaccagagta | 60 |
| gaggcctata | gaagaaactg | cgatacccttt | tgtgatggct | aaacaaacag | acatcttttt | 120 |
| atatgttttt | acttctgtat | atcgtgaagt | agtaagtgat | aagcgaattt | ggctaagaac | 180 |
| gttgtaagtg | aacaagggac | ctctttttgcc | tttcaaaaaa | ggattaaatg | gagttaatca | 240 |
| ttgagattta | gttttcgtta | gattctgtat | ccctaaataa | ctcccttacc | cgacgggaag | 300 |
| gcacaaaaga | cttgaataat | agcaaacggc | cagtagccaa | gaccaaataa | tactagagtt | 360 |
| aactgatggt | cttaaacagg | cattacgtgg | tgaactccaa | gaccaatata | caaaatatcg | 420 |
| ataagttatt | cttgcccacc | aatttaagga | gcctacatca | ggacagtagt | accattcctc | 480 |
| agagaagagg | tatacataac | aagaaaatcg | cgtgaacacc | ttatataact | tagcccgtta | 540 |
| ttgagctaaa | aaaccttgca | aaatttccta | tgaataagaa | tacttcagac | gtgataaaaa | 600 |
| tttactttct | aactcttctc | acgctgcccc | tatctgttct | tccgctctac | cgtgagaaat | 660 |
| aaagcatcga | gtacggcagt | tcgctgtcac | tgaactaaaa | caataaggct | agttcgaatg | 720 |
| atgaacttgc | ttgctgtcaa | acttctgagt | tgccgctgat | gtgacactgt | gacaataaat | 780 |
| tcaaaccggt | tatagcggtc | tcctccggta | ccggttctgc | cacctccaat | agagctcagt | 840 |
| aggagtcaga | acctctgcgg | tggctgtcag | tgactcatcc | gcgtttcgta | agttgtgcgc | 900 |

```
gtgcacattt cgcccgttcc cgctcatctt gcagcaggcg gaaattttca tcacgctgta    960
ggacgcaaaa aaaaaataat taatcgtaca agaatcttgg aaaaaaaatt gaaaaatttt   1020
gtataaaagg gatgacctaa cttgactcaa tggcttttac acccagtatt ttcccttttcc  1080 ttgtttgtta caattataga agcaagacaa aaacatatag acaacctatt cctaggagtt   1140 atatttttt accctaccag caatataagt aaaaaactag t                         1181
```

<210> SEQ ID NO 27
<211> LENGTH: 759
<212> TYPE: DNA
<213> ORGANISM: Saccharomyces cerevisiae

<400> SEQUENCE: 27

```
ggccctgcag gcctatcaag tgctggaaac tttttctctt ggaattttg caacatcaag       60 tcatagtcaa ttgaattgac ccaatttcac atttaagatt ttttttttt catccgacat      120 acatctgtac actaggaagc cctgttttc tgaagcagct tcaaatatat atatttttta     180
catatttatt atgattcaat gaacaatcta attaaatcga aaacaagaac cgaaacgcga     240
ataaataatt tatttagatg gtgacaagtg tataagtcct catcgggaca gctacgattt     300
ctctttcggt tttggctgag ctactggttg ctgtgacgca gcggcattag cgcggcgtta    360
tgagctaccc tcgtggcctg aaagatggcg ggaataaagc ggaactaaaa attactgact    420
gagccatatt gaggtcaatt tgtcaactcg tcaagtcacg tttggtggac ggccccttttc   480 caacgaatcg tatatactaa catgcgcgcg cttcctatat acacatatac atatatatat    540
atatatatat gtgtgcgtgt atgtgtacac ctgtatttaa ttttccttact cgcgggtttt   600 tctttttct caattcttgg cttcctcttt ctcgagtata taattttca ggtaaaattt      660 agtacgatag taaaatactt ctcgaactcg tcacatatac gtgtacataa tgtctgaacc    720
agctcaaaag aaacaaaagg ttgctaacaa ctctctaga                           759
```

<210> SEQ ID NO 28
<211> LENGTH: 643
<212> TYPE: DNA
<213> ORGANISM: Saccharomyces cerevisiae

<400> SEQUENCE: 28

```
gaaatgaata acaatactga cagtactaaa taattgccta cttggcttca catacgttgc     60
atacgtcgat atagataata atgataatga cagcaggatt atcgtaatac gtaatagttg   120
aaaatctcaa aaatgtgtgg gtcattacgt aaataatgat aggaatggga ttcttctatt    180 tttcctttt ccattctagc agccgtcggg aaaacgtggc atcctctctt tcgggctcaa     240
ttggagtcac gctgccgtga gcatcctctc tttccatatc taacaactga gcacgtaacc    300
aatggaaaag catgagctta gcgttgctcc aaaaaagtat tggatggtta ataccatttg   360
tctgttctct tctgactttg actcctcaaa aaaaaaaaat ctacaatcaa cagatcgctt    420
caattacgcc ctcacaaaaa cttttttcct tcttcttcgc ccacgttaaa ttttatccct   480
catgttgtct aacggatttc tgcacttgat ttattataaa aagacaaaga cataatactt    540
ctctatcaat ttcagttatt gttcttcctt gcgttattct tctgttcttc ttttctttt    600 gtcatatata accataacca agtaatacat attcaaatct aga                      643
```

<210> SEQ ID NO 29
<211> LENGTH: 548
<212> TYPE: PRT

<213> ORGANISM: Lactococcus lactis

<400> SEQUENCE: 29

```
Met Tyr Thr Val Gly Asp Tyr Leu Leu Asp Arg Leu His Glu Leu Gly
1               5                   10                  15
Ile Glu Glu Ile Phe Gly Val Pro Gly Asp Tyr Asn Leu Gln Phe Leu
            20                  25                  30
Asp Gln Ile Ile Ser His Lys Asp Met Lys Trp Val Gly Asn Ala Asn
        35                  40                  45
Glu Leu Asn Ala Ser Tyr Met Ala Asp Gly Tyr Ala Arg Thr Lys Lys
    50                  55                  60
Ala Ala Ala Phe Leu Thr Thr Phe Gly Val Gly Glu Leu Ser Ala Val
65                  70                  75                  80
Asn Gly Leu Ala Gly Ser Tyr Ala Glu Asn Leu Pro Val Val Glu Ile
            85                  90                  95
Val Gly Ser Pro Thr Ser Lys Val Gln Asn Glu Gly Lys Phe Val His
            100                 105                 110
His Thr Leu Ala Asp Gly Asp Phe Lys His Phe Met Lys Met His Glu
        115                 120                 125
Pro Val Thr Ala Ala Arg Thr Leu Leu Thr Ala Glu Asn Ala Thr Val
    130                 135                 140
Glu Ile Asp Arg Val Leu Ser Ala Leu Leu Lys Glu Arg Lys Pro Val
145                 150                 155                 160
Tyr Ile Asn Leu Pro Val Asp Val Ala Ala Ala Lys Ala Glu Lys Pro
            165                 170                 175
Ser Leu Pro Leu Lys Lys Glu Asn Ser Thr Ser Asn Thr Ser Asp Gln
            180                 185                 190
Glu Ile Leu Asn Lys Ile Gln Glu Ser Leu Lys Asn Ala Lys Lys Pro
        195                 200                 205
Ile Val Ile Thr Gly His Glu Ile Ile Ser Phe Gly Leu Glu Lys Thr
    210                 215                 220
Val Thr Gln Phe Ile Ser Lys Thr Lys Leu Pro Ile Thr Thr Leu Asn
225                 230                 235                 240
Phe Gly Lys Ser Ser Val Asp Glu Ala Leu Pro Ser Phe Leu Gly Ile
            245                 250                 255
Tyr Asn Gly Thr Leu Ser Glu Pro Asn Leu Lys Glu Phe Val Glu Ser
            260                 265                 270
Ala Asp Phe Ile Leu Met Leu Gly Val Lys Leu Thr Asp Ser Ser Thr
        275                 280                 285
Gly Ala Phe Thr His His Leu Asn Glu Asn Lys Met Ile Ser Leu Asn
    290                 295                 300
Ile Asp Glu Gly Lys Ile Phe Asn Glu Arg Ile Gln Asn Phe Asp Phe
305                 310                 315                 320
Glu Ser Leu Ile Ser Ser Leu Leu Asp Leu Ser Glu Ile Glu Tyr Lys
            325                 330                 335
Gly Lys Tyr Ile Asp Lys Lys Gln Glu Asp Phe Val Pro Ser Asn Ala
            340                 345                 350
Leu Leu Ser Gln Asp Arg Leu Trp Gln Ala Val Glu Asn Leu Thr Gln
        355                 360                 365
Ser Asn Glu Thr Ile Val Ala Glu Gln Gly Thr Ser Phe Phe Gly Ala
    370                 375                 380
Ser Ser Ile Phe Leu Lys Ser Lys Ser His Phe Ile Gly Gln Pro Leu
385                 390                 395                 400
```

```
Trp Gly Ser Ile Gly Tyr Thr Phe Pro Ala Ala Leu Gly Ser Gln Ile
            405                 410                 415

Ala Asp Lys Glu Ser Arg His Leu Leu Phe Ile Gly Asp Gly Ser Leu
        420                 425                 430

Gln Leu Thr Val Gln Glu Leu Gly Leu Ala Ile Arg Glu Lys Ile Asn
    435                 440                 445

Pro Ile Cys Phe Ile Ile Asn Asn Asp Gly Tyr Thr Val Glu Arg Glu
450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Glu Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545

<210> SEQ ID NO 30
<211> LENGTH: 1644
<212> TYPE: DNA
<213> ORGANISM: artificial sequence
<220> FEATURE:
<223> OTHER INFORMATION: codon optimized L. lactis kivD coding region
      for S. cerevisiae expression

<400> SEQUENCE: 30
atgtatacag taggtgacta tctgttggac agattacacg aattaggtat agaagaaata      60
ttcggagtac caggtgacta caatttgcaa tttctagatc aaattatttc acacaaagat     120
atgaaatggg tgggaaatgc taatgagtta atgcctcct atatgccga cgggtacgca      180 agaacgaaaa aggctgcggc attcttgact acatttggtg ttggcgaatt atccgcagtt     240
aatggcttag cgggctccta tgctgagaac ctgcctgttg ttgagatcgt gggatctcct     300
acctcgaaag tgcagaacga aggtaagttt gttcaccata cgttggctga tggtgatttc     360
aagcacttta tgaagatgca cgaaccggtt actgctgcca ggactttatt gacagccgag     420
aatgcaactg ttgaaattga tagagtgttg tctgccttac taaaggaaag aaagccggtt     480
tacatcaatt tacctgtaga tgtagctgcc gctaaggctg aaaaaccatc cttgcctctt     540
aagaaggaaa attccacgtc gaatacatct gatcaagaga ttctgaacaa atacaggaa      600 agtctgaaga atgccaagaa accaattgta atcacaggcc atgaaattat atcgttcggc     660
ctagagaaga ctgttactca gtttatttca aagactaagt tacctattac tactttgaac     720
tttggtaaat catctgttga tgaagcattg ccctcatttt ggggattta caacggtact      780 ctgtcagagc caaacttgaa ggaatttgtg gaatctgctg atttattct tatgtttggt      840 gtaaagctta ccgattctag tacgggtgca tttactcacc atcttaatga aaataaaatg     900
atttccttga atatcgatga aggtaaaatt ttcaacgaaa gaatccaaaa tttcgacttc     960
gaatccctga tatcatctct tcttgacttg tccgaaattg aatataaagg caagtacata    1020
gataaaaagc aagaagattt tgtaccttct aacgcgctgt tgtcacaaga tagactgtgg    1080
caagctgtcg aaaatttgac ccaaagtaat gagacgatcg tggctgaaca aggcacttct    1140
```

```
ttcttcggtg cctcatctat atttctgaaa tcgaaatcac attttattgg tcaacccttg    1200
tggggatcta taggatacac tttccccgca gctctaggca gccaaattgc agataaagaa    1260
tctagacatt tattgtttat cggagatgga tcattgcaac tgactgtcca agaattagga    1320
ctagccatta gagagaagat aaacccaatc tgctttatca ttaataacga tggttacacg    1380
gttgagaggg aaattcatgg tccgaaccag agttataatg acattcctat gtggaattac    1440
tcaaaactgc cagaaagttt cggggcaacg gaagacagag ttgtgtccaa aattgtgaga    1500
acagaaaatg aattcgtatc cgtgatgaaa gaagctcaag cagatccaaa taggatgtat    1560
tggatagaac ttattctagc aaaggagggt gcacctaaag ttttgaaaaa gatgggtaag    1620
ttatttgcag aacaaaacaa gagc                                          1644

<210> SEQ ID NO 31
<211> LENGTH: 1125
<212> TYPE: DNA
<213> ORGANISM: artificial sequence
<220> FEATURE:
<223> OTHER INFORMATION: horse ADH coding region codon optimized for S.
      cerevisiae expression

<400> SEQUENCE: 31
atgtcaacag ccggtaaagt tattaagtgt aaagcggcag ttttgtggga agagaaaaag      60
ccgtttagca tagaagaagt agaagtagcg ccaccaaaag cacacgaggt tagaatcaag     120
atggttgcca ccggaatctg tagatccgac gaccatgtgg tgagtggcac tctagttact     180
cctttgccag taatcgcggg acacgaggct gccggaatcg ttgaatccat aggtgaaggt     240
gttaccactg ttcgtcctgg tgataaagtg atcccactgt tcactcctca atgtggtaag    300
tgtagagtct gcaaacatcc tgagggtaat ttctgcctta aaaatgattt gtctatgcct    360
agaggtacta tgcaggatgg tacaagcaga tttacatgca gagggaaacc tatacaccat    420
ttccttggta cttctacatt ttcccaatac acagtggtgg acgagatatc tgtcgctaaa    480
atcgatgcag cttcaccact ggaaaaagtt tgcttgatag ggtgcggatt ttccaccggt    540
tacggttccg cagttaaagt tgcaaaggtt acacagggtt cgacttgtgc agtattcggt    600
ttaggaggag taggactaag cgttattatg gggtgtaaag ctgcaggcgc agcgaggatt    660
ataggtgtag acatcaataa ggacaaattt gcaaaagcta aggaggtcgg ggctactgaa    720
tgtgttaacc ctcaagatta taagaaacca atacaagaag tccttactga aatgtcaaac    780
ggtggagttg atttctcttt tgaagttata ggccgtcttg atactatggt aactgcgttg    840
tcctgctgtc aagaggcata tggagtcagt gtgatcgtag tgttcctcc tgattcacaa    900 aatttgtcga tgaatcctat gctgttgcta agcggtcgta catggaaggg agctatattt    960
ggcggtttta agagcaagga tagtgttcca aaacttgttg ccgactttat ggcgaagaag    1020
tttgctcttg atccttta at tacacatgta ttgccattcg agaaaatcaa tgaagggttt    1080
gatttgttaa gaagtggtga atctattcgt acaattttaa ctttt               1125

<210> SEQ ID NO 32
<211> LENGTH: 375
<212> TYPE: PRT
<213> ORGANISM: Equus caballus

<400> SEQUENCE: 32

Met Ser Thr Ala Gly Lys Val Ile Lys Cys Lys Ala Ala Val Leu Trp
1               5                   10                  15

Glu Glu Lys Lys Pro Phe Ser Ile Glu Glu Val Glu Val Ala Pro Pro
```

```
            20                  25                  30
Lys Ala His Glu Val Arg Ile Lys Met Val Ala Thr Gly Ile Cys Arg
            35                  40                  45

Ser Asp Asp His Val Val Ser Gly Thr Leu Val Thr Pro Leu Pro Val
        50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
            115                 120                 125

Ser Arg Phe Thr Cys Arg Gly Lys Pro Ile His His Phe Leu Gly Thr
        130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
        210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270

Leu Asp Thr Met Val Thr Ala Leu Ser Cys Cys Gln Glu Ala Tyr Gly
        275                 280                 285

Val Ser Val Ile Val Gly Val Pro Pro Asp Ser Gln Asn Leu Ser Met
        290                 295                 300

Asn Pro Met Leu Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
370                 375

<210> SEQ ID NO 33
<211> LENGTH: 15539
<212> TYPE: DNA
<213> ORGANISM: artificial sequence
<220> FEATURE:
<223> OTHER INFORMATION: constructed plasmid

<400> SEQUENCE: 33
tcgcgcgttt cggtgatgac ggtgaaaacc tctgacacat gcagctcccg gagacggtca     60
```

```
cagcttgtct gtaagcggat gccgggagca gacaagcccg tcaggcgcg tcagcgggtg    120 ttggcgggtg tcgggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tcttttcta    300 ttactcttgg cctcctctag tacactctat attttttat gcctcggtaa tgattttcat    360 ttttttttt ccacctagcg gatgactctt ttttttctt agcgattggc attatcacat    420
aatgaattat acattatata aagtaatgtg atttcttcga agaatatact aaaaaatgag    480
caggcaagat aaacgaaggc aaagatgaca gagcagaaag ccctagtaaa gcgtattaca    540
aatgaaacca agattcagat tgcgatctct ttaaagggtg gtccctagc gatagagcac    600 tcgatcttcc cagaaaaaga ggcagaagca gtagcagaac aggccacaca atcgcaagtg    660
attaacgtcc acacaggtat agggtttctg gaccatatga tacatgctct ggccaagcat    720
tccggctggt cgctaatcgt tgagtgcatt ggtgacttac atagacga ccatcacacc    780 actgaagact gcgggattgc tctcggtcaa gcttttaaag aggccctagg ggccgtgcgt    840
ggagtaaaaa ggtttggatc aggatttgcg ccttttggatg aggcactttc cagagcggtg    900
gtagatcttt cgaacaggcc gtacgcagtt gtcgaacttg gtttgcaaag ggagaaagta    960
ggagatctct cttgcgagat gatcccgcat tttcttgaaa gctttgcaga ggctagcaga   1020
attaccctcc acgttgattg tctgcgaggc aagaatgatc atcaccgtag tgagagtgcg   1080
ttcaaggctc ttgcggttgc cataagagaa gccacctcgc ccaatggtac caacgatgtt   1140
ccctccacca aggtgttct tatgtagtga caccgattat ttaaagctgc agcatacgat   1200
atatatacat gtgtatatat gtatacctat gaatgtcagt aagtatgtat acgaacagta   1260
tgatactgaa gatgacaagg taatgcatca ttctatacgt gtcattctga acgaggcgcg   1320 cttccttt tctttttgc ttttttcttt tttttctctt gaactcgacg gatctatgcg   1380
gtgtgaaata ccgcacagat gcgtaaggag aaaataccgc atcaggaaat tgtaagcgtt   1440
aatattttgt taaaattcgc gttaaatttt tgttaaatca gctcatttt taaccaatag   1500 gccgaaatcg gcaaaatccc ttataaatca aagaataga ccgagatagg gttgagtgtt   1560
gttccagttt ggaacaagag tccactatta aagaacgtgg actccaacgt caaagggcga   1620
aaaaccgtct atcagggcga tggcccacta cgtgaaccat caccctaatc aagttttttg   1680
gggtcgaggt gccgtaaagc actaaatcgg aaccctaaag ggagccccg atttagagct   1740 tgacggggaa agccggcgaa cgtggcgaga aggaaggga agaaagcgaa aggagcgggc   1800
gctagggcgc tggcaagtgt agcggtcacg ctgcgcgtaa ccaccacacc cgccgcgctt   1860
aatgcgccgc tacagggcgc gtccattcgc cattcaggct gcgcaactgt gggaagggc   1920 gcggtgcggg cctcttcgct attacgccag ctggcgaaag ggggatgtgc tgcaaggcga   1980
ttaagttggg taacgccagg gttttcccag tcacgacgtt gtaaaacgac ggccagtgag   2040
cgcgcgtaat acgactcact atagggcgaa ttgggtaccg gccccccct cgaggtcgac   2100 ggcgcgccac tggtagagag cgactttgta tgccccaatt gcgaaacccg cgatatcctt   2160
ctcgattctt tagtacccga ccaggacaag gaaaggagg tcgaaacgtt tttgaagaaa   2220
caagaggaac tacacggaag ctctaaagat ggcaaccagc cagaaactaa gaaaatgaag   2280
ttgatggatc caactggcac cgctggcttg aacaacaata ccagccttcc aacttctgta   2340
aataacggcg gtacgccagt gccaccagta ccgttacctt tcggtatacc tcctttcccc   2400
```

-continued

```
atgtttccaa tgcccttcat gcctccaacg gctactatca caaatcctca tcaagctgac    2460
gcaagcccta agaaatgaat aacaatactg acagtactaa ataattgcct acttggcttc    2520
acatacgttg catacgtcga tatagataat aatgataatg acagcaggat tatcgtaata    2580
cgtaatagct gaaaatctca aaaatgtgtg ggtcattacg taaataatga taggaatggg    2640
attcttctat ttttcctttt tccattctag cagccgtcgg gaaaacgtgg catcctctct    2700
ttcgggctca attggagtca cgctgccgtg agcatcctct ctttccatat ctaacaactg    2760
agcacgtaac caatggaaaa gcatgagctt agcgttgctc caaaaagta ttggatggtt     2820 ataccatttt gtctgttctc ttctgactt t gactcctcaa aaaaaaaaat ctacaatcaa    2880
cagatcgctt caattacgcc ctcacaaaaa cttttttcct tcttcttcgc ccacgttaaa    2940
ttttatccct catgttgtct aacggatttc tgcacttgat ttattataaa agacaaaga     3000 cataatactt ctctatcaat ttcagttatt gttcttcctt gcgttattct tctgttcttc    3060
tttttctttt gtcatatata accataacca agtaatacat attcaaacta gtatgactga    3120
caaaaaaact cttaaagact taagaaatcg tagttctgtt tacgattcaa tggttaaatc    3180
acctaatcgt gctatgttgc gtgcaactgg tatgcaagat gaagactttg aaaaacctat    3240
cgtcggtgtc atttcaactt gggctgaaaa cacaccttgt aatatccact acatgactt     3300 tggtaaacta gccaaagtcg gtgttaagga agctggtgct tggccagttc agttcggaac    3360
aatcacggtt tctgatggaa tcgccatggg aacccaagga atgcgtttct ccttgacatc    3420
tcgtgatatt attgcagatt ctattgaagc agccatggga ggtcataatg cggatgcttt    3480
tgtagccatt ggcggttgtg ataaaaacat gcccggttct gttatcgcta tggctaacat    3540
ggatatccca gccatttttg cttacggcgg aacaattgca cctggtaatt tagacggcaa    3600
agatatcgat ttagtctctg tctttgaagg tgtcggccat tggaaccacg cgatatgac    3660 caaagaagaa gttaaagctt tggaatgtaa tgcttgtccc ggtcctggag gctgcggtgg    3720
tatgtatact gctaacacaa tggcgacagc tattgaagtt ttgggactta gccttccggg    3780
ttcatcttct cacccggctg aatccgcaga aaagaaagca gatattgaag aagctggtcg    3840
cgctgttgtc aaaatgctcg aaatgggctt aaaaccttct gacattttaa cgcgtgaagc    3900
ttttgaagat gctattactg taactatggc tctgggaggt tcaaccaact caaccccttca   3960 cctcttagct attgcccatg ctgctaatgt ggaattgaca cttgatgatt tcaatacttt    4020
ccaagaaaaa gttcctcatt tggctgattt gaaaccttct ggtcaatatg tattccaaga    4080
cctttacaag gtcggagggg taccagcagt tatgaaatat ctccttaaaa atggcttcct    4140
tcatggtgac cgtatcactt gtactggcaa aacagtcgct gaaaatttga aggcttttga    4200
tgatttaaca cctggtcaaa aggttattat gccgcttgaa atcctaaac gtgaagatgg     4260 tccgctcatt attctccatg gtaacttggc tccagacggt gccgttgcca agtttctgg     4320 tgtaaaagtg cgtcgtcatg tcggtcctgc taaggtcttt aattctgaag aagaagccat    4380
tgaagctgtc ttgaatgatg atattgttga tggtgatgtt gttgtcgtac gttttgtagg    4440
accaaagggc ggtcctggta tgcctgaaat gctttcccct tcatcaatga ttgttggtaa    4500
agggcaaggt gaaaaagttg cccttctgac agatggccgc ttctcaggtg gtacttatgg    4560
tcttgtcgtg ggtcatatcg ctcctgaagc acaagatggc ggtccaatcg cctacctgca    4620
aacaggagac atagtcacta ttgaccaaga cactaaggaa ttacactttg atatctccga    4680
tgaagagtta aaacatcgtc aagagaccat tgaattgcca ccgctctatt cacgcggtat    4740
ccttggtaaa tatgctcaca tcgtttcgtc tgcttctagg ggagccgtaa cagacttttg    4800
```

-continued

```
gaagcctgaa gaaactggca aaaaatgttg tcctggttgc tgtggttaag cggccgcgtt    4860
aattcaaatt aattgatata gttttttaat gagtattgaa tctgtttaga aataatggaa    4920
tattattttt atttatttat ttatattatt ggtcggctct tttcttctga aggtcaatga    4980
caaaatgata tgaaggaaat aatgatttct aaaattttac aacgtaagat attttacaa     5040 aagcctagct catcttttgt catgcactat tttactcacg cttgaaatta acggccagtc    5100
cactgcggag tcatttcaaa gtcatcctaa tcgatctatc gttttgata gctcattttg     5160 gagttcgcga ttgtcttctg ttattcacaa ctgttttaat ttttatttca ttctggaact    5220
cttcgagttc tttgtaaagt ctttcatagt agcttacttt atcctccaac atatttaact    5280
tcatgtcaat ttcggctctt aaattttcca catcatcaag ttcaacatca tcttttaact    5340
tgaatttatt ctctagctct tccaaccaag cctcattgct ccttgattta ctggtgaaaa    5400
gtgatacact ttgcgcgcaa tccaggtcaa aactttcctg caaagaattc accaatttct    5460
cgacatcata gtacaatttg ttttgttctc ccatcacaat ttaatatacc tgatggattc    5520
ttatgaagcg ctgggtaatg acgtgtcac tctacttcgc ctttttccct actccttta     5580 gtacggaaga caatgctaat aaataagagg gtaataataa tattattaat cggcaaaaaa    5640
gattaaacgc caagcgttta attatcagaa agcaaacgtc gtaccaatcc ttgaatgctt    5700
cccaattgta tattaagagt catcacagca acatattctt gttattaaat taattattat    5760 tgattttga tattgtataa aaaaaccaaa tatgtataaa aaagtgaat aaaaaatacc      5820 aagtatggag aaatatatta gaagtctata cgttaaacca cccgggcccc cctcgaggt    5880 cgacggtatc gataagcttg atatcgaatt cctgcagccc gggggatcca ctagttctag    5940
agcggccgct ctagaactag taccacaggt gttgtcctct gaggacataa aatacacacc    6000
gagattcatc aactcattgc tggagttagc atatctacaa ttgggtgaaa tggggagcga    6060
tttgcaggca tttgctcggc atgccggtag aggtgtggtc aataagagcg acctcatgct    6120
atacctgaga aagcaacctg acctacagga aagagttact caagaataag aattttcgtt    6180
ttaaaaccta agagtcactt taaaatttgt atacacttat tttttttata acttatttaa    6240
taataaaaat cataaatcat aagaaaattcg cttactctta attaatcaaa aagttaaaat   6300
tgtacgaata gattcaccac ttcttaacaa atcaaaccct tcattgattt tctcgaatgg    6360
caatacatgt gtaattaaag gatcaagagc aaacttcttc gccataaagt cggcaacaag    6420
ttttggaaca ctatccttgc tcttaaaacc gccaaatata gctcccttcc atgtacgacc    6480
gcttagcaac agcataggat tcatcgacaa attttgtgaa tcaggaggaa cacctacgat    6540
cacactgact ccatatgcct cttgacagca ggacaacgca gttaccatag tatcaagacg    6600
gcctataact tcaaaagaga aatcaactcc accgtttgac atttcagtaa ggacttcttg    6660
tattggtttc ttataatctt gagggttaac acattcagta gccccgacct ccttagcttt    6720
tgcaaatttg tccttattga tgtctacacc tataatcctc gctgcgcctg cagcttaca    6780 ccccataata acgcttagtc ctactcctcc taaaccgaat actgcacaag tcgaaccctg    6840 tgtaacctt gcaactttaa ctgcggaacc gtaccggtg gaaatccgc accctatcaa      6900 gcaaactttt tccagtggtg aagctgcatc gattttagcg acagatatct cgtccaccac    6960
tgtgtattgg gaaatgtag aagtaccaag gaaatggtgt ataggtttcc ctctgcatgt    7020
aaatctgctt gtaccatcct gcatagtacc tctaggcata gacaaatcat ttttaaggca    7080
gaaattaccc tcaggatgtt tgcagactct acacttacca cattgaggag tgaacagtgg    7140
```

```
gatcacttta tcaccaggac gaacagtggt aacaccttca cctatggatt caacgattcc    7200
ggcagcctcg tgtcccgcga ttactggcaa aggagtaact agagtgccac tcaccacatg    7260
gtcgtcggat ctacagattc cggtggcaac catcttgatt ctaacctcgt gtgcttttgg    7320
tggcgctact tctacttctt ctatgctaaa cggcttttc tcttcccaca aaactgccgc     7380
tttacactta ataactttac cggctgttga catcctcagc tagctattgt aatatgtgtg    7440
tttgtttgga ttattaagaa gaataattac aaaaaaaatt acaaaggaag gtaattacaa    7500
cagaattaag aaaggacaag aaggaggaag agaatcagtt cattatttct tctttgttat    7560
ataacaaacc caagtagcga tttggccata cattaaaagt tgagaaccac cctccctggc    7620
aacagccaca actcgttacc attgttcatc acgatcatga aactcgctgt cagctgaaat    7680
ttcacctcag tggatctctc tttttattct tcatcgttcc actaaccttt ttccatcagc    7740
tggcagggaa cggaaagtgg aatcccattt agcgagcttc ctcttttctt caagaaaaga    7800
cgaagcttgt gtgtgggtgc gcgcgctagt atctttccac attaagaaat ataccataaa    7860
ggttacttag acatcactat ggctatatat atatatatat atatatgtaa cttagcacca    7920
tcgcgcgtgc atcactgcat gtgttaaccg aaaagtttgg cgaacacttc accgacacgg    7980
tcatttagat ctgtcgtctg cattgcacgt cccttagcct taaatcctag gcgggagcat    8040
tctcgtgtaa ttgtgcagcc tgcgtagcaa ctcaacatag cgtagtctac ccagtttttc    8100
aagggtttat cgttagaaga ttctcccttt tcttcctgct cacaaatctt aaagtcatac    8160
attgcacgac taaatgcaag catgcggatc ccccgggctg caggaattcg atatcaagct    8220
tatcgatacc gtcgactggc cattaatctt tcccatatta gatttcgcca agccatgaaa    8280
gttcaagaaa ggtctttaga cgaattaccc ttcatttctc aaactggcgt caagggatcc    8340
tggtatggtt ttatcgtttt atttctggtt cttatagcat cgttttggac ttctctgttc    8400
ccattaggcg gttcaggagc cagcgcagaa tcattctttg aaggatactt atccttttcca   8460
attttgattg tctgttacgt tggacataaa ctgtatacta gaaattggac tttgatggtg    8520
aaactagaag atatggatct tgataccggc agaaaacaag tagatttgac tcttcgtagg    8580
gaagaaatga ggattgagcg agaaacatta gcaaaaagat ccttcgtaac aagattttta    8640
catttctggt gttgaaggga agatatgag ctatacagcg gaatttccat atcactcaga     8700
ttttgttatc taattttttc cttcccacgt ccgcgggaat ctgtgtatat tactgcatct    8760
agatatatgt tatcttatct tggcgcgtac atttaatttt caacgtattc tataagaaat    8820
tgcgggagtt tttttcatgt agatgatact gactgcacgc aaatataggc atgatttata    8880
ggcatgattt gatggctgta ccgataggaa cgctaagagt aacttcagaa tcgttatcct    8940
ggcgaaaaa attcatttgt aaactttaaa aaaaaagcc aatatcccca aaattattaa      9000
gagcgcctcc attattaact aaaatttcac tcagcatcca caatgtatca ggtatctact    9060
acagatatta catgtggcga aaaagacaag aacaatgcaa tagcgcatca agaaaaaaca    9120
caaagctttc aatcaatgaa tcgaaaatgt cattaaaata gtatataaat tgaaactaag    9180
tcataaagct ataaaagaa aatttattta aatgcaagat ttaaagtaaa ttcacggccc     9240
tgcaggcctc agctcttgtt ttgttctgca ataacttac ccatcttttt caaaacttta     9300
ggtgcaccct cctttgctag aataagttct atccaataca tcctatttgg atctgcttga    9360
gcttctttca tcacggatac gaattcattt tctgttctca caattttgga cacaactctg    9420
tcttccgttg ccccgaaact ttctggcagt tttgagtaat tccacatagg aatgtcatta    9480
taactctggt tcggaccatg aatttccctc tcaaccgtgt aaccatcgtt attaatgata    9540
```

```
aagcagattg ggtttatctt ctctctaatg gctagtccta attcttggac agtcagttgc    9600
aatgatccat ctccgataaa caataaatgt ctagattctt tatctgcaat ttggctgcct    9660
agagctgcgg ggaaagtgta tcctatagat ccccacaagg gttgaccaat aaaatgtgat    9720
ttcgatttca gaaatataga tgaggcaccg aagaaagaag tgccttgttc agccacgatc    9780
gtctcattac tttgggtcaa attttcgaca gcttgccaca gtctatcttg tgacaacagc    9840
gcgttagaag gtacaaaatc ttcttgcttt ttatctatgt acttgccttt atattcaatt    9900
tcggacaagt caagaagaga tgatatcagg gattcgaagt cgaaattttg gattctttcg    9960
ttgaaaattt taccttcatc gatattcaag gaaatcattt tattttcatt aagatggtga   10020
gtaaatgcac ccgtactaga atcggtaagc tttacaccca acataagaat aaaatcagca   10080
gattccacaa attccttcaa gtttggctct gacagagtac cgttgtaaat ccccaaaaat   10140
gagggcaatg cttcatcaac agatgattta ccaaagttca aagtagtaat aggtaactta   10200
gtctttgaaa taaactgagt aacagtcttc tctaggccga acgatataat ttcatggcct   10260
gtgattacaa ttggtttctt ggcattcttc agactttcct gtattttgtt cagaatctct   10320
tgatcagatg tattcgacgt ggaattttcc ttcttaagag gcaaggatgg tttttcagcc   10380
ttagcggcag ctacatctac aggtaaattg atgtaaaccg gctttctttc ctttagtaag   10440
gcagacaaca ctctatcaat ttcaacagtt gcattctcgg ctgtcaataa agtcctggca   10500
gcagtaaccg gttcgtgcat cttcataaag tgcttgaaat caccatcagc caacgtatgg   10560
tgaacaaact taccttcgtt ctgcactttc gaggtaggag atcccacgat ctcaacaaca   10620
ggcaggttct cagcatagga gcccgctaag ccattaactg cggataattc gccaacacca   10680
aatgtagtca agaatgccgc agccttttc gttcttgcgt acccgtcggc catataggag   10740
gcatttaact cattagcatt tcccacccat ttcatatctt tgtgtgaaat aatttgatct   10800
agaaattgca aattgtagtc acctggtact ccgaatattt cttctatacc taattcgtgt   10860
aatctgtcca acagatagtc acctactgta tacattttgt ttactagttt atgtgtgttt   10920
attcgaaact aagttcttgg tgttttaaaa ctaaaaaaaa gactaactat aaaagtagaa   10980
tttaagaagt ttaagaaata gatttacaga attacaatca atacctaccg tctttatata   11040
cttattagtc aagtagggga ataatttcag ggaactggtt tcaacctttt ttttcagctt   11100
tttccaaatc agagagagca gaaggtaata gaaggtgtaa gaaaatgaga tagatacatg   11160
cgtgggtcaa ttgccttgtg tcatcattta ctccaggcag gttgcatcac tccattgagg   11220
ttgtgcccgt tttttgcctg tttgtgcccc tgttctctgt agttgcgcta agagaatgga   11280
cctatgaact gatggttggt gaagaaaaca atattttggt gctgggattc tttttttttc   11340
tggatgccag cttaaaaagc gggctccatt atatttagtg gatgccagga ataaactgtt   11400
cacccagaca cctacgatgt tatatattct gtgtaacccg cccctatttt gggcatgta    11460 cgggttacag cagaattaaa aggctaattt tttgactaaa taaagttagg aaaatcacta   11520
ctattaatta tttacgtatt cttgaaatg gcagtattga taatgataaa ctcgaactga    11580
aaaagcgtgt tttttattca aaatgattct aactccctta cgtaatcaag gaatcttttt   11640
gccttggcct ccgcgtcatt aaacttcttg ttgttgacgc taacattcaa cgctagtata   11700
tattcgtttt tttcaggtaa gttcttttca acgggtctta ctgatgaggc agtcgcgtct   11760
gaacctgtta agaggtcaaa tatgtcttct tgaccgtacg tgtcttgcat gttattagct   11820
ttgggaattt gcatcaagtc ataggaaaat ttaaatcttg gctctcttgg gctcaaggtg   11880
```

```
acaaggtcct cgaaaatagg gcgcgcccca ccgcggtgga gctccagctt ttgttccctt    11940
tagtgagggt taattgcgcg cttggcgtaa tcatggtcat agctgtttcc tgtgtgaaat    12000
tgttatccgc tcacaattcc acacaacata cgagccggaa gcataaagtg taaagcctgg    12060
ggtgcctaat gagtgagcta actcacatta attgcgttgc gctcactgcc cgctttccag    12120
tcgggaaacc tgtcgtgcca gctgcattaa tgaatcggcc aacgcgcggg gagaggcggt    12180
ttgcgtattg ggcgctcttc cgcttcctcg ctcactgact cgctgcgctc ggtcgttcgg    12240
ctgcggcgag cggtatcagc tcactcaaag gcggtaatac ggttatccac agaatcaggg    12300
gataacgcag gaaagaacat gtgagcaaaa ggccagcaaa aggccaggaa ccgtaaaaag    12360
gccgcgttgc tggcgttttt ccataggctc cgcccccctg acgagcatca caaaaatcga    12420
cgctcaagtc agaggtggcg aaacccgaca ggactataaa gataccaggc gtttccccct    12480
ggaagctccc tcgtgcgctc tcctgttccg accctgccgc ttaccggata cctgtccgcc    12540
tttctccctt cgggaagcgt ggcgctttct catagctcac gctgtaggta tctcagttcg    12600
gtgtaggtcg ttcgctccaa gctgggctgt gtgcacgaac cccccgttca gcccgaccgc    12660
tgcgccttat ccggtaacta tcgtcttgag tccaacccgg taagacacga cttatcgcca    12720
ctggcagcag ccactggtaa caggattagc agagcgaggt atgtaggcgg tgctacagag    12780
ttcttgaagt ggtggcctaa ctacggctac actagaagaa cagtatttgg tatctgcgct    12840
ctgctgaagc cagttacctt cggaaaaaga gttggtagct cttgatccgg caaacaaacc    12900
accgctggta gcggtggttt ttttgtttgc aagcagcaga ttacgcgcag aaaaaaagga    12960
tctcaagaag atcctttgat cttttctacg gggtctgacg ctcagtggaa cgaaaactca    13020
cgttaaggga ttttggtcat gagattatca aaaaggatct tcacctagat ccttttaaat    13080
taaaaatgaa gttttaaatc aatctaaagt atatatgagt aaacttggtc tgacagttac    13140
caatgcttaa tcagtgaggc acctatctca gcgatctgtc tatttcgttc atccatagtt    13200
gcctgactcc ccgtcgtgta gataactacg atacgggagg gcttaccatc tggccccagt    13260
gctgcaatga taccgcgaga cccacgctca ccggctccag atttatcagc aataaaccag    13320
ccagccggaa gggccgagcg cagaagtggt cctgcaactt tatccgcctc catccagtct    13380
attaattgtt gccgggaagc tagagtaagt agttcgccag ttaatagttt gcgcaacgtt    13440
gttgccattg ctacaggcat cgtggtgtca cgctcgtcgt ttggtatggc ttcattcagc    13500
tccggttccc aacgatcaag gcgagttaca tgatccccca tgttgtgcaa aaaagcggtt    13560
agctccttcg gtcctccgat cgttgtcaga agtaagttgg ccgcagtgtt atcactcatg    13620
gttatggcag cactgcataa ttctcttact gtcatgccat ccgtaagatg cttttctgtg    13680
actggtgagt actcaaccaa gtcattctga gaatagtgta tgcggcgacc gagttgctct    13740
tgcccggcgt caatacggga taataccgcg ccacatagca gaactttaaa agtgctcatc    13800
attggaaaac gttcttcggg gcgaaaactc tcaaggatct taccgctgtt gagatccagt    13860
tcgatgtaac ccactcgtgc acccaactga tcttcagcat cttttacttt caccagcgtt    13920
tctgggtgag caaaaacagg aaggcaaaat gccgcaaaaa agggaataag ggcgacacgg    13980
aaatgttgaa tactcatact cttcctttt caatattatt gaagcattta tcagggttat    14040
tgtctcatga gcggatacat atttgaatgt atttagaaaa ataaacaaat aggggttccg    14100
cgcacatttc cccgaaaagt gccacctgaa cgaagcatct gtgcttcatt tgtagaacaa    14160
aaaatgcaac gcgagagcgc taattttttca acaaagaat ctgagctgca ttttttacaga    14220 acagaaatgc aacgcgaaag cgctatttta ccaacgaaga atctgtgctt catttttgta    14280
```

```
aaacaaaaat gcaacgcgag agcgctaatt tttcaaacaa agaatctgag ctgcattttt    14340
acagaacaga aatgcaacgc gagagcgcta ttttaccaac aaagaatcta tacttctttt    14400
ttgttctaca aaaatgcatc ccgagagcgc tattttttcta acaaagcatc ttagattact   14460 tttttttctcc tttgtgcgct ctataatgca gtctcttgat aacttttttgc actgtaggtc  14520 cgttaaggtt agaagaaggc tactttggtg tctatttttct cttccataaa aaaagcctga   14580
ctccacttcc cgcgtttact gattactagc gaagctgcgg gtgcattttt tcaagataaa    14640 ggcatcccg attatattct ataccgatgt ggattgcgca actttgtga acagaaagtg      14700 atagcgttga tgattcttca ttggtcagaa aattatgaac ggtttcttct attttgtctc    14760
tatatactac gtataggaaa tgtttacatt ttcgtattgt tttcgattca ctctatgaat    14820
agttcttact acaatttttt tgtctaaaga gtaatactag agataaacat aaaaaatgta    14880
gaggtcgagt ttagatgcaa gttcaaggag cgaaaggtgg atgggtaggt tatataggga    14940
tatagcacag agatatatag caaagagata cttttgagca atgtttgtgg aagcggtatt    15000
cgcaatattt tagtagctcg ttacagtccg gtgcgttttt ggttttttga agtgcgtct     15060 tcagagcgct tttggttttc aaaagcgctc tgaagttcct atactttcta gagaatagga    15120
acttcggaat aggaacttca aagcgtttcc gaaaacgagc gcttccgaaa atgcaacgcg    15180
agctgcgcac atacagctca ctgttcacgt cgcacctata tctgcgtgtt gcctgtatat    15240
atatatacat gagaagaacg gcatagtgcg tgtttatgct taaatgcgta cttatatgcg    15300
tctatttatg taggatgaaa ggtagtctag tacctcctgt gatattatcc cattccatgc    15360
ggggtatcgt atgcttcctt cagcactacc ctttagctgt tctatatgct gccactcctc    15420
aattggatta gtctcatcct tcaatgctat catttccttt gatattggat catactaaga    15480
aaccattatt atcatgacat taacctataa aaataggcgt atcacgaggc cctttcgtc    15539
```

<210> SEQ ID NO 34
<211> LENGTH: 1047
<212> TYPE: DNA
<213> ORGANISM: Alcaligenes xylosoxydans

<400> SEQUENCE: 34

```
atgaaagctc tggtttatca cggtgaccac aagatctcgc ttgaagacaa gcccaagccc    60
acccttcaaa agcccacgga tgtagtagta cgggttttga agaccacgat ctgcggcacg    120
gatctcggca tctacaaagg caagaatcca gaggtcgccg acgggcgcat cctgggccat    180
gaaggggtag gcgtcatcga ggaagtgggc gagagtgtca cgcagttcaa gaaggcgac    240 aaggtcctga tttcctgcgt cacttcttgc ggctcgtgcg actactgcaa gaagcagctt    300
tactcccatt gccgcgacgg cggtggatc ctgggttaca tgatcgatgg cgtgcaggcc    360
gaatacgtcc gcatcccgca tgccgacaac agcctctaca agatcccccca gacaattgac    420 gacgaaatcg ccgtcctgct gagcgacatc ctgcccaccg gccacgaaat cggcgtccag    480
tatgggaatg tccagccggg cgatgcggtg gctattgtcg gcgcgggccc cgtcggcatg    540
tccgtactgt tgaccgccca gttctactcc ccctcgacca tcatcgtgat cgacatggac    600
gagaatcgcc tccagctcgc caaggagctc ggggcaacgc acaccatcaa ctccggcacg    660
gagaacgttg tcgaagccgt gcataggatt gcggcagagg gagtcgatgt tgcgatcgag    720
gcggtgggca taccgcgac ttgggacatc tgccaggaga tcgtcaagcc cggcgcgcac    780
atcgccaacg tcggcgtgca tggcgtcaag gttgacttcg agattcagaa gctctggatc    840
```

```
aagaacctga cgatcaccac gggactggtg aacacgaaca cgacgcccat gctgatgaag    900
gtcgcctcga ccgacaagct tccgttgaag aagatgatta cccatcgctt cgagctggcc    960
gagatcgagc acgcctatca ggtattcctc aatggcgcca aggagaaggc gatgaagatc   1020
atcctctcga acgcaggcgc tgcctga                                       1047
```

<210> SEQ ID NO 35
<211> LENGTH: 348
<212> TYPE: PRT
<213> ORGANISM: Alcaligenes xylosoxydans

<400> SEQUENCE: 35

```
Met Lys Ala Leu Val Tyr His Gly Asp His Lys Ile Ser Leu Glu Asp
1               5                   10                  15

Lys Pro Lys Pro Thr Leu Gln Lys Pro Thr Asp Val Val Arg Val
            20                  25                  30

Leu Lys Thr Thr Ile Cys Gly Thr Asp Leu Gly Ile Tyr Lys Gly Lys
        35                  40                  45

Asn Pro Glu Val Ala Asp Gly Arg Ile Leu Gly His Glu Gly Val Gly
    50                  55                  60

Val Ile Glu Glu Val Gly Glu Ser Val Thr Gln Phe Lys Lys Gly Asp
65                  70                  75                  80

Lys Val Leu Ile Ser Cys Val Thr Ser Cys Gly Ser Cys Asp Tyr Cys
                85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220

Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
                245                 250                 255

Pro Gly Ala His Ile Ala Asn Val Gly Val His Gly Val Lys Val Asp
            260                 265                 270

Phe Glu Ile Gln Lys Leu Trp Ile Lys Asn Leu Thr Ile Thr Thr Gly
        275                 280                 285

Leu Val Asn Thr Asn Thr Thr Pro Met Leu Met Lys Val Ala Ser Thr
    290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335
```

Ala Met Lys Ile Ile Leu Ser Asn Ala Gly Ala Ala
        340                 345

<210> SEQ ID NO 36
<211> LENGTH: 9089
<212> TYPE: DNA
<213> ORGANISM: artificial sequence
<220> FEATURE:
<223> OTHER INFORMATION: constructed plasmid

<400> SEQUENCE: 36

| | | | |
|---|---|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataccac agcttttcaa ttcaattcat cattttttt ttattctttt ttttgatttc | 240 |
| ggtttctttg aaatttttt gattcggtaa tctccgaaca aaggaagaa cgaaggaagg | 300 |
| agcacagact tagattggta tatatacgca tatgtagtgt tgaagaaaca tgaaattgcc | 360 |
| cagtattctt aacccaactg cacagaacaa aaacctgcag gaaacgaaga taaatcatgt | 420 |
| cgaaagctac atataaggaa cgtgctgcta ctcatcctag tcctgttgct gccaagctat | 480 |
| ttaatatcat gcacgaaaag caaacaaact tgtgtgcttc attggatgtt cgtaccacca | 540 |
| aggaattact ggagttagtt gaagcattag gtcccaaaat ttgttactta aaaacacatg | 600 |
| tggatatctt gactgatttt tccatggagg gcacagttaa gccgctaaag gcattatccg | 660 |
| ccaagtacaa ttttttactc ttcgaagaca gaaaatttgc tgacattggt aatacagtca | 720 |
| aattgcagta ctctgcgggt gtatacagaa tagcagaatg ggcagacatt acgaatgcac | 780 |
| acggtgtggt gggcccaggt attgttagcg gtttgaagca ggcggcagaa gaagtaacaa | 840 |
| aggaacctag aggcctttg atgttagcag aattgtcatg caagggctcc ctatctactg | 900 |
| gagaatatac taagggtact gttgacattg cgaagagcga caaagatttt gttatcggct | 960 |
| ttattgctca aagagacatg ggtggaagag atgaaggtta cgattggttg attatgacac | 1020 |
| ccggtgtggg tttagatgac aagggagacg cattgggtca acagtataga accgtggatg | 1080 |
| atgtggtctc tacaggatct gacattatta ttgttggaag aggactattt gcaaagggaa | 1140 |
| gggatgctaa ggtagagggt gaacgttaca gaaaagcagg ctgggaagca tatttgagaa | 1200 |
| gatgcggcca gcaaaactaa aaaactgtat tataagtaaa tgcatgtata ctaaactcac | 1260 |
| aaattagagc ttcaatttaa ttatatcagt tattacccta tgcggtgtga ataccgcac | 1320 |
| agatgcgtaa ggagaaaata ccgcatcagg aaattgtaaa cgttaatatt ttgttaaaat | 1380 |
| tcgcgttaaa ttttgttaa atcagctcat tttttaacca ataggccgaa atcggcaaaa | 1440 |
| tcccttataa atcaaaagaa tagaccgaga tagggttgag tgttgttcca gtttggaaca | 1500 |
| agagtccact attaaagaac gtggactcca acgtcaaagg gcgaaaaacc gtctatcagg | 1560 |
| gcgatggccc actacgtgaa ccatcaccct aatcaagttt tttggggtcg aggtgccgta | 1620 |
| aagcactaaa tcggaaccct aaagggagcc ccgatttag agcttgacgg ggaaagccgg | 1680 |
| cgaacgtggc gagaaaggaa gggaagaaag cgaaaggagc gggcgctagg gcgctggcaa | 1740 |
| gtgtagcggt cacgctgcgc gtaaccacca cacccgccgc gcttaatgcg ccgctacagg | 1800 |
| gcgcgtcgcg ccattcgcca ttcaggctgc gcaactgttg ggaagggcga tcggtgcggg | 1860 |
| cctcttcgct attacgccag ctggcgaaag gggatgtgc tgcaaggcga ttaagttggg | 1920 |
| taacgccagg gttttcccag tcacgacgtt gtaaaacgac ggccagtgag cgcgcgtaat | 1980 |

```
acgactcact ataqggcgaa ttgggtaccg ggccccccct cgaggtcgac tggccattaa    2040
tctttcccat attagatttc gccaagccat gaaagttcaa gaaaggtctt tagacgaatt    2100
acccttcatt tctcaaactg gcgtcaaggg atcctggtat ggttttatcg ttttatttct    2160
ggttcttata gcatcgtttt ggacttctct gttcccatta ggcggttcag gagccagcgc    2220
agaatcattc tttgaaggat acttatcctt tccaattttg attgtctgtt acgttggaca    2280
taaactgtat actagaaatt ggactttgat ggtgaaacta aagatatgg atcttgatac     2340 cggcagaaaa caagtagatt tgactcttcg tagggaagaa atgaggattg agcgagaaac    2400
attagcaaaa agatccttcg taacaagatt tttacatttc tggtgttgaa gggaaagata    2460
tgagctatac agcggaattt ccatatcact cagattttgt tatctaattt tttccttccc    2520
acgtccgcgg gaatctgtgt atattactgc atctagatat atgttatctt atcttggcgc    2580
gtacatttaa ttttcaacgt attctataag aaattgcggg agttttttc atgtagatga     2640 tactgactgc acgcaaatat aggcatgatt tataggcatg atttgatggc tgtaccgata    2700
ggaacgctaa gagtaacttc agaatcgtta tcctggcgga aaaaattcat tgtaaactt     2760 taaaaaaaaa agccaatatc cccaaaatta ttaagagcgc ctccattatt aactaaaatt    2820
tcactcagca tccacaatgt atcaggtatc tactacagat attacatgtg gcgaaaaaga    2880
caagaacaat gcaatagcgc atcaagaaaa aacacaaagc tttcaatcaa tgaatcgaaa    2940
atgtcattaa aatagtatat aaattgaaac taagtcataa agctataaaa agaaaattta    3000
tttaaatgca agatttaaag taaattcacg gccctgcagg ccctaacctg ctaggacaca    3060
acgtctttgc ctggtaaagt ttctagctga cgtgattcct tcacctgtgg atccggcaat    3120
tgtaaaggtt gtgaaaccct cagcttcata accgacacct gcaaatgact ttgcattctt    3180
aacaaagata gttgtatcaa tttcacgttc gaatctatta aggttatcga tgttcttaga    3240
ataaatgtag gcggaatgtt ttctattctg ctcagctatc ttggcgtatt taatggcttc    3300
atcaatgtcc ttcactctaa ctataggcaa aattggcatc atcaactccg tcataacgaa    3360
cggatggttt gcgttgactt cacaaataat acactttaca ttacttggtg actctacatc    3420
tatttcatcc aaaaacagtt tagcgtcctt accaacccac ttcttattaa tgaaatattc    3480
ttgagtttca ttgttctttt gaagaacaag gtctatcagc ttggatactt ggtcttcatt    3540
gataatgacg gcgttgtttt tcaacatgtt agagatcaga tcatctgcaa cgttttcaaa    3600
cacgaacact tcttttttccg cgatacaagg aagattgttg tcaaacgaac aaccttcaat    3660
aatgcttctg ccggccttct cgatatctgc tgtatcgtct acaataaccg gaggattacc    3720
cgcgccagct ccgatggcct ttttaccaga attaagaagg gttttttacca tacccgggcc    3780 acccgtaccg cacaacaatt ttatggatgg atgtttgata atagcgtcta aactttccat    3840
agttgggttc tttatagtag tgacaaggtt ttcaggtcca ccacagctaa ttatggcttt    3900
gtttatcatt tctactgcga aagcgacaca cttttttggcg catgggtgac cattaaatac    3960
aactgcattc cccgcagcta tcataccatat agaattgcag ataacggttt ctgttggatt    4020
cgtgcttgga gttatagcgc cgataactcc gtatggactc atttcaacca ctgttagtcc    4080
attatcgccg gaccatgctg ttgttgtcag atcttcagtg cctggggtat acttggccac    4140
taattcatgt ttcaagattt tatcctcata ccttcccatg tgggtttcct ccaggatcat    4200
tgtggctaag acctctttat tctgtaatgc ggctttttctt attcggtga ttattttctc     4260 tcttttgttcc tttgtgtagt gtagggaaag aatcttttgt gcatgtactg cagaagaaat    4320
ggcattctca acattttcaa atactccaaa acatgaagag ttatctttgt aattcttta     4380
```

```
gttgatgttt tcaccattag tcttcacttt caagtctttg gtggttggga ttaaggtatc    4440
tttatccatg gtgtttgttt atgtgtgttt attcgaaact aagttcttgg tgttttaaaa    4500
ctaaaaaaaa gactaactat aaaagtagaa tttaagaagt ttaagaaata gatttacaga    4560
attacaatca atacctaccg tctttatata cttattagtc aagtagggga ataatttcag    4620
ggaactggtt tcaacctttt ttttcagctt tttccaaatc agagagagca gaaggtaata    4680
gaaggtgtaa gaaaatgaga tagatacatg cgtgggtcaa ttgccttgtg tcatcattta    4740
ctccaggcag gttgcatcac tccattgagg ttgtgcccgt ttttgcctg tttgtgcccc     4800 tgttctctgt agttgcgcta agagaatgga cctatgaact gatggttggt gaagaaaaca    4860
atattttggt gctgggattc tttttttttc tggatgccag cttaaaaagc gggctccatt    4920
atatttagtg gatgccagga ataaactgtt cacccagaca cctacgatgt tatatattct    4980
gtgtaacccg cccctatttt gggcatgta cgggttacag cagaattaaa aggctaattt      5040
tttgactaaa taaagttagg aaaatcacta ctattaatta tttacgtatt ctttgaaatg    5100
gcagtattga taatgataaa ctcgaactga aaaagcgtgt ttttttattca aaatgattct   5160 aactccctta cgtaatcaag gaatcttttt gccttggcct ccgcgtcatt aaacttcttg    5220
ttgttgacgc taacattcaa cgctagtata tattcgtttt tttcaggtaa gttcttttca    5280
acgggtctta ctgatgaggc agtcgcgtct gaacctgtta agaggtcaaa tatgtcttct    5340
tgaccgtacg tgtcttgcat gttattagct ttgggaattt gcatcaagtc ataggaaaat    5400
ttaaatcttg gctctcttgg gctcaaggtg acaaggtcct cgaaaatagg gcgcgcccca    5460
ccgcggtgga gctccagctt ttgttcccctt tagtgagggt taattgcgcg cttggcgtaa    5520
tcatggtcat agctgtttcc tgtgtgaaat tgttatccgc tcacaattcc acacaacata    5580
ggagccggaa gcataaagtg taaagcctgg ggtgcctaat gagtgaggta actcacatta    5640
attgcgttgc gctcactgcc cgctttccag tcgggaaacc tgtcgtgcca gctgcattaa    5700
tgaatcggcc aacgcgcggg gagaggcggt ttgcgtattg ggcgctcttc cgcttcctcg    5760
ctcactgact cgctgcgctc ggtcgttcgg ctgcggcgag cggtatcagc tcactcaaag    5820
gcggtaatac ggttatccac agaatcaggg gataacgcag gaaagaacat gtgagcaaaa    5880
ggccagcaaa aggccaggaa ccgtaaaaag gccgcgttgc tggcgttttt ccataggctc    5940
cgcccccctg acgagcatca caaaaatcga cgctcaagtc agaggtggcg aaacccgaca    6000
ggactataaa gataccaggc gtttccccct ggaagctccc tcgtgcgctc tcctgttccg    6060
accctgccgc ttaccggata cctgtccgcc tttctccctt cgggaagcgt ggcgctttct    6120
catagctcac gctgtaggta tctcagttcg gtgtaggtcg ttcgctccaa gctgggctgt    6180
gtgcacgaac cccccgttca gcccgaccgc tgcgccttat ccggtaacta tcgtcttgag    6240
tccaacccgg taagacacga cttatcgcca ctggcagcag ccactggtaa caggattagc    6300
agagcgaggt atgtaggcgg tgctacagag ttcttgaagt ggtggcctaa ctacggctac    6360
actagaagga cagtatttgg tatctgcgct ctgctgaagc cagttacctt cggaaaaaga    6420
gttggtagct cttgatccgg caaacaaacc accgctggta gcggtggttt ttttgtttgc    6480
aagcagcaga ttacgcgcag aaaaaaagga tctcaagaag atcctttgat cttttctacg    6540
gggtctgacg ctcagtggaa cgaaaactca cgttaaggga ttttggtcat gagattatca    6600
aaaaggatct tcacctagat ccttttaaat taaaaatgaa gttttaaatc aatctaaagt    6660
atatatgagt aaacttggtc tgacagttac caatgcttaa tcagtgaggc acctatctca    6720
```

```
gcgatctgtc tatttcgttc atccatagtt gcctgactcc ccgtcgtgta gataactacg    6780
atacgggagg gcttaccatc tggcccagt  gctgcaatga taccgcgaga cccacgctca    6840
ccggctccag atttatcagc aataaaccag ccagccggaa gggccgagcg cagaagtggt    6900
cctgcaactt tatccgcctc catccagtct attaattgtt gccgggaagc tagagtaagt    6960
agttcgccag ttaatagttt gcgcaacgtt gttgccattg ctacaggcat cgtggtgtca    7020
cgctcgtcgt ttggtatggc ttcattcagc tccggttccc aacgatcaag gcgagttaca    7080
tgatccccca tgttgtgcaa aaaagcggtt agctccttcg gtcctccgat cgttgtcaga    7140
agtaagttgg ccgcagtgtt atcactcatg gttatggcag cactgcataa ttctcttact    7200
gtcatgccat ccgtaagatg cttttctgtg actggtgagt actcaaccaa gtcattctga    7260
gaatagtgta tgcggcgacc gagttgctct tgcccggcgt caatacggga taataccgcg    7320
ccacatagca gaactttaaa agtgctcatc attggaaaac gttcttcggg gcgaaaactc    7380
tcaaggatct taccgctgtt gagatccagt tcgatgtaac ccactcgtgc acccaactga    7440
tcttcagcat cttttacttt caccagcgtt tctgggtgag caaaaacagg aaggcaaaat    7500
gccgcaaaaa agggaataag ggcgacacgg aaatgttgaa tactcatact cttccttttt    7560
caatattatt gaagcattta tcaggggtat tgtctcatga gcggatacat atttgaatgt    7620
atttagaaaa ataaacaaat aggggttccg cgcacatttc cccgaaaagt gccacctgaa    7680
cgaagcatct gtgcttcatt tgtagaaca  aaaatgcaac gcgagagcgc taattttttca    7740 aacaaagaat ctgagctgca ttttacaga  acagaaatgc aacgcgaaag cgctatttta    7800
ccaacgaaga atctgtgctt cattttgta  aaacaaaaat gcaacgcgag agcgctaatt    7860
tttcaaacaa gaatctgag  ctgcattttt acagaacaga aatgcaacgc gagagcgcta    7920
ttttaccaac aaagaatcta tacttctttt ttgttctaca aaaatgcatc ccgagagcgc    7980
tatttttcta caaagcatc  ttagattact tttttctcc  tttgtgcgct ctataatgca    8040
gtctcttgat aacttttgc  actgtaggtc cgttaaggtt agaagaaggc tactttggtg    8100
tctattttct cttccataaa aaaagcctga ctccacttcc cgcgtttact gattactagc    8160
gaagctgcgg gtgcattttt tcaagataaa ggcatccccg attatattct ataccgatgt    8220
ggattgcgca tactttgtga acagaaagtg atagcgttga tgattcttca ttggtcagaa    8280
aattatgaac ggtttcttct attttgtctc tatatactac gtataggaaa tgtttacatt    8340
ttcgtattgt tttcgattca ctctatgaat agttcttact acaatttttt tgtctaaaga    8400
gtaatactag ataaaacat  aaaaaatgta gaggtcgagt ttagatgcaa gttcaaggag    8460 cgaaggtgg  atgggtaggt tatatagggga tatagcacag agatatatag caaagagata    8520
cttttgagca atgtttgtgg aagcggtatt cgcaatattt tagtagctcg ttacagtccg    8580
gtgcgttttt ggttttttga agtgcgtct  tcagagcgct tttggttttc aaaagcgctc    8640
tgaagttcct atactttcta gagaatagga acttcggaat aggaacttca aagcgtttcc    8700
gaaaacgagc gcttccgaaa atgcaacgcg agctgcgcac atacagctca ctgttcacgt    8760
cgcacctata tctgcgtgtt gcctgtatat atatatacat gagaagaacg gcatagtgcg    8820
tgtttatgct taaatgcgta cttatatgcg tctatttatg taggatgaaa ggtagtctag    8880
tacctcctgt gatattatcc cattccatgc ggggtatcgt atgcttcctt cagcactacc    8940
ctttagctgt tctatatgct gccactcctc aattggatta gtctcatcct tcaatgctat    9000
catttccttt gatattggat catactaaga accattatt  atcatgacat aacctataa     9060 aaataggcgt atcacgaggc cctttcgtc                                      9089
```

<210> SEQ ID NO 37
<211> LENGTH: 1023
<212> TYPE: DNA
<213> ORGANISM: Saccharomyces cerevisiae

<400> SEQUENCE: 37

```
caccgcggtg gggcgcgccc tattttcgag gaccttgtca ccttgagccc aagagagcca      60
agatttaaat tttcctatga cttgatgcaa attcccaaag ctaataacat gcaagacacg     120
tacggtcaag aagacatatt tgacctctta acaggttcag acgcgactgc ctcatcagta     180
agacccgttg aaaagaactt acctgaaaaa acgaatata tactagcgtt gaatgttagc     240
gtcaacaaca agaagtttaa tgacgcggag gccaaggcaa aaagattcct tgattacgta     300
agggagttag aatcattttg aataaaaaac acgcttttc agttcgagtt tatcattatc     360
aatactgcca tttcaaagaa tacgtaaata attaatagta gtgattttcc taactttatt     420
tagtcaaaaa attagccttt taattctgct gtaacccgta catgcccaaa ataggggggcg    480
ggttacacag aatatataac atcgtaggtg tctgggtgaa cagtttattc ctggcatcca     540
ctaaatataa tggagcccgc tttttaagct ggcatccaga aaaaaaaga atcccagcac     600
caaaatattg ttttcttcac caaccatcag ttcataggtc cattctctta gcgcaactac     660
agagaacagg ggcacaaaca ggcaaaaaac gggcacaacc tcaatggagt gatgcaacct     720
gcctggagta aatgatgaca caaggcaatt gacccacgca tgtatctatc tcattttctt     780
acaccttcta ttaccttctg ctctctctga tttggaaaaa gctgaaaaaa aaggttgaaa     840
ccagttccct gaaattattc ccctacttga ctaataagta tataaagacg gtaggtattg     900
attgtaattc tgtaaatcta tttcttaaac ttcttaaatt ctactttat agttagtctt     960
tttttagtt ttaaaacacc aagaacttag tttcgaataa acacacataa actagtaaac   1020
aaa                                                                1023
```

<210> SEQ ID NO 38
<211> LENGTH: 21
<212> TYPE: DNA
<213> ORGANISM: artificial sequence
<220> FEATURE:
<223> OTHER INFORMATION: primer

<400> SEQUENCE: 38

```
caaaagctga gctccaccgc g                                              21
```

<210> SEQ ID NO 39
<211> LENGTH: 44
<212> TYPE: DNA
<213> ORGANISM: artificial sequence
<220> FEATURE:
<223> OTHER INFORMATION: primer

<400> SEQUENCE: 39

```
gtttactagt ttatgtgtgt ttattcgaaa ctaagttctt ggtg                     44
```

<210> SEQ ID NO 40
<211> LENGTH: 8994
<212> TYPE: DNA
<213> ORGANISM: artificial sequence
<220> FEATURE:
<223> OTHER INFORMATION: constructed plasmid

<400> SEQUENCE: 40

```
ctagttctag agcggccgcc accgcggtgg agctccagct tttgttccct ttagtgaggg      60
ttaattgcgc gcttggcgta atcatggtca tagctgtttc ctgtgtgaaa ttgttatccg     120
ctcacaattc cacacaacat aggagccgga agcataaagt gtaaagcctg gggtgcctaa     180
tgagtgaggt aactcacatt aattgcgttg cgctcactgc ccgctttcca gtcgggaaac     240
ctgtcgtgcc agctgcatta atgaatcggc caacgcgcgg ggagaggcgg tttgcgtatt     300
gggcgctctt ccgcttcctc gctcactgac tcgctgcgct cggtcgttcg gctgcggcga     360
gcggtatcag ctcactcaaa ggcggtaata cggttatcca cagaatcagg ggataacgca     420
ggaaagaaca tgtgagcaaa aggccagcaa aaggccagga accgtaaaaa ggccgcgttg     480
ctggcgtttt tccataggct ccgcccccct gacgagcatc acaaaaatcg acgctcaagt     540
cagaggtggc gaaacccgac aggactataa agataccagg cgtttccccc tggaagctcc     600
ctcgtgcgct ctcctgttcc gaccctgccg cttaccggat acctgtccgc ctttctccct     660
tcggaagcg tggcgctttc tcatagctca cgctgtaggt atctcagttc ggtgtaggtc      720
gttcgctcca agctgggctg tgtgcacgaa ccccccgttc agcccgaccg ctgcgcctta     780
tccggtaact atcgtcttga gtccaacccg gtaagacacg acttatcgcc actggcagca     840
gccactggta acaggattag cagagcgagg tatgtaggcg gtgctacaga gttcttgaag     900
tggtggccta actacggcta cactagaagg acagtatttg gtatctgcgc tctgctgaag     960
ccagttacct tcggaaaaag agttggtagc tcttgatccg gcaaacaaac caccgctggt    1020
agcggtggtt ttttgtttg caagcagcag attacgcgca gaaaaaaagg atctcaagaa    1080
gatcctttga tcttttctac ggggtctgac gctcagtgga acgaaaactc acgttaaggg    1140
attttggtca tgagattatc aaaaaggatc ttcacctaga tccttttaaa ttaaaaatga    1200
agttttaaat caatctaaag tatatatgag taaacttggt ctgacagtta ccaatgctta    1260
atcagtgagg cacctatctc agcgatctgt ctatttcgtt catccatagt tgcctgactc    1320
cccgtcgtgt agataactac gatacgggag ggcttaccat ctggccccag tgctgcaatg    1380
ataccgcgag acccacgctc accggctcca gatttatcag caataaacca gccagccgga    1440
agggccgagc gcagaagtgg tcctgcaact ttatccgcct ccatccagtc tattaattgt    1500
tgccgggaag ctagagtaag tagttcgcca gttaatagtt tgcgcaacgt tgttgccatt    1560
gctacaggca tcgtggtgtc acgctcgtcg tttggtatgg cttcattcag ctccggttcc    1620
caacgatcaa ggcgagttac atgatccccc atgttgtgca aaaaagcggt tagctccttc    1680
ggtcctccga tcgttgtcag aagtaagttg gccgcagtgt tatcactcat ggttatggca    1740
gcactgcata attctcttac tgtcatgcca tccgtaagat gcttttctgt gactggtgag    1800
tactcaacca agtcattctg agaatagtgt atgcggcgac cgagttgctc ttgcccggcg    1860
tcaatacggg ataataccgc gccacatagc agaactttaa aagtgctcat cattggaaaa    1920
cgttcttcgg ggcgaaaact ctcaaggatc ttaccgctgt tgagatccag ttcgatgtaa    1980
cccactcgtg cacccaactg atcttcagca tcttttactt tcaccagcgt ttctgggtga    2040
gcaaaaacag gaaggcaaaa tgccgcaaaa aagggaataa gggcgacacg gaaatgttga    2100
atactcatac tcttcctttt tcaatattat tgaagcattt atcagggtta ttgtctcatg    2160
agcggataca tatttgaatg tatttagaaa aataaacaaa taggggttcc gcgcacattt    2220
ccccgaaaag tgccacctga cgaagcatc tgtgcttcat tttgtagaac aaaaatgcaa    2280
cgcgagagcg ctaattttc aaacaaagaa tctgagctgc attttacag aacagaaatg     2340
caacgcgaaa gcgctatttt accaacgaag aatctgtgct tcatttttgt aaaacaaaaa    2400
```

```
tgcaacgcga gagcgctaat ttttcaaaca aagaatctga gctgcatttt tacagaacag    2460
aaatgcaacg cgagagcgct attttaccaa caaagaatct atacttcttt tttgttctac    2520
aaaaatgcat cccgagagcg ctattttct aacaaagcat cttagattac ttttttctc     2580 ctttgtgcgc tctataatgc agtctcttga aacttttg cactgtaggt ccgttaaggt     2640
tagaagaagg ctactttggt gtctattttc tcttccataa aaaagcctg actccacttc    2700 ccgcgtttac tgattactag cgaagctgcg ggtgcatttt ttcaagataa aggcatcccc   2760
gattatattc tataccgatg tggattgcgc atactttgtg aacagaaagt gatagcgttg   2820
atgattcttc attggtcaga aaattatgaa cggttcttc tattttgtct ctatatacta    2880
cgtataggaa atgtttacat tttcgtattg ttttcgattc actctatgaa tagttcttac   2940
tacaattttt ttgtctaaag agtaatacta gagataaaca taaaaatgt agaggtcgag    3000 tttagatgca agttcaagga gcgaaaggtg gatgggtagg ttatataggg atatagcaca   3060
gagatatata gcaaagagat acttttgagc aatgtttgtg gaagcggtat tcgcaatatt   3120
ttagtagctc gttacagtcc ggtgcgtttt tggttttttg aaagtgcgtc ttcagagcgc   3180
ttttggtttt caaaagcgct ctgaagttcc tatacttct agagaatagg aacttcggaa    3240
taggaacttc aaagcgtttc cgaaaacgag cgcttccgaa aatgcaacgc gagctgcgca   3300
catacagctc actgttcacg tcgcacctat atctgcgtgt tgcctgtata tatatataca   3360
tgagaagaac ggcatagtgc gtgtttatgc ttaaatgcgt acttatatgc gtctatttat   3420
gtaggatgaa aggtagtcta gtacctcctg tgatattatc ccattccatg cggggtatcg   3480
tatgcttcct tcagcactac cctttagctg ttctatatgc tgccactcct caattggatt   3540
agtctcatcc ttcaatgcta tcatttcctt tgatattgga tcatactaag aaaccattat   3600
tatcatgaca ttaacctata aaaataggcg tatcacgagg cccttcgtc tcgcgcgttt    3660 cggtgatgac ggtgaaaacc tctgacacat gcagctcccg gagacggtca cagcttgtct   3720
gtaagcggat gccgggagca gacaagcccg tcagggcgcg tcagcgggtg ttggcgggtg   3780
tcggggctgg cttaactatg cggcatcaga gcagattgta ctgagagtgc accatatcga   3840
ctacgtcgta aggccgtttc tgacagagta aaattcttga gggaactttc accattatgg   3900
gaaatgcttc aagaaggtat tgacttaaac tccatcaaat ggtcaggtca ttgagtgttt   3960
tttatttgtt gtattttttt tttttagag aaaatcctcc aatatcaaat taggaatcgt    4020
agtttcatga ttttctgtta cacctaactt tttgtgtggt gccctcctcc ttgtcaatat   4080
taatgttaaa gtgcaattct ttttccttat cacgttgagc cattagtatc aatttgctta   4140
cctgtattcc tttactatcc tccttttct ccttcttgat aaatgtatgt agattgcgta    4200
tatagtttcg tctaccctat gaacatattc cattttgtaa tttcgtgtcg tttctattat   4260
gaatttcatt tataaagttt atgtacaaat atcataaaaa aagagaatct ttttaagcaa   4320
ggattttctt aacttcttcg gcgacagcat caccgacttc ggtggtactg ttggaaccac   4380
ctaaatcacc agttctgata cctgcatcca aaacctttt aactgcatct tcaatggcct    4440
taccttcttc aggcaagttc aatgacaatt tcaacatcat tgcagcagac aagatagtgg   4500
cgatagggtc aaccttattc tttggcaaat ctggagcaga accgtggcat ggttcgtaca   4560
aaccaaatgc ggtgttcttg tctggcaaag aggccaagga cgcagatggc aacaaaccca   4620
aggaacctgg gataacggag gcttcatcgg agatgatatc accaaacatg ttgctggtga   4680
ttataatacc atttaggtgg gttgggttct taactaggat catggcggca gaatcaatca   4740
```

```
attgatgttg aaccttcaat gtagggaatt cgttcttgat ggtttcctcc acagttttc    4800 tccataatct tgaagaggcc aaaagattag ctttatccaa ggaccaaata ggcaatggtg    4860
gctcatgttg tagggccatg aaagcggcca ttcttgtgat tctttgcact tctggaacgg    4920
tgtattgttc actatcccaa gcgacaccat caccatcgtc ttcctttctc ttaccaaagt    4980
aaatacctcc cactaattct ctgacaacaa cgaagtcagt acctttagca aattgtggct    5040
tgattggaga taagtctaaa agagagtcgg atgcaaagtt acatggtctt aagttggcgt    5100
acaattgaag ttcttttacgg atttttagta aaccttgttc aggtctaaca ctaccggtac    5160
cccatttagg accagccaca gcacctaaca aaacggcatc aaccttcttg gaggcttcca    5220
gcgcctcatc tggaagtggg cacctgtag catcgatagc agcaccacca attaaatgat    5280
tttcgaaatc gaacttgaca ttggaacgaa catcagaaat agctttaaga accttaatgg    5340
cttcggctgt gatttcttga ccaacgtggt cacctggcaa aacgacgatc ttcttagggg    5400
cagacatagg ggcagacatt agaatggtat atccttgaaa tatatatata tattgctgaa    5460
atgtaaaagg taagaaaagt tagaaagtaa gacgattgct aaccacctat tggaaaaaac    5520
aataggtcct taaataatat tgtcaacttc aagtattgtg atgcaagcat ttagtcatga    5580
acgcttctct attctatatg aaaagccggt tccggcctct caccttttcct ttttctccca    5640 atttttcagt tgaaaaggt atatgcgtca ggcgacctct gaaattaaca aaaaatttcc    5700
agtcatcgaa tttgattctg tgcgatacg ccctgtgtg ttctcgttat gttgaggaaa    5760
aaaataatgg ttgctaagag attcgaactc ttgcatctta cgatacctga gtattcccac    5820
agttaactgc ggtcaagata tttcttgaat caggcgcctt agaccgctcg gccaaacaac    5880
caattacttg ttgagaaata gagtataatt atcctataaa tataacgttt ttgaacacac    5940
atgaacaagg aagtacagga caattgattt tgaagagaat gtggattttg atgtaattgt    6000
tgggattcca ttttttaataa ggcaataata ttaggtatgt ggatatacta gaagttctcc    6060
tcgaccgtcg atatgcggtg tgaaataccg cacagatgcg taaggagaaa ataccgcatc    6120
aggaaattgt aaacgttaat attttgttaa aattcgcgtt aaattttgt taaatcagct    6180 cattttttaa ccaataggcc gaaatcggca aaatccctta taaatcaaaa gaatagaccg    6240
agatagggtt gagtgttgtt ccagtttgga acaagagtcc actattaaag aacgtggact    6300
ccaacgtcaa agggcgaaaa accgtctatc agggcgatgg cccactacgt gaaccatcac    6360
cctaatcaag ttttttgggg tcgaggtgcc gtaaagcact aaatcggaac cctaaaggga    6420
gcccccgatt tagagcttga cggggaaagc cggcgaacgt ggcgagaaag gaagggaaga    6480
aagcgaaagg agcgggcgct agggcgctgg caagtgtagc ggtcacgctg cgcgtaacca    6540
ccacacccgc cgcgcttaat gcgccgctac agggcgcgtc gcgccattcg ccattcaggc    6600
tgcgcaactg ttgggaaggg cgatcggtgc gggcctcttc gctattacgc cagctggcga    6660 aaggggatg tgctgcaagg cgattaagtt gggtaacgcc agggttttcc cagtcacgac    6720
gttgtaaaac gacggccagt gagcgcgcgt aatacgactc actatagggc gaattgggta    6780 ccgggcccccc cctcgaggtc gacggtatcg ataagcttga tatcgaattc ctgcagcccg    6840
ggggatccgc atgcttgcat ttagtcgtgc aatgtatgac tttaagattt gtgagcagga    6900
agaaaaggga gaatcttcta acgataaacc cttgaaaaac tgggtagact acgctatgtt    6960
gagttgctac gcaggctgca caattacacg agaatgctcc cgcctaggat ttaaggctaa    7020
gggacgtgca atgcagacga cagatctaaa tgaccgtgtc ggtgaagtgt tcgccaaact    7080
tttcggttaa cacatgcagt gatgcacgcg cgatggtgct aagttacata tatatatata    7140
```

```
tatatatata tagccatagt gatgtctaag taacctttat ggtatatttc ttaatgtgga    7200
aagatactag cgcgcgcacc cacacacaag cttcgtcttt tcttgaagaa aagaggaagc    7260
tcgctaaatg ggattccact ttccgttccc tgccagctga tggaaaaagg ttagtggaac    7320
gatgaagaat aaaagagag atccactgag gtgaaatttc agctgacagc gagtttcatg     7380
atcgtgatga acaatggtaa cgagttgtgg ctgttgccag ggagggtggt tctcaacttt    7440
taatgtatgg ccaaatcgct acttgggttt gttatataac aaagaagaaa taatgaactg    7500
attctcttcc tccttcttgt cctttcttaa ttctgttgta attaccttcc tttgtaattt    7560
tttttgtaat tattcttctt aataatccaa acaaacacac atattacaat agctagctga    7620
ggatgaaggc attagtttat catggggatc acaaaatttc gttagaagac aaaccaaaac    7680
ccactctgca gaaaccaaca gacgttgtgg ttagggtgtt gaaaacaaca atttgcggta    7740
ctgacttggg aatatacaaa ggtaagaatc ctgaagtggc agatggcaga atcctgggtc    7800
atgagggcgt tggcgtcatt gaagaagtgg gcgaatccgt gacacaattc aaaaaggggg    7860
ataaagtttt aatctcctgc gttactagct gtggatcgtg tgattattgc aagaagcaac    7920
tgtattcaca ctgtagagac ggtggctgga ttttaggtta catgatcgac ggtgtccaag    7980
ccgaatacgt cagaatacca catgctgaca attcattgta taagatcccg caaactatcg    8040
atgatgaaat tgcagtacta ctgtccgata ttttacctac tggacatgaa attggtgttc    8100
aatatggtaa cgttcaacca ggcgatgctg tagcaattgt aggagcaggt cctgttggaa    8160
tgtcagtttt gttaactgct caattttact cgcctagtac cattattgtt atcgacatgg    8220
acgaaaaccg tttacaatta gcgaaggagc ttggggccac acacactatt aactccggta    8280
ctgaaaatgt tgtcgaagct gtgcatcgta tagcagccga aggagtggat gtagcaatag    8340
aagctgttgg tatacccgca acctgggaca tctgtcagga aattgtaaaa cccggcgctc    8400
atattgccaa cgtgggagtt catggtgtta aggtggactt tgaaattcaa aagttgtgga    8460
ttaagaatct aaccatcacc actggtttgg ttaacactaa tactacccca atgttgatga    8520
aggtagcctc tactgataaa ttgcctttaa agaaaatgat tactcacagg tttgagttag    8580
ctgaaatcga acacgcatat caggttttct tgaatggcgc taaagaaaaa gctatgaaga    8640
ttattctatc taatgcaggt gccgcctaat taattaagag taagcgaatt tcttatgatt    8700
tatgattttt attattaaat aagttataaa aaaataagt gtatacaaat tttaaagtga    8760
ctcttaggtt ttaaaacgaa aattcttatt cttgagtaac tctttcctgt aggtcaggtt    8820
gctttctcag gtatagcatg aggtcgctct tattgaccac acctctaccg gcatgccgag    8880
caaatgcctg caaatcgctc cccatttcac ccaattgtag atatgctaac tccagcaatg    8940
agttgatgaa tctcggtgtg tattttatgt cctcagagga caacacctgt ggta           8994
```

<210> SEQ ID NO 41
<211> LENGTH: 753
<212> TYPE: DNA
<213> ORGANISM: Saccharomyces cerevisiae

<400> SEQUENCE: 41

```
gcatgcttgc atttagtcgt gcaatgtatg actttaagat ttgtgagcag gaagaaaagg     60
gagaatcttc taacgataaa cccttgaaaa actgggtaga ctacgctatg ttgagttgct    120
acgcaggctg cacaattaca cgagaatgct cccgcctagg atttaaggct aagggacgtg    180
caatgcagac gacagatcta aatgaccgtg tcggtgaagt gttcgccaaa cttttcggtt    240
```

```
aacacatgca gtgatgcacg cgcgatggtg ctaagttaca tatatatata tatagccata    300
gtgatgtcta agtaaccttt atggtatatt tcttaatgtg gaaagatact agcgcgcgca    360
cccacacaca agcttcgtct tttcttgaag aaaagaggaa gctcgctaaa tgggattcca    420
ctttccgttc cctgccagct gatggaaaaa ggttagtgga acgatgaaga ataaaaagag    480
agatccactg aggtgaaatt tcagctgaca gcgagtttca tgatcgtgat gaacaatggt    540
aacgagttgt ggctgttgcc agggagggtg gttctcaact tttaatgtat ggccaaatcg    600
ctacttgggt ttgttatata acaaagaaga aataatgaac tgattctctt cctccttctt    660
gtcctttctt aattctgttg taattacctt cctttgtaat ttttttttgta attattcttc    720 ttaataatcc aaacaaacac acatattaca ata                                 753
```

<210> SEQ ID NO 42
<211> LENGTH: 316
<212> TYPE: DNA
<213> ORGANISM: Saccharomyces cerevisiae

<400> SEQUENCE: 42

```
gagtaagcga atttcttatg atttatgatt tttattatta aataagttat aaaaaaaata     60
agtgtataca aattttaaag tgactcttag gttttaaaac gaaaattctt attcttgagt    120
aactctttcc tgtaggtcag gttgctttct caggtatagc atgaggtcgc tcttattgac    180
cacacctcta ccggcatgcc gagcaaatgc ctgcaaatcg ctccccattt cacccaattg    240
tagatatgct aactccagca atgagttgat gaatctcggt gtgtattttta tgtcctcaga    300 ggacaacacc tgtggt                                                   316
```

<210> SEQ ID NO 43
<211> LENGTH: 1713
<212> TYPE: DNA
<213> ORGANISM: Streptococcus mutans

<400> SEQUENCE: 43

```
atgactgaca aaaaaactct taaagactta agaaatcgta gttctgttta cgattcaatg     60
gttaaatcac ctaatcgtgc tatgttgcgt gcaactggta tgcaagatga agactttgaa    120
aaacctatcg tcggtgtcat ttcaacttgg gctgaaaaca caccttgtaa tatccactta    180
catgactttg gtaaactagc caaagtcggt gttaaggaag ctggtgcttg gccagttcag    240
ttcggaacaa tcacggtttc tgatggaatc gccatgggaa cccaaggaat gcgtttctcc    300
ttgacatctc gtgatattat tgcagattct attgaagcag ccatgggagg tcataatgcg    360
gatgcttttg tagccattgg cggttgtgat aaaaacatgc ccggttctgt tatcgctatg    420
gctaacatgg atatcccagc catttttgct tacggcggaa caattgcacc tggtaattta    480
gacggcaaag atatcgattt agtctctgtc tttgaaggtg tcggccattg gaaccacggc    540
gatatgacca agaagaagt taagctttg gaatgtaatg cttgtcccgg tcctggaggc    600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga catttttaacg    780 cgtgaagctt ttgaagatgc tattactgta actatggctc tgggaggttc aaccaactca    840
acccttcacc tcttagctat tgcccatgct gctaatgtgg aattgacact tgatgatttc    900
aatactttcc aagaaaaagt tcctcatttg gctgatttga aaccttctgg tcaatatgta    960
ttccaagacc tttacaaggt cggagggta ccagcagtta tgaaatatct ccttaaaaat   1020
```

-continued

```
ggcttccttc atggtgaccg tatcacttgt actggcaaaa cagtcgctga aaatttgaag    1080
gcttttgatg atttaacacc tggtcaaaag gttattatgc cgcttgaaaa tcctaaacgt    1140
gaagatggtc cgctcattat tctccatggt aacttggctc agacggtgc cgttgccaaa     1200 gtttctggtg taaaagtgcg tcgtcatgtc ggtcctgcta aggtctttaa ttctgaagaa    1260
gaagccattg aagctgtctt gaatgatgat attgttgatg gtgatgttgt tgtcgtacgt    1320
tttgtaggac caaagggcgg tcctggtatg cctgaaatgc tttcccttc atcaatgatt     1380 gttggtaaag gcaaggtga aaaagttgcc cttctgacag atggccgctt ctcaggtggt     1440
acttatggtc ttgtcgtggg tcatatcgct cctgaagcac aagatggcgg tccaatcgcc    1500
tacctgcaaa caggagacat agtcactatt gaccaagaca ctaaggaatt acactttgat    1560
atctccgatg aagagttaaa acatcgtcaa gagaccattg aattgccacc gctctattca    1620
cgcggtatcc ttggtaaata tgctcacatc gtttcgtctg cttctagggg agccgtaaca    1680
gacttttgga gcctgaaga aactggcaaa aaa                                   1713
```

<210> SEQ ID NO 44
<211> LENGTH: 571
<212> TYPE: PRT
<213> ORGANISM: Streptococcus mutans

<400> SEQUENCE: 44

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
            85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
            165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
    210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
```

```
                        245                 250                 255
Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
    290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Val Pro Ala Val Met Lys Tyr
                325                 330                 335

Leu Leu Lys Asn Gly Phe Leu His Gly Asp Arg Ile Thr Cys Thr Gly
                340                 345                 350

Lys Thr Val Ala Glu Asn Leu Lys Ala Phe Asp Leu Thr Pro Gly
                355                 360                 365

Gln Lys Val Ile Met Pro Leu Glu Asn Pro Lys Arg Glu Asp Gly Pro
    370                 375                 380

Leu Ile Ile Leu His Gly Asn Leu Ala Pro Asp Gly Ala Val Ala Lys
385                 390                 395                 400

Val Ser Gly Val Lys Val Arg Arg His Val Gly Pro Ala Lys Val Phe
                405                 410                 415

Asn Ser Glu Glu Glu Ala Ile Glu Ala Val Leu Asn Asp Asp Ile Val
                420                 425                 430

Asp Gly Asp Val Val Val Val Arg Phe Val Gly Pro Lys Gly Gly Pro
                435                 440                 445

Gly Met Pro Glu Met Leu Ser Leu Ser Ser Met Ile Val Gly Lys Gly
            450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
                485                 490                 495

Gly Pro Ile Ala Tyr Leu Gln Thr Gly Asp Ile Val Thr Ile Asp Gln
                500                 505                 510

Asp Thr Lys Glu Leu His Phe Asp Ile Ser Asp Glu Glu Leu Lys His
            515                 520                 525

Arg Gln Glu Thr Ile Glu Leu Pro Pro Leu Tyr Ser Arg Gly Ile Leu
    530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
                565                 570

<210> SEQ ID NO 45
<211> LENGTH: 39
<212> TYPE: DNA
<213> ORGANISM: artificial sequence
<220> FEATURE:
<223> OTHER INFORMATION: primer

<400> SEQUENCE: 45
cacacatatt acaatagcta gctgaggatg aaagctctg                              39

<210> SEQ ID NO 46
<211> LENGTH: 39
<212> TYPE: DNA
<213> ORGANISM: artificial sequence
```

```
<220> FEATURE:
<223> OTHER INFORMATION: primer

<400> SEQUENCE: 46
cagagctttc atcctcagct agctattgta atatgtgtg                              39

<210> SEQ ID NO 47
<211> LENGTH: 9491
<212> TYPE: DNA
<213> ORGANISM: artificial sequence
<220> FEATURE:
<223> OTHER INFORMATION: constructed plasmid

<400> SEQUENCE: 47
tcgcgcgttt cggtgatgac ggtgaaaacc tctgacacat gcagctcccg gagacggtca        60
cagcttgtct gtaagcggat gccgggagca gacaagcccg tcaggcgcg tcagcgggtg        120 ttggcgggtg tcgggctgg cttaactatg cggcatcaga gcagattgta ctgagagtgc        180
accataaatt cccgttttaa gagcttggtg agcgctagga gtcactgcca ggtatcgttt        240
gaacacggca ttagtcaggg aagtcataac acagtccttt cccgcaattt tcttttttcta      300 ttactcttgg cctcctctag tacactctat atttttttat gcctcggtaa tgattttcat      360
tttttttttt cccctagcgg atgactcttt tttttcttta gcgattggca ttatcacata      420
atgaattata cattatataa agtaatgtga tttcttcgaa gaatatacta aaaatgagc        480 aggcaagata acgaaggca aagatgacag agcagaaagc cctagtaaag cgtattacaa        540
atgaaaccaa gattcagatt gcgatctctt taaagggtgg tccctagcg atagagcact        600 cgatcttccc agaaaaagag gcagaagcag tagcagaaca ggccacacaa tcgcaagtga      660
ttaacgtcca cacaggtata gggtttctgg accatatgat acatgctctg gccaagcatt      720
ccggctggtc gctaatcgtt gagtgcattg gtgacttaca catagacgac catcacacca      780
ctgaagactg cgggattgct ctcggtcaag cttttaaaga ggccctactg gcgcgtggag      840
taaaaaggtt tggatcagga tttgcgcctt ggatgaggc actttccaga gcggtggtag      900
atctttcgaa caggccgtac gcagttgtcg aacttggttt gcaaagggag aaagtaggag      960
atctctcttg cgagatgatc ccgcattttc ttgaaagctt tgcagaggct agcagaatta    1020
ccctccacgt tgattgtctg cgaggcaaga atgatcatca ccgtagtgag agtgcgttca    1080
aggctcttgc ggttgccata agagaagcca cctcgcccaa tggtaccaac gatgttcccct    1140 ccaccaaagg tgttcttatg tagtgacacc gattatttaa agctgcagca tacgatatat    1200
atacatgtgt atatatgtat acctatgaat gtcagtaagt atgtatacga acagtatgat    1260
actgaagatg acaaggtaat gcatcattct atacgtgtca ttctgaacga ggcgcgcttt    1320
ccttttttct ttttgctttt tctttttttt tctcttgaac tcgacggatc tatgcggtgt    1380
gaaataccgc acagatgcgt aaggagaaaa taccgcatca ggaaattgta aacgttaata    1440
ttttgttaaa attcgcgtta aattttgtt aaatcagctc attttttaac caataggccg    1500
aaatcggcaa aatcccttat aaatcaaaag aatagaccga gatagggttg agtgttgttc    1560
cagtttggaa caagagtcca ctattaaaga acgtggactc caacgtcaaa gggcgaaaaa    1620
ccgtctatca gggcgatggc ccactacgtg aaccatcacc ctaatcaagt tttttggggt    1680
cgaggtgccg taaagcacta aatcggaacc ctaaagggag cccccgattt agagcttgac    1740
ggggaaagcc ggcgaacgtg gcgagaaagg aagggaagaa agcgaaagga gcgggcgcta    1800
gggcgctggc aagtgtagcg gtcacgctgc gcgtaaccac cacacccgcc gcgcttaatg    1860
```

```
cgccgctaca gggcgcgtcg cgccattcgc cattcaggct gcgcaactgt tgggaagggc  1920
gatcggtgcg ggcctcttcg ctattacgcc agctggcgaa aggggatgt gctgcaaggc   1980
gattaagttg ggtaacgcca gggttttccc agtcacgacg ttgtaaaacg acggccagtg  2040
agcgcgcgta atacgactca ctatagggcg aattgggtac cgggccccc ctcgaggtcg   2100
acggcgcgcc actggtagag agcgactttg tatgccccaa ttgcgaaacc cgcgatatcc  2160
ttctcgattc tttagtaccc gaccaggaca aggaaaagga ggtcgaaacg tttttgaaga  2220
aacaagagga actacacgga agctctaaag atggcaacca gccagaaact aagaaaatga  2280
agttgatgga tccaactggc accgctggct gaacaacaa taccagcctt ccaacttctg    2340
taaataacgg cggtacgcca gtgccaccag taccgttacc tttcggtata cctcctttcc  2400
ccatgtttcc aatgcccttc atgcctccaa cggctactat cacaaatcct catcaagctg  2460
acgcaagccc taagaaatga ataacaatac tgacagtact aaataattgc ctacttggct  2520
tcacatacgt tgcatacgtc gatatagata ataatgataa tgacagcagg attatcgtaa  2580
tacgtaatag ttgaaaatct caaaaatgtg tgggtcatta cgtaaataat gataggaatg  2640
ggattcttct attttccctt tttccattct agcagccgtc gggaaaacgt ggcatcctct  2700
ctttcgggct caattggagt cacgctgccg tgagcatcct ctctttccat atctaacaac  2760
tgagcacgta accaatggaa aagcatgagc ttagcgttgc tccaaaaaag tattggatgg  2820
ttaataccat ttgtctgttc tcttctgact ttgactcctc aaaaaaaaaa aatctacaat  2880
caacagatcg cttcaattac gccctcacaa aactttttt ccttcttctt cgcccacgtt    2940
aaatttatc cctcatgttg tctaacggat ttctgcactt gatttattat aaaaagacaa   3000
agacataata cttctctatc aatttcagtt attgttcttc cttgcgttat tcttctgttc  3060
ttcttttct tttgtcatat ataaccataa ccaagtaata catattcaaa ctagtatgac    3120
tgacaaaaaa actcttaaag acttaagaaa tcgtagttct gtttacgatt caatggttaa  3180
atcacctaat cgtgctatgt tgcgtgcaac tggtatgcaa gatgaagact ttgaaaaacc  3240
tatcgtcggt gtcatttcaa cttgggctga aaacacacct tgtaatatcc acttacatga  3300
cttggtaaa ctagccaaag tcggtgttaa ggaagctggt gcttggccag ttcagttcgg    3360
aacaatcacg gtttctgatg gaatcgccat gggaacccaa ggaatgcgtt tctccttgac  3420
atctcgtgat attattgcag attctattga agcagccatg ggaggtcata atgcggatgc  3480
ttttgtagcc attggcggtt gtgataaaaa catgcccggt tctgttatcg ctatggctaa  3540
catggatatc ccagccattt ttgcttacgg cggaacaatt gcacctggta atttagacgg  3600
caaagatatc gatttagtct ctgtctttga aggtgtcggc cattggaacc acggcgatat  3660
gaccaaagaa gaagttaaag ctttggaatg taatgcttgt cccggtcctg gaggctgcgg  3720
tggtatgtat actgctaaca caatggcgac agctattgaa gttttgggac ttagccttcc  3780
gggttcatct tctcacccgg ctgaatccgc agaaaagaaa gcagatattg aagaagctgg  3840
tcgcgctgtt gtcaaaatgc tcgaaatggg cttaaaacct tctgacattt taacgcgtga  3900
agcttttgaa gatgctatta ctgtaactat ggctctggga ggttcaacca actcaaccct  3960
tcacctctta gctattgccc atgctgctaa tgtggaattg acacttgatg atttcaatac  4020
tttccaagaa aaagttcctc atttggctga tttgaaacct tctggtcaat atgtattcca  4080
agaccttttac aaggtcggag gggtaccagc agttatgaaa tatctcctta aaaatggctt  4140
ccttcatggt gaccgtatca cttgtactgg caaaacagtc gctgaaaatt tgaaggcttt  4200
tgatgattta acacctggtc aaaaggttat tatgccgctt gaaaatccta aacgtgaaga  4260
```

```
tggtccgctc attattctcc atggtaactt ggctccagac ggtgccgttg ccaaagtttc    4320
tggtgtaaaa gtgcgtcgtc atgtcggtcc tgctaaggtc tttaattctg aagaagaagc    4380
cattgaagct gtcttgaatg atgatattgt tgatggtgat gttgttgtcg tacgttttgt    4440
aggaccaaag ggcggtcctg gtatgcctga aatgctttcc ctttcatcaa tgattgttgg    4500
taaagggcaa ggtgaaaaag ttgcccttct gacagatggc cgcttctcag gtggtactta    4560
tggtcttgtc gtgggtcata tcgctcctga agcacaagat ggcggtccaa tcgcctacct    4620
gcaaacagga gacatagtca ctattgacca agacactaag gaattacact tgatatctc     4680 cgatgaagag ttaaaacatc gtcaagagac cattgaattg ccaccgctct attcacgcgg    4740
tatccttggt aaatatgctc acatcgtttc gtctgcttct aggggagccg taacagactt    4800
ttggaagcct gaagaaactg gcaaaaaatg ttgtcctggt tgctgtggtt aagcggccgc    4860
gttaattcaa attaattgat atagttttt aatgagtatt gaatctgttt agaaataatg     4920
gaatattatt tttatttatt tatttatatt attggtcggc tcttttcttc tgaaggtcaa    4980
tgacaaaatg atatgaagga ataatgatt tctaaaattt tacaacgtaa gatattttta     5040
caaaagccta gctcatcttt tgtcatgcac tattttactc acgcttgaaa ttaacggcca    5100
gtccactgcg gagtcatttc aaagtcatcc taatcgatct atcgttttg atagctcatt     5160 ttggagttcg cgattgtctt ctgttattca caactgtttt aattttatt tcattctgga     5220 actcttcgag ttctttgtaa agtctttcat agtagcttac tttatcctcc aacatattta    5280
acttcatgtc aatttcggct cttaaatttt ccacatcatc aagttcaaca tcatctttta    5340
acttgaattt attctctagc tcttccaacc aagcctcatt gctccttgat ttactggtga    5400
aaagtgatac actttgcgcg caatccaggt caaaactttc ctgcaaagaa ttcaccaatt    5460
tctcgacatc atagtacaat ttgttttgtt ctcccatcac aatttaatat acctgatgga    5520
ttcttatgaa gcgctgggta atggacgtgt cactctactt cgccttttc cctactcctt     5580 ttagtacgga agacaatgct aataaataag agggtaataa taatattatt aatcggcaaa    5640
aaagattaaa cgccaagcgt ttaattatca gaaagcaaac gtcgtaccaa tccttgaatg    5700
cttcccaatt gtatattaag agtcatcaca gcaacatatt cttgttatta aattaattat    5760
tattgatttt tgatattgta taaaaaaacc aaatatgtat aaaaaaagtg aataaaaaat    5820
accaagtatg gagaaatata ttagaagtct atacgttaaa ccaccgcggt ggagctccag    5880
cttttgttcc ctttagtgag ggttaattgc gcgcttggcg taatcatggt catagctgtt    5940
tcctgtgtga attgttatc cgctcacaat tccacacaac ataggagccg gaagcataaa     6000
gtgtaaagcc tggggtgcct aatgagtgag gtaactcaca ttaattgcgt tgcgctcact    6060
gcccgctttc cagtcgggaa acctgtcgtg ccagctgcat taatgaatcg gccaacgcgc    6120
ggggagaggc ggtttgcgta ttgggcgctc ttccgcttcc tcgctcactg actcgctgcg    6180
ctcggtcgtt cggctgcggc gagcggtatc agctcactca aaggcggtaa tacgttatc     6240 cacagaatca ggggataacg caggaaagaa catgtgagca aaaggccagc aaaaggccag    6300
gaaccgtaaa aaggccgcgt tgctggcgtt tttccatagg ctccgccccc ctgacgagca    6360
tcacaaaaat cgacgctcaa gtcagaggtg gcgaaacccg acaggactat aaagatacca    6420
ggcgtttccc cctggaagct ccctcgtgcg ctctcctgtt ccgaccctgc cgcttaccgg    6480
atacctgtcc gcctttctcc cttcgggaag cgtggcgctt tctcatagct cacgctgtag    6540
gtatctcagt tcggtgtagg tcgttcgctc caagctgggc tgtgtgcacg aaccccccgt    6600
```

```
tcagcccgac cgctgcgcct tatccggtaa ctatcgtctt gagtccaacc cggtaagaca    6660
cgacttatcg ccactggcag cagccactgg taacaggatt agcagagcga ggtatgtagg    6720
cggtgctaca gagttcttga agtggtggcc taactacggc tacactagaa ggacagtatt    6780
tggtatctgc gctctgctga agccagttac cttcggaaaa agagttggta gctcttgatc    6840
cggcaaacaa accaccgctg gtagcggtgg ttttttttgtt tgcaagcagc agattacgcg    6900
cagaaaaaaa ggatctcaag aagatccttt gatcttttct acggggtctg acgctcagtg    6960
gaacgaaaac tcacgttaag ggattttggt catgagatta tcaaaaagga tcttcaccta    7020
gatcctttta aattaaaaat gaagttttaa atcaatctaa agtatatatg agtaaacttg    7080
gtctgacagt taccaatgct taatcagtga ggcacctatc tcagcgatct gtctatttcg    7140
ttcatccata gttgcctgac tccccgtcgt gtagataact acgatacggg agggcttacc    7200
atctggcccc agtgctgcaa tgataccgcg agacccacgc tcaccggctc cagatttatc    7260
agcaataaac cagccagccg gaagggccga gcgcagaagt ggtcctgcaa ctttatccgc    7320
ctccatccag tctattaatt gttgccggga agctagagta agtagttcgc cagttaatag    7380
tttgcgcaac gttgttgcca ttgctacagg catcgtggtg tcacgctcgt cgtttggtat    7440
ggcttcattc agctccggtt cccaacgatc aaggcgagtt acatgatccc ccatgttgtg    7500
caaaaaagcg gttagctcct tcggtcctcc gatcgttgtc agaagtaagt tggccgcagt    7560
gttatcactc atggttatgg cagcactgca taattctctt actgtcatgc catccgtaag    7620
atgcttttct gtgactggtg agtactcaac caagtcattc tgagaatagt gtatgcggcg    7680
accgagttgc tcttgcccgg cgtcaatacg ggataatacc gcgccacata gcagaacttt    7740
aaaagtgctc atcattggaa acgttcttc ggggcgaaaa ctctcaagga tcttaccgct    7800
gttgagatcc agttcgatgt aacccactcg tgcacccaac tgatcttcag catcttttac    7860
tttcaccagc gtttctgggt gagcaaaaac aggaaggcaa aatgccgcaa aaaagggaat    7920
aagggcgaca cggaaatgtt gaatactcat actcttcctt tttcaatatt attgaagcat    7980
ttatcagggt tattgtctca tgagcggata catatttgaa tgtatttaga aaataaaca    8040
aatagggggtt ccgcgcacat ttccccgaaa agtgccacct gaacgaagca tctgtgcttc    8100
attttgtaga acaaaaatgc aacgcgagag cgctaatttt tcaaacaaag aatctgagct    8160
gcattttta c agaacagaaa tgcaacgcga aagcgctatt ttaccaacga agaatctgtg    8220
cttcattttt gtaaaacaaa aatgcaacgc gagagcgcta attttttcaaa caaagaatct    8280
gagctgcatt tttacagaac agaaatgcaa cgcgagagcg ctattttacc aacaaagaat    8340
ctatacttct tttttgttct acaaaaatgc atcccgagag cgctattttt ctaacaaagc    8400
atcttagatt acttttttc tcctttgtgc gctctataat gcagtctctt gataactttt    8460
tgcactgtag gtccgttaag gttagaagaa ggctactttg gtgtctattt tctcttccat    8520
aaaaaaagcc tgactccact tcccgcgttt actgattact agcgaagctg cgggtgcatt    8580
ttttcaagat aaaggcatcc ccgattatat tctataccga tgtggattgc gcatactttg    8640
tgaacagaaa gtgatagcgt tgatgattct tcattggtca gaaaattatg aacggtttct    8700
tctattttgt ctctatatac tacgtatagg aaatgtttac attttcgtat tgttttcgat    8760
tcactctatg aatagttctt actacaattt ttttgtctaa agagtaatac tagagataaa    8820
cataaaaaat gtagaggtcg agtttagatg caagttcaag gagcgaaagg tggatgggta    8880
ggttatatag ggatatagca cagagatata tagcaaagag atacttttga gcaatgtttg    8940
tggaagcggt attcgcaata ttttagtagc tcgttacagt ccggtgcgtt tttggttttt    9000
```

```
tgaaagtgcg tcttcagagc gcttttggtt ttcaaaagcg ctctgaagtt cctatacttt    9060
ctagagaata ggaacttcgg aataggaact tcaaagcgtt tccgaaaacg agcgcttccg    9120
aaaatgcaac gcgagctgcg cacatacagc tcactgttca cgtcgcacct atatctgcgt    9180
gttgcctgta tatatatata catgagaaga acggcatagt gcgtgtttat gcttaaatgc    9240
gtacttatat gcgtctattt atgtaggatg aaaggtagtc tagtacctcc tgtgatatta    9300
tcccattcca tgcggggtat cgtatgcttc cttcagcact acccttagc tgttctatat     9360 gctgccactc ctcaattgga ttagtctcat ccttcaatgc tatcatttcc tttgatattg    9420
gatcatctaa gaaaccatta ttatcatgac attaacctat aaaaataggc gtatcacgag    9480
gccctttcgt c                                                         9491
```

<210> SEQ ID NO 48
<211> LENGTH: 1000
<212> TYPE: DNA
<213> ORGANISM: Saccharomyces cerevisiae

<400> SEQUENCE: 48

```
gttaattcaa attaattgat atagtttttt aatgagtatt gaatctgttt agaaataatg     60 gaatatatt tttatttatt tatttatatt attggtcggc tcttttcttc tgaaggtcaa     120
tgacaaaatg atatgaagga aataatgatt tctaaaattt tacaacgtaa gatattttta   180
caaaagccta gctcatcttt tgtcatgcac tattttactc acgcttgaaa ttaacggcca    240
gtccactgcg gagtcatttc aaagtcatcc taatcgatct atcgttttg atagctcatt     300 ttggagttcg cgattgtctt ctgttattca caactgtttt aatttttatt tcattctgga   360
actcttcgag ttcttttgtaa agtctttcat agtagcttac tttatcctcc aacatattta   420
acttcatgtc aatttcggct cttaaatttt ccacatcatc aagttcaaca tcatctttta   480
acttgaattt attctctagc tcttccaacc aagcctcatt gctccttgat ttactggtga   540
aaagtgatac actttgcgcg caatccaggt caaaactttc ctgcaaagaa ttcaccaatt    600
tctcgacatc atagtacaat ttgttttgtt ctcccatcac aatttaatat acctgatgga   660
ttcttatgaa gcgctgggta atggacgtgt cactctactt cgccttttc cctactcctt    720 ttagtacgga agacaatgct aataaataag agggtaataa taatattatt aatcggcaaa   780
aaagattaaa cgccaagcgt ttaattatca gaaagcaaac gtcgtaccaa tccttgaatg    840
cttcccaatt gtatattaag agtcatcaca gcaacatatt cttgttatta aattaattat    900
tattgatttt tgatattgta taaaaaaacc aaatatgtat aaaaaaagtg aataaaaaat    960
accaagtatg gagaaatata ttagaagtct atacgttaaa                         1000
```

<210> SEQ ID NO 49
<211> LENGTH: 643
<212> TYPE: DNA
<213> ORGANISM: Saccharomyces cerevisiae

<400> SEQUENCE: 49

```
gaaatgaata acaatactga cagtactaaa taattgccta cttggcttca catacgttgc     60
atacgtcgat atagataata atgataatga cagcaggatt atcgtaatac gtaatagttg   120
aaaatctcaa aaatgtgtgg gtcattacgt aaataatgat aggaatggga ttcttctatt    180
tttccttttt ccattctagc agccgtcggg aaaacgtggc atcctctctt tcgggctcaa   240
ttggagtcac gctgccgtga gcatcctctc tttccatatc taacaactga gcacgtaacc    300
```

| aatggaaaag catgagctta gcgttgctcc aaaaaagtat tggatggtta ataccatttg | 360 |
| tctgttctct tctgactttg actcctcaaa aaaaaaaaat ctacaatcaa cagatcgctt | 420 |
| caattacgcc ctcacaaaaa cttttttcct tcttcttcgc ccacgttaaa ttttatccct | 480 |
| catgttgtct aacggatttc tgcacttgat ttattataaa aagacaaaga cataatactt | 540 |
| ctctatcaat ttcagttatt gttcttcctt gcgttattct tctgttcttc ttttttcttt | 600 |
| gtcatatata accataacca agtaatacat attcaaatct aga | 643 |

```
<210> SEQ ID NO 50
<211> LENGTH: 2145
<212> TYPE: DNA
<213> ORGANISM: artificial sequence
<220> FEATURE:
<223> OTHER INFORMATION: constructed chimeric gene

<400> SEQUENCE: 50
```

| gcatgcttgc atttagtcgt gcaatgtatg actttaagat ttgtgagcag gaagaaaagg | 60 |
| gagaatcttc taacgataaa cccttgaaaa actgggtaga ctacgctatg ttgagttgct | 120 |
| acgcaggctg cacaattaca cgagaatgct cccgcctagg atttaaggct aagggacgtg | 180 |
| caatgcagac gacagatcta aatgaccgtg tcggtgaagt gttcgccaaa cttttcggtt | 240 |
| aacacatgca gtgatgcacg cgcgatggtg ctaagttaca tatatatata tatatatata | 300 |
| tatagccata gtgatgtcta agtaacccttt atggtatatt tcttaatgtg gaaagatact | 360 |
| agcgcgcgca cccacacaca agcttcgtct tttcttgaag aaaagaggaa gctcgctaaa | 420 |
| tgggattcca ctttccgttc cctgccagct gatggaaaaa ggttagtgga acgatgaaga | 480 |
| ataaaagag agatccactg aggtgaaatt tcagctgaca gcgagtttca tgatcgtgat | 540 |
| gaacaatggt aacgagttgt ggctgttgcc agggagggtg gttctcaact tttaatgtat | 600 |
| ggccaaatcg ctacttgggt tgttatata acaagaaga ataatgaac tgattctctt | 660 |
| cctccttctt gtccttttctt aattctgttg taattaccttt cctttgtaat ttttttttgta | 720 |
| attattcttc ttaataatcc aaacaaacac acatattaca atagctagct gaggatgaag | 780 |
| gcattagttt atcatgggga tcacaaaatt tcgttagaag acaaaccaaa acccactctg | 840 |
| cagaaaccaa cagacgttgt ggttagggtg ttgaaaacaa caatttgcgg tactgacttg | 900 |
| ggaatataca aaggtaagaa tcctgaagtg cagatggca gaatcctggg tcatgagggc | 960 |
| gttggcgtca ttgaagaagt gggcgaatcc gtgacacaat tcaaaagggg ggataaagtt | 1020 |
| ttaatctcct gcgttactag ctgtggatcg tgtgattatt gcaagaagca actgtattca | 1080 |
| cactgtagag acggtggctg gattttaggt tacatgatcg acggtgtcca agccgaatac | 1140 |
| gtcagaatac cacatgctga caattcattg tataagatcc cgcaaactat cgatgatgaa | 1200 |
| attgcagtac tactgtccga tatttaccct actggacatg aaattggtgt tcaatatggt | 1260 |
| aacgttcaac caggcgatgc tgtagcaatt gtaggagcag gtcctgttgg aatgtcagtt | 1320 |
| ttgttaactg ctcaattta ctcgcctagt accattattg ttatcgacat ggacgaaaac | 1380 |
| cgtttacaat tagcgaagga gcttggggcc acacacacta ttaactccgg tactgaaaat | 1440 |
| gttgtcgaag ctgtgcatcg tatagcagcc gaaggagtgg atgtagcaat agaagctgtt | 1500 |
| ggtatacccg caacctggga catctgtcag gaaattgtaa acccggcgc tcatattgcc | 1560 |
| aacgtgggag ttcatggtgt taaggtggac tttgaaattc aaaagttgtg gattaagaat | 1620 |
| ctaaccatca ccactggttt ggttaacact aatactaccc caatgttgat gaaggtagcc | 1680 |
| tctactgata aattgccttt aaagaaaatg attactcaca ggtttgagtt agctgaaatc | 1740 |

```
gaacacgcat atcaggtttt cttgaatggc gctaaagaaa aagctatgaa gattattcta   1800
tctaatgcag gtgccgccta attaattaag agtaagcgaa tttcttatga tttatgattt   1860
ttattattaa ataagttata aaaaaaataa gtgtatacaa attttaaagt gactcttagg   1920
ttttaaaacg aaaattctta ttcttgagta actctttcct gtaggtcagg ttgctttctc   1980
aggtatagca tgaggtcgct cttattgacc acacctctac cggcatgccg agcaaatgcc   2040
tgcaaatcgc tccccatttc acccaattgt agatatgcta actccagcaa tgagttgatg   2100
aatctcggtg tgtattttat gtcctcagag gacaacacct gtggt                  2145
```

<210> SEQ ID NO 51
<211> LENGTH: 4280
<212> TYPE: DNA
<213> ORGANISM: artificial sequence
<220> FEATURE:
<223> OTHER INFORMATION: vector

<400> SEQUENCE: 51

```
ggggatcctc tagagtcgac ctgcaggcat gcaagcttgg cgtaatcatg gtcatagctg     60
tttcctgtgt gaaattgtta tccgctcaca attccacaca acatacgagc cggaagcata    120
aagtgtaaag cctggggtgc ctaatgagtg agctaactca cattaattgc gttgcgctca    180
ctgcccgctt tccagtcggg aaacctgtcg tgccagctgc attaatgaat cggccaacgc    240
gcggggagag gcggtttgcg tattgggcgc tcttccgctt cctcgctcac tgactcgctg    300
cgctcggtcg ttcggctgcg gcgagcggta tcagctcact caaaggcggt aatacggtta    360
tccacagaat caggggataa cgcaggaaag aacatgtgag caaaaggcca gcaaaaggcc    420
aggaaccgta aaaaggccgc gttgctggcg tttttccata ggctccgccc ccctgacgag    480
catcacaaaa atcgacgctc aagtcagagg tggcgaaacc cgacaggact ataaagatac    540
caggcgtttc cccctggaag ctccctcgtg cgctctcctg ttccgaccct gccgcttacc    600
ggatacctgt ccgcctttct cccttcggga agcgtggcgc tttctcatag ctcacgctgt    660
aggtatctca gttcggtgta ggtcgttcgc tccaagctgg gctgtgtgca cgaaccccc    720 gttcagcccg accgctgcgc cttatccggt aactatcgtc ttgagtccaa cccggtaaga    780
cacgacttat cgccactggc agcagccact ggtaacagga ttagcagagc gaggtatgta    840
ggcggtgcta cagagttctt gaagtggtgg cctaactacg gctacactag aaggacagta    900
tttggtatct gcgctctgct gaagccagtt accttcggaa aaagagttgg tagctcttga    960
tccggcaaac aaaccaccgc tggtagcggt ggtttttttg tttgcaagca gcagattacg   1020
cgcagaaaaa aaggatctca agaagatcct ttgatctttt ctacggggtc tgacgctcag   1080
tggaacgaaa actcacgtta agggattttg gtcatgagat tatcaaaaag gatcttcacc   1140
tagatccttt taaattaaaa atgaagtttt aaatcaatct aaagtatata tgagtaaact   1200
tggtctgaca gttaccaatg cttaatcagt gaggcaccta tctcagcgat ctgtctattt   1260
cgttcatcca tagttgcctg actccccgtc gtgtagataa ctacgatacg ggagggctta   1320
ccatctggcc ccagtgctgc aatgataccg cgagacccac gctcaccggc tccagattta   1380
tcagcaataa accagccagc cggaagggcc gagcgcagaa gtggtcctgc aactttatcc   1440
gcctccatcc agtctattaa ttgttgccgg gaagctagag taagtagttc gccagttaat   1500
agtttgcgca acgttgttgc cattgctaca ggcatcgtgg tgtcacgctc gtcgtttggt   1560
atggcttcat tcagctccgg ttcccaacga tcaaggcgag ttacatgatc ccccatgttg   1620
```

```
tgcaaaaaag cggttagctc cttcggtcct ccgatcgttg tcagaagtaa gttggccgca    1680
gtgttatcac tcatggttat ggcagcactg cataattctc ttactgtcat gccatccgta    1740
agatgctttt ctgtgactgg tgagtactca accaagtcat tctgagaata gtgtatgcgg    1800
cgaccgagtt gctcttgccc ggcgtcaata cgggataata ccgcgccaca tagcagaact    1860
ttaaaagtgc tcatcattgg aaaacgttct tcggggcgaa aactctcaag gatcttaccg    1920
ctgttgagat ccagttcgat gtaacccact cgtgcaccca actgatcttc agcatctttt    1980
actttcacca gcgtttctgg gtgagcaaaa acaggaaggc aaaatgccgc aaaaaaggga    2040
ataagggcga cacggaaatg ttgaatactc atactcttcc tttttcaata ttattgaagc    2100
atttatcagg gttattgtct catgagcgga tacatatttg aatgtattta gaaaaataaa    2160
caaataggggg ttccgcgcac atttccccga aaagtgccac ctgacgtcta agaaaccatt    2220
attatcatga cattaaccta taaaaatagg cgtatcacga ggccctttcg tctcgcgcgt    2280
ttcggtgatg acggtgaaaa cctctgacac atgcagctcc cggagacggt cacagcttgt    2340
ctgtaagcgg atgccgggag cagacaagcc cgtcagggcg cgtcagcggg tgttggcggg    2400
tgtcggggct ggcttaacta tgcggcatca gagcagattg tactgagagt gcaccatatg    2460
cggtgtgaaa taccgcacag atgcgtaagg agaaaatacc gcatcaggcg ccattcgcca    2520
ttcaggctgc gcaactgttg ggaagggcga tcggtgcggg cctcttcgct attacgccag    2580
ctggcgaaag gggatgtgc tgcaaggcga ttaagttggg taacgccagg gttttcccag    2640
tcacgacgtt gtaaaacgac ggccagtgaa ttcgagctcg taccccggg ctctgagaca    2700
gtagtaggtt agtcatcgct ctaccgacgc gcaggaaaag aaagaagcat tgcggattac    2760
gtattctaat gttcagcccg cggaacgcca gcaaatcacc acccatgcgc atgatactga    2820
gtcttgtaca cgctgggctt ccagtgtact gagagtgcac cataccacag cttttcaatt    2880
caattcatca ttttttttt attctttttt ttgatttcgg tttctttgaa attttttga    2940
ttcggtaatc tccgaacaga aggaagaacg aaggaaggag cacagactta gattggtata    3000
tatacgcata tgtagtgttg aagaaacatg aaattgccca gtattcttaa cccaactgca    3060
cagaacaaaa acctgcagga aacgaagata atcatgtcg aaagctacat ataaggaacg    3120
tgctgctact catcctagtc ctgttgctgc caagctattt aatatcatgc acgaaaagca    3180
aacaaacttg tgtgcttcat tggatgttcg taccaccaag gaattactgg agttagttga    3240
agcattaggt cccaaaattt gtttactaaa aacacatgtg gatatcttga ctgatttttc    3300
catggagggc acagttaagc cgctaaaggc attatccgcc aagtacaatt ttttactctt    3360
cgaagacaga aaatttgctg acattggtaa tacagtcaaa ttgcagtact ctgcgggtgt    3420
atacagaata gcagaatggg cagacattac gaatgcacac ggtgtggtgg gcccaggtat    3480
tgttagcggt ttgaagcagg cggcagaaga agtaacaaag gaacctagag gccttttgat    3540
gttagcagaa ttgtcatgca agggctccct atctactgga gaatatacta agggtactgt    3600
tgacattgcg aagagcgaca aagattttgt tatcggcttt attgctcaaa gagacatggg    3660
tggaagagat gaaggttacg attggttgat tatgacaccc ggtgtgggtt tagatgacaa    3720
gggagacgca ttgggtcaac agtatagaac cgtggatgat gtggtctcta caggatctga    3780
cattattatt gttggaagag gactatttgc aaagggaagg gatgctaagg tagagggtga    3840
acgttacaga aaagcaggct gggaagcata tttgagaaga tgcggccagc aaaactaaaa    3900
aactgtatta taagtaaatg catgtatact aaactcacaa attagagctt caatttaatt    3960
atatcagtta ttaccctatg cggtgtgaaa taccgcacag atgcgtaagg agaaaatacc    4020
```

```
gcatcaggaa attgtaaacg ttaatatttt gttaaaattc gcgttaaatt tttgttaaat       4080
cagctcattt tttaaccaat aggccgaaat cggcaaaatc ttcagcccgc ggaacgccag       4140
caaatcacca cccatgcgca tgatactgag tcttgtacac gctgggcttc cagtgatgat       4200
acaacgagtt agccaaggtg agcacggatg tctaaattag aattacgttt taatatcttt       4260
ttttccatat ctagggctag                                                   4280

<210> SEQ ID NO 52
<211> LENGTH: 30
<212> TYPE: DNA
<213> ORGANISM: artificial sequence
<220> FEATURE:
<223> OTHER INFORMATION: primer

<400> SEQUENCE: 52
gcatgcttgc atttagtcgt gcaatgtatg                                          30

<210> SEQ ID NO 53
<211> LENGTH: 54
<212> TYPE: DNA
<213> ORGANISM: artificial sequence
<220> FEATURE:
<223> OTHER INFORMATION: primer

<400> SEQUENCE: 53
gaacattaga atacgtaatc cgcaatgcac tagtaccaca ggtgttgtcc tctg              54

<210> SEQ ID NO 54
<211> LENGTH: 54
<212> TYPE: DNA
<213> ORGANISM: artificial sequence
<220> FEATURE:
<223> OTHER INFORMATION: primer

<400> SEQUENCE: 54
cagaggacaa cacctgtggt actagtgcat tgcggattac gtattctaat gttc              54

<210> SEQ ID NO 55
<211> LENGTH: 28
<212> TYPE: DNA
<213> ORGANISM: artificial sequence
<220> FEATURE:
<223> OTHER INFORMATION: primer

<400> SEQUENCE: 55
caccttggct aactcgttgt atcatcac                                            28

<210> SEQ ID NO 56
<211> LENGTH: 100
<212> TYPE: DNA
<213> ORGANISM: artificial sequence
<220> FEATURE:
<223> OTHER INFORMATION: primer

<400> SEQUENCE: 56
ttttaagccg aatgagtgac agaaaaagcc cacaacttat caagtgatat tgaacaaagg        60
gcgaaacttc gcatgcttgc atttagtcgt gcaatgtatg                             100

<210> SEQ ID NO 57
<211> LENGTH: 98
<212> TYPE: DNA
<213> ORGANISM: artificial sequence
<220> FEATURE:
```

```
<223> OTHER INFORMATION: primer

<400> SEQUENCE: 57
cccaattggt aaatattcaa caagagacgc gcagtacgta acatgcgaat tgcgtaattc    60
acggcgataa caccttggct aactcgttgt atcatcac                            98

<210> SEQ ID NO 58
<211> LENGTH: 29
<212> TYPE: DNA
<213> ORGANISM: artificial sequence
<220> FEATURE:
<223> OTHER INFORMATION: primer

<400> SEQUENCE: 58
caaaagccca tgtcccacac caaaggatg                                      29

<210> SEQ ID NO 59
<211> LENGTH: 26
<212> TYPE: DNA
<213> ORGANISM: artificial sequence
<220> FEATURE:
<223> OTHER INFORMATION: primer

<400> SEQUENCE: 59
caccatcgcg cgtgcatcac tgcatg                                         26

<210> SEQ ID NO 60
<211> LENGTH: 28
<212> TYPE: DNA
<213> ORGANISM: artificial sequence
<220> FEATURE:
<223> OTHER INFORMATION: primer

<400> SEQUENCE: 60 tcggttttg caatatgacc tgtgggcc                                        28

<210> SEQ ID NO 61
<211> LENGTH: 22
<212> TYPE: DNA
<213> ORGANISM: artificial sequence
<220> FEATURE:
<223> OTHER INFORMATION: primer

<400> SEQUENCE: 61
gagaagatgc ggccagcaaa ac                                             22

<210> SEQ ID NO 62
<211> LENGTH: 2745
<212> TYPE: DNA
<213> ORGANISM: artificial sequence
<220> FEATURE:
<223> OTHER INFORMATION: constructed coding region-terminator segment

<400> SEQUENCE: 62
atgactgaca aaaaaactct aaagactta agaaatcgta gttctgttta cgattcaatg     60
gttaaatcac ctaatcgtgc tatgttgcgt gcaactggta tgcaagatga agactttgaa  120
aaacctatcg tcggtgtcat ttcaacttgg gctgaaaaca caccttgtaa tatccactta  180
catgactttg gtaaactagc caaagtcggt gttaaggaag ctggtgcttg gccagttcag  240
ttcggaacaa tcacggtttc tgatggaatc gccatgggaa cccaaggaat gcgtttctcc  300
ttgacatctc gtgatattat tgcagattct attgaagcag ccatggggagg tcataatgcg  360 gatgcttttg tagccattgg cggttgtgat aaaaacatgc ccggttctgt tatcgctatg  420
```

```
gctaacatgg atatcccagc cattttttgct tacggcggaa caattgcacc tggtaattta    480
gacggcaaag atatcgattt agtctctgtc tttgaaggtg tcggccattg gaaccacggc    540
gatatgacca aagaagaagt taaagctttg gaatgtaatg cttgtcccgg tcctggaggc    600
tgcggtggta tgtatactgc taacacaatg gcgacagcta ttgaagtttt gggacttagc    660
cttccgggtt catcttctca cccggctgaa tccgcagaaa agaaagcaga tattgaagaa    720
gctggtcgcg ctgttgtcaa aatgctcgaa atgggcttaa aaccttctga cattttaacg    780
cgtgaagctt ttgaagatgc tattactgta actatggctc tgggaggttc aaccaactca    840
acccttcacc tcttagctat tgcccatgct gctaatgtgg aattgacact tgatgatttc    900
aatactttcc aagaaaaagt tcctcatttg gctgatttga accttctgg tcaatatgta     960
ttccaagacc tttacaaggt cggaggggta ccagcagtta tgaaatatct ccttaaaaat   1020
ggcttccttc atggtgaccg tatcacttgt actggcaaaa cagtcgctga aaatttgaag   1080
cttttgatg atttaacacc tggtcaaaag gttattatgc cgcttgaaaa tcctaaacgt    1140
gaagatggtc cgctcattat tctccatggt aacttggctc cagacggtgc cgttgccaaa   1200
gtttctggtg taaaagtgcg tcgtcatgtc ggtcctgcta aggtctttaa ttctgaagaa   1260
gaagccattg aagctgtctt gaatgatgat attgttgatg gtgatgttgt tgtcgtacgt   1320
tttgtaggac caaagggcgg tcctggtatg cctgaaatgc tttcccttc atcaatgatt    1380
gttggtaaag ggcaaggtga aaaagttgcc cttctgacag atggccgctt ctcaggtggt   1440
acttatggtc ttgtcgtggg tcatatcgct cctgaagcac aagatggcgg tccaatcgcc   1500
tacctgcaaa caggagacat agtcactatt gaccaagaca ctaaggaatt acactttgat   1560
atctccgatg aagagttaaa acatcgtcaa gagaccattg aattgccacc gctctattca   1620
cgcggtatcc ttggtaaata tgctcacatc gtttcgtctg cttctagggg agccgtaaca   1680
gactttgga agcctgaaga aactggcaaa aaatgttgtc ctggttgctg tggttaagcg    1740
gccgcgttaa ttcaaattaa ttgatatagt tttttaatga gtattgaatc tgtttagaaa   1800
taatggaata ttattttttat ttatttattt atattattgg tcggctcttt tcttctgaag   1860
gtcaatgaca aaatgatatg aaggaaataa tgatttctaa aattttacaa cgtaagatat   1920
ttttacaaaa gcctagctca tcttttgtca tgcactattt tactcacgct tgaaattaac   1980
ggccagtcca ctgcggagtc atttcaaagt catcctaatc gatctatcgt ttttgatagc   2040
tcattttgga gttcgcgatt gtcttctgtt attcacaact gttttaattt ttatttcatt   2100
ctggaactct tcgagttctt tgtaaagtct ttcatagtag cttactttat cctccaacat   2160
atttaacttc atgtcaattt cggctcttaa attttccaca tcatcaagtt caacatcatc   2220
ttttaacttg aatttattct ctagctcttc caaccaagcc tcattgctcc ttgatttact   2280
ggtgaaaagt gatacacttt gcgcgcaatc caggtcaaaa cttttcctgca aagaattcac   2340
caatttctcg acatcatagt acaatttgtt ttgttctccc atcacaattt aatatacctg   2400
atggattctt atgaagcgct gggtaatgga cgtgtcactc tacttcgcct ttttccctac   2460
tcctttttagt acggaagaca atgctaataa ataagagggt aataataata ttattaatcg   2520
gcaaaaaaga ttaaacgcca agcgtttaat tatcagaaag caaacgtcgt accaatcctt   2580
gaatgcttcc caattgtata ttaagagtca tcacagcaac atattcttgt tattaaatta   2640
attattattg attttttgata ttgtataaaa aaaccaaata tgtataaaaa aagtgaataa   2700
aaaataccaa gtatggagaa atatattaga agtctatacg ttaaa                   2745
```

<210> SEQ ID NO 63
<211> LENGTH: 99
<212> TYPE: DNA
<213> ORGANISM: artificial sequence
<220> FEATURE:
<223> OTHER INFORMATION: primer

<400> SEQUENCE: 63
tcctttctca attattattt tctactcata acctcacgca aaataacaca gtcaaatcaa    60
tcaaagtatg actgacaaaa aaactcttaa agacttaag                            99

<210> SEQ ID NO 64
<211> LENGTH: 77
<212> TYPE: DNA
<213> ORGANISM: artificial sequence
<220> FEATURE:
<223> OTHER INFORMATION: primer

<400> SEQUENCE: 64
gaacattaga atacgtaatc cgcaatgctt ctttcttttc cgtttaacgt atagacttct    60
aatatatttc tccatac                                                    77

<210> SEQ ID NO 65
<211> LENGTH: 45
<212> TYPE: DNA
<213> ORGANISM: artificial sequence
<220> FEATURE:
<223> OTHER INFORMATION: primer

<400> SEQUENCE: 65
aaacggaaaa gaaagaagca ttgcggatta cgtattctaa tgttc                     45

<210> SEQ ID NO 66
<211> LENGTH: 88
<212> TYPE: DNA
<213> ORGANISM: artificial sequence
<220> FEATURE:
<223> OTHER INFORMATION: primer

<400> SEQUENCE: 66 tattttcgt tacataaaaa tgcttataaa actttaacta ataattagag attaaatcgc      60
caccttggct aactcgttgt atcatcac                                        88

<210> SEQ ID NO 67
<211> LENGTH: 27
<212> TYPE: DNA
<213> ORGANISM: artificial sequence
<220> FEATURE:
<223> OTHER INFORMATION: primer

<400> SEQUENCE: 67
gacttttgga agcctgaaga aactggc                                         27

<210> SEQ ID NO 68
<211> LENGTH: 20
<212> TYPE: DNA
<213> ORGANISM: artificial sequence
<220> FEATURE:
<223> OTHER INFORMATION: primer

<400> SEQUENCE: 68
cttggcagca acaggactag                                                 20

<210> SEQ ID NO 69
<211> LENGTH: 26
<212> TYPE: DNA
<213> ORGANISM: artificial sequence
<220> FEATURE:
<223> OTHER INFORMATION: primer

<400> SEQUENCE: 69
ccaggccaat tcaacagact gtcggc                                          26

<210> SEQ ID NO 70
<211> LENGTH: 2347
<212> TYPE: DNA
<213> ORGANISM: artificial sequence
<220> FEATURE:
<223> OTHER INFORMATION: constructed URA3 marker with flanking
      homologous repeat sequences for HIS gene replacement and marker
      excision

<400> SEQUENCE: 70
gcattgcgga ttacgtattc taatgttcag gtgctggaag aagagctgct taaccgccgc      60
gcccagggtg aagatccacg ctactttacc ctgcgtcgtc tggatttcgg cggctgtcgt    120
ctttcgctgg caacgccggt tgatgaagcc tgggacggtc cgctctcctt aaacggtaaa    180
cgtatcgcca cctcttatcc tcacctgctc aagcgttatc tcgaccagaa aggcatctct    240
tttaaatcct gcttactgaa cggttctgtt gaagtcgccc cgcgtgccgg actggcggat    300
gcgatttgcg atctggtttc caccggtgcc acgctggaag ctaacggcct gcgcgaagtc    360
gaagttatct atcgctcgaa agcctgcctg attcaacgcg atggcgaaat ggaagaatcc    420
aaacagcaac tgatcgacaa actgctgacc cgtattcagg gtgtgatcca ggcgcgcgaa    480
tcaaaataca tcatgatgca cgcaccgacc gaacgtctgg atgaagtcat ggtacctact    540
gagagtgcac cataccacag cttttcaatt caattcatca ttttttttt atctttttt      600
ttgatttcgg tttctttgaa attttttga ttcggtaatc tccgaacaga aggaagaacg    660
aaggaaggag cacagactta gattggtata tatacgcata tgtagtgttg aagaaacatg    720
aaattgccca gtattcttaa cccaactgca cagaacaaaa acctgcagga acgaagata    780
aatcatgtcg aaagctacat ataaggaacg tgctgctact catcctagtc ctgttgctgc    840
caagctatt  aatatcatgc acgaaaagca aacaaacttg tgtgcttcat tggatgttcg    900
taccaccaag gaattactgg agttagttga agcattaggt cccaaaattt gtttactaaa    960
aacacatgtg gatatcttga ctgattttc  catggagggc acagttaagc cgctaaaggc   1020
attatccgcc aagtacaatt ttttactctt cgaagacaga aaatttgctg acattggtaa   1080
tacagtcaaa ttgcagtact ctgcgggtgt atacagaata gcagaatggg cagacattac   1140
gaatgcacac ggtgtggtgg gcccaggtat tgttagcggt ttgaagcagg cggcagaaga   1200
agtaacaaag gaacctagag gccttttgat gttagcagaa ttgtcatgca agggctccct   1260
atctactgga gaatatacta agggtactgt tgacattgcg aagagcgaca agatttttgt   1320
tatcggcttt attgctcaaa gagacatggg tggaagagat gaaggttacg attggttgat   1380
tatgacaccc ggtgtgggtt tagatgacaa gggagacgca ttgggtcaac agtatagaac   1440
cgtggatgat gtggtctcta caggatctga cattattat  gttggaagag gactatttgc   1500
aaagggaagg gatgctaagg tagagggtga acgttacaga aaagcaggct gggaagcata   1560
tttgagaaga tgcggccagc aaaactaaaa aactgtatta taagtaaatg catgtatact   1620
aaactcacaa attagagctt caatttaatt atatcagtta ttacccctatg cggtgtgaaa   1680

-continued

| | |
|---|---|
| taccgcacag atgcgtaagg agaaaatacc gcatcaggaa attgtaaacg ttaatattt | 1740 |
| gttaaaattc gcgttaaatt tttgttaaat cagctcattt tttaaccaat aggccgaaat | 1800 |
| cggcaaaatc tctagagtgc tggaagaaga gctgcttaac cgccgcgccc agggtgaaga | 1860 |
| tccacgctac tttaccctgc gtcgtctgga tttcggcggc tgtcgtcttt cgctggcaac | 1920 |
| gccggttgat gaagcctggg acggtccgct ctccttaaac ggtaaacgta tcgccacctc | 1980 |
| ttatcctcac ctgctcaagc gttatctcga ccagaaaggc atctctttta aatcctgctt | 2040 |
| actgaacggt tctgttgaag tcgccccgcg tgccggactg gcggatgcga tttgcgatct | 2100 |
| ggtttccacc ggtgccacgc tggaagctaa cggcctgcgc gaagtcgaag ttatctatcg | 2160 |
| ctcgaaagcc tgcctgattc aacgcgatgg cgaaatggaa gaatccaaac agcaactgat | 2220 |
| cgacaaactg ctgacccgta ttcagggtgt gatccaggcg cgcgaatcaa aatacatcat | 2280 |
| gatgcacgca ccgaccgaac gtctggatga agtcatccag tgatgataca acgagttagc | 2340 |
| caaggtg | 2347 |

<210> SEQ ID NO 71
<211> LENGTH: 80
<212> TYPE: DNA
<213> ORGANISM: artificial sequence
<220> FEATURE:
<223> OTHER INFORMATION: primer

<400> SEQUENCE: 71

| | |
|---|---|
| cttcgaagaa tatactaaaa aatgagcagg caagataaac gaaggcaaag gcattgcgga | 60 |
| ttacgtattc taatgttcag | 80 |

<210> SEQ ID NO 72
<211> LENGTH: 81
<212> TYPE: DNA
<213> ORGANISM: artificial sequence
<220> FEATURE:
<223> OTHER INFORMATION: primer

<400> SEQUENCE: 72

| | |
|---|---|
| tatacacatg tatatatatc gtatgctgca gctttaaata atcggtgtca caccttggct | 60 |
| aactcgttgt atcatcactg g | 81 |

<210> SEQ ID NO 73
<211> LENGTH: 26
<212> TYPE: DNA
<213> ORGANISM: artificial sequence
<220> FEATURE:
<223> OTHER INFORMATION: primer

<400> SEQUENCE: 73

| | |
|---|---|
| gacttgaata atgcagcggc gcttgc | 26 |

<210> SEQ ID NO 74
<211> LENGTH: 30
<212> TYPE: DNA
<213> ORGANISM: artificial sequence
<220> FEATURE:
<223> OTHER INFORMATION: primer

<400> SEQUENCE: 74

| | |
|---|---|
| ccaccctctt caattagcta agatcatagc | 30 |

<210> SEQ ID NO 75
<211> LENGTH: 25

```
<212> TYPE: DNA
<213> ORGANISM: artificial sequence
<220> FEATURE:
<223> OTHER INFORMATION: primer

<400> SEQUENCE: 75
aaaaattgat tctcatcgta aatgc                                           25

<210> SEQ ID NO 76
<211> LENGTH: 20
<212> TYPE: DNA
<213> ORGANISM: artificial sequence
<220> FEATURE:
<223> OTHER INFORMATION: primer

<400> SEQUENCE: 76
ctgcagcgag gagccgtaat                                                 20

<210> SEQ ID NO 77
<211> LENGTH: 90
<212> TYPE: DNA
<213> ORGANISM: artificial sequence
<220> FEATURE:
<223> OTHER INFORMATION: primer

<400> SEQUENCE: 77
atggttcatt taggtccaaa aaaaccacaa gccagaaagg gttccatggc cgatgtgcca     60
gcattgcgga ttacgtattc taatgttcag                                      90

<210> SEQ ID NO 78
<211> LENGTH: 91
<212> TYPE: DNA
<213> ORGANISM: artificial sequence
<220> FEATURE:
<223> OTHER INFORMATION: primer

<400> SEQUENCE: 78
ttaagcaccg atgataccaa cggacttacc ttcagcaatt cttttttggg ccaaagcagc     60
caccttggct aactcgttgt atcatcactg g                                    91

<210> SEQ ID NO 79
<211> LENGTH: 24
<212> TYPE: DNA
<213> ORGANISM: artificial sequence
<220> FEATURE:
<223> OTHER INFORMATION: primer

<400> SEQUENCE: 79
ctaggatgag tagcagcacg ttcc                                            24

<210> SEQ ID NO 80
<211> LENGTH: 26
<212> TYPE: DNA
<213> ORGANISM: artificial sequence
<220> FEATURE:
<223> OTHER INFORMATION: primer

<400> SEQUENCE: 80
ccaattccgt gatgtctctt tgttgc                                          26

<210> SEQ ID NO 81
<211> LENGTH: 20
<212> TYPE: DNA
<213> ORGANISM: artificial sequence
<220> FEATURE:
```

```
<223> OTHER INFORMATION: primer

<400> SEQUENCE: 81
gtgaacgagt tcacaaccgc                                                  20

<210> SEQ ID NO 82
<211> LENGTH: 22
<212> TYPE: DNA
<213> ORGANISM: artificial sequence
<220> FEATURE:
<223> OTHER INFORMATION: primer

<400> SEQUENCE: 82
gttcgttcca gaattatcac gc                                               22

<210> SEQ ID NO 83
<211> LENGTH: 4236
<212> TYPE: DNA
<213> ORGANISM: artificial sequence
<220> FEATURE:
<223> OTHER INFORMATION: construct

<400> SEQUENCE: 83
gatccgcatt gcggattacg tattctaatg ttcagataac ttcgtatagc atacattata      60
cgaagttatg cagattgtac tgagagtgca ccataccaca gcttttcaat tcaattcatc    120
attttttttt tattcttttt tttgatttcg gtttctttga aatttttttg attcggtaat    180
ctccgaacag aaggaagaac gaaggaagga gcacagactt agattggtat atatacgcat    240
atgtagtgtt gaagaaacat gaaattgccc agtattctta acccaactgc acagaacaaa    300
aacctgcagg aaacgaagat aaatcatgtc gaaagctaca tataaggaac gtgctgctac    360
tcatcctagt cctgttgctg ccaagctatt taatatcatg cacgaaaagc aaacaaactt    420
gtgtgcttca ttggatgttc gtaccaccaa ggaattactg gagttagttg aagcattagg    480
tcccaaaatt tgtttactaa aaacacatgt ggatatcttg actgattttt ccatggaggg    540
cacagttaag ccgctaaagg cattatccgc caagtacaat ttttactct tcgaagacag    600 aaaatttgct gacattggta atacagtcaa attgcagtac tctgcgggtg tatacagaat    660
agcagaatgg gcagacatta cgaatgcaca cggtgtggtg ggcccaggta ttgttagcgg    720
tttgaagcag gcggcagaag aagtaacaaa ggaacctaga ggccttttga tgttagcaga    780
attgtcatgc aagggctccc tatctactgg agaatatact aagggtactg ttgacattgc    840
gaagagcgac aaagattttg ttatcggctt tattgctcaa agagacatgg gtggaagaga    900
tgaaggttac gattggttga ttatgacacc cggtgtgggt ttagatgaca agggagacgc    960
attgggtcaa cagtatagaa ccgtggatga tgtggtctct acaggatctg acattattat   1020
tgttggaaga ggactatttg caaagggaag ggatgctaag gtagagggtg aacgttacag   1080
aaaagcaggc tgggaagcat atttgagaag atgcggccag caaaactaaa aaactgtatt   1140
ataagtaaat gcatgtatac taaactcaca aattagagct tcaatttaat tatatcagtt   1200
attaccctat gcggtgtgaa ataccgcaca gatgcgtaag gagaaaatac cgcatcagga   1260
aattgtaaac gttaatattt tgttaaaatt cgcgttaaat ttttgttaaa tcagctcatt   1320
ttttaaccaa taggccgaaa tcggcaaaat cccttataaa tcaaaagaat agaccgagat   1380
agggttgagt gttgttccag tttggaacaa gagtccacta ttaaagaacg tggactccaa   1440
cgtcaagggg cgaaaaaccg tctatcaggg cgatggccca ctacgtgaac catcacccta   1500
atcaagataa cttcgtatag catacattat acgaagttat ccagtgatga tacaacgagt   1560
```

```
tagccaaggt gaattcactg gccgtcgttt tacaacgtcg tgactgggaa aaccctggcg   1620
ttacccaact taatcgcctt gcagcacatc cccctttcgc cagctggcgt aatagcgaag   1680
aggcccgcac cgatcgccct tcccaacagt tgcgcagcct gaatggcgaa tggcgcctga   1740
tgcggtattt tctccttacg catctgtgcg gtatttcaca ccgcatatgg tgcactctca   1800
gtacaatctg ctctgatgcc gcatagttaa gccagccccg acacccgcca cacccgctg    1860
acgcccctg acgggcttgt ctgctcccgg catccgctta cagacaagct gtgaccgtct    1920
ccgggagctg catgtgtcag aggttttcac cgtcatcacc gaaacgcgcg agacgaaagg   1980
gcctcgtgat acgcctattt ttataggtta atgtcatgat aataatggtt tcttagacgt   2040
caggtggcac ttttcgggga atgtgcgcg gaacccctat tgtttatttt tctaaatac    2100
attcaaatat gtatccgctc atgagacaat aaccctgata aatgcttcaa taatattgaa   2160
aaaggaagag tatgagtatt caacatttcc gtgtcgccct tattcccttt tttgcggcat   2220
tttgccttcc tgttttgct cacccagaaa cgctggtgaa agtaaaagat gctgaagatc    2280
agttgggtgc acgagtgggt tacatcgaac tggatctcaa cagcggtaag atccttgaga   2340
gttttcgccc cgaagaacgt tttccaatga tgagcacttt taaagttctg ctatgtggcg   2400
cggtattatc ccgtattgac gccgggcaag agcaactcgg tcgccgcata cactattctc   2460
agaatgactt ggttgagtac tcaccagtca cagaaaagca tcttacggat ggcatgacag   2520
taagagaatt atgcagtgct gccataacca tgagtgataa cactgcggcc aacttacttc   2580
tgacaacgat cggaggaccg aaggagctaa ccgcttttt gcacaacatg ggggatcatg    2640
taactcgcct tgatcgttgg gaaccggagc tgaatgaagc cataccaaac gacgagcgtg   2700
acaccacgat gcctgtagca atggcaacaa cgttgcgcaa actattaact ggcgaactac   2760
ttactctagc ttcccggcaa caattaatag actggatgga ggcggataaa gttgcaggac   2820
cacttctgcg ctcggccctt ccggctggct ggtttattgc tgataaatct ggagccggtg   2880
agcgtgggtc tcgcggtatc attgcagcac tggggccaga tggtaagccc tcccgtatcg   2940
tagttatcta cacgacgggg agtcaggcaa ctatggatga acgaaataga cagatcgctg   3000
agataggtgc ctcactgatt aagcattggt aactgtcaga ccaagtttac tcatatatac   3060
tttagattga tttaaaactt catttttaat ttaaaaggat ctaggtgaag atcctttttg   3120
ataatctcat gaccaaaatc ccttaacgtg agttttcgtt ccactgagcg tcagaccccg   3180
tagaaaagat caaaggatct tcttgagatc ctttttttct gcgcgtaatc tgctgcttgc   3240
aaacaaaaaa accaccgcta ccagcggtgg tttgtttgcc ggatcaagag ctaccaactc   3300
tttttccgaa ggtaactggc ttcagcagag cgcagatacc aaatactgtc cttctagtgt   3360
agccgtagtt aggccaccac ttcaagaact ctgtagcacc gcctacatac ctcgctctgc   3420
taatcctgtt accagtggct gctgccagtg gcgataagtc gtgtcttacc gggttggact   3480
caagacgata gttaccggat aaggcgcagc ggtcgggctg aacggggggt tcgtgcacac   3540
agcccagctt ggagcgaacg acctacaccg aactgagata cctacagcgt gagctatgag   3600
aaagcgccac gcttcccgaa gggagaaagg cggacaggta tccggtaagc ggcagggtcg   3660
gaacaggaga gcgcacgagg gagcttccag ggggaaacgc ctggtatctt tatagtcctg   3720
tcgggtttcg ccacctctga cttgagcgtc gatttttgtg atgctcgtca ggggggcgga   3780
gcctatggaa aaacgccagc aacgcggcct ttttacggtt cctggccttt tgctggcctt   3840
ttgctcacat gttctttcct gcgttatccc ctgattctgt ggataaccgt attaccgcct   3900
```

```
ttgagtgagc tgataccgct cgccgcagcc gaacgaccga gcgcagcgag tcagtgagcg    3960
aggaagcgga agagcgccca atacgcaaac cgcctctccc cgcgcgttgg ccgattcatt    4020
aatgcagctg gcacgacagg tttcccgact ggaaagcggg cagtgagcgc aacgcaatta    4080
atgtgagtta gctcactcat taggcacccc aggctttaca ctttatgctt ccggctcgta    4140
tgttgtgtgg aattgtgagc ggataacaat ttcacacagg aaacagctat gaccatgatt    4200
acgccaagct tgcatgcctg caggtcgact ctagag                              4236
```

<210> SEQ ID NO 84
<211> LENGTH: 7523
<212> TYPE: DNA
<213> ORGANISM: Artificial sequence
<220> FEATURE:
<223> OTHER INFORMATION: construct

<400> SEQUENCE: 84

```
ccagcttttg ttcccttta g tgagggttaa ttgcgcgctt ggcgtaatca tggtcatagc      60
tgtttcctgt gtgaaattgt tatccgctca caattccaca caacatagga gccggaagca     120
taaagtgtaa agcctggggt gcctaatgag tgaggtaact cacattaatt gcgttgcgct     180
cactgcccgc tttccagtcg ggaaacctgt cgtgccagct gcattaatga atcggccaac     240
gcgcggggag aggcggtttg cgtattgggc gctcttccgc ttcctcgctc actgactcgc     300
tgcgctcggt cgttcggctg cggcgagcgg tatcagctca ctcaaaggcg gtaatacggt     360
tatccacaga atcaggggat aacgcaggaa agaacatgtg agcaaaaggc cagcaaaagg     420
ccaggaaccg taaaaaggcc gcgttgctgg cgtttttcca taggctccgc cccctgacg     480 agcatcacaa aaatcgacgc tcaagtcaga ggtggcgaaa cccgacagga ctataaagat     540
accaggcgtt tccccctgga agctccctcg tgcgctctcc tgttccgacc ctgccgctta     600
ccggatacct gtccgccttt ctcccttcgg gaagcgtggc gctttctcat agctcacgct     660
gtaggtatct cagttcggtg taggtcgttc gctccaagct gggctgtgtg cacgaacccc     720
ccgttcagcc cgaccgctgc gccttatccg gtaactatcg tcttgagtcc aacccggtaa     780
gacacgactt atcgccactg gcagcagcca ctggtaacag gattagcaga gcgaggtatg     840
taggcggtgc tacagagttc ttgaagtggt ggcctaacta cggctacact agaaggacag     900
tatttggtat ctgcgctctg ctgaagccag ttaccttcgg aaaaagagtt ggtagctctt     960
gatccggcaa acaaaccacc gctggtagcg gtggtttttt tgtttgcaag cagcagatta    1020
cgcgcagaaa aaaaggatct caagaagatc ctttgatctt ttctacgggg tctgacgctc    1080
agtggaacga aaactcacgt taagggattt tggtcatgag attatcaaaa aggatcttca    1140
cctagatcct tttaaattaa aaatgaagtt ttaaatcaat ctaaagtata tatgagtaaa    1200
cttggtctga cagttaccaa tgcttaatca gtgaggcacc tatctcagcg atctgtctat    1260
ttcgttcatc catagttgcc tgactccccg tcgtgtagat aactacgata cgggagggct    1320
taccatctgg ccccagtgct gcaatgatac cgcgagaccc acgctcaccg gctccagatt    1380
tatcagcaat aaaccagcca gccggaaggg ccgagcgcag aagtggtcct gcaactttat    1440
ccgcctccat ccagtctatt aattgttgcc gggaagctag agtaagtagt tcgccagtta    1500
atagtttgcg caacgttgtt gccattgcta caggcatcgt ggtgtcacgc tcgtcgtttg    1560
gtatggcttc attcagctcc ggttcccaac gatcaaggcg agttacatga tcccccatgt    1620
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
```

```
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttgaatac tcatactctt ccttttttcaa tattattgaa    2100 gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa ttttttcaaac aaagaatctg    2280 agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg cattttttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta taatgcagtc tcttgataac    2580
tttttgcact gtaggtccgt taaggttaga agaaggctac tttggtgtct attttctctt    2640
ccataaaaaa agcctgactc cacttcccgc gtttactgat tactagcgaa gctgcgggtg    2700
cattttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacattttc gtattgtttt    2880
cgattcactc tatgaatagt tcttactaca atttttttgt ctaaagagta atactagaga    2940
taaacataaa aaatgtagag gtcgagttta gatgcaagtt caaggagcga aaggtggatg    3000
ggtaggttat atagggatat agcacagaga tatatagcaa agagatactt ttgagcaatg    3060
tttgtggaag cggtattcgc aatatttttag tagctcgtta cagtccggtg cgttttttggt    3120 tttttgaaag tgcgtcttca gagcgctttt ggttttcaaa agcgctctga agttcctata    3180 cttttctagag aataggaact tcggaatagg aacttcaaag cgtttccgaa aacgagcgct    3240
tccgaaaatg caacgcgagc tgcgcacata cagctcactg ttcacgtcgc acctatatct    3300
gcgtgttgcc tgtatatata tatacatgag aagaacggca tagtgcgtgt ttatgcttaa    3360
atgcgtactt atatgcgtct atttatgtag gatgaaaggt agtctagtac ctcctgtgat    3420
attatcccat tccatgcggg gtatcgtatg cttccttcag cactacccct tagctgttct    3480
atatgctgcc actcctcaat tggattagtc tcatccttca atgctatcat ttcctttgat    3540
attggatcat ctaagaaacc attattatca tgacattaac ctataaaaat aggcgtatca    3600
cgaggccctt tcgtctcgcg cgtttcggtg atgacggtga aaacctctga cacatgcagc    3660
tcccggagac ggtcacagct tgtctgtaag cggatgccgg gagcagacaa gcccgtcagg    3720
gcgcgtcagc gggtgttggc gggtgtcggg gctggcttaa ctatgcggca tcagagcaga    3780
ttgtactgag agtgcaccat aaattcccgt tttaagagct tggtgagcgc taggagtcac    3840
tgccaggtat cgtttgaaca cggcattagt cagggaagtc ataacacagt cctttcccgc    3900
aattttcttt ttctattact cttggcctcc tctagtacac tctatatttt tttatgcctc    3960
ggtaatgatt tcatttttt tttttcccct agcggatgac tctttttttt tcttagcgat    4020
tggcattatc acataatgaa ttatacatta tataaagtaa tgtgatttct tcgaagaata    4080
```

```
tactaaaaaa tgagcaggca agataaacga aggcaaagat gacagagcag aaagccctag    4140
taaagcgtat tacaaatgaa accaagattc agattgcgat ctctttaaag ggtggtcccc    4200
tagcgataga gcactcgatc ttcccagaaa aagaggcaga agcagtagca gaacaggcca    4260
cacaatcgca agtgattaac gtccacacag gtatagggtt tctggaccat atgatacatg    4320
ctctggccaa gcattccggc tggtcgctaa tcgttgagtg cattggtgac ttacacatag    4380
acgaccatca caccactgaa gactgcggga ttgctctcgg tcaagctttt aaagaggccc    4440
tactggcgcg tggagtaaaa aggtttggat caggatttgc gcctttggat gaggcacttt    4500
ccagagcggt ggtagatctt tcgaacaggc cgtacgcagt tgtcgaactt ggtttgcaaa    4560
gggagaaagt aggagatctc tcttgcgaga tgatcccgca ttttcttgaa agctttgcag    4620
aggctagcag aattaccctc cacgttgatt gtctgcgagg caagaatgat catcaccgta    4680
gtgagagtgc gttcaaggct cttgcggttg ccataagaga agccacctcg cccaatggta    4740
ccaacgatgt tccctccacc aaaggtgttc ttatgtagtg acaccgatta tttaaagctg    4800
cagcatacga tatatataca tgtgtatata tgtataccta tgaatgtcag taagtatgta    4860
tacgaacagt atgatactga agatgacaag gtaatgcatc attctatacg tgtcattctg    4920
aacgaggcgc gctttccttt tttcttttttg cttttctttt tttttctct tgaactcgac    4980 ggatctatgc ggtgtgaaat accgcacaga tgcgtaagga gaaataccg catcaggaaa    5040 ttgtaaacgt taatattttg ttaaaattcg cgttaaattt tgttaaaatc agctcatttt    5100
ttaaccaata ggccgaaatc ggcaaaatcc cttataaatc aaaagaatag accgagatag    5160
ggttgagtgt tgttccagtt tggaacaaga gtccactatt aaagaacgtg gactccaacg    5220
tcaaagggcg aaaaaccgtc tatcagggcg atggcccact acgtgaacca tcaccctaat    5280 caagttttt ggggtcgagg tgccgtaaag cactaaatcg gaaccctaaa gggagccccc    5340
gatttagagc ttgacgggga agccggcga acgtggcgag aaaggaaggg aagaaagcga    5400
aaggagcggg cgctagggcg ctggcaagtg tagcggtcac gctgcgcgta accaccacac    5460
ccgccgcgct taatgcgccg ctacagggcg cgtcgcgcca ttcgccattc aggctgcgca    5520
actgttggga agggcgatcg gtgcgggcct cttcgctatt acgccagctg gcgaaagggg    5580
gatgtgctgc aaggcgatta agttgggtaa cgccagggtt ttcccagtca cgacgttgta    5640
aaacgacggc cagtgagcgc gcgtaatacg actcactata gggcgaattg ggtaccgggc    5700
cccccctcga ggtattagaa gccgccgagc gggcgacagc cctccgacgg aagactctcc    5760
tccgtgcgtc ctcgtcttca ccggtcgcgt tcctgaaacg cagatgtgcc tcgcgccgca    5820
ctgctccgaa caataaagat tctacaatac tagcttttat ggttatgaag aggaaaaatt    5880
ggcagtaacc tggccccaca aaccttcaaa ttaacgaatc aaattaacaa ccataggatg    5940
ataatgcgat tagtttttta gccttatttc tggggtaatt aatcagcgaa gcgatgattt    6000
ttgatctatt aacagatata taatggaaa agctgcataa ccactttaac taatactttc    6060
aacattttca gtttgtatta cttcttattc aaatgtcata aaagtatcaa caaaaaattg    6120
ttaatatacc tctatacttt aacgtcaagg agaaaaatgt ccaatttact gcccgtacac    6180
caaaatttgc ctgcattacc ggtcgatgca acgagtgatg aggttcgcaa gaacctgatg    6240
gacatgttca gggatcgcca ggcgttttct gagcatacct ggaaaatgct tctgtccgtt    6300
tgccggtcgt gggcggcatg gtgcaagttg aataaccgga atggtttcc cgcagaacct    6360 gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
```

```
gacagcaatg ctgtttcact ggttatgcgg cggatccgaa agaaaaacgt tgatgccggt    6540
gaacgtgcaa aacaggctct agcgttcgaa cgcactgatt tcgaccaggt tcgttcactc    6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta aatattgtca tgaactatat ccgtaacctg    7140
gatagtgaaa caggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctctttcctg    7320
taggtcaggt tgctttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                            7523

<210> SEQ ID NO 85
<211> LENGTH: 11844
<212> TYPE: DNA
<213> ORGANISM: artificial sequence
<220> FEATURE:
<223> OTHER INFORMATION: constructed plasmid

<400> SEQUENCE: 85
tcccattacc gacatttggg cgctatacgt gcatatgttc atgtatgtat ctgtatttaa      60 aacactttg tattatttt cctcatatat gtgtataggt ttatacggat gatttaatta      120
ttacttcacc acccttatt tcaggctgat atcttagcct tgttactagt tagaaaaga      180 cattttgct gtcagtcact gtcaagagat tcttttgctg gcatttcttc tagaagcaaa      240
aagagcgatg cgtctttcc gctgaaccgt tccagcaaaa aagactacca acgcaatatg      300
gattgtcaga atcatataaa agagaagcaa ataactcctt gtcttgtatc aattgcatta      360
taatatcttc ttgttagtgc aatatcatat agaagtcatc gaaatagata ttaagaaaaa      420
caaactgtac aatcaatcaa tcaatcatcg ctgaggatgt tgacaaaagc aacaaaagaa      480
caaaaatccc ttgtgaaaaa cagaggggcg gagcttgttg ttgattgctt agtggagcaa      540
ggtgtcacac atgtatttgg cattccaggt gcaaaaattg atgcggtatt tgacgcttta      600
caagataaag gacctgaaat tatcgttgcc cggcacgaac aaaacgcagc attcatggcc      660
caagcagtcg gccgttaac tggaaaaccg ggagtcgtgt tagtcacatc aggaccgggt      720
gcctctaact tggcaacagg cctgctgaca gcgaacactg aaggagaccc tgtcgttgcg      780
cttgctggaa acgtgatccg tgcagatcgt ttaaacggac acatcaatc tttggataat      840 gcggcgctat tccagccgat tacaaaatac agtgtagaag ttcaagatgt aaaaaatata      900
ccggaagctg ttacaaatgc atttaggata gcgtcagcag ggcaggctgg ggccgctttt      960
```

-continued

```
gtgagctttc cgcaagatgt tgtgaatgaa gtcacaaata cgaaaaacgt gcgtgctgtt    1020
gcagcgccaa aactcggtcc tgcagcagat gatgcaatca gtgcggccat agcaaaaatc    1080
caaacagcaa aacttcctgt cgttttggtc ggcatgaaag gcggaagacc ggaagcaatt    1140
aaagcggttc gcaagctttt gaaaaaggtt cagcttccat tgttgaaaac atatcaagct    1200
gccggtaccc tttctagaga tttagaggat caatattttg gccgtatcgg tttgttccgc    1260
aaccagcctg gcgatttact gctagagcag gcagatgttg ttctgacgat cggctatgac    1320
ccgattgaat atgatccgaa attctggaat atcaatggag accggacaat tatccattta    1380
gacgagatta tcgctgacat tgatcatgct taccagcctg atcttgaatt gatcggtgac    1440
attccgtcca cgatcaatca tatcgaacac gatgctgtga agtggaatt tgcagagcgt    1500 gagcagaaaa tccttttctga tttaaaacaa tatatgcatg aaggtgagca ggtgcctgca    1560
gattggaaat cagacagagc gcaccctctt gaaatcgtta aagagttgcg taatgcagtc    1620
gatgatcatg ttacagtaac ttgcgatatc ggttcgcacg ccatttggat gtcacgttat    1680
ttccgcagct acgagccgtt aacattaatg atcagtaacg gtatgcaaac actcggcgtt    1740
gcgcttcctt gggcaatcgg cgcttcattg gtgaaaccgg gagaaaaagt ggtttctgtc    1800
tctggtgacg gcggtttctt attctcagca atggaattag acagcagt tcgactaaaa    1860 gcaccaattg tacacattgt atggaacgac agcacatatg acatggttgc attccagcaa    1920
ttgaaaaaat ataaccgtac atctgcggtc gatttcggaa atatcgatat cgtgaaatat    1980
gcggaaagct tcggagcaac tggcttgcgc gtagaatcac cagaccagct ggcagatgtt    2040
ctgcgtcaag gcatgaacgc tgaaggtcct gtcatcatcg atgtcccggt tgactacagt    2100
gataacatta atttagcaag tgacaagctt ccgaaagaat tcggggaact catgaaaacg    2160
aaagctctct agttaattaa tcatgtaatt agttatgtca cgcttacatt cacgccctcc    2220
ccccacatcc gctctaaccg aaaaggaagg agttagacaa cctgaagtct aggtccctat    2280
ttattttttt atagttatgt tagtattaag aacgttattt atatttcaaa ttttctttt    2340 ttttctgtac agacgcgtgt acgcatgtaa cattatactg aaaaccttgc ttgagaaggt    2400
tttgggacgc tcgaaggctt taatttgcgg gcggccgcac ctggtaaaac ctctagtgga    2460
gtagtagatg taatcaatga agcggaagcc aaaagaccag agtagaggcc tatagaagaa    2520
actgcgatac cttttgtgat ggctaaacaa acagacatct tttatatgt ttttacttct    2580 gtatatcgtg aagtagtaag tgataagcga atttggctaa gaacgttgta agtgaacaag    2640
ggacctcttt tgccttcaa aaaggattaa aatggagtta atcattgaga tttagttttc    2700
gttagattct gtatccctaa ataactccct tacccgacgg gaaggcacaa aagacttgaa    2760
taatagcaaa cggccagtag ccaagaccaa ataatactag agttaactga tggtcttaaa    2820
caggcattac gtggtgaact ccaagaccaa tatacaaaat atcgataagt tattcttgcc    2880
caccaattta aggagcctac atcaggacag tagtaccatt cctcagagaa gaggtataca    2940
taacaagaaa atcgcgtgaa caccttatat aacttagccc gttattgagc taaaaaacct    3000
tgcaaaattt cctatgaata agaatacttc agacgtgata aaatttact ttctaactct    3060 tctcacgctg cccctatctg ttcttccgct ctaccgtgag aaataaagca tcgagtacgg    3120
cagttcgctg tcactgaact aaaacaataa ggctagttcg aatgatgaac ttgcttgctg    3180
tcaaacttct gagttgccgc tgatgtgaca ctgtgacaat aaattcaaac cggttatagc    3240
ggtctcctcc ggtaccggtt ctgccacctc aatagagct cagtaggagt cagaacctct    3300
gcggtggctg tcagtgactc atccgcgttt cgtaagttgt gcgcgtgcac atttcgcccg    3360
```

```
ttcccgctca tcttgcagca ggcggaaatt ttcatcacgc tgtaggacgc aaaaaaaaaa   3420
taattaatcg tacaagaatc ttggaaaaaa aattgaaaaa ttttgtataa aagggatgac   3480
ctaacttgac tcaatggctt ttacacccag tattttccct ttccttgttt gttacaatta   3540
tagaagcaag acaaaaacat atagacaacc tattcctagg agttatattt ttttacccta   3600
ccagcaatat aagtaaaaaa ctgtttaaac agtatggcag ttacaatgta ttatgaagat   3660
gatgtagaag tatcagcact tgctggaaag caaattgcag taatcggtta tggttcacaa   3720
ggacatgctc acgcacagaa tttgcgtgat tctggtcaca acgttatcat tggtgtgcgc   3780
cacgaaaaat cttttgataa agcaaaagaa gatggctttg aaacatttga agtaggagaa   3840
gcagtagcta agctgatgt tattatggtt ttggcaccag atgaacttca acaatccatt   3900
tatgaagagg acatcaaacc aaacttgaaa gcaggttcag cacttggttt tgctcacgga   3960
tttaatatcc attttggcta tattaaagta ccagaagacg ttgacgtctt tatggttgcg   4020
cctaaggctc caggtcacct tgtccgtcgg acttatactg aaggttttgg tacaccagct   4080
ttgtttgttt cacaccaaaa tgcaagtggt catgcgcgtg aaatcgcaat ggattgggcc   4140
aaaggaattg gttgtgctcg agtgggaatt attgaaacaa cttttaaaga agaaacagaa   4200
gaagatttgt ttggagaaca agctgttcta tgtggaggtt tgacagcact tgttgaagcc   4260
ggttttgaaa cactgacaga agctggatac gctggcgaat tggcttactt tgaagttttg   4320
cacgaaatga aattgattgt tgacctcatg tatgaaggtg gttttactaa aatgcgtcaa   4380
tccatctcaa atactgctga gtttggcgat tatgtgactg gtccacggat tattactgac   4440
gaagttaaaa agaatatgaa gcttgttttg gctgatattc aatctggaaa atttgctcaa   4500
gatttcgttg atgacttcaa agcggggcgt ccaaaattaa tagcctatcg cgaagctgca   4560
aaaaatcttg aaattgaaaa aattggggca gagctacgtc aagcaatgcc attcacacaa   4620
tctggtgatg acgatgcctt taaaatctat cagtaaggcc ctgcaggcct atcaagtgct   4680
ggaaactttt tctcttggaa tttttgcaac atcaagtcat agtcaattga attgacccaa   4740
tttcacattt aagattttt tttttcatc cgacatacat ctgtacacta ggaagccctg   4800 ttttttctgaa gcagcttcaa atatatatat ttttacata tttattatga ttcaatgaac   4860
aatctaatta aatcgaaaac aagaaccgaa acgcgaataa ataatttatt tagatggtga   4920
caagtgtata agtcctcatc gggacagcta cgatttctct ttcggttttg gctgagctac   4980
tggttgctgt gacgcagcgg cattagcgcg gcgttatgag ctaccctcgt ggcctgaaag   5040
atggcgggaa taaagcggaa ctaaaaatta ctgactgagc catattgagg tcaatttgtc   5100
aactcgtcaa gtcacgtttg gtggacggcc ccttccaac gaatcgtata tactaacatg   5160
cgcgcgcttc ctatatacac atatacatat atatatatat atatatgtgt gcgtgtatgt   5220
gtacacctgt atttaatttc cttactcgcg ggttttcttt ttttctcaat tcttggcttc   5280
ctctttctcg agcggaccgg atcctccgcg gtgccggcag atctatttaa atggcgcgcc   5340
gacgtcaggt ggcactttc ggggaaatgt gcgcggaacc cctatttgtt tatttttcta   5400
aatacattca aatatgtatc cgctcatgag acaataaccc tgataaatgc ttcaataata   5460
ttgaaaaagg aagagtatga gtattcaaca tttccgtgtc gcccttattc ccttttttgc   5520
ggcattttgc cttcctgttt ttgctcaccc agaaacgctg gtgaaagtaa aagatgctga   5580
agatcagttg ggtgcacgag tgggttacat cgaactggat ctcaacagcg gtaagatcct   5640
tgagagtttt cgccccgaag aacgttttcc aatgatgagc acttttaaag ttctgctatg   5700
```

```
tggcgcggta ttatcccgta ttgacgccgg gcaagagcaa ctcggtcgcc gcatacacta    5760
ttctcagaat gacttggttg agtactcacc agtcacagaa aagcatctta cggatggcat    5820
gacagtaaga gaattatgca gtgctgccat aaccatgagt gataacactg cggccaactt    5880
acttctgaca acgatcggag gaccgaagga gctaaccgct tttttgcaca acatgggggga   5940 tcatgtaact cgccttgatc gttgggaacc ggagctgaat gaagccatac caaacgacga    6000
gcgtgacacc acgatgcctg tagcaatggc aacaacgttg cgcaaactat taactggcga    6060
actacttact ctagcttccc ggcaacaatt aatagactgg atggaggcgg ataaagttgc    6120
aggaccactt ctgcgctcgg cccttccggc tggctggttt attgctgata aatctggagc    6180
cggtgagcgt gggtctcgcg gtatcattgc agcactgggg ccagatggta agccctcccg    6240
tatcgtagtt atctacacga cggggagtca ggcaactatg gatgaacgaa atagacagat    6300
cgctgagata ggtgcctcac tgattaagca ttggtaactg tcagaccaag tttactcata    6360
tatactttag attgatttaa aacttcattt ttaatttaaa aggatctagg tgaagatcct    6420
ttttgataat ctcatgacca aaatccctta acgtgagttt cgttccact gagcgtcaga    6480 ccccgtagaa aagatcaaag gatcttcttg agatcctttt tttctgcgcg taatctgctg    6540
cttgcaaaca aaaaaaccac cgctaccagc ggtggtttgt ttgccggatc aagagctacc    6600
aactcttttt ccgaaggtaa ctggcttcag cagagcgcag ataccaaata ctgttcttct    6660
agtgtagccg tagttaggcc accacttcaa gaactctgta gcaccgccta catacctcgc    6720
tctgctaatc ctgttaccag tggctgctgc cagtggcgat aagtcgtgtc ttaccgggtt    6780
ggactcaaga cgatagttac cggataaggc gcagcggtcg gctgaacgg ggggttcgtg    6840 cacacagccc agcttggagc gaacgaccta caccgaactg agatacctac agcgtgagct    6900
atgagaaagc gccacgcttc ccgaagggag aaaggcggac aggtatccgg taagcggcag    6960
ggtcggaaca ggagagcgca cgagggagct tccaggggga aacgcctggt atctttatag    7020
tcctgtcggg tttcgccacc tctgacttga gcgtcgattt ttgtgatgct cgtcaggggg    7080
gcggagccta tggaaaaacg ccagcaacgc ggccttttta cggttcctgg ccttttgctg    7140
gccttttgct cacatgttct ttcctgcgtt atcccctgat tctgtggata accgtattac    7200
cgcctttgag tgagctgata ccgctcgccg cagccgaacg accgagcgca gcgagtcagt    7260
gagcgaggaa gcggaagagc gcccaatacg caaaccgcct ctccccgcgc gttggccgat    7320
tcattaatgc agctggcacg acaggtttcc cgactggaaa gcgggcagtg agcgcaacgc    7380
aattaatgtg agttagctca ctcattaggc accccaggct ttacacttta tgcttccggc    7440
tcgtatgttg tgtggaattg tgagcggata acaatttcac acaggaaaca gctatgacca    7500
tgattacgcc aagcttttc tttccaattt ttttttttc gtcattataa aaatcattac    7560
gaccgagatt cccgggtaat aactgatata attaaattga agctctaatt tgtgagttta    7620
gtatacatgc atttacttat aatacagttt tttagttttg ctggccgcat cttctcaaat    7680
atgcttccca gcctgctttt ctgtaacgtt caccctctac cttagcatcc cttccctttg    7740
caaatagtcc tcttccaaca ataataatgt cagatcctgt agagaccaca tcatccacgg    7800
ttctatactg ttgacccaat gcgtctccct tgtcatctaa acccacaccg ggtgtcataa    7860
tcaaccaatc gtaaccttca tctcttccac ccatgtctct tgagcaata aagccgataa    7920 caaaatcttt gtcgctcttc gcaatgtcaa cagtacccct tagtatattct ccagtagata    7980 gggagcccct tgcatgacaat tctgctaaca tcaaaaggcc tctaggttcc tttgttactt    8040
cttctgccgc ctgcttcaaa ccgctaacaa tacctgggcc caccacaccg tgtgcattcg    8100
```

```
taatgtctgc ccattctgct attctgtata cacccgcaga gtactgcaat ttgactgtat   8160
taccaatgtc agcaaatttt ctgtcttcga agagtaaaaa attgtacttg gcggataatg   8220
cctttagcgg cttaactgtg ccctccatgg aaaaatcagt caagatatcc acatgtgttt   8280
ttagtaaaca aattttggga cctaatgctt caactaactc cagtaattcc ttggtggtac   8340
gaacatccaa tgaagcacac aagtttgttt gcttttcgtg catgatatta aatagcttgg   8400
cagcaacagg actaggatga gtagcagcac gttccttata tgtagctttc gacatgattt   8460
atcttcgttt cctgcaggtt tttgttctgt gcagttgggt taagaatact gggcaatttc   8520
atgtttcttc aacactacat atgcgtatat ataccaatct aagtctgtgc tccttccttc   8580
gttcttcctt ctgttcggag attaccgaat caaaaaaatt tcaaggaaac cgaaatcaaa   8640
aaaaagaata aaaaaaaaat gatgaattga aaagcttgca tgcctgcagg tcgactctag   8700
tatactccgt ctactgtacg atacacttcc gctcaggtcc ttgtccttta acgaggcctt   8760
accactcttt tgttactcta ttgatccagc tcagcaaagg cagtgtgatc taagattcta   8820
tcttcgcgat gtagtaaaac tagctagacc gagaaagaga ctagaaatgc aaaaggcact   8880
tctacaatgg ctgccatcat tattatccga tgtgacgctg catttttttt tttttttttt   8940
tttttttttt tttttttttt tttttttttt ttttgtacaa atatcataaa aaagagaat   9000 cttttttaagc aaggattttc ttaacttctt cggcgacagc atcaccgact cggtggtac   9060 tgttggaacc acctaaatca ccagttctga tacctgcatc caaaaccttt ttaactgcat   9120
cttcaatggc tttaccttct tcaggcaagt tcaatgacaa tttcaacatc attgcagcag   9180
acaagatagt ggcgataggg ttgaccttat tctttggcaa atctggagcg gaaccatggc   9240
atggttcgta caaccaaat gcggtgttct tgtctggcaa agaggccaag gacgcagatg   9300
gcaacaaacc caaggagcct gggataacgg aggcttcatc ggagatgata tcaccaaaca   9360
tgttgctggt gattataata ccatttaggt gggttgggtt cttaactagg atcatggcgg   9420
cagaatcaat caattgatgt tgaactttca atgtagggaa ttcgttcttg atggtttcct   9480
ccacagtttt tctccataat cttgaagagg ccaaaacatt agctttatcc aaggaccaaa   9540
taggcaatgg tggctcatgt tgtagggcca tgaaagcggc cattcttgtg attctttgca   9600
cttctggaac ggtgtattgt tcactatccc aagcgacacc atcaccatcg tcttcctttc   9660
tcttaccaaa gtaaataccct cccactaatt ctctaacaac aacgaagtca gtacctttag   9720
caaattgtgg cttgattgga gataagtcta aagagagtc ggatgcaaag ttacatggtc   9780
ttaagttggc gtacaattga agttctttac ggattttttag taaaccttgt tcaggtctaa   9840
cactaccggt accccattta ggaccaccca cagcacctaa caaaacggca tcagccttct   9900
tggaggcttc cagcgcctca tctggaagtg aacacctgt agcatcgata gcagcaccac   9960
caattaaatg attttcgaaa tcgaacttga cattggaacg aacatcagaa atagctttaa  10020
gaaccttaat ggcttcggct gtgatttctt gaccaacgtg gtcacctggc aaaacgacga  10080
tcttcttagg ggcagacatt acaatggtat atccttgaaa tatatataaa aaaaaaaaa  10140 aaaaaaaaaa aaaaaaatgc agcttctcaa tgatattcga atacgctttg aggagataca  10200
gcctaatatc cgacaaactg ttttacagat ttacgatcgt acttgttacc catcattgaa  10260
ttttgaacat ccgaacctgg gagttttccc tgaaacagat agtatatttg aacctgtata  10320
ataatatata gtctagcgct ttacggaaga caatgtatgt atttcggttc ctggagaaac  10380
tattgcatct attgcatagg taatcttgca cgtcgcatcc ccggttcatt ttctgcgttt  10440
```

```
ccatcttgca cttcaatagc atatctttgt taacgaagca tctgtgcttc attttgtaga    10500
acaaaaatgc aacgcgagag cgctaatttt tcaaacaaag aatctgagct gcattttac     10560 agaacagaaa tgcaacgcga agcgctatt ttaccaacga agaatctgtg cttcattttt     10620
gtaaaacaaa aatgcaacgc gagagcgcta attttcaaa caagaatct gagctgcatt     10680 tttacagaac agaaatgcaa cgcgagagcg ctattttacc aacaagaat ctatacttct     10740 tttttgttct acaaaaatgc atcccgagag cgctattttt ctaacaaagc atcttagatt   10800 acttttttc tcctttgtgc gctctataat gcagtctctt gataacttt tgcactgtag      10860 gtccgttaag gttagaagaa ggctactttg gtgtctattt tctcttccat aaaaaaagcc    10920
tgactccact tcccgcgttt actgattact agcgaagctg cgggtgcatt ttttcaagat    10980
aaaggcatcc ccgattatat tctataccga tgtggattgc gcatactttg tgaacagaaa   11040
gtgatagcgt tgatgattct tcattggtca gaaaattatg aacggtttct tctatttgt    11100 ctctatatac tacgtatagg aaatgtttac attttcgtat tgttttcgat tcactctatg   11160
aatagttctt actacaattt ttttgtctaa agagtaaatac tagagataaa cataaaaaat  11220
gtagaggtcg agtttagatg caagttcaag gagcgaaagg tggatgggta ggttatatag   11280
ggatatagca cagagatata tagcaaagag atacttttga gcaatgtttg tggaagcggt   11340
attcgcaata ttttagtagc tcgttacagt ccggtgcgtt tttggttttt tgaaagtgcg   11400
tcttcagagc gcttttggtt tcaaaagcg ctctgaagtt cctatacttt ctagagaata    11460
ggaacttcgg aataggaact tcaaagcgtt tccgaaaacg agcgcttccg aaaatgcaac    11520
gcgagctgcg cacatacagc tcactgttca cgtcgcacct atatctgcgt gttgcctgta    11580
tatatatata catgagaaga acggcatagt gcgtgtttat gcttaaatgc gtacttatat    11640
gcgtctattt atgtaggatg aaaggtagtc tagtacctcc tgtgatatta tcccattcca    11700
tgcggggtat cgtatgcttc cttcagcact acccttagc tgttctatat gctgccactc    11760
ctcaattgga ttagtctcat ccttcaatgc tatcatttcc tttgatattg gatcatatgc   11820
atagtaccga gaaactagag gatc                                          11844
```

<210> SEQ ID NO 86
<211> LENGTH: 13114
<212> TYPE: DNA
<213> ORGANISM: artificial sequence
<220> FEATURE:
<223> OTHER INFORMATION: constructed plasmid

<400> SEQUENCE: 86

```
tcgcgcgttt cggtgatgac ggtgaaaacc tctgacacat gcagctcccg gagacggtca      60
cagcttgtct gtaagcggat gccgggagca gacaagcccg tcaggcgcg tcagcgggtg     120 ttggcgggtg tcggggctgg cttaactatg cggcatcaga gcagattgta ctgagagtgc    180
accataaatt cccgttttaa gagcttggtg agcgctagga gtcactgcca ggtatcgttt    240
gaacacggca ttagtcaggg aagtcataac acagtccttt cccgcaattt tctttttcta    300
ttactcttgg cctcctctag tacactctat attttttat gcctcggtaa tgattttcat    360
tttttttttt ccacctagcg gatgactctt tttttttctt agcgattggc attatcacat    420
aatgaattat acattatata agtaatgtg atttcttcga agaatatact aaaaaatgag     480
caggcaagat aaacgaaggc aaagatgaca gagcagaaag ccctagtaaa gcgtattaca    540
aatgaaacca agattcagat tgcgatctct ttaaagggtg gtcccctagc gatagagcac    600
tcgatcttcc cagaaaaaga ggcagaagca gtagcagaac aggccacaca atcgcaagtg    660
```

```
attaacgtcc acacaggtat agggtttctg gaccatatga tacatgctct ggccaagcat      720
tccggctggt cgctaatcgt tgagtgcatt ggtgacttac acatagacga ccatcacacc      780
actgaagact gcgggattgc tctcggtcaa gcttttaaag aggccctagg ggccgtgcgt      840
ggagtaaaaa ggtttggatc aggatttgcg cctttggatg aggcactttc cagagcggtg      900
gtagatcttt cgaacaggcc gtacgcagtt gtcgaacttg gtttgcaaag ggagaaagta      960
ggagatctct cttgcgagat gatcccgcat tttcttgaaa gctttgcaga ggctagcaga     1020
attaccctcc acgttgattg tctgcgaggc aagaatgatc atcaccgtag tgagagtgcg     1080
ttcaaggctc ttgcggttgc cataagagaa gccacctcgc ccaatggtac caacgatgtt     1140
ccctccacca aggtgttcct tatgtagtga caccgattat ttaaagctgc agcatacgat     1200
atatatacat gtgtatatat gtataccgat gaatgtcagt aagtatgtat acgaacagta     1260
tgatactgaa gatgacaagg taatgcatca ttctatacgt gtcattctga acgaggcgcg     1320
cttttccttt ttctttttgc ttttttcttt ttttctctt gaactcgacg gatctatgcg     1380
gtgtgaaata ccgcacagat gcgtaaggag aaaataccgc atcaggaaat tgtaagcgtt     1440
aatattttgt taaaattcgc gttaaatttt tgttaaatca gctcattttt taaccaatag     1500
gccgaaatcg gcaaaatccc ttataaatca aagaataga ccgagatagg gttgagtgtt     1560
gttccagttt ggaacaagag tccactatta agaacgtgg actccaacgt caaagggcga     1620
aaaaccgtct atcagggcga tggcccacta cgtggccggc ttcacatacg ttgcatacgt     1680
cgatatagat aataatgata atgacagcag gattatcgta atacgtaata gctgaaaatc     1740
tcaaaaatgt gtgggtcatt acgtaaataa tgataggaat gggattcttc tattttccct     1800
ttttccattc tagcagccgt cgggaaaacg tggcatcctc tctttcgggc tcaattggag     1860
tcacgctgcc gtgagcatcc tctctttcca tatctaacaa ctgagcacgt aaccaatgga     1920
aaagcatgag cttagcgttg ctccaaaaaa gtattggatg gttaatacca tttgtctgtt     1980
ctcttctgac tttgactcct caaaaaaaaa aatctacaat caacagatcg cttcaattac     2040
gccctcacaa aaacttttt ccttcttctt cgcccacgtt aaattttatc cctcatgttg     2100
tctaacggat ttctgcactt gatttattat aaaaagacaa agacataata cttctctatc     2160
aatttcagtt attgttcttc cttgcgttat tcttctgttc ttcttttct tttgtcatat     2220
ataaccataa ccaagtaata catattcaaa cacgtgagta tgactgacaa aaaaactctt     2280
aaagacttaa gaaatcgtag ttctgtttac gattcaatgg ttaaatcacc taatcgtgct     2340
atgttgcgtg caactggtat gcaagatgaa gactttgaaa aacctatcgt cggtgtcatt     2400
tcaacttggg ctgaaaacac accttgtaat atccacttac atgactttgg taaactagcc     2460
aaagtcggtg ttaaggaagc tggtgcttgg ccagttcagt tcggaacaat cacggtttct     2520
gatggaatcg ccatgggaac ccaaggaatg cgtttctcct tgacatctcg tgatattatt     2580
gcagattcta ttgaagcagc catgggaggt cataatgcgg atgcttttgt agccattggc     2640
ggttgtgata aaaacatgcc cggttctgtt atcgctatgg ctaacatgga tatcccagcc     2700
atttttgctt acggcggaac aattgcacct ggtaatttag acggcaaaga tatcgattta     2760
gtctctgtct ttgaaggtgt cggccattgg aaccacggcg atatgaccaa agaagaagtt     2820
aaagctttgg aatgtaatgc ttgtcccggt cctggaggct gcggtggtat gtatactgct     2880
aacacaatgg cgacagctat tgaagttttg ggacttagcc ttccgggttc atcttctcac     2940
ccggctgaat ccgcagaaaa gaaagcagat attgaagaag ctggtcgcgc tgttgtcaaa     3000
```

```
atgctcgaaa tgggcttaaa accttctgac attttaacgc gtgaagcttt tgaagatgct    3060
attactgtaa ctatggctct gggaggttca accaactcaa cccttcacct cttagctatt    3120
gcccatgctg ctaatgtgga attgacactt gatgatttca atactttcca agaaaaagtt    3180
cctcatttgg ctgatttgaa accttctggt caatatgtat ccaagacct ttacaaggtc     3240 ggaggggtac cagcagttat gaaatatctc cttaaaaatg gcttccttca tggtgaccgt    3300
atcacttgta ctggcaaaac agtcgctgaa aatttgaagg cttttgatga tttaacacct    3360
ggtcaaaagg ttattatgcc gcttgaaaat cctaaacgtg aagatggtcc gctcattatt    3420
ctccatggta acttggctcc agacggtgcc gttgccaaag tttctggtgt aaaagtgcgt    3480
cgtcatgtcg gtcctgctaa ggtctttaat tctgaagaag aagccattga agctgtcttg    3540
aatgatgata ttgttgatgg tgatgttgtt gtcgtacgtt ttgtaggacc aaagggcggt    3600
cctggtatgc ctgaaatgct ttcccttca tcaatgattg ttggtaaagg gcaaggtgaa    3660
aaagttgccc ttctgacaga tggccgcttc tcaggtggta cttatggtct tgtcgtgggt    3720
catatcgctc ctgaagcaca agatggcggt ccaatcgcct acctgcaaac aggagacata    3780
gtcactattg accaagacac taaggaatta cactttgata tctccgatga agagttaaaa    3840
catcgtcaag agaccattga attgccaccg ctctattcac gcggtatcct tggtaaatat    3900
gctcacatcg tttcgtctgc ttctagggga gccgtaacag acttttggaa gcctgaagaa    3960
actggcaaaa aatgttgtcc tggttgctgt ggttaagcgg ccgcgttaat tcaaattaat    4020
tgatatagtt ttttaatgag tattgaatct gtttagaaat aatggaatat tatttttatt    4080
tatttattta tattattggt cggctctttt cttctgaagg tcaatgacaa aatgatatga    4140
aggaaataat gatttctaaa attttacaac gtaagatatt tttacaaaag cctagctcat    4200
cttttgtcat gcactatttt actcacgctt gaaattaacg gccagtccac tgcggagtca    4260
tttcaaagtc atcctaatcg atctatcgtt tttgatagct cattttggag ttcgcgagga    4320
tccactagtt ctagagcggc cgctctagaa ctagtaccac aggtgttgtc ctctgaggac    4380
ataaaataca caccgagatt catcaactca ttgctggagt tagcatatct acaattgggt    4440
gaaatgggga gcgatttgca ggcatttgct cggcatgccg gtagaggtgt ggtcaataag    4500
agcgacctca tgctatacct gagaaagcaa cctgacctac aggaaagagt tactcaagaa    4560
taagaatttt cgttttaaaa cctaagagtc actttaaaat ttgtatacac ttattttttt    4620
tataacttat ttaataataa aaatcataaa tcataagaaa ttcgcttact cttaattaat    4680
caaaaagtta aaattgtacg aatagattca ccacttctta acaaatcaaa cccttcattg    4740
attttctcga atggcaatac atgtgtaatt aaaggatcaa gagcaaactt cttcgccata    4800
aagtcggcaa caagttttgg aacactatcc ttgctcttaa aaccgccaaa tatagctccc    4860
ttccatgtac gaccgcttag caacagcata ggattcatcg acaaattttg tgaatcagga    4920
ggaacaccta cgatcacact gactccatat gcctcttgac agcaggacaa cgcagttacc    4980
atagtatcaa gacggcctat aacttcaaaa gagaaatcaa ctccaccgtt tgacatttca    5040
gtaaggactt cttgtattgg tttcttataa tcttgagggt taacacattc agtagccccg    5100
acctccttag cttttgcaaa tttgtcctta ttgatgtcta cacctataat cctcgctgcg    5160
cctgcagctt tacaccccat aataacgctt agtcctactc ctcctaaacc gaatactgca    5220
caagtcgaac cctgtgtaac ctttgcaact ttaactgcgg aaccgtaacc ggtggaaaat    5280
ccgcacccta tcaagcaaac ttttttccagt ggtgaagctg catcgatttt agcgacagat    5340
atctcgtcca ccactgtgta ttgggaaaat gtagaagtac caaggaaatg gtgtataggt    5400
```

```
ttccctctgc atgtaaatct gcttgtacca tcctgcatag tacctctagg catagacaaa    5460
tcatttttaa ggcagaaatt accctcagga tgtttgcaga ctctacactt accacattga    5520
ggagtgaaca gtgggatcac tttatcacca ggacgaacag tggtaacacc ttcacctatg    5580
gattcaacga ttccggcagc ctcgtgtccc gcgattactg gcaaaggagt aactagagtg    5640
ccactcacca catggtcgtc ggatctacag attccggtgg caaccatctt gattctaacc    5700
tcgtgtgctt ttggtggcgc tacttctact tcttctatgc taaacggctt tttctcttcc    5760
cacaaaactg ccgctttaca cttaataact ttaccggctg ttgacatcct cagctagcta    5820
ttgtaatatg tgtgtttgtt tggattatta agaagaataa ttacaaaaaa aattacaaag    5880
gaaggtaatt acaacagaat taagaaagga caagaaggag gaagagaatc agttcattat    5940
ttcttctttg ttatataaca aacccaagta gcgatttggc catacattaa aagttgagaa    6000
ccaccctccc tggcaacagc cacaactcgt taccattgtt catcacgatc atgaaactcg    6060
ccgtcagctg aaatttcacc tcagtggatc tctcttttta ttcttcatcg ttccactaac    6120 cttttttccat cagctggcag ggaacggaaa gtggaatccc atttagcgag cttcctcttt    6180
tcttcaagaa aagacgaagc ttgtgtgtgg gtgcgcgcgc tagtatcttt ccacattaag    6240
aaatatacca taaaggttac ttagacatca ctatggctat atatatatat atatatatat    6300
gtaacttagc accatcgcgc gtgcatcact gcatgtgtta accgaaaagt ttggcgaaca    6360
cttcaccgac acggtcattt agatctgtcg tctgcattgc acgtcccta gccttaaatc    6420 ctaggcggga gcattctcgt gtaattgtgc agcctgcgta gcaactcaac atagcgtagt    6480
ctacccagtt tttcaagggt ttatcgttag aagattctcc cttttcttcc tgctcacaaa    6540
tcttaaagtc atacattgca cgactaaatg caagcgacgt cagggaaaga tatgagctat    6600
acagcggaat ttccatatca ctcagatttt gttatctaat ttttccttc ccacgtccgc    6660 gggaatctgt gtatattact gcatctagat atatgttatc ttatcttggc gcgtacattt    6720
aattttcaac gtattctata agaaattgcg ggagtttttt tcatgtagat gatactgact    6780
gcacgcaaat ataggcatga tttataggca tgatttgatg gctgtaccga taggaacgct    6840
aagagtaact tcagaatcgt tatcctggcg gaaaaaattc atttgtaaac tttaaaaaaa    6900
aaagccaata tccccaaaat tattaagagc gcctccatta ttaactaaaa tttcactcag    6960
catccacaat gtatcaggta tctactacag atattacatg tggcgaaaaa gacaagaaca    7020
atgcaatagc gcatcaagaa aaaacacaaa gctttcaatc aatgaatcga aaatgtcatt    7080
aaaatagtat ataaattgaa actaagtcat aaagctataa aaagaaaatt tatttaaatg    7140
caagatttaa agtaaattca cggccctgca ggcctcagct cttgttttgt tctgcaaata    7200
acttacccat cttttcaaa actttaggtg caccctcctt tgctagaata agttctatcc    7260
aatacatcct atttggatct gcttgagctt ctttcatcac ggatacgaat tcattttctg    7320
ttctcacaat tttggacaca actctgtctt ccgttgcccc gaaactttct ggcagttttg    7380
agtaattcca cataggaatg tcattataac tctggttcgg accatgaatt tccctctcaa    7440
ccgtgtaacc atcgttatta atgataaagc agattgggtt tatcttctct ctaatggcta    7500
gtcctaattc ttgacagtc agttgcaatg atccatctcc gataaacaat aaatgtctag    7560
attctttatc tgcaatttgg ctgcctagag ctgcggggaa agtgtatcct atagatcccc    7620
acaagggttg accaataaaa tgtgatttcg atttcagaaa tatagatgag gcaccgaaga    7680
aagaagtgcc ttgttcagcc acgatcgtct cattactttg ggtcaaattt tcgacagctt    7740
```

```
gccacagtct atcttgtgac aacagcgcgt tagaaggtac aaaatcttct tgcttttat    7800
ctatgtactt gcctttatat tcaatttcgg acaagtcaag aagagatgat atcagggatt   7860
cgaagtcgaa attttggatt ctttcgttga aattttacc ttcatcgata ttcaaggaaa    7920
tcattttatt ttcattaaga tggtgagtaa atgcacccgt actagaatcg gtaagcttta   7980
cacccaacat aagaataaaa tcagcagatt ccacaaattc cttcaagttt ggctctgaca   8040
gagtaccgtt gtaaatcccc aaaaatgagg gcaatgcttc atcaacagat gatttaccaa   8100
agttcaaagt agtaataggt aacttagtct ttgaaataaa ctgagtaaca gtcttctcta   8160
ggccgaacga tataatttca tggcctgtga ttacaattgg tttcttggca ttcttcagac   8220
tttcctgtat tttgttcaga atctcttgat cagatgtatt cgacgtggaa ttttccttct   8280
taagaggcaa ggatggtttt tcagccttag cggcagctac atctacaggt aaattgatgt   8340
aaaccggctt tctttccttt agtaaggcag acaacactct atcaatttca acagttgcat   8400
tctcggctgt caataaagtc ctggcagcag taaccggttc gtgcatcttc ataaagtgct   8460
tgaaatcacc atcagccaac gtatggtgaa caaacttacc ttcgttctgc actttcgagg   8520
taggagatcc cacgatctca acaacaggca ggttctcagc ataggagccc gctaagccat   8580
taactgcgga taattcgcca acaccaaatg tagtcaagaa tgccgcagcc ttttcgttc    8640
ttgcgtaccc gtcggccata taggaggcat ttaactcatt agcatttccc acccatttca   8700
tatctttgtg tgaaataatt tgatctagaa attgcaaatt gtagtcacct ggtactccga   8760
atatttcttc tatacctaat tcgtgtaatc tgtccaacag atagtcacct actgtataca   8820
tgtttaaact ttgtttacta gtttatgtgt gtttattcga aactaagttc ttggtgtttt   8880
aaaactaaaa aaagactaa ctataaagt agaatttaag agtttaaga aatagattta    8940
cagaattaca atcaatacct accgtcttta tatacttat agtcaagtag gggaataatt   9000
tcagggaact ggtttcaacc ttttttttca gcttttcca aatcagagag agcagaaggt    9060
aatagaaggt gtaagaaaat gagatagata catgcgtggg tcaattgcct tgtgtcatca   9120
tttactccag gcaggttgca tcactccatt gaggttgtgc ccgttttttg cctgtttgtg   9180
cccctgttct ctgtagttgc gctaagagaa tggacctatg aactgatggt tggtgaagaa   9240
aacaatattt tggtgctggg attcttttt tttctggatg ccagcttaaa aagcgggctc     9300
cattatattt agtggatgcc aggaataaac tgttcaccca gacacctacg atgttatata   9360
ttctgtgtaa cccgccccct attttgggca tgtacgggtt acagcagaat taaaaggcta   9420
atttttgac taaataaagt taggaaaatc actactatta attatttcg tattctttga    9480
aatggcagta ttggagctcc agcttttgtt ccctttagtg agggttaatt gcgcgcttgg   9540
cgtaatcatg gtcatagctg tttcctgtgt gaaattgtta ccgctcaca attccacaca    9600
acatacgagc cggaagcata agtgtaaag cctggggtgc ctaatgagtg agctaactca    9660
cattaattgc gttgcgctca ctgcccgctt tccagtcggg aaacctgtcg tgccagctgc   9720
attaatgaat cggccaacgc gcggggagag gcggtttgcg tattgggcgc tcttccgctt   9780
cctcgctcac tgactcgctg cgctcggtcg ttcggctgcg gcgagcggta tcagctcact   9840
caaaggcggt aatacggtta tccacagaat caggggataa cgcaggaaag aacatgtgag   9900
caaaaggcca gcaaaaggcc aggaaccgta aaaaggccgc gttgctggcg ttttccata    9960
ggctccgccc cctgacgag catcacaaaa atcgacgctc aagtcagagg tggcgaaacc   10020
cgacaggact ataagatac caggcgtttc ccctggaag ctccctcgtg cgctctcctg   10080
ttccgaccct gccgcttacc ggatacctgt ccgcctttct cccttcggga agcgtggcgc   10140
```

```
tttctcatag ctcacgctgt aggtatctca gttcggtgta ggtcgttcgc tccaagctgg   10200
gctgtgtgca cgaaccgccc gttcagcccg accgctgcgc cttatccggt aactatcgtc   10260
ttgagtccaa cccggtaaga cacgacttat cgccactggc agcagccact ggtaacagga   10320
ttagcagagc gaggtatgta ggcggtgcta cagagttctt gaagtggtgg cctaactacg   10380
gctacactag aagaacagta tttggtatct gcgctctgct gaagccagtt accttcggaa   10440
aaagagttgg tagctcttga tccggcaaac aaaccaccgc tggtagcggt ggttttttg    10500 tttgcaagca gcagattacg cgcagaaaaa aaggatctca agaagatcct ttgatctttt   10560
ctacggggtc tgacgctcag tggaacgaaa actcacgtta agggattttg gtcatgagat   10620
tatcaaaaag gatcttcacc tagatccttt taaattaaaa atgaagtttt aaatcaatct   10680
aaagtatata tgagtaaact tggtctgaca gttaccaatg cttaatcagt gaggcaccta   10740
tctcagcgat ctgtctattt cgttcatcca tagttgcctg actccccgtc gtgtagataa   10800
ctacgatacg ggagggctta ccatctggcc ccagtgctgc aatgataccg cgagacccac   10860
gctcaccggc tccagattta tcagcaataa accagccagc cggaagggcc gagcgcagaa   10920
gtggtcctgc aactttatcc gcctccatcc agtctattaa ttgttgccgg gaagctagag   10980
taagtagttc gccagttaat agtttgcgca acgttgttgc cattgctaca ggcatcgtgg   11040
tgtcacgctc gtcgtttggt atggcttcat tcagctccgg ttcccaacga tcaaggcgag   11100
ttacatgatc ccccatgttg tgcaaaaaag cggttagctc cttcggtcct ccgatcgttg   11160
tcagaagtaa gttggccgca gtgttatcac tcatggttat ggcagcactg cataattctc   11220
ttactgtcat gccatccgta agatgctttt ctgtgactgg tgagtactca accaagtcat   11280
tctgagaata gtgtatgcgg cgaccgagtt gctcttgccc ggcgtcaata cgggataata   11340
ccgcgccaca tagcagaact ttaaaagtgc tcatcattgg aaaacgttct cggggcgaa    11400 aactctcaag gatcttaccg ctgttgagat ccagttcgat gtaacccact cgtgcaccca   11460
actgatcttc agcatctttt actttcacca gcgtttctgg gtgagcaaaa acaggaaggc   11520
aaaatgccgc aaaaaaggga ataagggcga cacggaaatg ttgaatactc atactcttcc   11580
tttttcaata ttattgaagc atttatcagg gttattgtct catgagcgga tacatatttg   11640
aatgtattta gaaaaataaa caaataggg ttccgcgcac atttccccga aaagtgccac    11700
ctgaacgaag catctgtgct tcattttgta gaacaaaaat gcaacgcgag agcgctaatt   11760
tttcaaacaa gaatctgag ctgcattttt acagaacaga aatgcaacgc gaaagcgcta    11820
ttttaccaac gaagaatctg tgcttcattt tgtaaaaca aaaatgcaac gcgagagcgc    11880 taattttca acaaagaat ctgagctgca tttttacaga acagaaatgc aacgcgagag    11940
cgctatttta ccaacaaaga atctatactt ctttttgtt ctacaaaaat gcatcccgag    12000
agcgctattt ttctaacaaa gcatcttaga ttactttttt tctcctttgt gcgctctata   12060
atgcagtctc ttgataactt tttgcactgt aggtccgtta aggttagaag aaggctactt   12120
tggtgtctat tttctcttcc ataaaaaaag cctgactcca cttcccgcgt ttactgatta   12180
ctagcgaagc tgcgggtgca ttttttcaag ataaaggcat ccccgattat attctatacc   12240
gatgtggatt gcgcatactt tgtgaacaga aagtgatagc gttgatgatt cttcattggt   12300
cagaaaatta tgaacggttt cttctatttt gtctctatat actacgtata ggaaatgttt   12360
acattttcgt attgttttcg attcactcta tgaatagttc ttactacaat tttttgtct   12420 aaagagtaat actagagata aacataaaaa atgtagaggt cgagtttaga tgcaagttca   12480
```

```
aggagcgaaa ggtggatggg taggttatat agggatatag cacagagata tatagcaaag    12540 agatacttt  gagcaatgtt tgtggaagcg gtattcgcaa tattttagta gctcgttaca    12600
gtccggtgcg ttttggttt  tttgaaagtg cgtcttcaga gcgcttttgg ttttcaaaag    12660
cgctctgaag ttcctatact ttctagagaa taggaacttc ggaataggaa cttcaaagcg    12720
tttccgaaaa cgagcgcttc cgaaaatgca acgcgagctg cgcacataca gctcactgtt    12780
cacgtcgcac ctatatctgc gtgttgcctg tatatatata tacatgagaa gaacggcata    12840
gtgcgtgttt atgcttaaat gcgtacttat atgcgtctat ttatgtagga tgaaaggtag    12900
tctagtacct cctgtgatat tatcccattc catgcgggt  atcgtatgct tccttcagca    12960 ctaccctta  gctgttctat atgctgccac tcctcaattg gattagtctc atccttcaat    13020
gctatcattt cctttgatat tggatcatac taagaaacca ttattatcat gacattaacc    13080
tataaaaata ggcgtatcac gaggccctt  cgtc                                13114
```

<210> SEQ ID NO 87
<211> LENGTH: 90
<212> TYPE: DNA
<213> ORGANISM: Artificial sequence
<220> FEATURE:
<223> OTHER INFORMATION: primer

<400> SEQUENCE: 87

```
gtattttggt agattcaatt ctctttccct ttccttttcc ttcgctcccc ttccttatca     60
gcattgcgga ttacgtattc taatgttcag                                      90
```

<210> SEQ ID NO 88
<211> LENGTH: 90
<212> TYPE: DNA
<213> ORGANISM: Artificial sequence
<220> FEATURE:
<223> OTHER INFORMATION: Primer

<400> SEQUENCE: 88

```
ttggttgggg gaaaagagg  caacaggaaa gatcagaggg ggagggggg  ggagagtgtc     60 accttggcta actcgttgta tcatcactgg                                      90
```

<210> SEQ ID NO 89
<211> LENGTH: 29
<212> TYPE: DNA
<213> ORGANISM: Artificial sequence
<220> FEATURE:
<223> OTHER INFORMATION: Primer

<400> SEQUENCE: 89

```
ctcgaaacaa taagacgacg atggctctg                                       29
```

<210> SEQ ID NO 90
<211> LENGTH: 86
<212> TYPE: DNA
<213> ORGANISM: Artificial sequence
<220> FEATURE:
<223> OTHER INFORMATION: Primer

<400> SEQUENCE: 90

```
aggataaaaa aagcttgtga ataaaaatct ttcgctaaaa atcaatataa gaaaatggta     60
caccttggct aactcgttgt atcatc                                          86
```

<210> SEQ ID NO 91
<211> LENGTH: 90

```
<212> TYPE: DNA
<213> ORGANISM: Artificial sequence
<220> FEATURE:
<223> OTHER INFORMATION: Primer

<400> SEQUENCE: 91
tgcatacttt atgcgtttat gcgttttgcg ccccttggaa aaaaattgat tctcatcgta    60
gcattgcgga ttacgtattc taatgttcag                                    90

<210> SEQ ID NO 92
<211> LENGTH: 29
<212> TYPE: DNA
<213> ORGANISM: Artificial sequence
<220> FEATURE:
<223> OTHER INFORMATION: Primer

<400> SEQUENCE: 92
gtctagacca gaagttaaga aggctgtag                                     29

<210> SEQ ID NO 93
<211> LENGTH: 26
<212> TYPE: DNA
<213> ORGANISM: Artificial sequence
<220> FEATURE:
<223> OTHER INFORMATION: Primer

<400> SEQUENCE: 93
tagcacccaa tagagcgccg actgtg                                        26

<210> SEQ ID NO 94
<211> LENGTH: 4519
<212> TYPE: DNA
<213> ORGANISM: Artificial sequence
<220> FEATURE:
<223> OTHER INFORMATION: Plasmid

<400> SEQUENCE: 94
caccttggct aactcgttgt atcatcactg gataacttcg tataatgtat gctatacgaa    60
gttatcgaac agagaaacta atccacatt aattgagagt tctatctatt agaaaatgca   120
aactccaact aaatgggaaa acagataacc tcttttatttt ttttttaatg tttgatattc   180 gagtctttttt cttttgttag gtttatattc atcatttcaa tgaataaaag aagcttctta   240
ttttggttgc aaagaatgaa aaaaaaggat tttttcatac ttctaaagct tcaattataa   300
ccaaaaattt tataaatgaa gagaaaaaat ctagtagtat caagttaaac ttagaaaaac   360
tcatcgagca tcaaatgaaa ctgcaattta ttcatatcag gattatcaat accatatttt   420
tgaaaaagcc gtttctgtaa tgaaggagaa aactcaccga ggcagttcca taggatggca   480
agatcctggt atcggtctgc gattccgact cgtccaacat caatacaacc tattaatttc   540
ccctcgtcaa aataaggtt atcaagtgag aaatcaccat gagtgacgac tgaatccggt   600
gagaatggca aaagcttatg catttctttc cagacttgtt caacaggcca gccattacgc   660
tcgtcatcaa aatcactcgc atcaaccaaa ccgttattca ttcgtgattg cgcctgagcg   720
agacgaaata cgcgatcgct gttaaaagga caattacaaa caggaatcga atgcaaccgg   780
cgcaggaaca ctgccagcgc atcaacaata ttttcacctg aatcaggata ttcttctaat   840
acctggaatg ctgtttttgcc ggggatcgca gtggtgagta accatgcatc atcaggagta   900
cggataaaat gcttgatggt cggaagaggc ataaattccg tcagccagtt tagtctgacc   960
atctcatctg taacatcatt ggcaacgcta cctttgccat gtttcagaaa caactctggc  1020
```

-continued

```
gcatcgggct tcccatacaa tcgatagatt gtcgcacctg attgcccgac attatcgcga      1080
gcccatttat acccatataa atcagcatcc atgttggaat ttaatcgcgg cctcgaaacg      1140
tgagtctttt ccttacccat ctcgagtttt aatgttactt ctcttgcagt tagggaacta      1200
taatgtaact caaaataaga ttaaacaaac taaaataaaa agaagttata cagaaaaacc      1260
catataaacc agtactaatc cataataata atacacaaaa aaactatcaa ataaaaccag      1320
aaaacagatt gaatagaaaa attttttcga tctcctttta tattcaaaat tcgatatatg      1380
aaaaagggaa ctctcagaaa atcaccaaat caatttaatt agatttttct tttccttcta      1440
gcgttggaaa gaaaaatttt tctttttttt tttagaaatg aaaaattttt gccgtaggaa      1500
tcaccgtata aaccctgtat aaacgctact ctgttcacct gtgtaggcta tgattgaccc      1560
agtgttcatt gttattgcga gagagcggga gaaagaacc gatacaagag atccatgctg       1620
gtatagttgt ctgtccaaca ctttgatgaa cttgtaggac gatgatgtgt atttagacga      1680
gtacgtgtgt gactattaag tagttatgat agagaggttt gtacggtgtg ttctgtgtaa      1740
ttcgattgag aaaatggtta tgaatcccta gataacttcg tataatgtat gctatacgaa      1800
gttatctgaa cattagaata cgtaatccgc aatgcgggga tcctctagag tcgacctgca      1860
ggcatgcaag cttggcgtaa tcatggtcat agctgtttcc tgtgtgaaat tgttatccgc      1920
tcacaattcc acacaacata cgagccggaa gcataaagtg taaagcctgg ggtgcctaat      1980
gagtgagcta actcacatta attgcgttgc gctcactgcc cgctttccag tcgggaaacc      2040
tgtcgtgcca gctgcattaa tgaatcggcc aacgcgcggg gagaggcggt ttgcgtattg      2100
ggcgctcttc cgcttcctcg ctcactgact cgctgcgctc ggtcgttcgg ctgcggcgag      2160
cggtatcagc tcactcaaag gcggtaatac ggttatccac agaatcaggg gataacgcag      2220
gaaagaacat gtgagcaaaa ggccagcaaa aggccaggaa ccgtaaaaag gccgcgttgc      2280
tggcgttttt ccataggctc cgcccccctg acgagcatca caaaaatcga cgctcaagtc      2340
agaggtggcg aaacccgaca ggactataaa gataccaggc gtttccccct ggaagctccc      2400
tcgtgcgctc tcctgttccg accctgccgc ttaccggata cctgtccgcc tttctccctt      2460
cgggaagcgt ggcgctttct catagctcac gctgtaggta tctcagttcg gtgtaggtcg      2520
ttcgctccaa gctgggctgt gtgcacgaac cccccgttca gcccgaccgc tgcgccttat      2580
ccggtaacta tcgtcttgag tccaacccgg taagacacga cttatcgcca ctggcagcag      2640
ccactggtaa caggattagc agagcgaggt atgtaggcgg tgctacagag ttcttgaagt      2700
ggtggcctaa ctacggctac actagaagga cagtatttgg tatctgcgct ctgctgaagc      2760
cagttacctt cggaaaaaga gttggtagct cttgatccgg caaacaaacc accgctggta      2820
gcggtggttt ttttgtttgc aagcagcaga ttacgcgcag aaaaaaagga tctcaagaag      2880
atcctttgat cttttctacg gggtctgacg ctcagtggaa cgaaaactca cgttaaggga      2940
ttttggtcat gagattatca aaaggatct tcacctagat ccttttaaat taaaaatgaa      3000
gttttaaatc aatctaaagt atatatgagt aaacttggtc tgacagttac caatgcttaa      3060
tcagtgaggc acctatctca gcgatctgtc tatttcgttc atccatagtt gcctgactcc      3120
ccgtcgtgta gataactacg atacgggagg gcttaccatc tggccccagt gctgcaatga      3180
taccgcgaga cccacgctca ccggctccag atttatcagc aataaaccag ccagccggaa      3240
gggccgagcg cagaagtggt cctgcaactt tatccgcctc catccagtct attaattgtt      3300
gccgggaagc tagagtaagt agttcgccag ttaatagttt gcgcaacgtt gttgccattg      3360
ctacaggcat cgtggtgtca cgctcgtcgt ttggtatggc ttcattcagc tccggttccc      3420
```

| | |
|---|---|
| aacgatcaag gcgagttaca tgatccccca tgttgtgcaa aaaagcggtt agctccttcg | 3480 |
| gtcctccgat cgttgtcaga agtaagttgg ccgcagtgtt atcactcatg gttatggcag | 3540 |
| cactgcataa ttctcttact gtcatgccat ccgtaagatg cttttctgtg actggtgagt | 3600 |
| actcaaccaa gtcattctga aatagtgta tgcggcgacc gagttgctct tgcccggcgt | 3660 |
| caatacggga taataccgcg ccacatagca gaactttaaa agtgctcatc attggaaaac | 3720 |
| gttcttcggg gcgaaaactc tcaaggatct taccgctgtt gagatccagt tcgatgtaac | 3780 |
| ccactcgtgc acccaactga tcttcagcat cttttacttt caccagcgtt tctgggtgag | 3840 |
| caaaaacagg aaggcaaaat gccgcaaaaa agggaataag ggcgacacgg aaatgttgaa | 3900 |
| tactcatact cttccttttt caatattatt gaagcattta tcagggttat tgtctcatga | 3960 |
| gcggatacat atttgaatgt atttagaaaa ataaacaaat aggggttccg cgcacatttc | 4020 |
| cccgaaaagt gccacctgac gtctaagaaa ccattattat catgacatta acctataaaa | 4080 |
| ataggcgtat cacgaggccc tttcgtctcg cgcgtttcgg tgatgacggt gaaaacctct | 4140 |
| gacacatgca gctcccggag acggtcacag cttgtctgta agcggatgcc gggagcagac | 4200 |
| aagcccgtca gggcgcgtca gcgggtgttg gcgggtgtcg gggctggctt aactatgcgg | 4260 |
| catcagagca gattgtactg agagtgcacc atatgcggtg tgaaataccg cacagatgcg | 4320 |
| taaggagaaa ataccgcatc aggcgccatt cgccattcag gctgcgcaac tgttgggaag | 4380 |
| ggcgatcggt gcgggcctct tcgctattac gccagctggc gaaaggggga tgtgctgcaa | 4440 |
| ggcgattaag ttgggtaacg ccagggtttt cccagtcacg acgttgtaaa acgacggcca | 4500 |
| gtgaattcga gctcggtac | 4519 |

<210> SEQ ID NO 95
<211> LENGTH: 1716
<212> TYPE: DNA
<213> ORGANISM: Bacillus subtilis

<400> SEQUENCE: 95

| | |
|---|---|
| atgttgacaa aagcaacaaa agaacaaaaa tcccttgtga aaaacagagg ggcggagctt | 60 |
| gttgttgatt gcttagtgga gcaaggtgtc acacatgtat ttggcattcc aggtgcaaaa | 120 |
| attgatgcgg tatttgacgc tttacaagat aaaggacctg aaattatcgt tgcccggcac | 180 |
| gaacaaaacg cagcattcat ggcccaagca gtcggccgtt taactggaaa accgggagtc | 240 |
| gtgttagtca catcaggacc gggtgcctct aacttggcaa caggcctgct gacagcgaac | 300 |
| actgaaggag accctgtcgt tgcgcttgct ggaaacgtga tccgtgcaga tcgtttaaaa | 360 |
| cggacacatc aatctttgga taatgcggcg ctattccagc cgattacaaa atacagtgta | 420 |
| gaagttcaag atgtaaaaaa tataccggaa gctgttacaa atgcatttag atagcgtca | 480 |
| gcagggcagg ctggggccgc ttttgtgagc tttccgcaag atgttgtgaa tgaagtcaca | 540 |
| aatacgaaaa acgtgcgtgc tgttcagcg ccaaaactcg gtcctgcagc agatgatgca | 600 |
| atcagtgcgg ccatagcaaa atccaaaca gcaaaacttc ctgtcgtttt ggtcggcatg | 660 |
| aaaggcggaa gaccggaagc aattaaagcg gttcgcaagc ttttgaaaaa ggttcagctt | 720 |
| ccatttgttg aaacatatca agctgccggt acccttctag agatttaga ggatcaatat | 780 |
| tttggccgta tcggtttgtt ccgcaaccag cctggcgatt tactgctaga gcaggcagat | 840 |
| gttgttctga cgatcggcta tgacccgatt gaatatgatc cgaaattctg gaatatcaat | 900 |
| ggagaccgga caattatcca tttagacgag attatcgctg acattgatca tgcttaccag | 960 |

```
cctgatcttg aattgatcgg tgacattccg tccacgatca atcatatcga acacgatgct   1020
gtgaaagtgg aatttgcaga gcgtgagcag aaaatccttt ctgatttaaa acaatatatg   1080
catgaaggtg agcaggtgcc tgcagattgg aaatcagaca gagcgcaccc tcttgaaatc   1140
gttaaagagt tgcgtaatgc agtcgatgat catgttacag taacttgcga tatcggttcg   1200
cacgccattt ggatgtcacg ttatttccgc agctacgagc cgttaacatt aatgatcagt   1260
aacggtatgc aaacactcgg cgttgcgctt ccttgggcaa tcggcgcttc attggtgaaa   1320
ccgggagaaa aagtggtttc tgtctctggt gacggcggtt tcttattctc agcaatggaa   1380
ttagagacag cagttcgact aaaagcacca attgtacaca ttgtatggaa cgacagcaca   1440
tatgacatgg ttgcattcca gcaattgaaa aaatataacc gtacatctgc ggtcgatttc   1500
ggaaatatcg atatcgtgaa atatgcggaa agcttcggag caactggctt gcgcgtagaa   1560
tcaccagacc agctggcaga tgttctgcgt caaggcatga acgctgaagg tcctgtcatc   1620
atcgatgtcc cggttgacta cagtgataac attaatttag caagtgacaa gcttccgaaa   1680
gaattcgggg aactcatgaa aacgaaagct ctctag                             1716
```

<210> SEQ ID NO 96
<211> LENGTH: 571
<212> TYPE: PRT
<213> ORGANISM: Bacillus subtilis

<400> SEQUENCE: 96

```
Met Leu Thr Lys Ala Thr Lys Glu Gln Lys Ser Leu Val Lys Asn Arg
1               5                   10                  15

Gly Ala Glu Leu Val Val Asp Cys Leu Val Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ala Ile Ala Lys Ile
        195                 200                 205

Gln Thr Ala Lys Leu Pro Val Val Leu Val Gly Met Lys Gly Gly Arg
    210                 215                 220

Pro Glu Ala Ile Lys Ala Val Arg Lys Leu Leu Lys Lys Val Gln Leu
225                 230                 235                 240
```

Pro Phe Val Glu Thr Tyr Gln Ala Ala Gly Thr Leu Ser Arg Asp Leu
                245                 250                 255

Glu Asp Gln Tyr Phe Gly Arg Ile Gly Leu Phe Arg Asn Gln Pro Gly
            260                 265                 270

Asp Leu Leu Leu Glu Gln Ala Asp Val Val Leu Thr Ile Gly Tyr Asp
        275                 280                 285

Pro Ile Glu Tyr Asp Pro Lys Phe Trp Asn Ile Asn Gly Asp Arg Thr
    290                 295                 300

Ile Ile His Leu Asp Glu Ile Ile Ala Asp Ile Asp His Ala Tyr Gln
305                 310                 315                 320

Pro Asp Leu Glu Leu Ile Gly Asp Ile Pro Ser Thr Ile Asn His Ile
                325                 330                 335

Glu His Asp Ala Val Lys Val Glu Phe Ala Glu Arg Glu Gln Lys Ile
            340                 345                 350

Leu Ser Asp Leu Lys Gln Tyr Met His Glu Gly Glu Gln Val Pro Ala
        355                 360                 365

Asp Trp Lys Ser Asp Arg Ala His Pro Leu Glu Ile Val Lys Glu Leu
    370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
                405                 410                 415

Leu Met Ile Ser Asn Gly Met Gln Thr Leu Gly Val Ala Leu Pro Trp
            420                 425                 430

Ala Ile Gly Ala Ser Leu Val Lys Pro Gly Glu Lys Val Val Ser Val
        435                 440                 445

Ser Gly Asp Gly Gly Phe Leu Phe Ser Ala Met Glu Leu Glu Thr Ala
    450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
                485                 490                 495

Ala Val Asp Phe Gly Asn Ile Asp Ile Val Lys Tyr Ala Glu Ser Phe
            500                 505                 510

Gly Ala Thr Gly Leu Arg Val Glu Ser Pro Asp Gln Leu Ala Asp Val
        515                 520                 525

Leu Arg Gln Gly Met Asn Ala Glu Gly Pro Val Ile Ile Asp Val Pro
    530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
                565                 570

<210> SEQ ID NO 97
<211> LENGTH: 540
<212> TYPE: PRT
<213> ORGANISM: Escherichia coli

<400> SEQUENCE: 97

Met Asn Thr Leu Pro Glu His Ser Cys Asp Val Leu Ile Ile Gly Ser
1               5                   10                  15

Gly Ala Ala Gly Leu Ser Leu Ala Leu Arg Leu Ala Asp Gln His Gln
            20                  25                  30

Val Ile Val Leu Ser Lys Gly Pro Val Thr Glu Gly Ser Thr Phe Tyr
        35                  40                  45

-continued

```
Ala Gln Gly Gly Ile Ala Ala Val Phe Asp Glu Thr Asp Ser Ile Asp
         50                  55                  60

Ser His Val Glu Asp Thr Leu Ile Ala Gly Ala Gly Ile Cys Asp Arg
 65                  70                  75                  80

His Ala Val Glu Phe Val Ala Ser Asn Ala Arg Ser Cys Val Gln Trp
                 85                  90                  95

Leu Ile Asp Gln Gly Val Leu Phe Asp Thr His Ile Gln Pro Asn Gly
             100                 105                 110

Glu Glu Ser Tyr His Leu Thr Arg Glu Gly Gly His Ser His Arg Arg
             115                 120                 125

Ile Leu His Ala Ala Asp Ala Thr Gly Arg Glu Val Glu Thr Thr Leu
            130                 135                 140

Val Ser Lys Ala Leu Asn His Pro Asn Ile Arg Val Leu Glu Arg Ser
145                 150                 155                 160

Asn Ala Val Asp Leu Ile Val Ser Asp Lys Ile Gly Leu Pro Gly Thr
                165                 170                 175

Arg Arg Val Val Gly Ala Trp Val Trp Asn Arg Asn Lys Glu Thr Val
                180                 185                 190

Glu Thr Cys His Ala Lys Ala Val Val Leu Ala Thr Gly Gly Ala Ser
            195                 200                 205

Lys Val Tyr Gln Tyr Thr Thr Asn Pro Asp Ile Ser Ser Gly Asp Gly
            210                 215                 220

Ile Ala Met Ala Trp Arg Ala Gly Cys Arg Val Ala Asn Leu Glu Phe
225                 230                 235                 240

Asn Gln Phe His Pro Thr Ala Leu Tyr His Pro Gln Ala Arg Asn Phe
                245                 250                 255

Leu Leu Thr Glu Ala Leu Arg Gly Glu Gly Ala Tyr Leu Lys Arg Pro
                260                 265                 270

Asp Gly Thr Arg Phe Met Pro Asp Phe Asp Glu Arg Gly Glu Leu Ala
            275                 280                 285

Pro Arg Asp Ile Val Ala Arg Ala Ile Asp His Glu Met Lys Arg Leu
290                 295                 300

Gly Ala Asp Cys Met Phe Leu Asp Ile Ser His Lys Pro Ala Asp Phe
305                 310                 315                 320

Ile Arg Gln His Phe Pro Met Ile Tyr Glu Lys Leu Leu Gly Leu Gly
                325                 330                 335

Ile Asp Leu Thr Gln Glu Pro Val Pro Ile Val Pro Ala Ala His Tyr
            340                 345                 350

Thr Cys Gly Gly Val Met Val Asp His Gly Arg Thr Asp Val Glu
            355                 360                 365

Gly Leu Tyr Ala Ile Gly Glu Val Ser Tyr Thr Gly Leu His Gly Ala
            370                 375                 380

Asn Arg Met Ala Ser Asn Ser Leu Leu Glu Cys Leu Val Tyr Gly Trp
385                 390                 395                 400

Ser Ala Ala Glu Asp Ile Thr Arg Arg Met Pro Tyr Ala His Asp Ile
                405                 410                 415

Ser Thr Leu Pro Pro Trp Asp Glu Ser Arg Val Glu Asn Pro Asp Glu
            420                 425                 430

Arg Val Val Ile Gln His Asn Trp His Glu Leu Arg Leu Phe Met Trp
                435                 440                 445

Asp Tyr Val Gly Ile Val Arg Thr Thr Lys Arg Leu Glu Arg Ala Leu
            450                 455                 460
```

```
Arg Arg Ile Thr Met Leu Gln Gln Glu Ile Asp Glu Tyr Tyr Ala His
465                 470                 475                 480

Phe Arg Val Ser Asn Asn Leu Leu Glu Leu Arg Asn Leu Val Gln Val
            485                 490                 495

Ala Glu Leu Ile Val Arg Cys Ala Met Met Arg Lys Glu Ser Arg Gly
            500                 505                 510

Leu His Phe Thr Leu Asp Tyr Pro Glu Leu Leu Thr His Ser Gly Pro
            515                 520                 525

Ser Ile Leu Ser Pro Gly Asn His Tyr Ile Asn Arg
530                 535                 540

<210> SEQ ID NO 98
<211> LENGTH: 531
<212> TYPE: PRT
<213> ORGANISM: Bacillus subtilis

<400> SEQUENCE: 98

Met Ser Lys Lys Thr Ile Ala Val Ile Gly Ser Gly Ala Ala Ala Leu
1               5                   10                  15

Ser Leu Ala Ala Ala Phe Pro Pro Ser Tyr Glu Val Thr Val Ile Thr
            20                  25                  30

Lys Lys Ser Val Lys Asn Ser Asn Ser Val Tyr Ala Gln Gly Gly Ile
            35                  40                  45

Ala Ala Ala Tyr Ala Lys Asp Asp Ser Ile Glu Ala His Leu Glu Asp
        50                  55                  60

Thr Leu Tyr Ala Gly Cys Gly His Asn Asn Leu Ala Ile Val Ala Asp
65                  70                  75                  80

Val Leu His Asp Gly Lys Met Met Val Gln Ser Leu Leu Glu Arg Gly
                85                  90                  95

Phe Pro Phe Asp Arg Asn Glu Arg Gly Gly Val Cys Leu Gly Arg Glu
            100                 105                 110

Gly Ala His Ser Tyr Asn Arg Ile Phe His Ala Gly Gly Asp Ala Thr
            115                 120                 125

Gly Arg Leu Leu Ile Asp Tyr Leu Leu Lys Arg Ile Asn Ser Lys Ile
    130                 135                 140

Lys Leu Ile Glu Asn Glu Thr Ala Ala Asp Leu Leu Ile Glu Asp Gly
145                 150                 155                 160

Arg Cys Ile Gly Val Met Thr Lys Asp Ser Lys Gly Arg Leu Lys Val
                165                 170                 175

Arg His Ala Asp Glu Val Val Leu Ala Ala Gly Gly Cys Gly Asn Leu
            180                 185                 190

Phe Leu His His Thr Asn Asp Leu Thr Val Thr Gly Asp Gly Leu Ser
        195                 200                 205

Leu Ala Tyr Arg Ala Gly Ala Glu Leu Thr Asp Leu Glu Phe Thr Gln
    210                 215                 220

Phe His Pro Thr Leu Leu Val Lys Asn Gly Val Ser Tyr Gly Leu Val
225                 230                 235                 240

Ser Glu Ala Val Arg Gly Glu Gly Gly Cys Leu Val Asp Glu Asn Gly
                245                 250                 255

Arg Arg Ile Met Ala Glu Arg His Pro Leu Gly Asp Leu Ala Pro Arg
            260                 265                 270

Asp Ile Val Ser Arg Val Ile His Glu Glu Met Ala Lys Gly Asn Arg
        275                 280                 285

Val Tyr Ile Asp Phe Ser Ala Ile Ser Asp Phe Glu Thr Arg Phe Pro
    290                 295                 300
```

```
Thr Ile Thr Ala Ile Cys Glu Lys Ala Gly Ile Asp Ile His Ser Gly
305                 310                 315                 320

Lys Ile Pro Val Ala Pro Gly Met His Phe Leu Met Gly Gly Val Ser
                325                 330                 335

Val Asn Arg Trp Gly Glu Thr Thr Val Pro Gly Leu Tyr Ala Ile Gly
            340                 345                 350

Glu Thr Ala Cys Ser Gly Leu His Gly Ala Asn Arg Leu Ala Ser Asn
        355                 360                 365

Ser Leu Leu Glu Ala Leu Val Phe Gly Lys Arg Ala Ala Glu His Ile
370                 375                 380

Ile Gln Lys Pro Val Tyr Asn Arg Gln Tyr Gln Ser Gly Leu Glu Thr
385                 390                 395                 400

Ser Val Phe Tyr Glu Val Pro Asp Ile Glu Gly His Glu Leu Gln Ser
                405                 410                 415

Lys Met Thr Ser His Met Ser Ile Leu Arg Glu Gln Ser Ser Leu Ile
            420                 425                 430

Glu Leu Ser Ile Trp Leu His Thr Leu Pro Phe Gln Glu Val Asn Val
        435                 440                 445

Lys Asp Ile Thr Ile Arg Gln Met Glu Leu Ser His Leu Trp Gln Thr
450                 455                 460

Ala Lys Leu Met Thr Phe Ser Ala Leu Leu Arg Glu Glu Ser Arg Gly
465                 470                 475                 480

Ala His Phe Arg Thr Asp Phe Pro His Ala Glu Val Ser Trp Gln Gly
                485                 490                 495

Arg Gln Ile Val His Thr Lys Lys Gly Thr Lys Ile Arg Lys Asn Glu
            500                 505                 510

Gly Ile Trp Asn Asn Glu Ser Phe Thr Ala Lys Ile Thr Glu Ser
        515                 520                 525

Leu Phe Ser
    530

<210> SEQ ID NO 99
<211> LENGTH: 241
<212> TYPE: PRT
<213> ORGANISM: thermophilic bacterium PS3

<400> SEQUENCE: 99

Met Thr Val Leu Ile Ile Gly Met Gly Asn Ile Gly Lys Lys Leu Val
1               5                   10                  15

Glu Leu Gly Asn Phe Glu Lys Ile Tyr Ala Tyr Asp Arg Ile Ser Lys
            20                  25                  30

Asp Ile Pro Gly Val Val Arg Leu Asp Glu Phe Gln Val Pro Ser Asp
        35                  40                  45

Val Ser Thr Val Val Glu Cys Ala Ser Pro Glu Ala Val Lys Glu Tyr
    50                  55                  60

Ser Leu Gln Ile Leu Lys Asn Pro Val Asn Tyr Ile Ile Ser Thr
65                  70                  75                  80

Ser Ala Phe Ala Asp Glu Val Phe Arg Glu Arg Phe Ser Glu Leu
                85                  90                  95

Lys Asn Ser Pro Ala Arg Val Phe Phe Pro Ser Gly Ala Ile Gly Gly
            100                 105                 110

Leu Asp Val Leu Ser Ser Ile Lys Asp Phe Val Lys Asn Val Arg Ile
        115                 120                 125

Glu Thr Ile Lys Pro Pro Lys Ser Leu Gly Leu Asp Leu Lys Gly Lys
```

```
                130                 135                 140
Thr Val Val Phe Glu Gly Ser Val Glu Ala Ser Lys Leu Phe Pro
145                 150                 155                 160

Arg Asn Ile Asn Val Ala Ser Thr Ile Gly Leu Ile Val Gly Phe Glu
                165                 170                 175

Lys Val Lys Val Thr Ile Val Ala Asp Pro Ala Met Asp His Asn Ile
                180                 185                 190

His Ile Val Arg Ile Ser Ser Ala Ile Gly Asn Tyr Glu Phe Lys Ile
                195                 200                 205

Glu Asn Ile Pro Ser Pro Glu Asn Pro Lys Thr Ser Met Leu Thr Val
                210                 215                 220

Tyr Ser Ile Leu Arg Thr Leu Arg Asn Leu Glu Ser Lys Ile Ile Phe
225                 230                 235                 240

Gly

<210> SEQ ID NO 100
<211> LENGTH: 347
<212> TYPE: PRT
<213> ORGANISM: Escherichia coli

<400> SEQUENCE: 100

Met Ser Val Met Phe Asp Pro Asp Thr Ala Ile Tyr Pro Phe Pro Pro
1               5                   10                  15

Lys Pro Thr Pro Leu Ser Ile Asp Glu Lys Ala Tyr Tyr Arg Glu Lys
                20                  25                  30

Ile Lys Arg Leu Leu Lys Glu Arg Asn Ala Val Met Val Ala His Tyr
                35                  40                  45

Tyr Thr Asp Pro Glu Ile Gln Gln Leu Ala Glu Glu Thr Gly Gly Cys
            50                  55                  60

Ile Ser Asp Ser Leu Glu Met Ala Arg Phe Gly Ala Lys His Pro Ala
65              70                  75                  80

Ser Thr Leu Leu Val Ala Gly Val Arg Phe Met Gly Glu Thr Ala Lys
                85                  90                  95

Ile Leu Ser Pro Glu Lys Thr Ile Leu Met Pro Thr Leu Gln Ala Glu
                100                 105                 110

Cys Ser Leu Asp Leu Gly Cys Pro Val Glu Glu Phe Asn Ala Phe Cys
            115                 120                 125

Asp Ala His Pro Asp Arg Thr Val Val Val Tyr Ala Asn Thr Ser Ala
130                 135                 140

Ala Val Lys Ala Arg Ala Asp Trp Val Val Thr Ser Ser Ile Ala Val
145                 150                 155                 160

Glu Leu Ile Asp His Leu Asp Ser Leu Gly Glu Lys Ile Ile Trp Ala
                165                 170                 175

Pro Asp Lys His Leu Gly Arg Tyr Val Gln Lys Gln Thr Gly Gly Asp
                180                 185                 190

Ile Leu Cys Trp Gln Gly Ala Cys Ile Val His Asp Glu Phe Lys Thr
                195                 200                 205

Gln Ala Leu Thr Arg Leu Gln Glu Glu Tyr Pro Asp Ala Ala Ile Leu
                210                 215                 220

Val His Pro Glu Ser Pro Gln Ala Ile Val Asp Met Ala Asp Ala Val
225                 230                 235                 240

Gly Ser Thr Ser Gln Leu Ile Ala Ala Ala Lys Thr Leu Pro His Gln
                245                 250                 255

Arg Leu Ile Val Ala Thr Asp Arg Gly Ile Phe Tyr Lys Met Gln Gln
```

```
              260                 265                 270
Ala Val Pro Asp Lys Glu Leu Leu Glu Ala Pro Thr Ala Gly Glu Gly
            275                 280                 285

Ala Thr Cys Arg Ser Cys Ala His Cys Pro Trp Met Ala Met Asn Gly
        290                 295                 300

Leu Gln Ala Ile Ala Glu Ala Leu Glu Gln Glu Gly Ser Asn His Glu
305                 310                 315                 320

Val His Val Asp Glu Arg Leu Arg Glu Arg Ala Leu Val Pro Leu Asn
                325                 330                 335

Arg Met Leu Asp Phe Ala Ala Thr Leu Arg Gly
                340                 345

<210> SEQ ID NO 101
<211> LENGTH: 368
<212> TYPE: PRT
<213> ORGANISM: Bacillus subtilis

<400> SEQUENCE: 101

Met Ser Ile Leu Asp Val Ile Lys Gln Ser Asn Asp Met Met Pro Glu
1               5                   10                  15

Ser Tyr Lys Glu Leu Ser Arg Lys Asp Met Glu Thr Arg Val Ala Ala
            20                  25                  30

Ile Lys Lys Lys Phe Gly Ser Arg Leu Phe Ile Pro Gly His His Tyr
        35                  40                  45

Gln Lys Asp Glu Val Ile Gln Phe Ala Asp Gln Thr Gly Asp Ser Leu
    50                  55                  60

Gln Leu Ala Gln Val Ala Glu Lys Asn Lys Glu Ala Asp Tyr Ile Val
65                  70                  75                  80

Phe Cys Gly Val His Phe Met Ala Glu Thr Ala Asp Met Leu Thr Ser
                85                  90                  95

Glu Gln Gln Thr Val Val Leu Pro Asp Met Arg Ala Gly Cys Ser Met
            100                 105                 110

Ala Asp Met Ala Asp Met Gln Gln Thr Asn Arg Ala Trp Lys Lys Leu
        115                 120                 125

Gln His Ile Phe Gly Asp Thr Ile Ile Pro Leu Thr Tyr Val Asn Ser
    130                 135                 140

Thr Ala Glu Ile Lys Ala Phe Val Gly Lys His Gly Gly Ala Thr Val
145                 150                 155                 160

Thr Ser Ser Asn Ala Lys Lys Val Leu Glu Trp Ala Phe Thr Gln Lys
                165                 170                 175

Lys Arg Ile Leu Phe Leu Pro Asp Gln His Leu Gly Arg Asn Thr Ala
            180                 185                 190

Tyr Asp Leu Gly Ile Ala Leu Glu Asp Met Ala Val Trp Asp Pro Met
        195                 200                 205

Lys Asp Glu Leu Val Ala Glu Ser Gly His Thr Asn Val Lys Val Ile
    210                 215                 220

Leu Trp Lys Gly His Cys Ser Val His Glu Lys Phe Thr Thr Lys Asn
225                 230                 235                 240

Ile His Asp Met Arg Glu Arg Asp Pro Asp Ile Gln Ile Val His
                245                 250                 255

Pro Glu Cys Ser His Glu Val Val Thr Leu Ser Asp Asp Asn Gly Ser
            260                 265                 270

Thr Lys Tyr Ile Ile Asp Thr Ile Asn Gln Ala Pro Ala Gly Ser Lys
        275                 280                 285
```

Trp Ala Ile Gly Thr Glu Met Asn Leu Val Gln Arg Ile Ile His Glu
290                 295                 300

His Pro Asp Lys Gln Ile Glu Ser Leu Asn Pro Asp Met Cys Pro Cys
305                 310                 315                 320

Leu Thr Met Asn Arg Ile Asp Leu Pro His Leu Leu Trp Ser Leu Glu
            325                 330                 335

Gln Ile Glu Lys Gly Glu Pro Ser Gly Val Ile Lys Val Pro Lys Ala
            340                 345                 350

Ile Gln Glu Asp Ala Leu Leu Ala Leu Asn Arg Met Leu Ser Ile Thr
            355                 360                 365

<210> SEQ ID NO 102
<211> LENGTH: 298
<212> TYPE: PRT
<213> ORGANISM: Thermotoga maritima

<400> SEQUENCE: 102

Met Val Asp Glu Ile Leu Lys Leu Lys Lys Glu Lys Gly Tyr Ile Ile
1               5                   10                  15

Leu Ala His Asn Tyr Gln Ile Pro Glu Leu Gln Asp Ile Ala Asp Phe
            20                  25                  30

Val Gly Asp Ser Leu Gln Leu Ala Arg Lys Ala Met Glu Leu Ser Glu
        35                  40                  45

Lys Lys Ile Leu Phe Leu Gly Val Asp Phe Met Ala Glu Leu Val Lys
    50                  55                  60

Ile Leu Asn Pro Asp Lys Lys Val Ile Val Pro Asp Arg Ser Ala Thr
65                  70                  75                  80

Cys Pro Met Ala Asn Arg Leu Thr Pro Glu Ile Ile Arg Glu Tyr Arg
                85                  90                  95

Glu Lys Phe Pro Asp Ala Pro Val Val Leu Tyr Val Asn Ser Thr Ser
            100                 105                 110

Glu Cys Lys Thr Leu Ala Asp Val Ile Cys Thr Ser Ala Asn Ala Val
        115                 120                 125

Glu Val Val Lys Lys Leu Asp Ser Ser Val Val Ile Phe Gly Pro Asp
    130                 135                 140

Arg Asn Leu Gly Glu Tyr Val Ala Glu Lys Thr Gly Lys Lys Val Ile
145                 150                 155                 160

Thr Ile Pro Glu Asn Gly His Cys Pro Val His Gln Phe Asn Ala Glu
                165                 170                 175

Ser Ile Asp Ala Val Arg Lys Lys Tyr Pro Asp Ala Lys Val Ile Val
            180                 185                 190

His Pro Glu Cys Pro Lys Pro Val Arg Asp Lys Ala Asp Tyr Val Gly
        195                 200                 205

Ser Thr Gly Gln Met Glu Lys Ile Pro Glu Lys Asp Pro Ser Arg Ile
    210                 215                 220

Phe Val Ile Gly Thr Glu Ile Gly Met Ile His Lys Leu Lys Lys Lys
225                 230                 235                 240

Phe Pro Asp Arg Glu Phe Val Pro Leu Glu Met Ala Val Cys Val Asn
                245                 250                 255

Met Lys Lys Asn Thr Leu Glu Asn Thr Leu His Ala Leu Gln Thr Glu
            260                 265                 270

Ser Phe Glu Val Ile Leu Pro Lys Glu Val Ile Glu Lys Ala Lys Lys
        275                 280                 285

Pro Ile Leu Arg Met Phe Glu Leu Met Gly
    290                 295

<210> SEQ ID NO 103
<211> LENGTH: 4586
<212> TYPE: DNA
<213> ORGANISM: Artificial Sequence
<220> FEATURE:
<223> OTHER INFORMATION: Plasmid pLA54

<400> SEQUENCE: 103

| | | | | |
|---|---|---|---|---|
| gggtaccgag ctcgaattca ctggccgtcg ttttacaacg tcgtgactgg gaaaaccctg | | | | 60 |
| gcgttaccca acttaatcgc cttgcagcac atccccttt cgccagctgg cgtaatagcg | | | | 120 |
| aagaggcccg caccgatcgc ccttcccaac agttgcgcag cctgaatggc gaatggcgcc | | | | 180 |
| tgatgcggta ttttctcctt acgcatctgt gcggtatttc acaccgcata tggtgcactc | | | | 240 |
| tcagtacaat ctgctctgat gccgcatagt taagccagcc ccgacacccg ccaacacccg | | | | 300 |
| ctgacgcgcc ctgacgggct tgtctgctcc cggcatccgc ttacagacaa gctgtgaccg | | | | 360 |
| tctccgggag ctgcatgtgt cagaggtttt caccgtcatc accgaaacgc gcgagacgaa | | | | 420 |
| agggcctcgt gatacgccta ttttttatagg ttaatgtcat gataataatg gtttcttaga | | | | 480 |
| cgtcaggtgg cacttttcgg ggaaatgtgc gcggaacccc tatttgttta tttttctaaa | | | | 540 |
| tacattcaaa tatgtatccg ctcatgagac aataaccctg ataaatgctt caataatatt | | | | 600 |
| gaaaaaggaa gagtatgagt attcaacatt tccgtgtcgc ccttattccc ttttttgcgg | | | | 660 |
| cattttgcct tcctgttttt gctcacccag aaacgctggt gaaagtaaaa gatgctgaag | | | | 720 |
| atcagttggg tgcacgagtg ggttacatcg aactggatct caacagcggt aagatccttg | | | | 780 |
| agagttttcg ccccgaagaa cgttttccaa tgatgagcac ttttaaagtt ctgctatgtg | | | | 840 |
| gcgcggtatt atcccgtatt gacgccgggc aagagcaact cggtcgccgc atacactatt | | | | 900 |
| ctcagaatga cttggttgag tactcaccag tcacagaaaa gcatcttacg gatggcatga | | | | 960 |
| cagtaagaga attatgcagt gctgccataa ccatgagtga taacactgcg gccaacttac | | | | 1020 |
| ttctgacaac gatcggagga ccgaaggagc taaccgcttt tttgcacaac atgggggatc | | | | 1080 |
| atgtaactcg ccttgatcgt tgggaaccgg agctgaatga agccatacca aacgacgagc | | | | 1140 |
| gtgacaccac gatgcctgta gcaatggcaa caacgttgcg caaactatta actggcgaac | | | | 1200 |
| tacttactct agcttcccgg caacaattaa tagactggat ggaggcggat aaagttgcag | | | | 1260 |
| gaccacttct gcgctcggcc cttccggctg gctggtttat tgctgataaa tctggagccg | | | | 1320 |
| gtgagcgtgg gtctcgcggt atcattgcag cactggggcc agatggtaag ccctcccgta | | | | 1380 |
| tcgtagttat ctacacgacg gggagtcagg caactatgga tgaacgaaat agacagatcg | | | | 1440 |
| ctgagatagg tgcctcactg attaagcatt ggtaactgtc agaccaagtt tactcatata | | | | 1500 |
| tactttagat tgatttaaaa cttcattttt aatttaaaag gatctaggtg aagatccttt | | | | 1560 |
| ttgataatct catgaccaaa atcccttaac gtgagttttc gttccactga gcgtcagacc | | | | 1620 |
| ccgtagaaaa gatcaaagga tcttcttgag atcctttttt tctgcgcgta atctgctgct | | | | 1680 |
| tgcaaacaaa aaaaccaccg ctaccagcgg tggtttgttt gccggatcaa gagctaccaa | | | | 1740 |
| ctctttttcc gaaggtaact ggcttcagca gagcgcagat accaaatact gtccttctag | | | | 1800 |
| tgtagccgta gttaggccac cacttcaaga actctgtagc accgcctaca tacctcgctc | | | | 1860 |
| tgctaatcct gttaccagtg gctgctgcca gtggcgataa gtcgtgtctt accgggttgg | | | | 1920 |
| actcaagacg atagttaccg gataaggcgc agcggtcggg ctgaacgggg ggttcgtgca | | | | 1980 |
| cacagcccag cttggagcga acgacctaca ccgaactgag atacctacag cgtgagctat | | | | 2040 |

```
gagaaagcgc cacgcttccc gaagggagaa aggcggacag gtatccggta agcggcaggg    2100
tcggaacagg agagcgcacg agggagcttc caggggaaa  cgcctggtat ctttatagtc    2160
ctgtcgggtt tcgccacctc tgacttgagc gtcgatttt  gtgatgctcg tcagggggc    2220 ggagcctatg gaaaaacgcc agcaacgcgg ccttttacg  gttcctggcc ttttgctggc    2280
cttttgctca catgttcttt cctgcgttat ccctgattc  tgtggataac cgtattaccg    2340
cctttgagtg agctgatacc gctcgccgca gccgaacgac cgagcgcagc gagtcagtga    2400
gcgaggaagc ggaagagcgc ccaatacgca aaccgcctct ccccgcgcgt tggccgattc    2460
attaatgcag ctggcacgac aggtttcccg actggaaagc gggcagtgag cgcaacgcaa    2520
ttaatgtgag ttagctcact cattaggcac cccaggcttt acactttatg cttccggctc    2580
gtatgttgtg tggaattgtg agcggataac aatttcacac aggaaacagc tatgaccatg    2640
attacgccaa gcttgcatgc ctgcaggtcg actctagagg atccccgcat tgcggattac    2700
gtattctaat gttcagataa cttcgtatag catacattat acgaagttat ctagggattc    2760
ataaccattt tctcaatcga attacacaga acacaccgta caaacctctc tatcataact    2820
acttaatagt cacacacgta ctcgtctaaa tacacatcat cgtcctacaa gttcatcaaa    2880
gtgttggaca gacaactata ccagcatgga tctcttgtat cggttctttt ctcccgctct    2940
ctcgcaataa caatgaacac tgggtcaatc atagcctaca caggtgaaca gagtagcgtt    3000
tatacagggt ttatacggtg attcctacgg caaaaatttt tcatttctaa aaaaaaaag    3060 aaaaattttt cttccaacg  ctagaaggaa aagaaaaatc taattaaatt gatttggtga    3120
ttttctgaga gttcccttt  tcatatatcg aattttgaat ataaaaggag atcgaaaaaa    3180
tttttctatt caatctgttt tctggtttta tttgatagtt ttttttgtgta ttattattat    3240 ggattagtac tggtttatat gggttttct  gtataacttc ttttatttt agtttgttta    3300 atcttatttt gagttacatt atagttccct aactgcaaga gaagtaacat taaaactcga    3360
gatgggtaag gaaaagactc acgtttcgag gccgcgatta aattccaaca tggatgctga    3420
tttatatggg tataaatggg ctcgcgataa tgtcgggcaa tcaggtgcga caatctatcg    3480
attgtatggg aagcccgatg cgccagagtt gtttctgaaa catggcaaag gtagcgttgc    3540
caatgatgtt acagatgaga tggtcagact aaactggctg acggaattta tgcctcttcc    3600
gaccatcaag cattttatcc gtactcctga tgatgcatgg ttactcacca ctgcgatccc    3660
cggcaaaaca gcattccagg tattagaaga atatcctgat tcaggtgaaa atattgttga    3720
tgcgctggca gtgttcctgc gccggttgca ttcgattcct gtttgtaatt gtccttttaa    3780
cagcgatcgc gtatttcgtc tcgctcaggc gcaatcacga atgaataacg gtttggttga    3840
tgcgagtgat tttgatgacg agcgtaatgg ctggcctgtt gaacaagtct ggaaagaaat    3900
gcataagctt ttgccattct caccggattc agtcgtcact catggtgatt tctcacttga    3960
taaccttatt tttgacgagg ggaaattaat aggttgtatt gatgttggac gagtcggaat    4020
cgcagaccga taccaggatc ttgccatcct atggaactgc ctcggtgagt tttctccttc    4080
attacagaaa cggctttttc aaaaatatgg tattgataat cctgatatga ataaattgca    4140
gtttcatttg atgctcgatg agtttttcta agttaactt  gatactacta gattttttct    4200
cttcatttat aaaattttg  gttataattg aagctttaga agtatgaaaa atccttttt    4260 tttcattctt tgcaaccaaa ataagaagct tcttttattc attgaaatga tgaatataaa    4320
cctaacaaaa gaaaaagact cgaatatcaa acattaaaaa aaaataaaag aggttatctg    4380
ttttcccatt tagttggagt ttgcattttc taatagatag aactctcaat taatgtggat    4440
```

```
ttagtttctc tgttcgtttt tttttgtttt gttctcactg tatttacatt tctatttagt      4500
atttagttat tcatataatc tataacttcg tatagcatac attatacgaa gttatccagt      4560
gatgatacaa cgagttagcc aaggtg                                           4586
```

<210> SEQ ID NO 104
<211> LENGTH: 80
<212> TYPE: DNA
<213> ORGANISM: Artificial sequence
<220> FEATURE:
<223> OTHER INFORMATION: Primer

<400> SEQUENCE: 104

```
ttccggtttc tttgaaattt ttttgattcg gtaatctccg agcagaagga gcattgcgga       60
ttacgtattc taatgttcag                                                   80
```

<210> SEQ ID NO 105
<211> LENGTH: 81
<212> TYPE: DNA
<213> ORGANISM: Artificial sequence
<220> FEATURE:
<223> OTHER INFORMATION: Primer

<400> SEQUENCE: 105

```
gggtaataac tgatataatt aaattgaagc tctaatttgt gagtttagta caccttggct       60
aactcgttgt atcatcactg g                                                 81
```

<210> SEQ ID NO 106
<211> LENGTH: 38
<212> TYPE: DNA
<213> ORGANISM: Artificial sequence
<220> FEATURE:
<223> OTHER INFORMATION: Primer

<400> SEQUENCE: 106

```
gcctcgagtt ttaatgttac ttctcttgca gttaggga                               38
```

<210> SEQ ID NO 107
<211> LENGTH: 31
<212> TYPE: DNA
<213> ORGANISM: Artificial sequence
<220> FEATURE:
<223> OTHER INFORMATION: Primer

<400> SEQUENCE: 107

```
gctaaattcg agtgaaacac aggaagacca g                                      31
```

<210> SEQ ID NO 108
<211> LENGTH: 21
<212> TYPE: DNA
<213> ORGANISM: Artificial sequence
<220> FEATURE:
<223> OTHER INFORMATION: primer

<400> SEQUENCE: 108

```
tcggtgcggg cctcttcgct a                                                 21
```

<210> SEQ ID NO 109
<211> LENGTH: 21
<212> TYPE: DNA
<213> ORGANISM: Artificial sequence
<220> FEATURE:
<223> OTHER INFORMATION: Primer

<400> SEQUENCE: 109
aatgtgagtt agctcactca t                                         21

<210> SEQ ID NO 110
<211> LENGTH: 57
<212> TYPE: DNA
<213> ORGANISM: Artificial sequence
<220> FEATURE:
<223> OTHER INFORMATION: Primer

<400> SEQUENCE: 110
aattggatcc ggcgcgccgt ttaaacggcc ggccaatgtg gctgtggttt cagggtc    57

<210> SEQ ID NO 111
<211> LENGTH: 49
<212> TYPE: DNA
<213> ORGANISM: Artificial sequence
<220> FEATURE:
<223> OTHER INFORMATION: Primer

<400> SEQUENCE: 111
aatttctaga ttaattaagc ggccgcaagg ccatgaagct ttttctttc            49

<210> SEQ ID NO 112
<211> LENGTH: 24
<212> TYPE: DNA
<213> ORGANISM: Artificial sequence
<220> FEATURE:
<223> OTHER INFORMATION: Primer

<400> SEQUENCE: 112
ttctcgacgt gggccttttt cttg                                      24

<210> SEQ ID NO 113
<211> LENGTH: 49
<212> TYPE: DNA
<213> ORGANISM: Artificial sequence
<220> FEATURE:
<223> OTHER INFORMATION: Primer

<400> SEQUENCE: 113
tgcagcttta aataatcggt gtcactactt tgccttcgtt tatcttgcc            49

<210> SEQ ID NO 114
<211> LENGTH: 49
<212> TYPE: DNA
<213> ORGANISM: Artificial sequence
<220> FEATURE:
<223> OTHER INFORMATION: Primer

<400> SEQUENCE: 114
gagcaggcaa gataaacgaa ggcaaagtag tgacaccgat tatttaaag            49

<210> SEQ ID NO 115
<211> LENGTH: 49
<212> TYPE: DNA
<213> ORGANISM: Artificial sequence
<220> FEATURE:
<223> OTHER INFORMATION: Primer

<400> SEQUENCE: 115
tatggaccct gaaaccacag ccacattgta accaccacga cggttgttg            49

<210> SEQ ID NO 116
<211> LENGTH: 49

```
<212> TYPE: DNA
<213> ORGANISM: Artificial sequence
<220> FEATURE:
<223> OTHER INFORMATION: Primer

<400> SEQUENCE: 116
tttagcaaca accgtcgtgg tggttacaat gtggctgtgg tttcagggt            49

<210> SEQ ID NO 117
<211> LENGTH: 49
<212> TYPE: DNA
<213> ORGANISM: Artificial sequence
<220> FEATURE:
<223> OTHER INFORMATION: Primer

<400> SEQUENCE: 117
ccagaaaccc tatacctgtg tggacgtaag gccatgaagc tttttcttt            49

<210> SEQ ID NO 118
<211> LENGTH: 49
<212> TYPE: DNA
<213> ORGANISM: Artificial sequence
<220> FEATURE:
<223> OTHER INFORMATION: Primer

<400> SEQUENCE: 118
attggaaaga aaagcttca tggccttacg tccacacagg tatagggtt             49

<210> SEQ ID NO 119
<211> LENGTH: 22
<212> TYPE: DNA
<213> ORGANISM: Artificial sequence
<220> FEATURE:
<223> OTHER INFORMATION: Primer

<400> SEQUENCE: 119
cataagaaca cctttggtgg ag                                         22

<210> SEQ ID NO 120
<211> LENGTH: 22
<212> TYPE: DNA
<213> ORGANISM: Artificial sequence
<220> FEATURE:
<223> OTHER INFORMATION: Primer

<400> SEQUENCE: 120
aggattatca ttcataagtt tc                                         22

<210> SEQ ID NO 121
<211> LENGTH: 23
<212> TYPE: DNA
<213> ORGANISM: Artificial sequence
<220> FEATURE:
<223> OTHER INFORMATION: Primer

<400> SEQUENCE: 121
ttcttggagc tgggacatgt ttg                                        23

<210> SEQ ID NO 122
<211> LENGTH: 22
<212> TYPE: DNA
<213> ORGANISM: Artificial sequence
<220> FEATURE:
<223> OTHER INFORMATION: Primer

<400> SEQUENCE: 122
```
tgatgatatt tcataaataa tg                                              22

<210> SEQ ID NO 123
<211> LENGTH: 23
<212> TYPE: DNA
<213> ORGANISM: Artificial sequence
<220> FEATURE:
<223> OTHER INFORMATION: Primer

<400> SEQUENCE: 123
atgcgtccat ctttacagtc ctg                                             23

<210> SEQ ID NO 124
<211> LENGTH: 22
<212> TYPE: DNA
<213> ORGANISM: Artificial sequence
<220> FEATURE:
<223> OTHER INFORMATION: Primer

<400> SEQUENCE: 124
tacgtacgga ccaatcgaag tg                                              22

<210> SEQ ID NO 125
<211> LENGTH: 49
<212> TYPE: DNA
<213> ORGANISM: Artificial sequence
<220> FEATURE:
<223> OTHER INFORMATION: Primer

<400> SEQUENCE: 125
aattcgtttg agtacactac taatggcttt gttggcaata tgttttttgc                49

<210> SEQ ID NO 126
<211> LENGTH: 49
<212> TYPE: DNA
<213> ORGANISM: Artificial sequence
<220> FEATURE:
<223> OTHER INFORMATION: Primer

<400> SEQUENCE: 126
atatagcaaa aacatattgc caacaaagcc attagtagtg tactcaaac                 49

<210> SEQ ID NO 127
<211> LENGTH: 49
<212> TYPE: DNA
<213> ORGANISM: Artificial sequence
<220> FEATURE:
<223> OTHER INFORMATION: Primer

<400> SEQUENCE: 127
tatggaccct gaaaccacag ccacattctt gttatttata aaaagacac                 49

<210> SEQ ID NO 128
<211> LENGTH: 49
<212> TYPE: DNA
<213> ORGANISM: Artificial sequence
<220> FEATURE:
<223> OTHER INFORMATION: Primer

<400> SEQUENCE: 128
ctcccgtgtc tttttataaa taacaagaat gtggctgtgg tttcagggt                 49

<210> SEQ ID NO 129
<211> LENGTH: 49
<212> TYPE: DNA
<213> ORGANISM: Artificial sequence

```
<220> FEATURE:
<223> OTHER INFORMATION: Primer

<400> SEQUENCE: 129
taccgtaggc gtccttagga aagatagaag gccatgaagc tttttcttt                49

<210> SEQ ID NO 130
<211> LENGTH: 49
<212> TYPE: DNA
<213> ORGANISM: Artificial sequence
<220> FEATURE:
<223> OTHER INFORMATION: Primer

<400> SEQUENCE: 130
attggaaaga aaaagcttca tggccttcta tctttcctaa ggacgccta                49

<210> SEQ ID NO 131
<211> LENGTH: 21
<212> TYPE: DNA
<213> ORGANISM: Artificial sequence
<220> FEATURE:
<223> OTHER INFORMATION: Primer

<400> SEQUENCE: 131
ttattgtttg gcatttgtag c                                              21

<210> SEQ ID NO 132
<211> LENGTH: 22
<212> TYPE: DNA
<213> ORGANISM: Artificial sequence
<220> FEATURE:
<223> OTHER INFORMATION: Primer

<400> SEQUENCE: 132
ccaagcatct cataaaccta tg                                             22

<210> SEQ ID NO 133
<211> LENGTH: 22
<212> TYPE: DNA
<213> ORGANISM: Artificial sequence
<220> FEATURE:
<223> OTHER INFORMATION: Primer

<400> SEQUENCE: 133
tgtgcagatg cagatgtgag ac                                             22

<210> SEQ ID NO 134
<211> LENGTH: 17
<212> TYPE: DNA
<213> ORGANISM: Artificial sequence
<220> FEATURE:
<223> OTHER INFORMATION: Primer

<400> SEQUENCE: 134
agttattgat accgtac                                                   17

<210> SEQ ID NO 135
<211> LENGTH: 19
<212> TYPE: DNA
<213> ORGANISM: Artificial sequence
<220> FEATURE:
<223> OTHER INFORMATION: Primer

<400> SEQUENCE: 135
cgagataccg taggcgtcc                                                 19
```

<210> SEQ ID NO 136
<211> LENGTH: 24
<212> TYPE: DNA
<213> ORGANISM: Artificial sequence
<220> FEATURE:
<223> OTHER INFORMATION: Primer

<400> SEQUENCE: 136
ttatgtatgc tcttctgact tttc                                            24

<210> SEQ ID NO 137
<211> LENGTH: 49
<212> TYPE: DNA
<213> ORGANISM: Artificial sequence
<220> FEATURE:
<223> OTHER INFORMATION: Primer

<400> SEQUENCE: 137
aataattaga gattaaatcg ctcattttttt gccagtttct tcaggcttc                49

<210> SEQ ID NO 138
<211> LENGTH: 49
<212> TYPE: DNA
<213> ORGANISM: Artificial sequence
<220> FEATURE:
<223> OTHER INFORMATION: Primer

<400> SEQUENCE: 138
agcctgaaga aactggcaaa aaatgagcga tttaatctct aattattag                49

<210> SEQ ID NO 139
<211> LENGTH: 49
<212> TYPE: DNA
<213> ORGANISM: Artificial sequence
<220> FEATURE:
<223> OTHER INFORMATION: Primer

<400> SEQUENCE: 139
tatggaccct gaaaccacag ccacattttt caatcattgg agcaatcat                49

<210> SEQ ID NO 140
<211> LENGTH: 49
<212> TYPE: DNA
<213> ORGANISM: Artificial sequence
<220> FEATURE:
<223> OTHER INFORMATION: Primer

<400> SEQUENCE: 140
taaaatgatt gctccaatga ttgaaaaatg tggctgtggt ttcagggtc                49

<210> SEQ ID NO 141
<211> LENGTH: 49
<212> TYPE: DNA
<213> ORGANISM: Artificial sequence
<220> FEATURE:
<223> OTHER INFORMATION: Primer

<400> SEQUENCE: 141
accgtaggtg ttgtttggga aagtggaagg ccatgaagct ttttctttc                49

<210> SEQ ID NO 142
<211> LENGTH: 49
<212> TYPE: DNA
<213> ORGANISM: Artificial sequence
<220> FEATURE:
<223> OTHER INFORMATION: Primer

<400> SEQUENCE: 142
ttggaaagaa aaagcttcat ggccttccac tttcccaaac aacacctac      49

<210> SEQ ID NO 143
<211> LENGTH: 23
<212> TYPE: DNA
<213> ORGANISM: Artificial sequence
<220> FEATURE:
<223> OTHER INFORMATION: Primer

<400> SEQUENCE: 143
ttattgctta gcgttggtag cag                                  23

<210> SEQ ID NO 144
<211> LENGTH: 21
<212> TYPE: DNA
<213> ORGANISM: Artificial sequence
<220> FEATURE:
<223> OTHER INFORMATION: Primer

<400> SEQUENCE: 144
tttttggtgg ttccggcttc c                                    21

<210> SEQ ID NO 145
<211> LENGTH: 22
<212> TYPE: DNA
<213> ORGANISM: Artificial sequence
<220> FEATURE:
<223> OTHER INFORMATION: Primer

<400> SEQUENCE: 145
aaagttggca tagcggaaac tt                                   22

<210> SEQ ID NO 146
<211> LENGTH: 16
<212> TYPE: DNA
<213> ORGANISM: Artificial sequence
<220> FEATURE:
<223> OTHER INFORMATION: Primer

<400> SEQUENCE: 146
gtcattgaca ccatct                                          16

<210> SEQ ID NO 147
<211> LENGTH: 19
<212> TYPE: DNA
<213> ORGANISM: Artificial sequence
<220> FEATURE:
<223> OTHER INFORMATION: Primer

<400> SEQUENCE: 147
agagataccg taggtgttg                                       19

<210> SEQ ID NO 148
<211> LENGTH: 33
<212> TYPE: DNA
<213> ORGANISM: Artificial sequence
<220> FEATURE:
<223> OTHER INFORMATION: Primer

<400> SEQUENCE: 148
aattggcgcg ccatgaaagc tctggtttat cac                       33

<210> SEQ ID NO 149

```
<211> LENGTH: 49
<212> TYPE: DNA
<213> ORGANISM: Artificial sequence
<220> FEATURE:
<223> OTHER INFORMATION: Primer

<400> SEQUENCE: 149
tgaatcatga gttttatgtt aattagctca ggcagcgcct gcgttcgag         49

<210> SEQ ID NO 150
<211> LENGTH: 49
<212> TYPE: DNA
<213> ORGANISM: Artificial sequence
<220> FEATURE:
<223> OTHER INFORMATION: Primer

<400> SEQUENCE: 150
atcctctcga acgcaggcgc tgcctgagct aattaacata aaactcatg         49

<210> SEQ ID NO 151
<211> LENGTH: 34
<212> TYPE: DNA
<213> ORGANISM: Artificial sequence
<220> FEATURE:
<223> OTHER INFORMATION: Primer

<400> SEQUENCE: 151
aattgtttaa acaagtaaat aaattaatca gcat                          34

<210> SEQ ID NO 152
<211> LENGTH: 49
<212> TYPE: DNA
<213> ORGANISM: Artificial sequence
<220> FEATURE:
<223> OTHER INFORMATION: Primer

<400> SEQUENCE: 152
acacaataca ataacaagaa gaacaaaatg aaagctctgg tttatcacg         49

<210> SEQ ID NO 153
<211> LENGTH: 49
<212> TYPE: DNA
<213> ORGANISM: Artificial sequence
<220> FEATURE:
<223> OTHER INFORMATION: Primer

<400> SEQUENCE: 153
agcgtataca tctgttggga aagtagaagg ccatgaagct ttttcttc          49

<210> SEQ ID NO 154
<211> LENGTH: 49
<212> TYPE: DNA
<213> ORGANISM: Artificial sequence
<220> FEATURE:
<223> OTHER INFORMATION: Primer

<400> SEQUENCE: 154
ttggaaagaa aaagcttcat ggccttctac tttcccaaca gatgtatac         49

<210> SEQ ID NO 155
<211> LENGTH: 22
<212> TYPE: DNA
<213> ORGANISM: Artificial sequence
<220> FEATURE:
<223> OTHER INFORMATION: Primer

<400> SEQUENCE: 155
```
ttattgttta gcgttagtag cg								22

<210> SEQ ID NO 156
<211> LENGTH: 72
<212> TYPE: DNA
<213> ORGANISM: Artificial sequence
<220> FEATURE:
<223> OTHER INFORMATION: Primer

<400> SEQUENCE: 156
cataatcaat ctcaaagaga acaacacaat acaataacaa gaagaacaaa atgaaagctc								60 tggtttatca cg								72

<210> SEQ ID NO 157
<211> LENGTH: 21
<212> TYPE: DNA
<213> ORGANISM: Artificial sequence
<220> FEATURE:
<223> OTHER INFORMATION: primer

<400> SEQUENCE: 157
taggcataat caccgaagaa g								21

<210> SEQ ID NO 158
<211> LENGTH: 21
<212> TYPE: DNA
<213> ORGANISM: Artificial sequence
<220> FEATURE:
<223> OTHER INFORMATION: primer

<400> SEQUENCE: 158
aaaatggtaa gcagctgaaa g								21

<210> SEQ ID NO 159
<211> LENGTH: 17
<212> TYPE: DNA
<213> ORGANISM: Artificial sequence
<220> FEATURE:
<223> OTHER INFORMATION: primer

<400> SEQUENCE: 159
agttgttaga actgttg								17

<210> SEQ ID NO 160
<211> LENGTH: 19
<212> TYPE: DNA
<213> ORGANISM: Artificial sequence
<220> FEATURE:
<223> OTHER INFORMATION: Primer

<400> SEQUENCE: 160
gacgatagcg tatacatct								19

<210> SEQ ID NO 161
<211> LENGTH: 22
<212> TYPE: DNA
<213> ORGANISM: Artificial sequence
<220> FEATURE:
<223> OTHER INFORMATION: Primer

<400> SEQUENCE: 161
cttagcctct agccatagcc at								22

<210> SEQ ID NO 162

```
<211> LENGTH: 23
<212> TYPE: DNA
<213> ORGANISM: Artificial sequence
<220> FEATURE:
<223> OTHER INFORMATION: Primer

<400> SEQUENCE: 162
ttagttttgc tggccgcatc ttc                                          23

<210> SEQ ID NO 163
<211> LENGTH: 21
<212> TYPE: DNA
<213> ORGANISM: Artificial sequence
<220> FEATURE:
<223> OTHER INFORMATION: Primer

<400> SEQUENCE: 163
cccattaata tactattgag a                                            21

<210> SEQ ID NO 164
<211> LENGTH: 7523
<212> TYPE: DNA
<213> ORGANISM: Artificial sequence
<220> FEATURE:
<223> OTHER INFORMATION: Plasmid

<400> SEQUENCE: 164
ccagcttttg ttccctttag tgagggttaa ttgcgcgctt ggcgtaatca tggtcatagc    60
tgtttcctgt gtgaaattgt tatccgctca caattccaca acatagga gccggaagca    120 taaagtgtaa agcctggggt gcctaatgag tgaggtaact cacattaatt gcgttgcgct   180
cactgcccgc tttccagtcg ggaaacctgt cgtgccagct gcattaatga atcggccaac   240
gcgcggggag aggcggtttg cgtattgggc gctcttccgc ttcctcgctc actgactcgc   300
tgcgctcggt cgttcggctg cggcgagcgg tatcagctca ctcaaaggcg gtaatacggt   360
tatccacaga atcaggggat aacgcaggaa agaacatgtg agcaaaaggc cagcaaaagg   420
ccaggaaccg taaaaaggcc gcgttgctgg cgtttttcca taggctccgc cccctgacg   480 agcatcacaa aaatcgacgc tcaagtcaga ggtggcgaaa cccgacagga ctataaagat   540
accaggcgtt tcccctgga agctccctcg tgcgctctcc tgttccgacc ctgccgctta   600
ccggatacct gtccgccttt ctcccttcgg aagcgtggc gctttctcat agctcacgct   660
gtaggtatct cagttcggtg taggtcgttc gctccaagct gggctgtgtg cacgaacccc   720
ccgttcagcc cgaccgctgc gccttatccg gtaactatcg tcttgagtcc aacccggtaa   780
gacacgactt atcgccactg gcagcagcca ctggtaacag gattagcaga gcgaggtatg   840
taggcggtgc tacagagttc ttgaagtggt ggcctaacta cggctacact agaaggacag   900
tatttggtat ctgcgctctg ctgaagccag ttaccttcgg aaaaagagtt ggtagctctt   960
gatccggcaa acaaaccacc gctggtagcg tggtttttt tgtttgcaag cagcagatta   1020
cgcgcagaaa aaaggatct caagaagatc ctttgatctt ttctacgggg tctgacgctc   1080
agtggaacga aaactcacgt taagggattt tggtcatgag attatcaaaa aggatcttca   1140
cctagatcct tttaaattaa aaatgaagtt ttaaatcaat ctaaagtata tatgagtaaa   1200
cttggtctga cagttaccaa tgcttaatca gtgaggcacc tatctcagcg atctgtctat   1260
ttcgttcatc catagttgcc tgactcccg tcgtgtagat aactacgata cgggagggct   1320
taccatctgg ccccagtgct gcaatgatac cgcgagaccc acgctcaccg gctccagatt   1380
tatcagcaat aaaccagcca gccggaaggg ccgagcgcag aagtggtcct gcaactttat   1440
```

```
ccgcctccat ccagtctatt aattgttgcc gggaagctag agtaagtagt tcgccagtta    1500
atagtttgcg caacgttgtt gccattgcta caggcatcgt ggtgtcacgc tcgtcgtttg    1560
gtatggcttc attcagctcc ggttcccaac gatcaaggcg agttacatga tcccccatgt    1620
tgtgcaaaaa agcggttagc tccttcggtc ctccgatcgt tgtcagaagt aagttggccg    1680
cagtgttatc actcatggtt atggcagcac tgcataattc tcttactgtc atgccatccg    1740
taagatgctt ttctgtgact ggtgagtact caaccaagtc attctgagaa tagtgtatgc    1800
ggcgaccgag ttgctcttgc ccggcgtcaa tacgggataa taccgcgcca catagcagaa    1860
ctttaaaagt gctcatcatt ggaaaacgtt cttcggggcg aaaactctca aggatcttac    1920
cgctgttgag atccagttcg atgtaaccca ctcgtgcacc caactgatct tcagcatctt    1980
ttactttcac cagcgtttct gggtgagcaa aaacaggaag gcaaaatgcc gcaaaaaagg    2040
gaataagggc gacacggaaa tgttgaatac tcatactctt cctttttcaa tattattgaa    2100
gcatttatca gggttattgt ctcatgagcg gatacatatt tgaatgtatt tagaaaaata    2160
aacaaatagg ggttccgcgc acatttcccc gaaaagtgcc acctgaacga agcatctgtg    2220
cttcattttg tagaacaaaa atgcaacgcg agagcgctaa ttttcaaac aaagaatctg    2280 agctgcattt ttacagaaca gaaatgcaac gcgaaagcgc tattttacca acgaagaatc    2340
tgtgcttcat ttttgtaaaa caaaaatgca acgcgagagc gctaattttt caaacaaaga    2400
atctgagctg cattttttaca gaacagaaat gcaacgcgag agcgctattt taccaacaaa    2460
gaatctatac ttcttttttg ttctacaaaa atgcatcccg agagcgctat ttttctaaca    2520
aagcatctta gattactttt tttctccttt gtgcgctcta atgcagtc tcttgataac    2580 ttttgcact gtaggtccgt taaggttaga agaaggctac tttggtgtct attttctctt    2640
ccataaaaaa agcctgactc cacttcccgc gtttactgat tactagcgaa gctgcgggtg    2700 catttttca agataaaggc atccccgatt atattctata ccgatgtgga ttgcgcatac    2760
tttgtgaaca gaaagtgata gcgttgatga ttcttcattg gtcagaaaat tatgaacggt    2820
ttcttctatt ttgtctctat atactacgta taggaaatgt ttacattttc gtattgtttt    2880
cgattcactc tatgaatagt tcttactaca atttttttgt ctaaagagta atactagaga    2940
taaacataaa aaatgtagag gtcgagttta gatgcaagtt caaggagcga aaggtggatg    3000
ggtaggttat atagggatat agcacagaga tatatagcaa agagatactt ttgagcaatg    3060
tttgtggaag cggtattcgc aatattttag tagctcgtta cagtccggtg cgttttggt    3120 tttttgaaag tgcgtcttca gagcgcttt ggttttcaaa agcgctctga agttcctata    3180
ctttctagag aataggaact tcggaatagg aacttcaaag cgtttccgaa acgagcgct    3240 tccgaaaatg caacgcgagc tgcgcacata cagctcactg ttcacgtcgc acctatatct    3300
gcgtgttgcc tgtatatata tacatgag aagaacggca tagtgcgtgt ttatgcttaa    3360
atgcgtactt atatgcgtct atttatgtag gatgaaaggt agtctagtac ctcctgtgat    3420
attatcccat tccatgcggg gtatcgtatg cttccttcag cactaccctt tagctgttct    3480
atatgctgcc actcctcaat tggattagtc tcatccttca atgctatcat ttcctttgat    3540
attggatcat ctaagaaacc attattatca tgacattaac ctataaaaat aggcgtatca    3600
cgaggccctt tcgtctcgcg cgtttcggtg atgacggtga aaacctctga cacatgcagc    3660
tcccggagac ggtcacagct tgtctgtaag cggatgccgg gagcagacaa gcccgtcagg    3720
gcgcgtcagc gggtgttggc gggtgtcggg gctggcttaa ctatgcggca tcagagcaga    3780
```

```
ttgtactgag agtgcaccat aaattcccgt tttaagagct tggtgagcgc taggagtcac    3840
tgccaggtat cgtttgaaca cggcattagt cagggaagtc ataacacagt cctttcccgc    3900
aattttcttt ttctattact cttggcctcc tctagtacac tctatatttt tttatgcctc    3960
ggtaatgatt ttcattttt ttttcccct agcggatgac tcttttttt tcttagcgat      4020 tggcattatc acataatgaa ttatacatta tataaagtaa tgtgatttct tcgaagaata    4080
tactaaaaaa tgagcaggca agataaacga aggcaaagat gacagagcag aaagccctag    4140
taaagcgtat tacaaatgaa accaagattc agattgcgat ctcttaaag ggtggtcccc     4200 tagcgataga gcactcgatc ttcccagaaa aagaggcaga agcagtagca gaacaggcca    4260
cacaatcgca agtgattaac gtccacacag gtataggggtt tctggaccat atgatacatg   4320
ctctggccaa gcattccggc tggtcgctaa tcgttgagtg cattggtgac ttacacatag    4380
acgaccatca caccactgaa gactgcggga ttgctctcgg tcaagctttt aaagaggccc    4440
tactggcgcg tggagtaaaa aggtttggat caggatttgc gcctttggat gaggcacttt    4500
ccagagcggt ggtagatctt tcgaacaggc cgtacgcagt tgtcgaactt ggtttgcaaa    4560
gggagaaagt aggagatctc tcttgcgaga tgatcccgca ttttcttgaa gctttgcag    4620 aggctagcag aattaccctc cacgttgatt gtctgcgagg caagaatgat catcaccgta    4680
gtgagagtgc gttcaaggct cttgcggttg ccataagaga agccacctcg cccaatggta    4740
ccaacgatgt tccctccacc aaaggtgttc ttatgtagtg acaccgatta tttaaagctg    4800
cagcatacga tatatataca tgtgtatata tgtataccta tgaatgtcag taagtatgta    4860
tacgaacagt atgatactga agatgacaag gtaatgcatc attctatacg tgtcattctg    4920
aacgaggcgc gctttccttt ttctttttg cttttctt tttttctct tgaactcgac       4980 ggatctatgc ggtgtgaaat accgcacaga tgcgtaagga aaaataccg catcaggaaa    5040 ttgtaaacgt taatattttg ttaaaattcg cgttaaattt tgttaaatc agctcatttt    5100 ttaaccaata ggccgaaatc ggcaaaatcc cttataaatc aaaagaatag accgagatag   5160
ggttgagtgt tgttccagtt tggaacaaga gtccactatt aaagaacgtg gactccaacg   5220
tcaaagggcg aaaaaccgtc tatcagggcg atggcccact acgtgaacca tcaccctaat   5280
caagtttttt ggggtcgagg tgccgtaaag cactaaatcg gaaccctaaa gggagccccc   5340
gatttagagc ttgacgggga aagccggcga acgtggcgag aaaggaaggg aagaaagcga   5400
aaggagcggg cgctagggcg ctggcaagtg tagcggtcac gctgcgcgta accaccacac   5460
ccgccgcgct taatgcgccg ctacaggcg cgtcgcgcca ttcgccattc aggctgcgca    5520
actgttggga agggcgatcg gtgcgggcct cttcgctatt acgccagctg gcgaaagggg   5580
gatgtgctgc aaggcgatta agttgggtaa cgccagggtt ttcccagtca cgacgttgta   5640
aaacgacggc cagtgagcgc gcgtaatacg actcactata gggcgaattg ggtaccgggc   5700
cccccctcga ggtattagaa gccgccgagc gggcgacagc cctccgacgg aagactctcc   5760
tccgtgcgtc ctcgtcttca ccggtcgcgt tcctgaaacg cagatgtgcc tcgcgccgca   5820
ctgctccgaa caataaagat tctacaatac tagctttat ggttatgaag aggaaaaatt    5880
ggcagtaacc tggccccaca aaccttcaaa ttaacgaatc aaattaacaa ccataggatg    5940
ataatgcgat tagttttta gccttatttc tggggtaatt aatcagcgaa gcgatgattt     6000
ttgatctatt aacagatata taaatggaaa agctgcataa ccactttaac taatactttc    6060
aacattttca gtttgtatta cttcttattc aaatgtcata aaagtatcaa caaaaaattg   6120
ttaatatacc tctatacttt aacgtcaagg agaaaaatgt ccaatttact gcccgtacac   6180
```

-continued

```
caaaatttgc ctgcattacc ggtcgatgca acgagtgatg aggttcgcaa gaacctgatg    6240
gacatgttca gggatcgcca ggcgttttct gagcatacct ggaaaatgct tctgtccgtt    6300
tgccggtcgt gggcggcatg gtgcaagttg aataaccgga aatggtttcc cgcagaacct    6360
gaagatgttc gcgattatct tctatatctt caggcgcgcg gtctggcagt aaaaactatc    6420
cagcaacatt tgggccagct aaacatgctt catcgtcggt ccgggctgcc acgaccaagt    6480
gacagcaatg ctgtttcact ggttatgcgg cggatccgaa agaaaacgt tgatgccggt     6540 gaacgtgcaa acaggctct agcgttcgaa cgcactgatt tcgaccaggt tcgttcactc     6600
atggaaaata gcgatcgctg ccaggatata cgtaatctgg catttctggg gattgcttat    6660
aacaccctgt tacgtatagc cgaaattgcc aggatcaggg ttaaagatat ctcacgtact    6720
gacggtggga gaatgttaat ccatattggc agaacgaaaa cgctggttag caccgcaggt    6780
gtagagaagg cacttagcct gggggtaact aaactggtcg agcgatggat ttccgtctct    6840
ggtgtagctg atgatccgaa taactacctg ttttgccggg tcagaaaaaa tggtgttgcc    6900
gcgccatctg ccaccagcca gctatcaact cgcgccctgg aagggatttt tgaagcaact    6960
catcgattga tttacggcgc taaggatgac tctggtcaga gatacctggc ctggtctgga    7020
cacagtgccc gtgtcggagc cgcgcgagat atggcccgcg ctggagtttc aataccggag    7080
atcatgcaag ctggtggctg gaccaatgta aatattgtca tgaactatat ccgtaacctg    7140
gatagtgaaa caggggcaat ggtgcgcctg ctggaagatg gcgattagga gtaagcgaat    7200
ttcttatgat ttatgatttt tattattaaa taagttataa aaaaaataag tgtatacaaa    7260
ttttaaagtg actcttaggt tttaaaacga aaattcttat tcttgagtaa ctctttcctg    7320
taggtcaggt tgcttttctca ggtatagcat gaggtcgctc ttattgacca cacctctacc    7380
ggcatgccga gcaaatgcct gcaaatcgct ccccatttca cccaattgta gatatgctaa    7440
ctccagcaat gagttgatga atctcggtgt gtattttatg tcctcagagg acaacacctg    7500
tggtccgcca ccgcggtgga gct                                            7523
```

<210> SEQ ID NO 165
<211> LENGTH: 15456
<212> TYPE: DNA
<213> ORGANISM: Artificial sequence
<220> FEATURE:
<223> OTHER INFORMATION: Template

<400> SEQUENCE: 165

```
aaagagtaat actagagata aacataaaaa atgtagaggt cgagtttaga tgcaagttca      60
aggagcgaaa ggtggatggg taggttatat agggatatag cacagagata tatagcaaag     120
agatactttt gagcaatgtt tgtggaagcg gtattcgcaa tattttagta gctcgttaca     180
gtccggtgcg ttttggttt tttgaaagtg cgtcttcaga gcgcttttgg ttttcaaaag     240
cgctctgaag ttcctatact ttctagagaa taggaacttc ggaataggaa cttcaaagcg     300
tttccgaaaa cgagcgcttc cgaaaatgca acgcgagctg cgcacataca gctcactgtt     360
cacgtcgcac ctatatctgc gtgttgcctg tatatatata tacatgagaa gaacggcata     420
gtgcgtgttt atgcttaaat gcgtacttat atgcgtctat ttatgtagga tgaaaggtag     480
tctagtacct cctgtgatat tatcccattc catgcggggt atcgtatgct tccttcagca     540
ctacccttta gctgttctat atgctgccac tcctcaattg gattagtctc atccttcaat     600
gctatcattt cctttgatat tggatcatac taagaaacca ttattatcat gacattaacc     660
```

```
tataaaaata ggcgtatcac gaggcccttt cgtctcgcgc gtttcggtga tgacggtgaa    720
aacctctgac acatgcagct cccggagacg tcacagctt gtctgtaagc ggatgccggg     780
agcagacaag cccgtcaggg cgcgtcagcg ggtgttggcg ggtgtcgggg ctggcttaac    840
tatgcggcat cagagcagat tgtactgaga gtgcaccata aattcccgtt ttaagagctt    900
ggtgagcgct aggagtcact gccaggtatc gtttgaacac ggcattagtc agggaagtca    960
taacacagtc ctttcccgca attttctttt tctattactc ttggcctcct ctagtacact   1020 ctatatttt ttatgcctcg gtaatgattt tcatttttt ttttccacct agcggatgac     1080
tctttttttt tcttagcgat tggcattatc acataatgaa ttatacatta tataaagtaa   1140
tgtgatttct tcgaagaata tactaaaaaa tgagcaggca agataaacga aggcaaagat   1200
gacagagcag aaagccctag taaagcgtat tacaaatgaa accaagattc agattgcgat   1260
ctctttaaag ggtggtcccc tagcgataga gcactcgatc ttcccagaaa aagaggcaga   1320
agcagtagca gaacaggcca cacaatcgca agtgattaac gtccacacag gtatagggtt   1380
tctggaccat atgatacatg ctctggccaa gcattccggc tggtcgctaa tcgttgagtg   1440
cattggtgac ttacacatag acgaccatca caccactgaa gactgcggga ttgctctcgg   1500
tcaagctttt aaagaggccc tagggccgt gcgtggagta aaaaggtttg gatcaggatt    1560
tgcgcctttg gatgaggcac tttccagagc ggtggtagat cttttcgaaca ggccgtacgc  1620 agttgtcgaa cttggtttgc aaagggagaa agtaggagat ctctcttgcg agatgatccc   1680
gcattttctt gaaagctttg cagaggctag cagaattacc ctccacgttg attgtctgcg   1740
aggcaagaat gatcatcacc gtagtgagag tgcgttcaag gctcttgcgg ttgccataag   1800
agaagccacc tcgcccaatg gtaccaacga tgttccctcc accaaaggtg ttcttatgta   1860
gtgacaccga ttatttaaag ctgcagcata cgatatatat acatgtgtat atatgtatac   1920
ctatgaatgt cagtaagtat gtatacgaac agtatgatac tgaagatgac aaggtaatgc   1980
atcattctat acgtgtcatt ctgaacgagg cgcgctttcc tttttttcttt ttgctttttc  2040 ttttttttttc tcttgaactc gacggatcta tgcggtgtga ataccgcac agatgcgtaa   2100 ggagaaaata ccgcatcagg aaattgtaag cgttaatatt ttgttaaaat tcgcgttaaa   2160 ttttttgttaa atcagctcat tttttaacca ataggccgaa atcggcaaaa tcccttataa   2220
atcaaaagaa tagaccgaga tagggttgag tgttgttcca gtttggaaca agagtccact   2280
attaaagaac gtggactcca acgtcaaagg gcgaaaaacc gtctatcagg gcgatggccc   2340
actacgtgaa ccatcaccct aatcaagttt tttggggtcg aggtgccgta aagcactaaa   2400
tcggaaccct aaagggagcc ccgatttag agcttgacgg ggaaagccgg cgaacgtggc   2460
gagaaaggaa gggaagaaag cgaaaggagc gggcgctagg gcgctggcaa gtgtagcggt   2520
cacgctgcgc gtaaccacca cacccgccgc gcttaatgcg ccgctacagg gcgcgtccat   2580
tcgccattca ggctgcgcaa ctgttgggaa gggcgcggtg cgggcctctt cgctattacg   2640
ccagctggcg aaagggggat gtgctgcaag gcgattaagt tgggtaacgc cagggttttc   2700
ccagtcacga cgttgtaaaa cgacggccag tgagcgcgcg taatacgact cactataggg   2760
cgaattgggt accggccccc cctcgaggt cgacggcgcg ccactggtag agagcgactt    2820
tgtatgcccc aattgcgaaa cccgcgatat ccttctcgat tctttagtac ccgaccagga   2880
caaggaaaag gaggtcgaaa cgttttgaa gaaacaagag gaactacacg gaagctctaa    2940
agatggcaac cagccagaaa ctaagaaat gaagttgatg gatccaactg gcaccgctgg   3000
cttgaacaac aataccagcc ttccaacttc tgtaaataac ggcggtacgc cagtgccacc   3060
```

```
agtaccgtta cctttcggta tacctccttt ccccatgttt ccaatgccct tcatgcctcc   3120
aacggctact atcacaaatc ctcatcaagc tgacgcaagc cctaagaaat gaataacaat   3180
actgacagta ctaaataatt gcctacttgg cttcacatac gttgcatacg tcgatataga   3240
taataatgat aatgacagca ggattatcgt aatacgtaat agctgaaaat ctcaaaaatg   3300
tgtgggtcat tacgtaaata atgataggaa tgggattctt ctattttttcc tttttccatt  3360 ctagcagccg tcgggaaaac gtggcatcct ctctttcggg ctcaattgga gtcacgctgc   3420
cgtgagcatc ctctctttcc atatctaaca actgagcacg taaccaatgg aaaagcatga   3480
gcttagcgtt gctccaaaaa agtattggat ggttaatacc atttgtctgt tctcttctga   3540
ctttgactcc tcaaaaaaaa aaatctacaa tcaacagatc gcttcaatta cgccctcaca   3600
aaaacttttt tccttcttct tcgcccacgt taaattttat ccctcatgtt gtctaacgga   3660
tttctgcact tgatttatta taaaaagaca aagacataat acttctctat caatttcagt   3720
tattgttctt ccttgcgtta ttcttctgtt cttctttttc ttttgtcata taaccata    3780 accaagtaat acatattcaa actagtatga ctgacaaaaa aactcttaaa gacttaagaa   3840
atcgtagttc tgtttacgat tcaatggtta aatcacctaa tcgtgctatg ttgcgtgcaa   3900
ctggtatgca agatgaagac tttgaaaaac ctatcgtcgg tgtcatttca acttgggctg   3960
aaaacacacc ttgtaatatc cacttacatg actttggtaa actagccaaa gtcggtgtta   4020
aggaagctgg tgcttggcca gttcagttcg gaacaatcac ggtttctgat ggaatcgcca   4080
tgggaaccca aggaatgcgt ttctccttga catctcgtga tattattgca gattctattg   4140
aagcagccat gggaggtcat aatgcggatg cttttgtagc cattggcggt tgtgataaaa   4200
acatgcccgg ttctgttatc gctatggcta acatggatat cccagccatt tttgcttacg   4260
gcggaacaat tgcacctggt aatttagacg gcaaagatat cgatttagtc tctgtctttg   4320
aaggtgtcgg ccattggaac cacggcgata tgaccaaaga agaagttaaa gctttggaat   4380
gtaatgcttg tcccggtcct ggaggctgcg gtggtatgta tactgctaac acaatggcga   4440
cagctattga agttttggga cttagccttc cgggttcatc ttctcacccg gctgaatccg   4500
cagaaaagaa agcagatatt gaagaagctg gtcgcgctgt tgtcaaaatg ctcgaaatgg   4560
gcttaaaacc ttctgacatt ttaacgcgtg aagcttttga agatgctatt actgtaacta   4620
tggctctggg aggttcaacc aactcaaccc ttcacctctt agctattgcc catgctgcta   4680
atgtggaatt gacacttgat gatttcaata cttttccaaga aaagttcct catttggctg   4740 atttgaaacc ttctggtcaa tatgtattcc aagacctttta caaggtcgga ggggtaccag   4800
cagttatgaa atatctcctt aaaaatggct tccttcatgg tgaccgtatc acttgtactg   4860
gcaaaacagt cgctgaaaat ttgaaggctt ttgatgattt aacacctggt caaaaggtta   4920
ttatgccgct tgaaaatcct aaacgtgaag atggtccgct cattattctc catggtaact   4980
tggctccaga cggtgccgtt gccaaagttt ctggtgtaaa agtgcgtcgt catgtcggtc   5040
ctgctaaggt ctttaattct gaagaagaag ccattgaagc tgtcttgaat gatgatattg   5100
ttgatggtga tgttgttgtc gtacgttttg taggaccaaa gggcggtcct ggtatgcctg   5160
aaatgctttc cctttcatca atgattgttg gtaaaggca aggtgaaaaa gttgcccttc    5220
tgacagatgg ccgcttctca ggtggtactt atggtcttgt cgtgggtcat atcgctcctg   5280
aagcacaaga tggcggtcca atcgcctacc tgcaaacagg agacatagtc actattgacc   5340
aagacactaa ggaattacac tttgatatct ccgatgaaga gttaaaacat cgtcaagaga   5400
```

```
ccattgaatt gccaccgctc tattcacgcg gtatccttgg taaatatgct cacatcgttt    5460
cgtctgcttc taggggagcc gtaacagact tttggaagcc tgaagaaact ggcaaaaaat    5520
gttgtcctgg ttgctgtggt taagcggccg cgttaattca aattaattga tatagttttt    5580
taatgagtat tgaatctgtt tagaaataat ggaatattat ttttatttat ttatttatat    5640
tattggtcgg ctcttttctt ctgaaggtca atgacaaaat gatatgaagg aaataatgat    5700
ttctaaaatt ttacaacgta agatatttt acaaaagcct agctcatctt ttgtcatgca    5760
ctatttact cacgcttgaa attaacggcc agtccactgc ggagtcattt caaagtcatc    5820
ctaatcgatc tatcgttttt gatagctcat tttggagttc gcgattgtct tctgttattc    5880
acaactgttt taattttat ttcattctgg aactcttcga gttctttgta aagtctttca    5940
tagtagctta ctttatcctc caacatattt aacttcatgt caatttcggc tcttaaattt    6000
tccacatcat caagttcaac atcatctttt aacttgaatt tattctctag ctcttccaac    6060
caagcctcat tgctccttga tttactggtg aaaagtgata cactttgcgc gcaatccagg    6120
tcaaaacttt cctgcaaaga attcaccaat ttctcgacat catagtacaa tttgttttgt    6180
tctcccatca caatttaata tacctgatgg attcttatga agcgctgggt aatggacgtg    6240
tcactctact tcgcctttt ccctactcct tttagtacgg aagacaatgc taataaataa    6300
gagggtaata ataatattat taatcggcaa aaaagattaa acgccaagcg tttaattatc    6360
agaaagcaaa cgtcgtacca atccttgaat gcttcccaat tgtatattaa gagtcatcac    6420
agcaacatat tcttgttatt aaattaatta ttattgattt ttgatattgt ataaaaaaac    6480
caaatatgta taaaaaagt gaataaaaaa taccaagtat ggagaaatat attagaagtc    6540
tatacgttaa accacccggg cccccctcg aggtcgacgg tatcgataag cttgatatcg    6600
aattcctgca gcccggggga tccactagtt ctagagcggc cgctctagaa ctagtaccac    6660
aggtgttgtc ctctgaggac ataaaataca caccgagatt catcaactca ttgctggagt    6720
tagcatatct acaattgggt gaatggggga gcgatttgca ggcatttgct cggcatgccg    6780
gtagaggtgt ggtcaataag agcgacctca tgctatacct gagaaagcaa cctgacctac    6840
aggaaagagt tactcaagaa taagaattt cgttttaaaa cctaagagtc actttaaaat    6900
ttgtatacac ttatttttt tataacttat ttaataataa aaatcataaa tcataagaaa    6960
ttcgcttact cttaattaat caggcagcgc ctgcgttcga gaggatgatc ttcatcgcct    7020
tctccttggc gccattgagg aatacctgat aggcgtgctc gatctcggcc agctcgaagc    7080
gatgggtaat catcttcttc aacggaagct tgtcggtcga ggcgaccttc atcagcatgg    7140
gcgtcgtgtt cgtgttcacc agtcccgtgg tgatcgtcag gttcttgatc cagagcttct    7200
gaatctcgaa gtcaaccttg acgccatgca cgccgacgtt ggcgatgtgc gcgccgggct    7260
tgacgatctc ctggcagatg tcccaagtcg ccggtatgcc caccgcctcg atcgcaacat    7320
cgactccctc tgccgcaatc ctatgcacgg cttcgacaac gttctccgtg ccggagttga    7380
tggtgtgcgt tgccccgagc tccttggcga gctgaggcg attctcgtcc atgtcgatca    7440
cgatgatggt cgagggggag tagaactggg cggtcaacag tacggacatg ccgacggggc    7500
ccgcgccgac aatagccacc gcatcgcccg gctggacatt cccatactgg acgccgattt    7560
cgtggccggt gggcaggatg tcgctcagca ggacggcgat ttcgtcgtca attgtctggg    7620
ggatcttgta gaggctgttg tcggcatgcg ggatgcggac gtattcggcc tgcacgccat    7680
cgatcatgta acccaggatc cacccgccgt cgcggcaatg ggagtaaagc tgcttcttgc    7740
agtagtcgca cgagccgcaa gaagtgacgc aggaaatcag gaccttgtcg cctttcttga    7800
```

```
actgcgtgac actctcgccc acttcctcga tgacgcctac cccttcatgg cccaggatgc    7860
gcccgtcggc gacctctgga ttcttgcctt tgtagatgcc gagatccgtg ccgcagatcg    7920
tggtcttcaa aacccgtact actacatccg tgggcttttg aagggtgggc ttgggcttgt    7980
cttcaagcga gatcttgtgg tcaccgtgat aaaccagagc tttcatcctc agctattgta    8040
atatgtgtgt ttgtttggat tattaagaag aataattaca aaaaaaatta caaaggaagg    8100
taattacaac agaattaaga aaggacaaga aggaggaaga gaatcagttc attatttctt    8160
ctttgttata taacaaaccc aagtagcgat ttggccatac attaaaagtt gagaaccacc    8220
ctccctggca acagccacaa ctcgttacca ttgttcatca cgatcatgaa actcgctgtc    8280
agctgaaatt tcacctcagt ggatctctct ttttattctt catcgttcca ctaacctttt    8340
tccatcagct ggcagggaac ggaaagtgga atcccattta gcgagcttcc tcttttcttc    8400
aagaaaagac gaagcttgtg tgtgggtgcg cgcgctagta tctttccaca ttaagaaata    8460
taccataaag gttacttaga catcactatg gctatatata tatatatata tatatatgta    8520
acttagcacc atcgcgcgtg catcactgca tgtgttaacc gaaaagtttg gcgaacactt    8580
caccgacacg gtcatttaga tctgtcgtct gcattgcacg tcccttagcc ttaaatccta    8640
ggcgggagca ttctcgtgta attgtgcagc ctgcgtagca actcaacata gcgtagtcta    8700
cccagttttt caagggttta tcgttagaag attctccctt ttcttcctgc tcacaaatct    8760
taaagtcata cattgcacga ctaaatgcaa gcatgcggat ccccgggct gcaggaattc     8820 gatatcaagc ttatcgatac cgtcgactgg ccattaatct ttcccatatt agatttcgcc    8880
aagccatgaa agttcaagaa aggtctttag acgaattacc cttcatttct caaactggcg    8940
tcaagggatc ctggtatggt tttatcgttt tatttctggt tcttatagca tcgttttgga    9000
cttctctgtt cccattaggc ggttcaggag ccagcgcaga atcattcttt gaaggatact    9060
tatcctttcc aattttgatt gtctgttacg ttggacataa actgtatact agaaattgga    9120
ctttgatggt gaaactagaa gatatggatc ttgataccgg cagaaaacaa gtagatttga    9180
ctcttcgtag ggaagaaatg aggattgagc gagaaacatt agcaaaaaga tccttcgtaa    9240
caagattttt acatttctgg tgttgaaggg aaagatatga gctatacagc ggaatttcca    9300
tatcactcag attttgttat ctaatttttt ccttcccacg tccgcgggaa tctgtgtata    9360
ttactgcatc tagatatatg ttatcttatc ttggcgcgta catttaattt tcaacgtatt    9420
ctataagaaa ttgcgggagt ttttttcatg tagatgatac tgactgcacg caaatatagg    9480
catgatttat aggcatgatt tgatggctgt accgatagga acgctaagag taacttcaga    9540
atcgttatcc tggcggaaaa aattcatttg taaactttaa aaaaaaagc caatatcccc      9600 aaaattatta agagcgcctc cattattaac taaaatttca ctcagcatcc acaatgtatc    9660
aggtatctac tacagatatt acatgtggcg aaaaagacaa gaacaatgca atagcgcatc    9720
aagaaaaaac acaaagcttt caatcaatga atcgaaaatg tcattaaaat agtatataaa    9780
ttgaaactaa gtcataaagc tataaaaaga aaatttattt aaatgcaaga tttaaagtaa    9840
attcacggcc ctgcaggcct cagctcttgt tttgttctgc aaataactta cccatcttt     9900 tcaaaacttt aggtgcaccc tcctttgcta gaataagttc tatccaatac atcctatttg    9960
gatctgcttg agcttctttc atcacggata cgaattcatt ttctgttctc acaattttgg   10020
acacaactct gtcttccgtt gccccgaaac tttctggcag ttttgagtaa ttccacatag   10080
gaatgtcatt ataactctgg ttcggaccat gaatttccct ctcaaccgtg taaccatcgt   10140
```

```
tattaatgat aaagcagatt gggtttatct tctctctaat ggctagtcct aattcttgga    10200
cagtcagttg caatgatcca tctccgataa acaataaatg tctagattct ttatctgcaa    10260
tttggctgcc tagagctgcg gggaaagtgt atcctataga tccccacaag ggttgaccaa    10320
taaaatgtga tttcgatttc agaaatatag atgaggcacc gaagaaagaa gtgccttgtt    10380
cagccacgat cgtctcatta ctttgggtca aattttcgac agcttgccac agtctatctt    10440
gtgacaacag cgcgttagaa ggtacaaaat cttcttgctt tttatctatg tacttgcctt    10500
tatattcaat ttcggacaag tcaagaagag atgatatcag ggattcgaag tcgaaatttt    10560
ggattctttc gttgaaaatt ttaccttcat cgatattcaa ggaaatcatt ttattttcat    10620
taagatggtg agtaaatgca cccgtactag aatcggtaag ctttacaccc aacataagaa    10680
taaaatcagc agattccaca aattccttca agtttggctc tgacagagta ccgttgtaaa    10740
tccccaaaaa tgagggcaat gcttcatcaa cagatgattt accaaagttc aaagtagtaa    10800
taggtaactt agtctttgaa ataaactgag taacagtctt ctctaggccg aacgatataa    10860
tttcatggcc tgtgattaca attggtttct tggcattctt cagactttcc tgtattttgt    10920
tcagaatctc ttgatcagat gtattcgacg tggaattttc cttcttaaga ggcaaggatg    10980 gttttcagc cttagcggca gctacatcta caggtaaatt gatgtaaacc ggctttcttt    11040
cctttagtaa ggcagacaac actctatcaa tttcaacagt tgcattctcg gctgtcaata    11100
aagtcctggc agcagtaacc ggttcgtgca tcttcataaa gtgcttgaaa tcaccatcag    11160
ccaacgtatg gtgaacaaac ttaccttcgt tctgcacttt cgaggtagga gatcccacga    11220
tctcaacaac aggcaggttc tcagcatagg agcccgctaa gccattaact gcggataatt    11280
cgccaacacc aaatgtagtc aagaatgccg cagccttttt cgttcttgcg tacccgtcgg    11340
ccatatagga ggcatttaac tcattagcat ttcccaccca tttcatatct ttgtgtgaaa    11400
taatttgatc tagaaattgc aaattgtagt cacctggtac tccgaatatt tcttctatac    11460
ctaattcgtg taatctgtcc aacagatagt cacctactgt atacattttg tttactagtt    11520
tatgtgtgtt tattcgaaac taagttcttg gtgttttaaa actaaaaaaa agactaacta    11580
taaaagtaga atttaagaag tttaagaaat agatttacag aattacaatc aatacctacc    11640
gtctttatat acttattagt caagtagggg aataatttca gggaactggt ttcaaccttt    11700 ttttcagct ttttccaaat cagagagagc agaaggtaat agaaggtgta agaaaatgag    11760
atagatacat gcgtgggtca attgccttgt gtcatcattt actccaggca ggttgcatca    11820
ctccattgag gttgtgcccg tttttgcct gtttgtgccc ctgttctctg tagttgcgct    11880
aagagaatgg acctatgaac tgatggttgg tgaagaaaac aatattttgg tgctgggatt    11940
cttttttttt ctggatgcca gcttaaaaag cgggctccat tatatttagt ggatgccagg    12000
aataaactgt tcacccagac acctacgatg ttatatattc tgtgtaaccc gcccctatt    12060 ttgggcatgt acgggttaca gcagaattaa aaggctaatt ttttgactaa ataaagttag    12120
gaaaatcact actattaatt atttacgtat tctttgaaat ggcagtattg ataatgataa    12180
actcgaactg aaaaagcgtg tttttttattc aaaatgattc taactcccctt acgtaatcaa    12240 ggaatctttt tgccttggcc tccgcgtcat taaacttctt gttgttgacg ctaacattca    12300
acgctagtat atattcgttt ttttcaggta agttcttttc aacgggtctt actgatgagg    12360
cagtcgcgtc tgaacctgtt aagaggtcaa atatgtcttc ttgaccgtac gtgtcttgca    12420
tgttattagc tttgggaatt tgcatcaagt cataggaaaa tttaaatctt ggctctcttg    12480
ggctcaaggt gacaaggtcc tcgaaaatag ggcgcgcccc accgcggtgg agctccagct    12540
```

```
tttgttccct ttagtgaggg ttaattgcgc gcttggcgta atcatggtca tagctgtttc   12600
ctgtgtgaaa ttgttatccg ctcacaattc cacacaacat acgagccgga agcataaagt   12660
gtaaagcctg gggtgcctaa tgagtgagct aactcacatt aattgcgttg cgctcactgc   12720
ccgctttcca gtcgggaaac ctgtcgtgcc agctgcatta atgaatcggc caacgcgcgg   12780
ggagaggcgg tttgcgtatt gggcgctctt ccgcttcctc gctcactgac tcgctgcgct   12840
cggtcgttcg gctgcggcga gcggtatcag ctcactcaaa ggcggtaata cggttatcca   12900
cagaatcagg ggataacgca ggaaagaaca tgtgagcaaa aggccagcaa aaggccagga   12960
accgtaaaaa ggccgcgttg ctggcgtttt tccataggct ccgcccccct gacgagcatc   13020
acaaaaatcg acgctcaagt cagaggtggc gaaacccgac aggactataa agataccagg   13080
cgtttccccc tggaagctcc ctcgtgcgct ctcctgttcc gaccctgccg cttaccggat   13140
acctgtccgc ctttctccct tcgggaagcg tggcgctttc tcatagctca cgctgtaggt   13200
atctcagttc ggtgtaggtc gttcgctcca agctgggctg tgtgcacgaa ccccccgttc   13260
agcccgaccg ctgcgcctta tccggtaact atcgtcttga gtccaacccg gtaagacacg   13320
acttatcgcc actggcagca gccactggta acaggattag cagagcgagg tatgtaggcg   13380
gtgctacaga gttcttgaag tggtggccta actacggcta cactagaaga acagtatttg   13440
gtatctgcgc tctgctgaag ccagttacct tcggaaaaag agttggtagc tcttgatccg   13500
gcaaacaaac caccgctggt agcggtggtt tttttgtttg caagcagcag attacgcgca   13560
gaaaaaaagg atctcaagaa gatcctttga tcttttctac ggggtctgac gctcagtgga   13620
acgaaaactc acgttaaggg attttggtca tgagattatc aaaaaggatc ttcacctaga   13680
tccttttaaa ttaaaaatga agttttaaat caatctaaag tatatatgag taaacttggt   13740
ctgacagtta ccaatgctta atcagtgagg cacctatctc agcgatctgt ctatttcgtt   13800
catccatagt tgcctgactc cccgtcgtgt agataactac gatacgggag ggcttaccat   13860
ctggccccag tgctgcaatg ataccgcgag acccacgctc accggctcca gatttatcag   13920
caataaacca gccagccgga agggccgagc gcagaagtgg tcctgcaact ttatccgcct   13980
ccatccagtc tattaattgt tgccgggaag ctagagtaag tagttcgcca gttaatagtt   14040
tgcgcaacgt tgttgccatt gctacaggca tcgtggtgtc acgctcgtcg tttggtatgg   14100
cttcattcag ctccggttcc caacgatcaa ggcgagttac atgatccccc atgttgtgca   14160
aaaaagcggt tagctccttc ggtcctccga tcgttgtcag aagtaagttg gccgcagtgt   14220
tatcactcat ggttatggca gcactgcata attctcttac tgtcatgcca tccgtaagat   14280
gcttttctgt gactggtgag tactcaacca agtcattctg agaatagtgt atgcggcgac   14340
cgagttgctc ttgcccggcg tcaatacggg ataataccgc gccacatagc agaactttaa   14400
aagtgctcat cattggaaaa cgttcttcgg ggcgaaaact ctcaaggatc ttaccgctgt   14460
tgagatccag ttcgatgtaa cccactcgtg cacccaactg atcttcagca tcttttactt   14520
tcaccagcgt ttctgggtga gcaaaaacag gaaggcaaaa tgccgcaaaa aagggaataa   14580
gggcgacacg gaaatgttga atactcatac tcttcctttt tcaatattat tgaagcattt   14640
atcagggtta ttgtctcatg agcggataca tatttgaatg tatttagaaa aataaacaaa   14700
taggggttcc gcgcacattt ccccgaaaag tgccacctga cgaagcatc tgtgcttcat   14760 tttgtagaac aaaaatgcaa cgcgagagcg ctaattttc aaacaaagaa tctgagctgc   14820
atttttacag aacagaaatg caacgcgaaa gcgctatttt accaacgaag aatctgtgct   14880
```

| | |
|---|---:|
| tcatttttgt aaaacaaaaa tgcaacgcga gagcgctaat ttttcaaaca aagaatctga | 14940 |
| gctgcatttt tacagaacag aaatgcaacg cgagagcgct attttaccaa caaagaatct | 15000 |
| atacttcttt tttgttctac aaaaatgcat cccgagagcg ctattttct aacaaagcat | 15060 |
| cttagattac ttttttctc ctttgtgcgc tctataatgc agtctcttga taacttttg | 15120 |
| cactgtaggt ccgttaaggt tagaagaagg ctactttggt gtctattttc tcttccataa | 15180 |
| aaaaagcctg actccacttc ccgcgtttac tgattactag cgaagctgcg ggtgcatttt | 15240 |
| ttcaagataa aggcatcccc gattatattc tataccgatg tggattgcgc atactttgtg | 15300 |
| aacagaaagt gatagcgttg atgattcttc attggtcaga aaattatgaa cggtttcttc | 15360 |
| tattttgtct ctatatacta cgtataggaa atgtttacat tttcgtattg ttttcgattc | 15420 |
| actctatgaa tagttcttac tacaattttt ttgtct | 15456 |

<210> SEQ ID NO 166
<211> LENGTH: 1559
<212> TYPE: DNA
<213> ORGANISM: Artificial sequence
<220> FEATURE:
<223> OTHER INFORMATION: Template

<400> SEQUENCE: 166

| | |
|---|---:|
| gcattgcgga ttacgtattc taatgttcag taccgttcgt ataatgtatg ctatacgaag | 60 |
| ttatgcagat tgtactgaga gtgcaccata ccacctttc aattcatcat ttttttta | 120 |
| ttctttttt tgatttcggt ttccttgaaa ttttttgat tcggtaatct ccgaacagaa | 180 |
| ggaagaacga aggaaggagc acagacttag attggtatat atacgcatat gtagtgttga | 240 |
| agaaacatga aattgcccag tattcttaac ccaactgcac agaacaaaaa cctgcaggaa | 300 |
| acgaagataa atcatgtcga aagctacata taaggaacgt gctgctactc atcctagtcc | 360 |
| tgttgctgcc aagctatta atatcatgca cgaaaagcaa acaaacttgt gtgcttcatt | 420 |
| ggatgttcgt accaccaagg aattactgga gttagttgaa gcattaggtc ccaaaatttg | 480 |
| tttactaaaa acacatgtgg atatcttgac tgattttcc atggagggca cagttaagcc | 540 |
| gctaaaggca ttatccgcca agtacaattt tttactcttc gaagacagaa atttgctga | 600 |
| cattggtaat acagtcaaat tgcagtactc tgcgggtgta tacagaatag cagaatgggc | 660 |
| agacattacg aatgcacacg gtgtggtggg cccaggtatt gttagcggtt tgaagcaggc | 720 |
| ggcagaagaa gtaacaaagg aacctagagg cctttgatg ttagcagaat tgtcatgcaa | 780 |
| gggctcccta tctactggag aatatactaa gggtactgtt gacattgcga gagcgacaa | 840 |
| agatttgtt atcggcttta ttgctcaaag agacatgggt ggaagagatg aaggttacga | 900 |
| ttggttgatt atgacacccg gtgtgggttt agatgacaag ggagacgcat tgggtcaaca | 960 |
| gtatagaacc gtggatgatg tggtctctac aggatctgac attattattg ttggaagagg | 1020 |
| actatttgca aagggaaggg atgctaaggt agagggtgaa cgttacagaa aagcaggctg | 1080 |
| ggaagcatat ttgagaagat gcggccagca aaactaaaaa actgtattat aagtaaatgc | 1140 |
| atgtatacta aactcacaaa ttagagcttc aatttaatta tatcagttat taccctatgc | 1200 |
| ggtgtgaaat accgcacaga tgcgtaagga gaaaataccg catcaggaaa ttgtaaacgt | 1260 |
| taatattttg ttaaaattcg cgttaaattt ttgttaaatc agctcatttt ttaaccaata | 1320 |
| ggccgaaatc ggcaaaatcc cttataaatc aaaagaatag accgagatag ggttgagtgt | 1380 |
| tgttccagtt tggaacaaga gtccactatt aaagaacgtg gactccaacg tcaaggggcg | 1440 |
| aaaaaccgtc tatcagggcg atggcccact acgtgaacca tcaccctaat caagataact | 1500 |

<210> SEQ ID NO 167
<211> LENGTH: 2237
<212> TYPE: DNA
<213> ORGANISM: Artificial Sequence
<220> FEATURE:
<223> OTHER INFORMATION: PDC1 Fragment A-ilvDSm

<400> SEQUENCE: 167

```
tcgtataatg tatgctatac gaacggtacc agtgatgata caacgagtta gccaaggtg    1559
```

```
ttatgtatgc tcttctgact tttcgtgtga tgaggctcgt ggaaaaaatg aataatttat      60
gaatttgaga acaattttgt gttgttacgg tattttacta tggaataatc aatcaattga     120
ggattttatg caaatatcgt ttgaatattt ttccgaccct ttgagtactt ttcttcataa     180
ttgcataata ttgtccgctg ccccttttc tgttagacgg tgtcttgatc tacttgctat      240
cgttcaacac caccttattt tctaactatt tttttttag ctcatttgaa tcagcttatg      300
gtgatggcac attttgcat aaacctagct gtcctcgttg aacataggaa aaaaaaatat     360
ataaacaagg ctctttcact ctccttgcaa tcagatttgg gtttgttccc tttatttca      420
tatttcttgt catattcctt tctcaattat tattttctac tcataacctc acgcaaaata     480
acacagtcaa atcaatcaaa atgactgaca aaaaaactct taagactta agaaatcgta      540
gttctgttta cgattcaatg gttaaatcac ctaatcgtgc tatgttgcgt gcaactggta    600
tgcaagatga agactttgaa aaacctatcg tcggtgtcat ttcaacttgg gctgaaaaca     660
caccttgtaa tatccactta catgactttg gtaaactagc caaagtcggt gttaaggaag     720
ctggtgcttg gccagttcag ttcggaacaa tcacggtttc tgatggaatc gccatgggaa     780
cccaaggaat gcgtttctcc ttgacatctc gtgatattat tgcagattct attgaagcag     840
ccatgggagg tcataatgcg gatgctttg tagccattgg cggttgtgat aaaaacatgc     900
ccggttctgt tatcgctatg gctaacatgg atatcccagc catttttgct tacgcggaa     960
caattgcacc tggtaattta gacggcaaag atatcgattt agtctctgtc tttgaaggtg    1020
tcggccattg gaaccacggc gatatgacca agaagaagt taaagctttg gaatgtaatg     1080
cttgtcccgg tcctggaggc tgcggtggta tgtatactgc taacacaatg gcgacagcta    1140
ttgaagttt gggacttagc cttccggggtt catcttctca cccggctgaa tccgcagaaa    1200
agaaagcaga tattgaagaa ctggtcgcg ctgttgtcaa aatgctcgaa atgggcttaa     1260
aaccttctga cattttaacg cgtgaagctt ttgaagatgc tattactgta actatggctc    1320
tgggaggttc aaccaactca acccttcacc tcttagctat gcccatgct gctaatgtgg    1380
aattgacact tgatgatttc aatactttcc aagaaaaagt tcctcatttg ctgatttga    1440
aaccttctgg tcaatatgta ttccaagacc tttacaaggt cggaggggta ccagcagtta    1500
tgaaatatct ccttaaaaat ggcttccttc atggtgaccg tatcacttgt actggcaaaa    1560
cagtcgctga aaatttgaag cttttgatg atttaacacc tggtcaaaag gttattatgc    1620
cgcttgaaaa tcctaaacgt gaagatggtc cgctcattat tctccatggt aacttggctc    1680
cagacggtgc cgttgccaaa gtttctggtg taaaagtgcg tcgtcatgtc ggtcctgcta    1740
aggtctttaa ttctgaagaa gaagccattg aagctgtctt gaatgatgat attgttgatg    1800
gtgatgttgt tgtcgtacgt tttgtaggac caaagggcgg tcctggtatg cctgaaatgc    1860
tttcccttc atcaatgatt gttggtaaag ggcaaggtga aaaagttgcc cttctgacag    1920
atggccgctt ctcaggtggt acttatggtc ttgtcgtggg tcatatcgct cctgaagcac    1980
```

-continued

```
aagatggcgg tccaatcgcc tacctgcaaa caggagacat agtcactatt gaccaagaca    2040
ctaaggaatt acactttgat atctccgatg aagagttaaa acatcgtcaa gagaccattg    2100
aattgccacc gctctattca cgcggtatcc ttggtaaata tgctcacatc gtttcgtctg    2160
cttctagggg agccgtaaca gacttttgga agcctgaaga aactggcaaa aaatgagcga    2220
tttaatctct aattatt                                                   2237
```

USE OF THIAMINE AND NICOTINE ADENINE DINUCLEOTIDE FOR BUTANOL PRODUCTION

FIELD OF THE INVENTION

The invention relates generally to the field of industrial microbiology and fermentative alcohol production. More specifically, the invention relates to the use of thiamine or biosynthetic precursors of thiamine, nicotinic acid, nicotinamid, nicotinic acid riboside, nicotinamid riboside, or other biosynthetic precursors of nicotine adenine dinucleotide (NAD) to improve the ability of a recombinant host cell to produce a product alcohol such as butanol. Recombinant host cells of the invention can produce butanol.

Additionally, the invention relates to methods of increasing butanol yield and methods for increasing specific butanol production rates.

BACKGROUND OF THE INVENTION

Global demand for liquid transportation fuel is projected to strain the ability to meet certain environmentally driven goals, for example, the conservation of oil reserves and limitation of green house gas emissions. Such demand has driven the development of technology which allows utilization of renewable resources to mitigate the depletion of oil reserves and to minimize green house gas emissions. This invention addresses the need for improved processes for the conversion of plant-derived raw materials to a product stream useful as a liquid transportation fuel. Such processes would satisfy both fuel demands and environmental concerns.

Butanol is an important industrial chemical and is useful as a fuel additive, as a feedstock chemical in the plastics industry, and as a food grade extractant in the food and flavor industry. Each year 10 to 12 billion pounds of butanol are produced by petrochemical means and the need for this commodity chemical will likely increase in the future.

Methods for the chemical synthesis of isobutanol are known such as oxo synthesis, catalytic hydrogenation of carbon monoxide (Ullmann's Encyclopedia of Industrial Chemistry, 6th edition, 2003, Wiley-VCH Verlag GmbH and Co., Weinheim, Germany, Vol. 5, pp. 716-719) and Guerbet condensation of methanol with n-propanol (Carlini, et al., J. Molec. Catal. A: Chem. 220:215-220, 2004). These processes use starting materials derived from petrochemicals, are generally expensive, and are not environmentally friendly. The production of butanol from plant-derived raw materials would minimize green house gas emissions and would represent an advance in the art.

Some fungi desire supplementation of the vitamin biotin, like many wild isolates of the yeast *Saccharomyces cerevisiae* (Leonian, et al., Science 95:658, 1942; Stolz, et al., J. Biol. Chem. 274:18741-18746, 1999; Hall, et al. Genetics 177: 2293-2307, 2007). For a biotin auxotrophic organisms to grow, sufficient amount of biotin is provided exogenously. Alternatively, endogenous biosynthesis of biotin can be accomplished, for example, by directed evolution (Leonian, et al., supra) or complementing the retained biosynthesis pathway of yeast with the missing enzyme activities (Hall, et al., supra).

Another vitamin that is often supplemented to yeast cultures is pantothenic acid (Leonian, et al., supra). However, although *Saccharomyces cerevisiae* is capable of de novo pantothenic acid biosynthesis, an increase of biosynthesis, especially the enzyme activity in the rate-limiting step of amine oxidase, may be achieved by directed evolution (Leonian, et al., supra) or recombinant DNA technology (White, et al., J. Biol. Chem. 276:10794-10800, 2001) which is typically required to provide sufficient activity to remedy growth, respectively. No further vitamin requirements for aerobic growth of *Saccharomyces cerevisiae* have been identified (Henry, Appl. Environ. Microbiol. 31:395-398, 1976).

A commercial defined medium without yeast extract and containing only the vitamins inositol, biotin, pantothenic acid, and pyridoxine was used to aerobically produce factor XIII with *Saccharomyces cerevisiae* (see, e.g., U.S. Pat. No. 6,750,045). A commercial medium for the aerobic production of protein in *Saccharomyces cerevisiae* supplemented with a vitamin mixture comprising biotin, pantothenic acid, myo-inositol, and pyridoxine is described in U.S. Pat. No. 5,795,771. U.S. Patent Application Publication No. 2005/0112737 reports a chemically defined medium supplemented with the vitamins biotin, inositol, and thiamine to grow a pyruvate-decarboxylase (PDC)-negative *Saccharomyces cerevisiae* with an exogenous lactate dehydrogenase activity. The non-Crabtree and PDC-KO yeast *Kluyveromyces marxianus* has been shown to produce lactic acid in shake flask cultivations with complex yeast extract peptone-dextrose medium (YPD) media comprising 10 g/L yeast extract, 20 g/L peptone, additionally glucose, and occasionally agar. No additional specific media requirements are described (see, e.g., U.S. Pat. No. 7,534,597). An example of a non-Crabtree yeast *Kluyveromyces marxianus* capable of generating biomass when cultured with corn fiber hydrolyzate supplemented with yeast minimal medium and a vitamin cocktail (Kiers, et al., Yeast 14:459-469, 1998) where 5 mg/L of nicotinic acid was added to the fiber hydrolysate is described in U.S. Pat. No. 7,700,332. However, no link of bioprocess performance to specific compounds of the vitamin mixture is made.

Very high gravity (VHG) fermentation with *Saccharomyces cerevisiae* and corn flour mash for the production of ethanol was optimized through supplementations of $Mg^{2+}$, glycine, yeast extract, biotin, acetaldehyde, and peptone (Wang, et al., Biotechnol. Lett. 29:233-236, 2007). Ethanol production with brewing yeast was also improved by adding a nitrogen source, ergosterol, and oleic acid to high-gravity worts of 16 to 18% dissolved solids (Casey, et al., Appl. Environ. Microbiol. 48:639-646, 1984). It is also reported that in a high cell density fermentation, feeding biotin in combination with a vitamin mixture containing pantothenic acid, meso-inositol, nicotinic acid, thiamine, pyridoxine, and para-aminobenzoic acid during aerated fed-batch processes improves ethanol production and viability of *Saccharomyces cerevisiae* (Alfenore, et al., Appl. Microbiol. Biotechnol. 60:67-72, 2002). However, apart from biotin, the composition of the vitamin mixture was not further investigated to link observed performance increases to specific components.

A complex YPD medium consisting of 10 g/L yeast extract, 20 g/L peptone, and variable amounts of glucose was described in examples for culturing the yeasts *Kluyveromyces marxianus* and *Saccharomyces cerevisiae* to produce butanol (see, e.g., WO 2010/075504). No specific requirements or analyses of vitamin requirements are mentioned. Examples of butanol production in yeasts *Kluyveromyces marxianus* and *Saccharomyces cerevisiae*, some with reduced or completely deleted PDC-activities, were described using 6.7 g/L YNB medium without amino acids and 0.076 g/L histidine with nicotinic acid concentrations of about 0.4 mg/L (see, e.g., WO 2010/051527). An economic comparison of nutrient costs in example fermentations is disclosed in U.S. Patent Application Publication No. 2009/0215137. Synthetic fermentation medium (mineral medium) (SFM) is described for butanol production with a yeast cell using a vitamin mixture according to Verduyn, et al., (Yeast 8:501-517, 1992) with the medium containing 1 mg/L nicotinic acid (see, e.g., WO 2009/103533).

Genetic modification of microorganisms to produce new products frequently comes with changed and/or new nutritional requirements to ensure optimum performance of the biocatalyst. Identifying and optimizing nutritional requirements can be complex and feeding complex multi-vitamin mixtures to address nutritional needs can be costly. Consequently, technical inventions are necessary to address and solve these hurdles.

BRIEF SUMMARY OF THE INVENTION

Provided herein are methods for producing a fermentation product comprising: providing a production culture comprising recombinant cells capable of producing butanol and production media comprising 1) thiamine or a biosynthetic precursor thereof, 2) optionally nicotinic acid, nicotinamid, or a biosynthetic precursor of NAD, and 3) a production feed derived from biomass comprising a fermentable carbon source wherein the production media contains less than 1 g/L of multi-component media additives. Methods further comprise contacting the production culture with the production media and the production feed in a fermentation vessel to form a production broth under conditions whereby a fermentation product is produced. In some embodiments, the production media is substantially free of multi-component media additives.

In some embodiments, the production broth contains at least about 5 mg/L thiamine or a biosynthetic precursor thereof. In other embodiments, the production broth comprises about 100 mg/L nicotinic acid and about 20 mg/L thiamine. In some embodiments, the production broth contains at least about 50 mg/L thiamine or a biosynthetic precursor thereof. In some embodiments, the production media contains at least about 20 mg/L thiamine or a biosynthetic precursor thereof. In other embodiments, the production broth contains at least about 0.1 mg/g dcw thiamine or a biosynthetic precursor thereof.

In some embodiments, the thiamine or a biosynthetic precursor thereof is present in an amount sufficient to provide at least about 30% of the rate, titer, or specific productivity observed in media that contains about 10 g/L yeast extract.

In some embodiments, the thiamine or a biosynthetic precursor thereof and/or nicotinic acid, nicotinamid, or a biosynthetic precursor of NAD are components of the production feed.

Also, provided herein are methods for producing a fermentation product comprising: providing a production culture comprising recombinant cells capable of producing butanol and a production media comprising 1) nicotinic acid, nicotinamid, or a biosynthetic precursor of NAD, 2) optionally thiamine or a biosynthetic precursor thereof, and 3) a production feed derived from biomass comprising a fermentable carbon source wherein the production media contains less than 1 g/L of multi-component media additives. Methods further comprise contacting the production culture with the production media and the production feed in a fermentation vessel to form a production broth under conditions whereby a fermentation product is produced. In some embodiments, the production media is substantially free of multi-component media additives.

In some embodiments, the production broth contains at least about 5 mg/L nicotinic acid, nicotinamid, or a biosynthetic precursor of NAD. In other embodiments, the production broth contains at least about 10 mg/L nicotinic acid, nicotinamid, or a biosynthetic precursor of NAD. In some embodiments, the production media contains at least about 20 mg/L nicotinic acid, nicotinamid, or a biosynthetic precursor of NAD. In some embodiments, the production broth comprises about 100 mg/L nicotinic acid and about 20 mg/L thiamine. In some embodiments, the production broth contains at least about 0.1 mg/g dcw nicotinic acid, nicotinamid, or a biosynthetic precursor of NAD.

In embodiments, nicotinic acid, nicotinamid, or a biosynthetic precursor of NAD is present in an amount sufficient to provide at least about 30% of the rate, titer, or specific productivity observed in media that contains about 10 g/L yeast extract.

In some embodiments the nicotinic acid, nicotinamid, or a biosynthetic precursor of NAD and/or thiamine or a biosynthetic precursor thereof are components of the production feed.

In some embodiments, the cell density in the fermentation vessel is at least about 10 g dcw/L. In other embodiments, the cell density in the fermentation vessel is less than about 10 g dcw/L.

In some embodiments, the recombinant cells are yeast. In some embodiments, the yeast is *Saccharomyces, Zygosaccharomyces, Schizosaccharomyces, Dekkera, Torulopsis, Brettanomyces, Torulaspora, Hanseniaspora, Kluveromyces, Issatchenkia, Ashbya,* or *Candida*. In some embodiments, the yeast is crabtree positive and in other embodiments, the yeast is crabtree negative.

In some embodiments, the recombinant cell comprises a modification of an endogenous gene encoding a thiaminephyrophosphate-dependent (TPP) gene. In some embodiments, the TPP-dependent gene is a pyruvate decarboxylase gene. In some embodiments, the modification is a deletion. In some embodiments, the recombinant cell comprises a modification in a gene encoding PDC1, PDC5, PDC6, or combinations thereof. In embodiments, the modification is a deletion.

In some embodiments of the methods provided, the recombinant cell comprises a butanol biosynthetic pathway. In some embodiments, the butanol biosynthetic pathway may be comprised of at least one heterologous polynucleotide encoding a polypeptide that catalyzes a substrate to product conversion of the pathway. The butanol biosynthetic pathway may be an isobutanol biosynthetic pathway. The isobutanol biosynthetic pathway may comprise the following substrate to product conversions:

a) pyruvate to acetolactate;
b) acetolactate to 2,3-dihydroxyisovalerate;
c) 2,3-dihydroxyisovalerate to α-ketoisovalerate;
d) α-ketoisovalerate to isobutyraldehyde; and
e) isobutyraldehyde to isobutanol.

In another embodiment, the recombinant host cell may comprise at least one DNA molecule encoding a polypeptide having aspartate oxidase or aspartate dehydrogenase activity. In one embodiment, the recombinant host cell may comprise at least one DNA molecule encoding a polypeptide having quinolinate synthase activity.

In some embodiments, butanol is produced at a specific butanol production rate of at least about 0.10 g/g/h In some embodiments, the product is produced under aerobic conditions and in other embodiments, the product is produced under anaerobic conditions.

In some embodiments, the fermentation broth further comprises at least about 5 mg/L thiamine or other biosynthetic precursors of thiamine. In other embodiments, the media further comprises at least about 10 mg/L thiamine or other biosynthetic precursors of thiamine. In some embodiments, the product is produced at a titer of at least about 50% of the titer when the host cell is grown in media containing about 10 g/L yeast extract and no supplemental thiamine or nicotinic acid, nicotinamid, or other biosynthetic precursor of NAD. In some embodiments, the product is produced at a specific production rate of at least about 50% of the rate when the host cell is grown in media containing about 10 g/L yeast extract and no supplemental thiamine or nicotinic acid, nicotinamid, or other biosynthetic precursor of NAD.

Also provided are compositions comprising: production media consisting essentially of greater than about 10 mg/L nicotinic acid, nicotinamid, or other biosynthetic precursor of NAD and, optionally, greater than about 10 mg/L thiamine or a biosynthetic precursor thereof; a production culture comprising a recombinant microorganism which comprises a butanol biosynthetic pathway; and liquefied biomass comprising a fermentable carbon substrate. In some embodiments, the production media consists essentially of greater than about 20 mg/L nicotinic acid, nicotinamid, or other biosynthetic precursor of NAD and greater than about 20 mg/L thiamine or a biosynthetic precursor thereof. In other embodiments, the production broth comprises about 100 mg/L nicotinic acid and about 20 mg/L thiamine.

In addition, provided herein are compositions comprising: production media consisting essentially of greater than about 10 mg/L thiamine or a biosynthetic precursor thereof and, optionally, greater than about 10 mg/L nicotinic acid, nicotinamid, or other biosynthetic precursor of NAD; a production culture comprising a recombinant microorganism which comprises a butanol biosynthetic pathway; and liquefied biomass comprising a fermentable carbon substrate. In some embodiments, the production media consists essentially of greater than about 20 mg/L thiamine or a biosynthetic precursor thereof and greater than about 20 mg/L nicotinic acid, nicotinamid, or other biosynthetic precursor of NAD. In other embodiments, the production broth comprises about 100 mg/L thiamine and about 20 mg/L nicotinic acid.

Provided herein are methods for producing butanol comprising: (a) providing a production culture comprising recombinant cells comprising a butanol biosynthetic pathway; (b) providing production media containing greater than about 1 mg/L thiamine or a thiamine biosynthetic precursor; and (c) contacting said production culture with said media under conditions whereby butanol is produced. In some embodiments, the production culture has a cell density less than about 10 g dcw/L.

Also provided are methods for producing butanol comprising: (a) providing a production culture comprising recombinant cells comprising a butanol biosynthetic pathway; (b) providing production media containing greater than about 1 mg/L thiamine or a thiamine biosynthetic precursor; and (c) contacting said production culture with said media under conditions whereby butanol is produced. In some embodiments, the production culture has a cell density greater than about 10 g dcw/L Also provided are methods for producing butanol comprising: (a) providing a production culture comprising recombinant cells comprising a butanol biosynthetic pathway; (b) providing production media containing greater than about 0.1 mg/gdcw thiamine or a thiamine biosynthetic precursor; and (c) contacting said production culture with said media under conditions whereby butanol is produced. In some embodiments, the production culture has a cell density greater than about 10 g dcw/L Provided herein are methods for producing butanol comprising: (a) providing a production culture comprising recombinant cells comprising a butanol biosynthetic pathway; (b) providing production media containing greater than about 1 mg/L nicotinic acid, nicotinamid, or other biosynthetic precursor of NAD; and (c) contacting said production culture with said media under conditions whereby butanol is produced. In some embodiments, the production culture has a cell density less than about 10 g dcw/L.

Also provided are methods for producing butanol comprising: (a) providing a production culture comprising recombinant cells comprising a butanol biosynthetic pathway; (b) providing production media containing greater than about 1 mg/L nicotinic acid, nicotinamid, or other biosynthetic precursor of NAD; and (c) contacting said production culture with said media under conditions whereby butanol is produced. In some embodiments, the production culture has a cell density greater than about 10 g dcw/L Also provided are methods for producing butanol comprising: (a) providing a production culture comprising recombinant cells comprising a butanol biosynthetic pathway; (b) providing production media containing greater than about 0.1 mg/gdcw nicotinic acid, nicotinamid, or other biosynthetic precursor of NAD; and (c) contacting said production culture with said media under conditions whereby butanol is produced. In some embodiments, the production culture has a cell density greater than about 10 g dcw/L In some embodiments, the amount of ketoisovaleric acid accumulated is less than that observed in media that contains about 10 g/L yeast extract. In some embodiments, the host cell further comprises ketoisovalerate decarboxylase.

In some embodiments, butanol is produced in a commercial scale fermentation and in some embodiments, the commercial scale is greater than about 1000 L.

In some embodiments, a production broth is provided with less than 1 g/L of multi-component media additives.

In some embodiments a butanol fermentation production media comprising;
1. thiamine or a biosynthetic precursor thereof;
2. optionally nicotinic acid, nicotinamid, or a biosynthetic precursor of NAD; and
3. a production feed derived from biomass comprising a fermentable carbon source; and wherein the production media comprises less than 1 g/L of multi-component media additives is provided.

In some embodiments a butanol fermentation production media comprising;
1. nicotinic acid, nicotinamid, or a biosynthetic precursor of NAD;
2. optionally thiamine or a biosynthetic precursor thereof; and
3. a production feed derived from biomass comprising a fermentable carbon source; and wherein the production media comprises less than 1 g/L of multi-component media additives is provided.

BRIEF DESCRIPTION OF THE DRAWINGS/FIGURES

The various embodiments of the invention can be more fully understood from the following detailed description, the figures, and the accompanying sequence descriptions, which form a part of this application.

Figure 7:
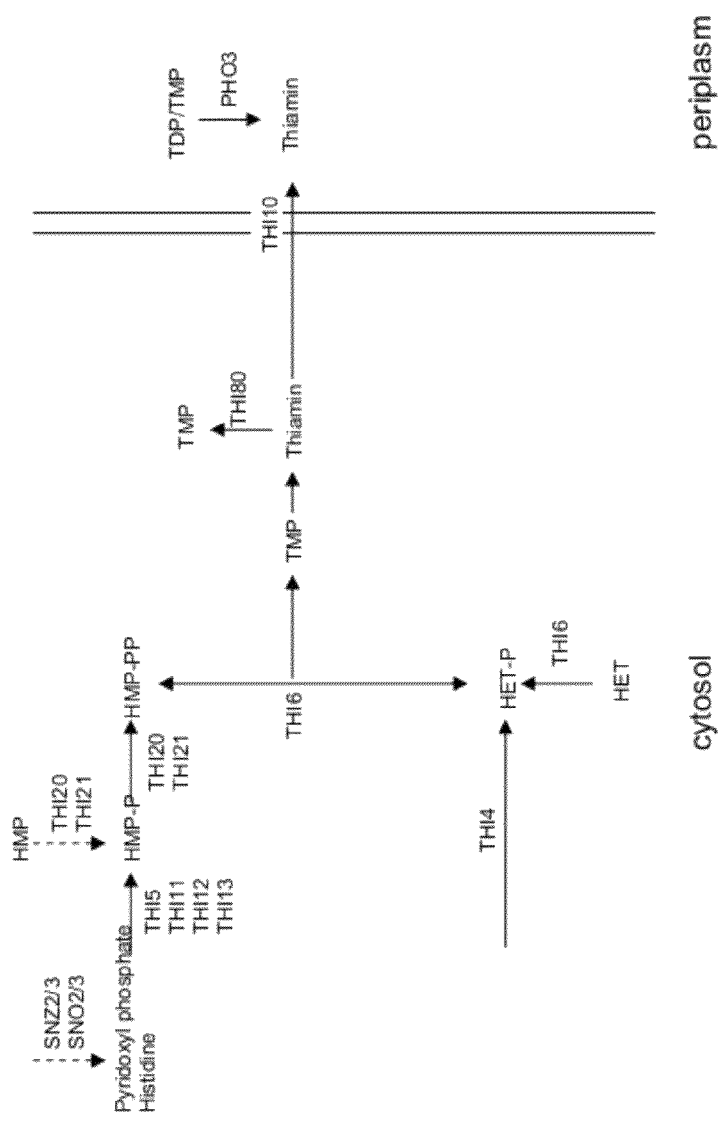

FIG. 7 depicts the pathway of thiamin biosynthesis in yeast. The major intermediates and products are written in bold, and the genes involved are written in italics. The dashed arrows indicate processes whose steps have not yet been fully identified.

Figure 8:
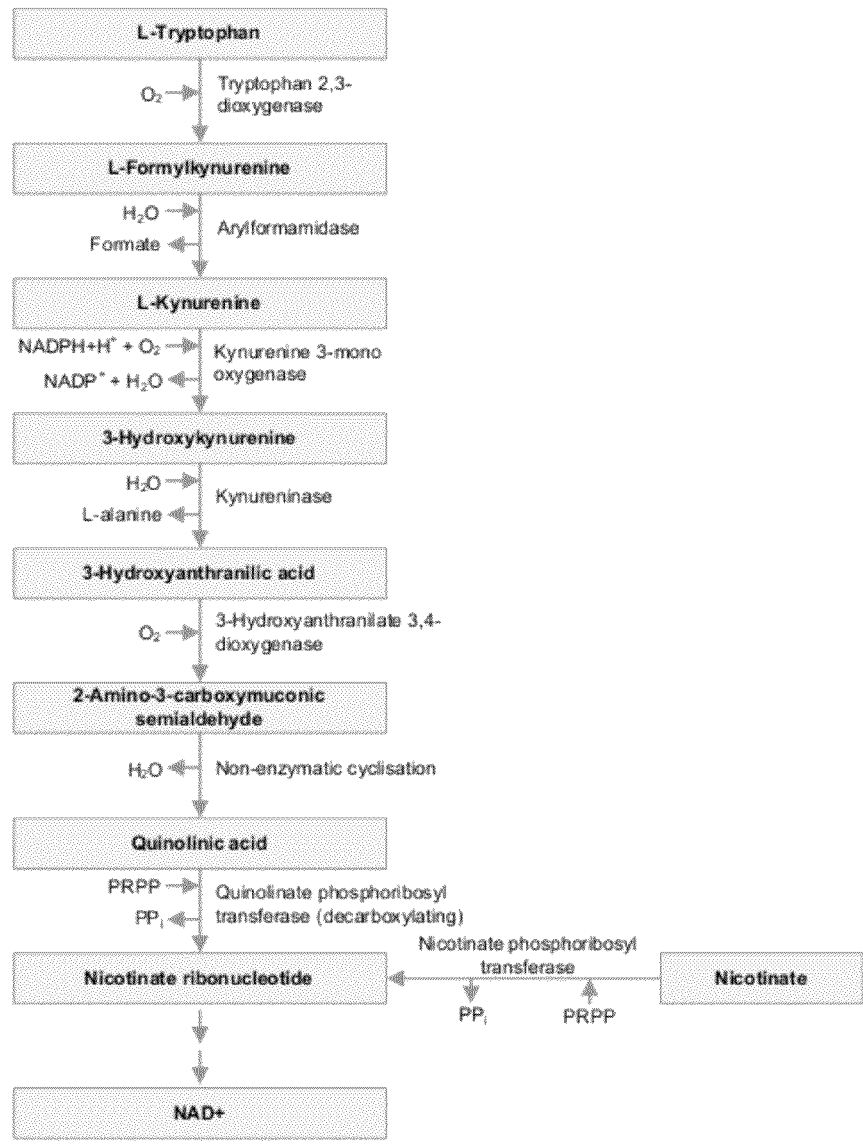

FIG. 8 depicts the biosynthesis pathway of NAD+ via the kynurenine pathway or by direct incorporation of nicotinic acid in *Saccharomyces cerevisiae*.

Figure 9:
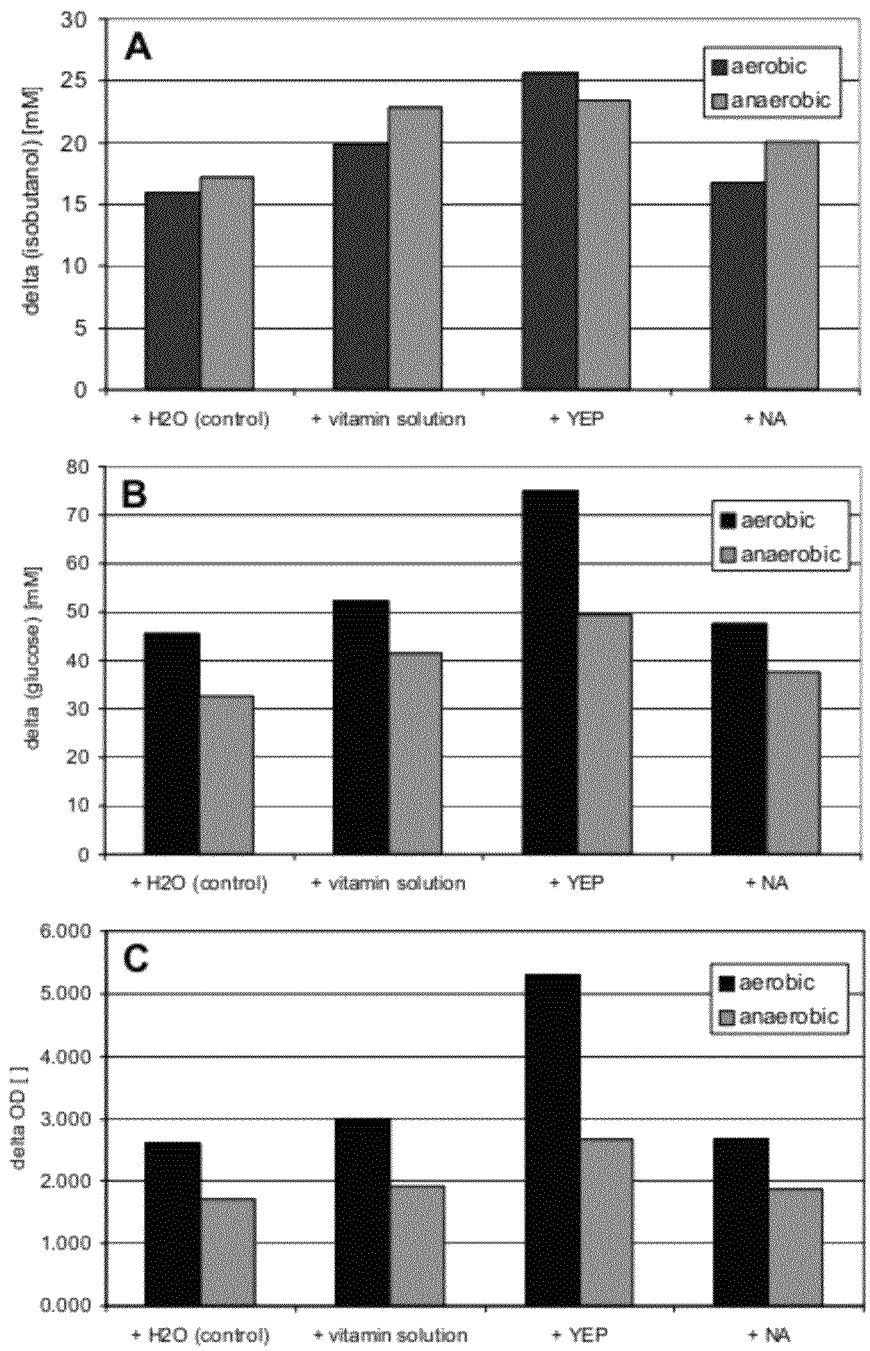

FIG. 9 depicts the increase in isobutanol concentration (delta c(isobutanol); mM), decrease of glucose concentration (delta (glucose); mM), and increase in biomass concentration (delta (OD);) in aerobic (solid black bars) and anaerobic (striped gray bars) shake flask cultivations with the addition of either water (H2O, control), vitamin solution, yeast extract and peptone solution (YEP), or nicotinic acid (NA).

Figure 10:
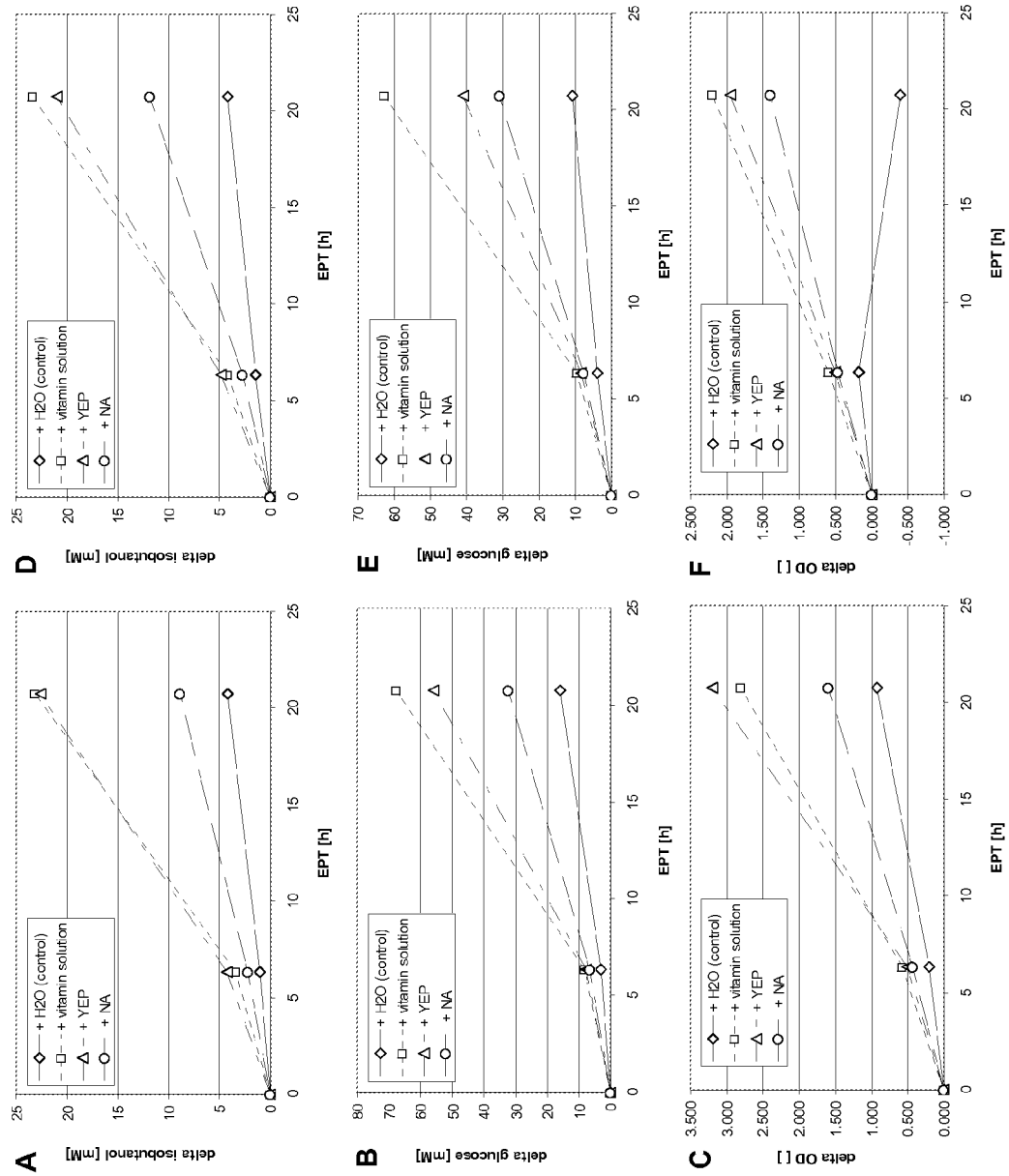

FIG. 10 depicts the increase in isobutanol concentration (delta c(isobutanol); mM), decrease of glucose concentration (delta (glucose); mM), and increase in biomass concentration (delta (OD);) in aerobic (A-C) and anaerobic (D-F) shake flask cultivations with the addition of either water (H2O, control) (Δ), vitamin solution (□), yeast extract and peptone solution (YEP) (Δ), or nicotinic acid (NA) (o).

Figure 11:
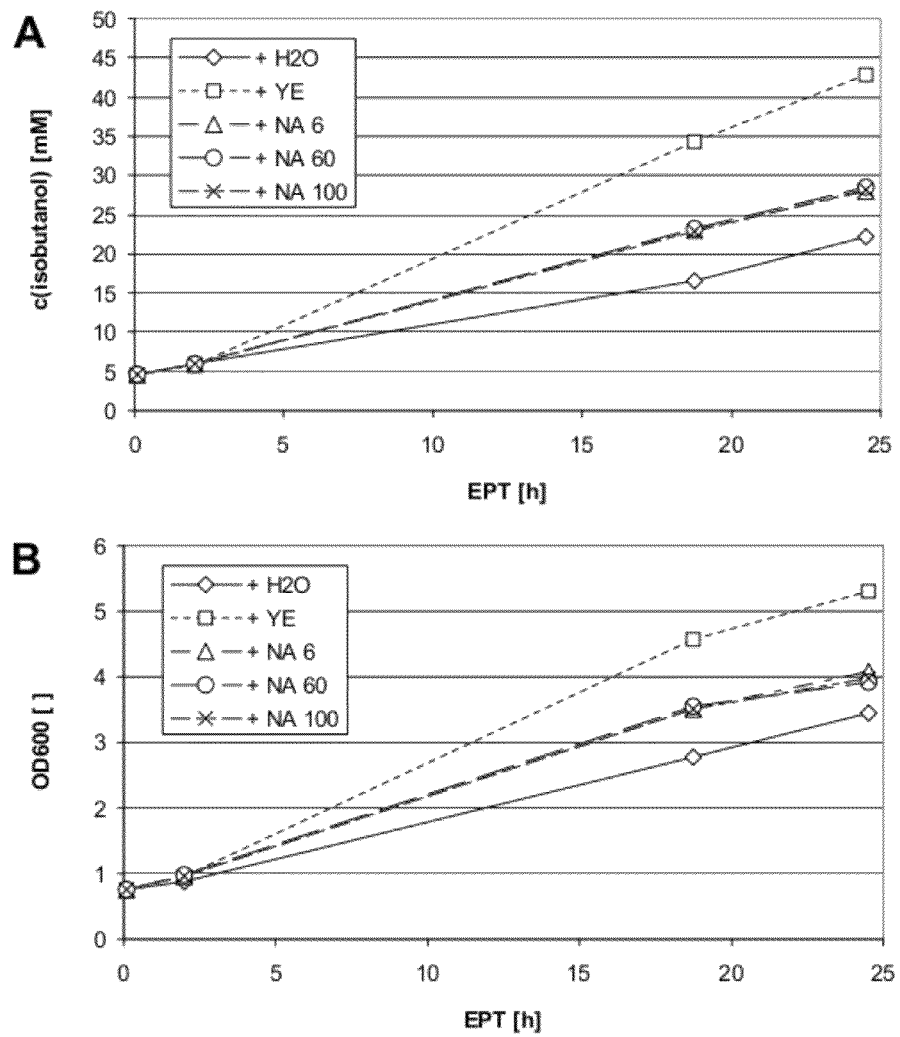

FIG. 11 depicts the isobutanol concentrations (c(isobutanol); mM) and biomass concentration (OD600;) in aerobic shake flask cultivations with nicotinic acid (NA) added ad 0 mg/L (◇; +H2O), ad 6 mg/L (Δ; +NA 6), ad 60 mg/L (o; +NA 60), or ad 100 mg/L (x; +NA 600) or yeast extract supplementation (YE) (□).

Figure 12:
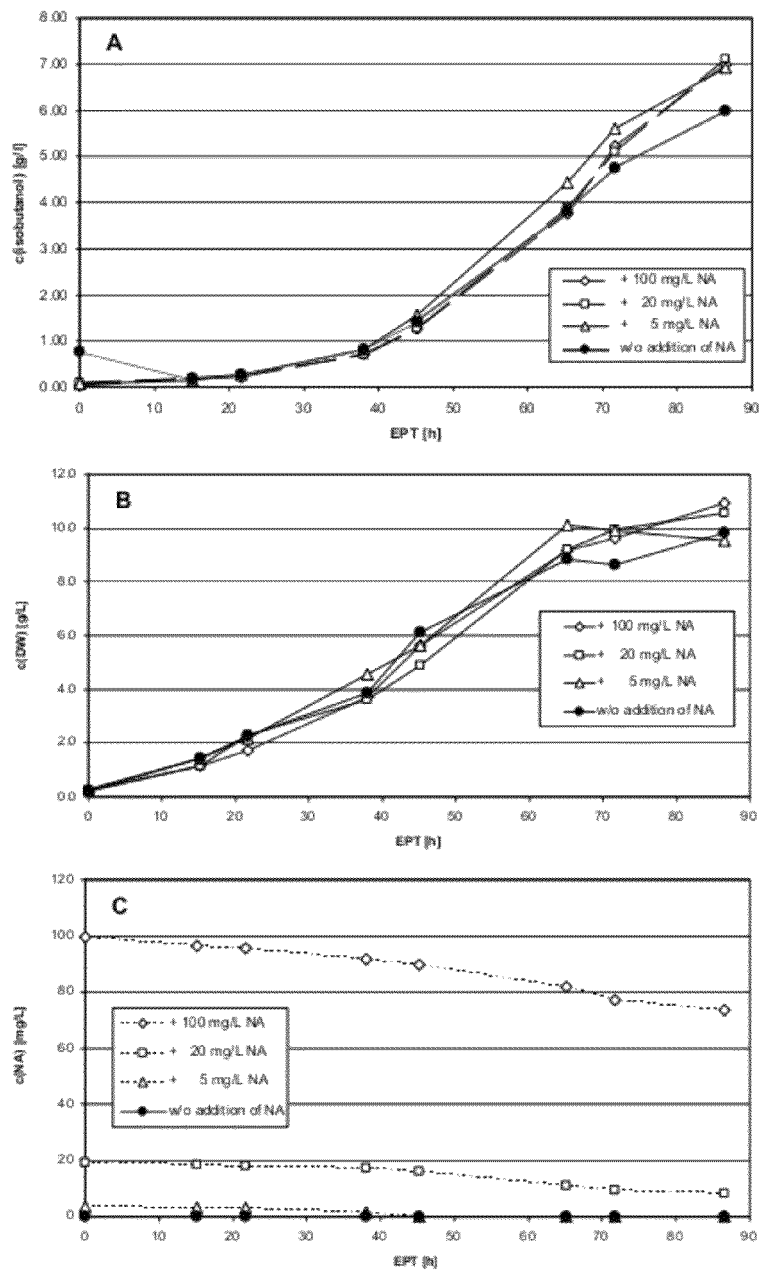

FIG. 12 depicts (A) the isobutanol concentration (c(isobutanol); g/L), (B) the biomass concentration (c(DE); g/L), and (C) the nicotinic acid (NA) concentration (c(NA); g/L) during fermentations described in the Example 9 with initial nicotinic acid supplementation of about 100 mg/L (◇), about 20 mg/L (□), about 5 mg/L (Δ), and about 0 mg/L (●).

The invention can be more fully understood from the following detailed description and the accompanying sequence descriptions which form a part of this application.

DETAILED DESCRIPTION OF THE INVENTION

Genetic modification of yeast to produce products other than biomass and ethanol, like e.g. butanol, requires genetic modification of the yeast biochemical network, resulting in changes of the genome, transcriptome, proteome and metabolome. Additionally, different products like butanol exert different physiological effects on cells due to their different physical properties.

Thiamine pyrophosphate (TPP) is an essential cofactor for a variety of metabolic enzymes. Such metabolic enzymes may be necessary for host organism production of fermentation products from a carbon substrate. Applicants have discovered that providing media with thiamine or biosynthetic precursors of thiamine leads to improved butanol production in a fermentation. Supplementation with thiamine has also been found to reduce or eliminate the need to supplement fermentation media with yeast extract. This is believed to be particularly advantageous for commercial scale fermentations. Furthermore, because the composition of yeast extract may vary from lot to lot, reducing or eliminating the need to provide yeast extract can advantageously reduce or eliminate variability of fermentation media composition and thus, variability in production of fermentation products.

Host cells such as yeast possess a biochemical pathway for the production of thiamine, but if thiamine or precursors are available in the medium, yeast typically use the externally provided compounds preferentially. Typically only minimal differences in aerobic growth are observed regardless of whether the thiamine is produced endogenously or provided in the medium. However, as shown herein, it has been surprisingly discovered that the addition of thiamine and/or its biosynthetic precursors improves butanol production in both aerobic and anaerobic conditions.

Applicants have also discovered that increased nicotine adenine dinucleotide (NAD) precursor availability improves alcohol production by recombinant microorganisms such as yeast under aerobic and/or anaerobic conditions. These findings come as a surprise, as it is known that yeast possesses the biochemical capability to endogenously produce NAD from carbon substrates. The major pathway for NAD biosynthesis in yeast is assumed to be the kynurenine pathway, starting from tryptophane. Accordingly, provided herein are methods of increasing the production of alcohols such as butanol using recombinant yeast organisms by increasing available nicotine adenine dinucleotide (NAD) via supplementation of NAD precursors to media and/or recombinant expression of genes involved in the synthesis of NAD precursors.

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All publications, patents, and other references mentioned herein are incorporated by reference in their entireties for all purposes as if each individual publication or patent application were specifically and individually indicated to be incorporated by reference, unless only specific sections of patents or patent publications are indicated to be incorporated by reference.

Although methods and materials similar or equivalent to those disclosed herein can be used in practice or testing of the present invention, suitable methods and materials are disclosed below. The materials, methods, and examples are illustrative only and are not intended to be limiting. Other features and advantages of the invention will be apparent from the detailed description and from the claims.

In order to further define this invention, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as disclosed in the application.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or to carry out the methods; and the like. The term "about" also encompasses amounts that differ due to different equilibrium conditions for a composition resulting from a particular initial mixture. Whether or not modified by the term "about," the claims include equivalents to the quantities. In one embodiment, the term "about" means within 10% of the reported numerical value, preferably within 5% of the reported numerical value.

The term "butanol" as used herein refers to 2-butanol, 1-butanol, isobutanol, or mixtures thereof.

The term "isobutanol biosynthetic pathway" refers to an enzyme pathway to produce isobutanol from pyruvate.

The terms "PDC-," "PDC knockout," or "PDC-KO" as used herein, refer to a cell that has a genetic modification to inactivate or reduce expression of a gene encoding pyruvate decarboxylase (PDC) so that the cell substantially or completely lacks pyruvate decarboxylase enzyme activity. If the cell has more than one expressed (active) PDC gene, then each of the active PDC genes may be inactivated or have minimal expression thereby producing a PDC-cell. For example, PDC1, PDC5, and PDC6 may be knocked out in a PDC knockout.

"Multi-component media additives" as used herein, encompasses complex media additives such as yeast extract and concentrated plant hydrolysates. Also included are multi-vitamin cocktails which, when added to production media, provide 2 or more of the following vitamins at final concentrations of greater than about 0.1 mg/L: biotin, pantothenate, myoinositol, pyridoxine, riboflavin, p-aminobenzoic acid, and folic acid. Production feed is not a multi-component media additive.

"Production feed" as used herein, refers to the portion of the fermentation broth that is provided from the biomass and may be a component of the production media. The biomass is also the source of the carbon substrate. The term "carbon substrate" refers to a carbon source capable of being metabolized by the recombinant host cells disclosed herein. Non-limiting examples of carbon substrates are provided herein and include, but are not limited to, monosaccharides, oligosaccharides, polysaccharides, ethanol, lactate, succinate, glycerol, carbon dioxide, methanol, glucose, fructose, sucrose, xylose, arabinose, dextrose, or mixtures thereof.

"Production broth" as used herein, refers to the contents of the fermentation vessel and comprises the production media with production feed and the production culture.

The term "polynucleotide" is intended to encompass a singular nucleic acid as well as plural nucleic acids, and refers to a nucleic acid molecule or construct, for example, messenger RNA (mRNA) or plasmid DNA (pDNA). A polynucleotide can contain the nucleotide sequence of the full-length cDNA sequence, or a fragment thereof, including the untranslated 5' and 3' sequences and the coding sequences. The polynucleotide can be composed of any polyribonucleotide or polydeoxyribonucleotide, which can be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or more typically, double-stranded or a mixture of single- and double-stranded regions. "Polynucleotide" embraces chemically, enzymatically, or metabolically modified forms.

A polynucleotide sequence can be referred to as "isolated," in which it has been removed from its native environment. For example, a heterologous polynucleotide encoding a polypeptide or polypeptide fragment having dihydroxy-acid dehydratase activity contained in a vector is considered isolated for the purposes of the present invention. Further examples of an isolated polynucleotide include recombinant polynucleotides maintained in heterologous host cells or purified (partially or substantially) polynucleotides in solution. Isolated polynucleotides or nucleic acids according to the present invention further include such molecules produced synthetically. An isolated polynucleotide fragment in the form of a polymer of DNA can be comprised of one or more segments of cDNA, genomic DNA, or synthetic DNA.

The term "gene" refers to a nucleic acid fragment that is capable of being expressed as a specific protein, optionally including regulatory sequences preceding (5' non-coding sequences) and following (3' non-coding sequences) the coding sequence.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences can include promoters, translation leader sequences, introns, polyadenylation recognition sequences, RNA processing site, effector binding site and stem-loop structure.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. A polypeptide can be derived from a natural biological source or produced by recombinant technology, but is not necessarily translated from a designated nucleic acid sequence. It can be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

As used herein, "pyruvate decarboxylase activity" refers to any polypeptide having a biological function of a pyruvate decarboxylase enzyme, including the examples provided herein. Such polypeptides include a polypeptide that catalyzes the conversion of pyruvate to acetaldehyde. Such polypeptides also include a polypeptide that corresponds to Enzyme Commission Number 4.1.1.1. Such polypeptides can be determined by methods well known in the art and disclosed herein.

As used herein, "reduced activity" can refer to any measurable decrease in a known biological activity of a polypeptide when compared to the same biological activity of the polypeptide prior to the change resulting in the reduced activity. Such a change can include a modification of a polypeptide or a polynucleotide encoding a polypeptide as described herein. A reduced activity of a polypeptide disclosed herein can be determined by methods well known in the art and disclosed herein. "Reduced activity" can also refer to any measurable decrease in a known biological activity in a cell when compared to the same biological activity in the cell prior to the change resulting in the decreased activity.

As used herein, "substantially eliminated activity" refers to measurable decrease in a known biological activity of a polypeptide that results in nearly complete abolishment of the activity when compared to the same biological activity of the polypeptide prior to the change resulting in the substantially eliminated activity. Such a change can include a modification of a polypeptide or a polynucleotide encoding a polypeptide as described herein. A substantially eliminated activity of a polypeptide disclosed herein can be determined by methods well known in the art and disclosed herein.

As used herein, "eliminated activity" refers to the complete abolishment of a known biological activity of a polypeptide when compared to the same biological activity of the polypeptide prior to the change resulting in the eliminated activity. Such a change can include a modification of a polypeptide or a polynucleotide encoding a polypeptide as described herein. An eliminated activity includes a biological activity of a polypeptide that is not measurable when compared to the same biological activity of the polypeptide prior to the change resulting in the eliminated activity. An eliminated activity of a polypeptide disclosed herein can be determined by methods well known in the art and disclosed herein.

As used herein, "native" refers to the form of a polynucleotide, gene, or polypeptide as found in nature with its own regulatory sequences, if present.

As used herein, "endogenous" refers to the native form of a polynucleotide, gene, or polypeptide in its natural location in the organism or in the genome of an organism. "Endogenous polynucleotide" includes a native polynucleotide in its natural location in the genome of an organism. "Endogenous gene" includes a native gene in its natural location in the genome of an organism. "Endogenous polypeptide" includes a native polypeptide in its natural location in the organism.

As used herein, "heterologous" refers to a polynucleotide, gene, or polypeptide not normally found in the host organism but that is introduced into the host organism. "Heterologous polynucleotide" includes a native coding region, or portion thereof, that is reintroduced into the source organism in a form that is different from the corresponding native polynucleotide. "Heterologous gene" includes a native coding region, or portion thereof, that is reintroduced into the source organism in a form that is different from the corresponding native gene. For example, a heterologous gene can include a native coding region that is a portion of a chimeric gene including non-native regulatory regions that is reintroduced into the native host. "Heterologous polypeptide" includes a native polypeptide that is reintroduced into the source organism in a form that is different from the corresponding native polypeptide.

As used herein, the term "modification" refers to a change in a polynucleotide disclosed herein that results in reduced, substantially eliminated or eliminated activity of a polypeptide encoded by the polynucleotide, as well as a change in a polypeptide disclosed herein that results in reduced, substantially eliminated or eliminated activity of the polypeptide. Such changes can be made by methods well known in the art including, but not limited to, deleting, mutating (e.g., spontaneous mutagenesis, random mutagenesis, mutagenesis caused by mutator genes, or transposon mutagenesis), substituting, inserting, down-regulating, altering the cellular location, altering the state of the polynucleotide or polypeptide (e.g., methylation, phosphorylation or ubiquitination), removing a cofactor, introduction of an antisense RNA/DNA, introduction of an interfering RNA/DNA, chemical modification, covalent modification, irradiation with UV or X-rays, homologous recombination, mitotic recombination, promoter replacement methods, and/or combinations thereof. Guidance in determining which nucleotides or amino acid residues can be modified, can be found by comparing the sequence of the particular polynucleotide or polypeptide with that of homologous polynucleotides or polypeptides, for example, yeast or bacterial, and maximizing the number of modifications made in regions of high homology (conserved regions) or consensus sequences.

As used herein, the term "variant" refers to a polypeptide differing from a specifically recited polypeptide of the invention by amino acid insertions, deletions, mutations, and substitutions, created using, for example, recombinant DNA techniques, such as mutagenesis. Guidance in determining which amino acid residues can be replaced, added, or deleted without abolishing activities of interest, can be found by comparing the sequence of the particular polypeptide with that of homologous polypeptides, for example, yeast or bacterial, and minimizing the number of amino acid sequence changes made in regions of high homology (conserved regions) or by replacing amino acids with consensus sequences.

Alternatively, recombinant polynucleotide variants encoding these same or similar polypeptides can be synthesized or selected by making use of the "redundancy" in the genetic code. Various codon substitutions, such as silent changes which produce various restriction sites, can be introduced to optimize cloning into a plasmid or viral vector for expression. Mutations in the polynucleotide sequence can be reflected in the polypeptide or domains of other peptides added to the polypeptide to modify the properties of any part of the polypeptide.

Amino acid "substitutions" can be the result of replacing one amino acid with another amino acid having similar structural and/or chemical properties, i.e., conservative amino acid replacements, or they can be the result of replacing one amino acid with an amino acid having different structural and/or chemical properties, i.e., non-conservative amino acid replacements. "Conservative" amino acid substitutions can be made on the basis of similarity in polarity, charge, solubility, hydrophobicity, hydrophilicity, or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. Alternatively, "non-conservative" amino acid substitutions can be made by selecting the differences in polarity, charge, solubility, hydrophobicity, hydrophilicity, or the amphipathic nature of any of these amino acids. "Insertions" or "deletions" can be within the range of variation as structurally or functionally tolerated by the recombinant proteins. The variation allowed can be experimentally determined by systematically making insertions, deletions, or substitutions of amino acids in a polypeptide molecule using recombinant DNA techniques and assaying the resulting recombinant variants for activity.

The term "promoter" refers to a DNA sequence capable of controlling the expression of a coding sequence or functional RNA. In general, a coding sequence is located 3' to a promoter sequence. Promoters can be derived in their entirety from a native gene, or be composed of different elements derived from different promoters found in nature, or even comprise synthetic DNA segments. It is understood by those skilled in the art that different promoters can direct the expression of a gene in different tissues or cell types, or at different stages of development, or in response to different environmental or physiological conditions. Promoters which cause a gene to be expressed in most cell types at most times are commonly referred to as "constitutive promoters." It is further recognized that since in most cases the exact boundaries of regulatory sequences have not been completely defined, DNA fragments of different lengths can have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression," as used herein, refers to the transcription and stable accumulation of sense (mRNA) or antisense RNA derived from the nucleic acid fragment of the invention. Expression can also refer to translation of mRNA into a polypeptide.

The term "overexpression," as used herein, refers to an increase in the level of nucleic acid or protein in a host cell. Thus, overexpression can result from increasing the level of transcription or translation of an endogenous sequence in a host cell or can result from the introduction of a heterologous sequence into a host cell. Overexpression can also result from increasing the stability of a nucleic acid or protein sequence.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements can be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Such optimization includes replacing at least one, or more than one, or a significant number, of codons with one or more codons that are more frequently used in the genes of that organism.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the proteins encoded by the DNA.

TABLE 1

The Standard Genetic Code

|   | T | C | A | G |
|---|---|---|---|---|
| T | TTT Phe (F) | TCT Ser (S) | TAT Tyr (Y) | TGT Cys (C) |
|   | TTC Phe (F) | TCC Ser (S) | TAC Tyr (Y) | TGC |
|   | TTA Leu (L) | TCA Ser (S) | TAA Stop | TGA Stop |
|   | TTG Leu (L) | TCG Ser (S) | TAG Stop | TGG Trp (W) |
| C | CTT Leu (L) | CCT Pro (P) | CAT His (H) | CGT Arg (R) |
|   | CTC Leu (L) | CCC Pro (P) | CAC His (H) | CGC Arg (R) |
|   | CTA Leu (L) | CCA Pro (P) | CAA Gln (Q) | CGA Arg (R) |
|   | CTG Leu (L) | CCG Pro (P) | CAG Gln (Q) | CGG Arg (R) |
| A | ATT Ile (I) | ACT Thr (T) | AAT Asn (N) | AGT Ser (S) |
|   | ATC Ile (I) | ACC Thr (T) | AAC Asn (N) | AGC Ser (S) |
|   | ATA Ile (I) | ACA Thr (T) | AAA Lys (K) | AGA Arg (R) |
|   | ATG Met (M) | ACG Thr (T) | AAG Lys (K) | AGG Arg (R) |
| G | GTT Val (V) | GCT Ala (A) | GAT Asp (D) | GGT Gly (G) |
|   | GTC Val (V) | GCC Ala (A) | GAC Asp (D) | GGC Gly (G) |
|   | GTA Val (V) | GCA Ala (A) | GAA Glu (E) | GGA Gly (G) |
|   | GTG Val (V) | GCG Ala (A) | GAG Glu (E) | GGG Gly (G) |

Many organisms display a bias for use of particular codons to code for insertion of a particular amino acid in a growing peptide chain. Codon preference, or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant, and microbial species, it is possible to calculate the relative frequencies of codon usage. Codon usage tables are readily available, for example, at the "Codon Usage Database" available at http://www.kazusa.or.jp/codon/ (visited Mar. 20, 2008), and these tables can be adapted in a number of ways (see, e.g., Nakamura, et al., Nucl. Acids Res. 28:292, 2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. Table 2 has been adapted so that frequencies are calculated for each amino acid, rather than for all 64 codons.

TABLE 2

Codon Usage Table for *Saccharomyces cerevisiae* Genes

| Amino Acid | Codon | Number | Frequency per thousand |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |

TABLE 2-continued

Codon Usage Table for *Saccharomyces cerevisiae* Genes

| Amino Acid | Codon | Number | Frequency per thousand |
|---|---|---|---|
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the Vector NTI Suite, available from InforMax, Inc., Bethesda, Md., and the "backtranslate" function in the GCG-Wisconsin Package, available from Accelrys, Inc., San Diego, Calif. In addition, various resources are publicly available to codon-optimize coding region sequences, for example, the "backtranslation" function at http://www.entelechon.com/bioinformatics/backtranslation.php?lang=eng (visited Apr. 15, 2008) and the "backtranseq" function available at http://bioinfo.pbi.nrc.ca:8090/EMBOSS/index.html (visited Jul. 9, 2002). Constructing a rudimentary algorithm to assign codons based on a given frequency can also easily be accomplished with basic mathematical functions by one of ordinary skill in the art.

Codon-optimized coding regions can be designed by various methods known to those skilled in the art including software packages such as "synthetic gene designer" (http://phenotype.biosci.umbc.edu/codon/sgd/index.php).

The term "percent identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods including, but not limited to, those disclosed in: 1.) *Compu-* tational Molecular Biology (Lesk, A. M., Ed.) Oxford University: NY (1988); 2.) Biocomputing: Informatics and Genome Projects (Smith, D. W., Ed.) Academic: NY (1993); 3.) Computer Analysis of Sequence Data, Part I (Griffin, A. M., and Griffin, H. G., Eds.) Humania: NJ (1994); 4.) Sequence Analysis in Molecular Biology (von Heinje, G., Ed.) Academic (1987); and 5.) Sequence Analysis Primer (Gribskov, M. and Devereux, J., Eds.) Stockton: NY (1991).

Preferred methods to determine identity are designed to give the best match between the sequences tested. Methods to determine identity and similarity are codified in publicly available computer programs. Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (disclosed by Higgins and Sharp, CABIOS. 5:151-153, 1989; Higgins, et al., Comput. Appl. Biosci., 8:189-191, 1992) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, supra; Higgins, et al., supra) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 55%, 60%, 65%, 70%, 75%, 80%, 85%, 90%, or 95%, or any integer percentage from 55% to 100% may be useful in describing the present invention, such as 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul, et al., J. Mol. Biol., 215:403-410, 1990); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Press, Cold Spring Harbor, N.Y. (1984); and by Ausubel, F. M. et al., Current Protocols in Molecular Biology, published by Greene Publishing Assoc. and Wiley-Interscience (1987). Additional suitable methods are in Methods in Enzymology, Volume 194, Guide to Yeast Genetics and Molecular and Cell Biology (Part A, 2004, Christine Guthrie and Gerald R. Fink (Eds.), Elsevier Academic Press, San Diego, Calif.).

The genetic manipulations of a recombinant host cell disclosed herein can be performed using standard genetic techniques and screening and can be made in any host cell that is suitable to genetic manipulation (Methods in Yeast Genetics, 2005, Cold Spring Harbor Laboratory Press, Cold Spring Harbor, N.Y., pp. 201-202). In some embodiments, the recombinant host cell disclosed herein can be bacterial or fungal. In some embodiments, the recombinant host cell disclosed herein can be E. coli. In some embodiments, a recombinant host cell disclosed herein can be any yeast or fungi host useful for genetic modification and recombinant gene expression. In other embodiments, a recombinant host cell can be a member of the genera Saccharomyces, Zygosaccharomyces, Schizosaccharomyces, Dekkera, Torulopsis, Brettanomyces, Torulaspora, Hanseniaspora, Kluveromyces, Issatchenkia, and some species of Candida. In another embodiment, a recombinant host cell can be Saccharomyces cerevisiae.

Exogenous Thiamine and/or Thiamine Biosynthetic Precursor Supplementation

The main biologically active thiamine derivative is thiaminediphosphate (TDP). Its primary function, recognized early after its discovery, is its contribution to the universal metabolic pathways including glycolysis, the pentose phosphate pathway, and the tricarboxylic acid cycle, where TDP serves as a cofactor of enzymes such as pyruvate dehydrogenases, α-ketoglutarate dehydrogenases, branched-chain α-ketoacid dehydrogenases, transketolases, and pyruvate decarboxylases. The roles of thiamin and its phosphate derivatives are described in Kowalska and Kozik, (Cell Mol. Biol. Lett. 13:271-82, 2008).

A regulatory activity of TDP has been reported, but the mechanisms of this regulation at the nucleic acid and protein levels is still poorly understood, as elaborated by Hohmann and Meacock (Biochim Biophys Acta 1385:201-19, 1998).

More recently, TDP was shown to bind to mRNA domains called "riboswitches" and to affect mRNA structure resulting in gene expression regulation, particularly regulation of the genes involved in thiamin biosynthesis (Lai, Curr. Biol. 13:R285-91, 2003).

A recent report on the accumulation of TTP in *Escherichia coli* in response to amino acid starvation raises a hypothesis that TTP may play a more universal role as a signal molecule in prokaryotic and eukaryotic cells (Lakaye, et al., J. Biol. Chem. 279:17142-7, 2004).

It has also recently been hypothesized that thiamin and its derivatives contribute to organism responses to various stress conditions, such as UV illumination when thiamin may be involved in the repair of DNA damage, or under conditions of oxidative stress and heat shock when thiamin may increase mitochondrial stability (Machado, et al., J. Mol. Biol. 273: 114-21, 1997) and Medina-Silva, et al., Res. Microbiol. 157: 275-81, 2006).

Knowledge on thiamin biosynthesis in yeast has been reviewed by Kowalska and Kozik (Cell Mol. Biol. Lett. 13: 271-82, 2008). According to Kowalska and Kozik, similar to other thiamin-synthesizing organisms, yeast first separately synthesize two precursors, 5-(2-hydroxyethyl)-4-methylthiazole phosphate (HET-P) and 4-amino-5-hydroxymethyl-2 methylpyrimidine diphosphate (HMP-PP), which are then condensed into TMP. In the absence of experimental evidence of the early steps of thiazole (HET-P) and pyrimidine (HMP-P) synthesis in yeast, intermediates have been predicted only by extrapolations from prokaryotic thiamin biosynthesis (Begley, et al., Arch. Microbiol. 171:293-300, 1999).

Kowalska and Kozik also indicate that substrates for yeast thiazole synthesis include cysteine as a sulfur donor, glycine, and D-pentulose-5-phosphate. The latter may be D-ribulose-5-phosphate or D-xylulose-5-phosphate, indicative of a link between thiamin biosynthesis and the pentose phosphate pathway (Hohmann and Meacock, supra). A mechanism of thiazole synthesis has been proposed in which NAD+ serves as the early source of a five-carbon carbohydrate and the advanced intermediate is an ADP adduct of 5-(2-hydroxyethyl)-4-methylthiazole-2-carboxylic acid (Chatterjee, et al., J. Am. Chem. Soc. 129:2914-22, 2007). The final product of the thiazole synthesis pathway is HET-P.

Furthermore, according to Kowalska and Kozik, yeast also possess a salvage pathway through which external 5-(2-hydroxyethyl)-4-methylthiazole (HET) is taken up and then phosphorylated to HET-P (Nosaka, et al., J. Biol. Chem. 269:30510-6, 1994). HMP-P is synthesized in yeast cells from histidine and pyridoxal-5-phosphate, the latter linking the thiamin and vitamin B6 (pyridoxine) biosynthesis pathways (Zeidler, et al., J. Am. Chem. Soc. 125:13094-105, 2003). Yeast can also salvage HMP-P by uptake of 4-amino-5-hydroxymethyl-2-methylpyrimidine (HMP) from the environment followed by its phosphorylation (Kawasak, et al., Curr. Genet. 47:156-62, 2005). The next phosphorylation step yields HMP-PP ready for condensation with HET-P to produce TMP.

Finally, Kowalska and Kozik state that unlike many bacteria, yeast cannot directly phosphorylate TMP to obtain the bioactive coenzyme, TDP. Therefore, TMP must first be dephosphorylated to free thiamin, which is then activated via one-step diphosphorylation (Nosaka, et al., J. Biol. Chem. 268: 17440-7, 1993). TDP may also be produced from free thiamin taken up by the yeast cells from the environment (Enjo, et al., J. Biol. Chem. 272: 19165-70, 1997). External thiamin phosphates, which cannot be transported across the cell membrane, are first dephosphorylated in the periplasm to be utilized by the yeast cells.

Provided herein are methods of increasing the production of butanol using recombinant host organisms by increasing available thiamine via addition of thiamine and/or its biosynthetic precursors to media. In some embodiments, the butanol is 1-butanol, 2-butanol, or isobutanol. In some embodiments, the host cell is *E. coli*. In other embodiments, the host cell is *S. cerevisiae*. At least two metabolic enzymes which can be expressed in host cells for butanol production, acetolactate synthase (AlsS) and ketoisovalerate decarboxylase, are TPP-dependent enzymes. Thus, the present invention provides methods for providing media containing sufficient thiamine for butanol production. The addition of thiamine or other biosynthetic precursors of thiamine to production media for recombinant butanol-producing yeast cells can increase butanol production. The thiamine or other biosynthetic precursor of thiamine can be added to the production media in the absence of other multi-component media additives such as yeast extract, corn steep liquor, and sugar cane concentrate. Thus, in some embodiments, the concentration of yeast extract in the production media is less than about 3 g/L, less than about 2 g/L, less than about 1 g/L, or less than about 0.5 g/L. In some embodiments, the production media is substantially free of yeast extract. In some embodiments, the concentration of multi-component media additives in the production media is less than about 3 g/L, less than about 2 g/L, less than about 1 g/L, or less than about 0.5 g/L. In some embodiments, the production media is substantially free of multi-component media additives. In some embodiments, the production broth contains less than about 3 g/L, less than about 2 g/L, less than about 1 g/L, less than about 0.5 g/L, or less than about 0.2 g/L of multi-component media additives.

Thiamine or a biosynthetic precursor of thiamine can be added to the production media at a concentration of at least about 0.4 mg/L, at least about 1.2 mg/L, at least about 2 mg/L, at least about 5 mg/L, at least about 6 mg/L, at least about 10 mg/L, at least about 50 mg/L, at least about 60 mg/L, at least about 80 mg/L, at least about 100 mg/L, at least about 150 mg/L, at least about 250 mg/L, or at least about at least about 300 mg/L. In one aspect, thiamine or a biosynthetic precursor of thiamine is provided in the production media in an amount greater than about 1 mg/L. In another aspect, thiamine or a biosynthetic precursor of thiamine is provided in the production media based on the cell density. Thiamine or a biosynthetic precursor of thiamine may be provided in an amount greater than about 0.1 g/g of dry cell weight (dcw) in the production media. In some embodiments, the concentration of thiamine is determined in the production broth (which comprises the production media). Accordingly, the concentration of thiamine may be at least about 0.2 mg/L, at least about 1 mg/L, at least about 5 mg/L, at least about 10 mg/L, at least about 50 mg/L, or at least about 100 mg/L in the production broth.

In some embodiments, the amount of thiamine or biosynthetic precursor is greater than about 0.1 g/g of dry cell weight and the cell density is greater than about 7 gdcw/L, about 10 g dcw/L, or about 20 gdcw/L. In some embodiments, the amount of thiamine or biosynthetic precursor is greater than about 1 g/L of dry cell weight and the cell density is less than about 7 g dcw/L, less than about 10 g dcw/L, or less than about 20 g dcw/L.

Cell density can be determined using techniques known in the art. Dry weight of the cell suspension is determined, for example, by centrifugation of 5 mL cell broth in a pre-weighed centrifuge tube, followed by washing with distilled water and drying to constant weight at 80° C. in an oven In some embodiments, the addition of thiamine and/or other biosynthetic precursor of thiamine improves fermentation product production parameters in aerobic conditions, anaerobic conditions, or both in aerobic and in anaerobic conditions. The addition of thiamine or other biosynthetic precursor of thiamine can increase butanol production as measured by butanol titer or specific butanol production rate. The addition of thiamine or other biosynthetic precursor of thiamine can increase butanol production as measured by butanol concentration or specific butanol production rate in aerobic conditions, anaerobic conditions, or both in aerobic and in anaerobic conditions. The addition of thiamine or other biosynthetic precursor of thiamine can increase butanol production as measured by less accumulation of the isobutanol pathway intermediates like α-ketoisovalerate.

In some embodiments, the host cell cultured in the media supplemented with thiamine or other biosynthetic precursor of thiamine can be a recombinant butanol producing host cell. In some embodiments, the recombinant butanol producing host cell can be an S. cerevisiae host cell. In other embodiments, the recombinant host cell can comprise a butanol biosynthetic pathway as described herein. In other embodiments, the butanol biosynthetic pathway can comprise polynucleotides encoding polypeptides having acetolactate synthase and ketoisovalerate decarboxylase and, optionally, alcohol dehydrogenase activity. In a particular embodiment, the butanol producing strain is S. cerevisiae.

In some embodiments, thiamine is added to the media prior to or at the beginning of a fermentation. In other embodiments, thiamine is added over the course of a fermentation or during a fermentation. Concentrations of thiamine provided may be achieved, for example, via addition of a bolus of thiamine to production media or via aliquots to production broth.

In some embodiments, nicotinic acid, nicotinamid, or other biosynthetic precursor of NAD is added to the production media in addition to the thiamine or other biosynthetic precursor of thiamine. Nicotinic acid, nicotinamid, or other biosynthetic precursor of NAD can be added to the production media at a concentration of at least about 5 mg/L, at least about 6 mg/L, at least about 7 mg/L, at least about 8 mg/L, at least about 9 mg/L, at least about 10 mg/L, at least about 20 mg/L, at least about 50 mg/L, at least about 80 mg/L, at least about 100 mg/L, at least about 150 mg/L, at least about 250 mg/L, at least about 250 mg/L, or at least about at least about 300 mg/L.

Because the methods provided herein are believed to be particularly advantageous for commercial scale fermentations, some embodiments include production media comprising added thiamine or biosynthetic precursors thereof and added nicotinic acid, nicotinamid, or biosynthetic precursor of NAD wherein the production media is substantially free of multi-component media additives. In some embodiments, the production media consists essentially of thiamine or biosynthetic precursors thereof and optionally nicotinic acid, nicotinamid, or biosynthetic precursor of NAD. In other embodiments, the production media consists essentially of thiamine or biosynthetic precursors thereof, and nicotinic acid, nicotinamid, or biosynthetic precursor of NAD. Some embodiments also include media for commercial-scale fermentations such as fermentations of volume greater than about 1000 L, greater than about 10,000 L, or greater than about 50,000 L.

Thi2, Thi3, and Pdc2 Activity

Pdc2 is a transcriptional regulator that coordinates the expression of THI (thiamine biosynthesis) regulon and the TPP-dependent enzymes (PDC1 and PDC5). Pdc2 interacts with Thi2 and Thi3 proteins in controlling the expression of many genes in the THI regulon. Thi2 is a transcription factor with a zinc finger DNA-binding motif. Overexpression of PDC2 protein has been shown to upregulate many genes in the THI regulon in a Thi2-independent manner, for example, THI4, THI5, THI7, THI13, PHO3, and PDC5. In addition, Thi2-dependent upregulation of THI6 and THI73 require Pdc2. Thi3 is an essential regulatory protein of the THI regulon. It binds to the TPP cofactor at high thiamine concentrations and leads to repression of THI genes. At low thiamine concentrations, it binds Thi2 and Pdc2 to activate THI gene transcription. Pdc2 mediates the upregulation of certain THI genes (e.g., THI20, PET18) together with Thi3.

Thus, in order to improve isobutanol production, a host cell such as yeast can be engineered to increase the activity of Thi2, Thi3, and/or Pdc2. The overall Thi2, Thi3, and/or Pdc2 activity in a yeast cell can be increased by increasing the levels of Thi2, Thi3, and/or Pdc2 or by increasing the activity of individual Thi2, Thi3, and/or Pdc2 molecules. Thus, for example, the levels of Thi2, Thi3, and/or Pdc2 can be increased by introducing sequences encoding Thi2, Thi3, and/or Pdc2 into a host cell, which may or may not express Thi2, Thi3, and/or Pdc2 endogenously. The levels of Thi2, Thi3, and/or Pdc2 can also be increased by increasing transcription of endogenous Thi2, Thi3, and/or Pdc2 sequences, for example, by creating mutations in the Thi2, Thi3, and/or Pdc2 promoter sequences that allow for increased transcription of Thi2, Thi3, and/or Pdc2. The activity of individual Thi2, Thi3, and/or Pdc2 molecules can be increased, for example, by introducing mutations into Thi2, Thi3, and/or Pdc2 coding sequences or proteins that result in increased transcriptional activity. For example, it has been demonstrated that a C-terminally truncated Pdc2 protein can transactivate THI11 gene transcription in a Thi3-independent manner (Nosaka, et al., FEBS Letters, 582:3991-3996, 2008). Thus, mutation of an endogenous Pdc2-coding sequence that results in the production of a C-terminally truncated Pdc2 protein increases Pdc2 activity. Similarly, introducing heterologous sequences encoding the truncated Pdc2 protein into a host cell can also increase Pdc2 activity. Therefore, the overall activity of Thi2, Thi3, and/or Pdc2 in a host cell can be increased by the introduction of heterologous nucleic acid and/or protein sequences or by mutation of endogenous nucleic acid and/or protein sequences. The introduction of Thi2, Thi3, and/or Pdc2 activity into a recombinant host cell can have the same, similar, or improved effects on butanol production as supplementation with thiamine or biosynthetic precursors thereof.

Heterologous Aspartate Oxidase/Dehydrogenase Activity

The introduction of heterologous aspartate oxidase and/or aspartate dehydrogenase activity into a recombinant host cell can increase isobutanol production. In some embodiments of the methods described herein, a heterologous polynucleotide encoding an aspartate oxidase and/or a heterologous polynucleotide encoding an aspartate dehydrogenase can be introduced into a cell using recombinant DNA technologies that are well known in the art. In some embodiments, the introduction of a heterologous polynucleotide encoding a polypeptide having aspartate oxidase or aspartate dehydrogenase activity results in an improved isobutanol concentrations and increased specific isobutanol production rates. In other embodiments, the NAD biosynthetic pathway can comprise a polynucleotide encoding a polypeptide that catalyzes the conversion of aspartic acid to iminoaspartic acid.

Examples of aspartate oxidase or aspartate dehydrogenase polynucleotides, genes and polypeptides that can be heterologously expressed in a host cell disclosed herein include, but are not limited to, those of the following Table 3.

TABLE 3

Aspartate Oxidase or Aspartate Dehydrogenase Sequences

| | |
|---|---|
| L-aspartate oxidase from *E. coli* | Amino acid (SEQ ID NO: 97)<br>MNTLPEHSCDVLIIGSGAAGLSLALRLADQHQVIVLSKGPVTEGST<br>FYAQGGIAAVFDETDSIDSHVEDTLIAGAGICDRHAVEFVASNAR<br>SCVQWLIDQGVLFDTHIQPNGEESYHLTREGGHSHRRILHAADAT<br>GREVETTLVSKALNHPNIRVLERSNAVDLIVSDKIGLPGTRRVVG<br>AWVWNRNKETVETCHAKAVVLATGGASKVYQYTTNPDISSGDG<br>IAMAWRAGCRVANLEFNQFHPTALYHPQARNFLLTEALRGEGAY<br>LKRPDGTRFMPDFDERGELAPRDIVARAIDHEMKRLGADCMFLDI<br>SHKPADFIRQHFPMIYEKLLGLGIDLTQEPVPIVPAAHYTCGGVM<br>VDDHGRTDVEGLYAIGEVSYTGLHGANRMASNSLLECLVYGWS<br>AAEDITRRMPYAHDISTLPPWDESRVENPDERVVIQHNWHELRLF<br>MWDYVGIVRTTKRLERALRRITMLQQEIDEYYAHFRVSNNLLEL<br>RNLVQVAELIVRCAMMRKESRGLHFTLDYPELLTHSGPSILSPGN<br>HYINR |
| L-aspartate oxidase from *B. subtilis* | Amino acid (SEQ ID NO: 98):<br>MSKKTIAVIGSGAAALSLAAAFPPSYEVTVITKKSVKNSNSVYAQ<br>GGIAAAYAKDDSIEAHLEDTLYAGCGHNNLAIVADVLHDGKMM<br>VQSLLERGFPFDRNERGGVCLGREGAHSYNRIFHAGGDATGRLLI<br>DYLLKRINSKIKLIENETAADLLIEDGRCIGVMTKDSKGRLKVRHA<br>DEVVLAAGGCGNLFLHHTNDLTVTGDGLSLAYRAGAELTDLEFT<br>QFHPTLLVKNGVSYGLVSEAVRGEGGCLVDENGRRIMAERHPLG<br>DLAPRDIVSRVIHEEMAKGNRVYIDFSAISDFETRFPTITAICEKAGI<br>DIHSGKIPVAPGMHFLMGGVSVNRWGETTVPGLYAIGETACSGL<br>HGANRLASNSLLEALVFGKRAAEHIIQKPVYNRQYQSGLETSVFY<br>EVPDIEGHELQSKMTSHMSILREQSSLIELSIWLHTLPFQEVNVKDI<br>TIRQMELSHLWQTAKLMTFSALLREESRGAHFRTDFPHAEVSWQ<br>GRQIVHTKKGTKIRKNEGIWNNESFTAEKITESLFS |
| Aspartate dehydrogenase from *T. maritime* | Amino acid (SEQ ID NO: 99):<br>MTVLIIGMGNIGKKLVELGNFEKIYAYDRISKDIPGVVRLDEFQVP<br>SDVSTVVECASPEAVKEYSLQILKNPVNYIIISTSAFADEVFRERFF<br>SELKNSPARVFFPSGAIGGLDVLSSIKDFVKNVRIETIKPPKSLGLD<br>LKGKTVVFEGSVEEASKLFPRNINVASTIGLIVGFEKVKVTIVADP<br>AMDHNIHIVRISSAIGNYEFKIENIPSPENPKTSMLTVYSILRTLRNL<br>ESKIIFG |

Heterologous Quinolinate Synthase Activity

The introduction of heterologous quinolinate synthase activity into a recombinant host cell can increase alcohol production. In some embodiments of the methods described herein, a heterologous polynucleotide encoding a quinolinate synthase can be introduced into a cell using recombinant DNA technologies that are well known in the art. In some embodiments, the introduction of a heterologous polynucleotide encoding a polypeptide having quinolinate synthase activity results in an improved isobutanol concentrations and increased specific isobutanol production rates. In other embodiments, the NAD biosynthetic pathway can comprise a polynucleotide encoding a polypeptide that catalyzes the conversion of iminoaspartic acid to quinolate.

Examples of quinolinate synthase polynucleotides, genes and polypeptides that can be heterologously expressed in a host cell disclosed herein include, but are not limited to, those of the following Table 4.

TABLE 4

Quinolinate Synthase Sequences

| | |
|---|---|
| Quinolinate synthase from *E. coli* | Amino acid (SEQ ID NO: 100):<br>MSVMFDPDTAIYPFPPPKPTPLSIDEKAYYREKIKRLLKERNAVMV<br>AHYYTDPEIQQLAEETGGCISDSLEMARFGAKHPASTLLVAGVRF<br>MGETAKILSPEKTILMPTLQAECSLDLGCPVEEFNAFCDAHPDRT<br>VVVYANTSAAVKARADWVVTSSIAVELIDHLDSLGEKIIWAPDK<br>HLGRYVQKQTGGDILCWQGACIVHDEFKTQALTRLQEEYPDAAI<br>LVHPESPQAIVDMADAVGSTSQLIAAAKTLPHQRLIVATDRGIFY<br>KMQQAVPDKELLEAPTAGEGATCRSCAHCPWMAMNGLQAIAEA<br>LEQEGSNHEVHVDERLRERALVPLNRMLDFAATLRG |
| Quinolinate synthase from *B. subtilis* | Amino acid (SEQ ID NO: 101):<br>MSILDVIKQSNDMMPESYKELSRKDMETRVAAIKKKFGSRLFIPG<br>HHYQKDEVIQFADQTGDSLQLAQVAEKNKEADYIVFCGVHFMA<br>ETADMLTSEQQTVVLPDMRAGCSMADMADMQQTNRAWKKLQ<br>HIFGDTIIPLTYVNSTAEIKAFVGKHGGATVTSSNAKKVLEWAFTQ<br>KKRILFLPDQHLGRNTAYDLGIALEDMAVWDPMKDELVAESGHT<br>NVKVILWKGHCSVHEKFTTKNIHDMRERDPDIQIIVHPECSHEVV<br>TLSDDNGSTKYIIDTINQAPAGSKWAIGTEMNLVQRIIHEHPDKQI<br>ESLNPDMCPCLTMNRIDLPHLLWSLEQIEKGEPSGVIKVPKAIQED<br>ALLALNRMLSIT |

TABLE 4-continued

Quinolinate Synthase Sequences

| | |
|---|---|
| Quinolinate synthase from T. maritime | Amino acid (SEQ ID NO: 102):<br>MVDEILKLKKEKGYIILAHNYQIPELQDIADFVGDSLQLARKAME<br>LSEKKILFLGVDFMAELVKILNPD-<br>KKVIVPDRSATCPMANRLTPEII<br>REYREKFPDAPVVLYVNSTSECKTLADVICTSANAVEVVKKLDSS<br>VVIFGPDRNLGEYVAEKTGKKVITIPENGHCPVHQFNAESIDAVR<br>KKYPDAKVIVHPECPKPVRDKADYVGSTGQMEKIPEKDPSRIFVI<br>GTEIGMIHKLKKKFPDREFVPLEMAVCVNMKKNTLENTLHALQT<br>ESFEVILPKEVIEKAKKPILRMFELMG |

Nicotinic Acid and/or Nicotinamid Supplementation

The addition of nicotinic acid, nicotinamid, or other biosynthetic precursors of nicotine adenine dinucleotide (NAD) to production media where recombinant alcohol-producing cells are cultured can increase alcohol production. In some embodiments, the alcohol is butanol and in other embodiments, the butanol is 1-butanol, 2-butanol, or isobutanol. In some embodiments, the host cell is yeast. In embodiments, the host cell is the yeast S. cerevisiae. The nicotinic acid, nicotinamid, or other biosynthetic precursor of NAD including, but not limited to, nicotinic acid riboside or nicotinamid riboside can be added to the production media in the absence of other multi-component media additives such as yeast extract, corn steep liquor, and sugar cane concentrate. Thus, in some embodiments, the concentration of yeast extract in the production media is less than about 20 g/L, less than about 10 g/L, less than about 5 g/L, less than about 4 g/L, less than about 3 g/L, less than about 2 g/L, less than about 1 g/L, or less than about 0.5 g/L. In some embodiments, the production media is substantially free of yeast extract. In some embodiments, the concentration of multi-component media additives in the production media is less than about 3 g/L, less than about 2 g/L, less than about 1 g/L, or less than about 0.5 g/L. In some embodiments, the production media is substantially free of multi-component media additives. In some embodiments, the production broth contains less than about 3 g/L, less than about 2 g/L, less than about 1 g/L, less than about 0.5 g/L, or less than about 0.2 g/L of multi-component media additives.

In another aspect, nicotinic acid, nicotinamid, nicotinic acid riboside, nicotinamid riboside, or other biosynthetic precursor of NAD is provided in the production media based on the cell density. The nicotinic acid, nicotinamid, or other biosynthetic precursor of NAD may be provided in an amount greater than about 0.5 mg/g of dry cell weight in the production media, greater than about 0.4 mg/g of dry cell weight in the production media, greater than about 0.3 mg/g of dry cell weight in the production media, greater than about 0.2 mg/g of dry cell weight in the production media, or greater than about 0.1 mg/g of dry cell weight in the production media.

In some embodiments, the amount of nicotinic acid, nicotinamid, or other biosynthetic precursor of NAD is greater than about 0.1 g/g of dry cell weight and the cell density is greater than about 5 gdcw/L, about 7 g dcw/L, about 10 g dcw/L, or about 20 gdcw/L. In some embodiments, the amount of nicotinic acid, nicotinamid, or other biosynthetic precursor of NAD is greater than about 5 mg/L of dry cell weight and the cell density is less than about 5 g dcw/L, less than about 7 g dcw/L, less than about 10 g dcw/L, or less than about 20 g dcw/L. Cell density may be determined as described above.

The nicotinic acid, nicotinamid, or other biosynthetic precursor of NAD can be added to the production media at a total concentration of at least about 5 mg/L, at least about 6 mg/L, at least about 7 mg/L, at least about 8 mg/L, at least about 9 mg/L, at least about 10 mg/L, at least about 15 mg/L, at least about 20 mg/L, at least about 25 mg/L, at least about 30 mg/L, at least about 40 mg/L, at least about 50 mg/L, at least about 60 mg/L, at least about 80 mg/L, or at least about 100 mg/L, at least about 120 mg/L, at least about 150 mg/L, or at least about 300 mg/L. In some embodiments, the concentration of nicotinic acid, nicotinamid, or other biosynthetic precursor of NAD is determined in the production broth (which comprises the production media). Accordingly, the concentration of nicotinic acid, nicotinamid, or other biosynthetic precursor of NAD may be at least about 0.2 mg/L, at least about 1 mg/L, at least about 5 mg/L, at least about 10 mg/L, at least about 50 mg/L, or at least about 70 mg/L in the production broth.

In some embodiments, the addition of nicotinic acid, nicotinamid, or other biosynthetic precursor of NAD improves one or more product production parameters like volumetric rate, specific rate, titer, or yield in aerobic conditions, anaerobic conditions, or both in aerobic and in anaerobic conditions. The addition of nicotinic acid, nicotinamid, or other biosynthetic precursor of NAD can increase alcohol production as measured by alcohol titer or specific alcohol production rate. In some embodiments, the addition of nicotinic acid, nicotinamid, or other biosynthetic precursor of NAD may increase cell mass. In some embodiments, the host cell cultured in the media supplemented with nicotinic acid, nicotinamid, or other biosynthetic precursor of NAD can be a recombinant butanol producing host cell. In some embodiments, the recombinant butanol producing host cell can be an S. cerevisiae host cell. In other embodiments, the recombinant host cell can comprise a butanol biosynthetic pathway as described further herein. In other embodiments, the butanol biosynthetic pathway can comprise polynucleotides encoding polypeptides having acetolactate synthase and ketoisovalerate decarboxylase, and, optionally, alcohol dehydrogenase activity. In a particular embodiment, the butanol producing strain is S. cerevisiae.

In some embodiments, the nicotinic acid, nicotinamid, or other biosynthetic precursor of NAD is added to the media prior to or at the beginning of a fermentation. In other embodiments, the nicotinic acid, nicotinamid, or other biosynthetic precursor of NAD is added over the course of a fermentation or during a fermentation. Concentrations of nicotinic acid, nicotinamid, or other biosynthetic precursor of NAD provided may be achieved, for example, via addition of a bolus of nicotinic acid, nicotinamid, or other biosynthetic precursor of NAD to media or via aliquots.

In some embodiments, thiamine or a biosynthetic precursor thereof is added to the production media in addition to the nicotinic acid, nicotinamid, or other biosynthetic precursor of NAD. Thiamine or a biosynthetic precursor thereof can be added to the production media at a concentration of at least about 1 mg/L, at least about 2 mg/L, at least about 3 mg/L, at least about 4 mg/L, at least about 5 mg/L, at least about 6 mg/L, at least about 7 mg/L, at least about 8 mg/L, at least about 10 mg/L, at least about 15 mg/L, at least about 20 mg/L, at least about 30 mg/L, at least about 50 mg/L, at least about 70 mg/L, at least about 100 mg/L, or at least about at least about 200 mg/L.

In some embodiments, the production media contacts recombinant microorganisms and a fermentable carbon source in a fermentation vessel. Thus, provided herein is a composition comprising i) production media, the media comprising thiamine and nicotinic acid, ii) recombinant microorganisms comprising a biosynthetic pathway, and iii) liquefied biomass comprising a fermentable carbon source. In some embodiments, the production media consists essentially of thiamine and nicotinic acid. In some embodiments, the production media consists essentially of nicotinic acid, nicotinamid, or other biosynthetic precursor of NAD and optionally thiamine or a biosynthetic precursor thereof. In some embodiments, the production media consists essentially of thiamine or biosynthetic precursors thereof and nicotinic acid, nicotinamid, or other biosynthetic precursor of NAD.

Modification of Pyruvate Decarboxylase

Functional deletion of the pyruvate decarboxylase gene has been used to increase the availability of pyruvate for utilization in biosynthetic product pathways. For example, U.S. Patent Application Publication No. 2007/0031950 A1 discloses a yeast strain with a disruption of one or more pyruvate decarboxylase genes and expression of a D-lactate dehydrogenase gene which is used for production of D-lactic acid. U.S. Patent Application Publication No. 2005/0059136 A1 discloses glucose tolerant two carbon source independent (GCSI) yeast strains with no pyruvate decarboxylase activity, which may have an exogenous lactate dehydrogenase gene. Nevoigt and Stahl (Yeast 12:1331-1337, 1996) describe the impact of reduced pyruvate decarboxylase and increased NAD-dependent glycerol-3-phosphate dehydrogenase in Saccharomyces cerevisiae on glycerol yield. U.S. patent application Ser. No. 12/477,942 discloses increased conversion of pyruvate to acetolactate by engineering yeast for expression of a cytosol-localized acetolactate synthase and substantial elimination of pyruvate decarboxylase activity.

In some embodiments of the invention, a recombinant host cell disclosed herein can comprise a modification in an endogenous polynucleotide encoding a polypeptide having pyruvate decarboxylase (PDC) activity or a modification in an endogenous polypeptide having PDC activity. In some embodiments, a recombinant host cell disclosed herein can have a modification or disruption of a polynucleotide, gene, and/or polypeptide encoding PDC. In some embodiments, a recombinant host cell comprises a deletion, mutation, and/or substitution in an endogenous polynucleotide or gene encoding a polypeptide having PDC activity, or in an endogenous polypeptides having PDC activity. Such modifications, disruptions, deletions, mutations, and/or substitutions can result in PDC activity that is reduced, substantially eliminated, or eliminated resulting, for example, in a PDC knock-out (PDC-KO) phenotype.

In some embodiments of the invention, an endogenous pyruvate decarboxylase activity of a recombinant host cell disclosed herein converts pyruvate to acetaldehyde which can then be converted to ethanol or to acetyl-CoA via acetate. In other embodiments, a recombinant host cell is Kluyveromyces lactis containing one gene encoding pyruvate decarboxylase, Candida glabrata containing one gene encoding pyruvate decarboxylase, or Schizosaccharomyces pombe containing one gene encoding pyruvate decarboxylase.

In other embodiments, a recombinant host cell is Saccharomyces cerevisiae containing three isozymes of pyruvate decarboxylase encoded by the PDC1, PDC5, and PDC6 genes. In a non-limiting example in S. cerevisiae, the PDC1 and PDC5 genes or the PDC1, PDC5, and PDC6 genes, are disrupted. In another non-limiting example in S. cerevisiae, polynucleotides or genes encoding pyruvate decarboxylase proteins such as those having about 70% to about 75%, about 75% to about 80%, about 80% to about 85%, about 85% to about 90%, about 90% to about 95%, about 96%, about 97%, about 98%, or about 99% sequence identity to PDC1, PDC5, and/or PDC6 can be disrupted.

In some embodiments, a polypeptide having PDC activity or a polynucleotide or gene encoding a polypeptide having PDC activity corresponds to Enzyme Commission Number EC 4.1.1.1. In other embodiments, a PDC gene of a recombinant host cell disclosed herein is not active under the fermentation conditions used, and therefore such a gene would not need to be modified or inactivated.

Examples of recombinant host cells with reduced pyruvate decarboxylase activity due to disruption of pyruvate decarboxylase encoding genes have been reported, such as for Saccharomyces in Flikweert, et al. (Yeast 12:247-257, 1996), for Kluyveromyces in Bianchi, et al. (Mol. Microbiol. 19(1): 27-36, 1996), and disruption of the regulatory gene in Hohmann (Mol. Gen. Genet. 241:657-666, 1993). Saccharomyces strains having no pyruvate decarboxylase activity are available from the ATCC with Accession No. 200027 and Accession No. 200028.

Examples of PDC polynucleotides, genes, and/or polypeptides that can be targeted for modification or inactivation in the recombinant host cells disclosed herein include, but are not limited to, those of the following Table 5.

TABLE 5

Pyruvate Decarboxylase Target Gene Coding Regions and Proteins

| Description | SEQ ID NO: Nucleic acid | SEQ ID NO: Amino acid |
|---|---|---|
| PDC1 pyruvate decarboxylase from Saccharomyces cerevisiae | 1 | 2 |
| PDC5 pyruvate decarboxylase from Saccharomyces cerevisiae | 3 | 4 |
| PDC6 pyruvate decarboxylase from Saccharomyces cerevisiae | 5 | 6 |
| pyruvate decarboxylase from Candida glabrata | 7 | 8 |
| PDC1 pyruvate decarboxylase from Pichia stipitis | 9 | 10 |
| PDC2 pyruvate decarboxylase from Pichia stipitis | 11 | 12 |
| pyruvate decarboxylase from Kluyveromyces lactis | 13 | 14 |
| pyruvate decarboxylase from Yarrowia lipolytica | 15 | 16 |
| pyruvate decarboxylase from Schizosaccharomyces pombe | 17 | 18 |
| pyruvate decarboxylase from Zygosaccharomyces rouxii | 18 | 20 |

Other examples of PDC polynucleotides, genes, and polypeptides that can be targeted for modification or inactivation in a recombinant host cell disclosed herein include, but are not limited to, PDC polynucleotides, genes and/or polypeptides having at least about 70% to about 75%, about 75% to about 80%, about 80% to about 85%, about 85% to about 90%, about 90% to about 95%, about 96%, about 97%, about 98%, or about 99% sequence identity (or identity) to any one of the sequences of Table 5, wherein such a polynucleotide or gene encodes, or such a polypeptide has, PDC activity. Still other examples of PDC polynucleotides, genes, and polypeptides that can be targeted for modification or inactivation in a recombinant host cell disclosed herein include, but are not limited to, an active variant, fragment, or derivative of any one of the sequences of Table 5, wherein such a polynucleotide or gene encodes, or such a polypeptide has, PDC activity.

In some embodiments, the sequences of other PDC polynucleotides, genes, and/or polypeptides can be identified in the literature and in bioinformatics databases well known to the skilled person using sequences disclosed herein and available in the art. For example, such sequences can be identified through BLAST (as described above) searching of publicly available databases with known PDC encoding polynucleotide or polypeptide sequences. In such a method, identities can be based on the Clustal W method of alignment using the default parameters of GAP PENALTY=10, GAP LENGTH PENALTY=0.1, and Gonnet 250 series of protein weight matrix.

Additionally, the PDC polynucleotide or polypeptide sequences described herein or known the art can be used to identify other PDC homologs in nature. For example, each of the PDC encoding nucleic acid fragments described herein can be used to isolate genes encoding homologous proteins. Isolation of homologous genes using sequence-dependent protocols is well known in the art. Examples of sequence-dependent protocols include, but are not limited to, (1) methods of nucleic acid hybridization; (2) methods of DNA and RNA amplification, as exemplified by various uses of nucleic acid amplification technologies [e.g., polymerase chain reaction (PCR), Mullis, et al., U.S. Pat. No. 4,683,202; ligase chain reaction (LCR), Tabor, et al., Proc. Natl. Acad. Sci. USA 82:1074, 1985; or strand displacement amplification (SDA), Walker, et al., Proc. Natl. Acad. Sci. USA 89:392, 1992]; and (3) methods of library construction and screening by complementation.

In some embodiments, pyruvate decarboxylase polynucleotides, genes, and/or polypeptides related to a recombinant host cell disclosed herein can be modified or disrupted. Many methods for genetic modification and disruption of target genes to reduce or eliminate expression are known to one of ordinary skill in the art and can be used to create a recombinant host cell disclosed herein. Modifications that can be used include, but are not limited to, deletion of the entire gene or a portion of the gene encoding a pyruvate decarboxylase protein, inserting a DNA fragment into the encoding gene (in either the promoter or coding region) so that the protein is not expressed or expressed at lower levels, introducing a mutation into the coding region which adds a stop codon or frame shift such that a functional protein is not expressed, and introducing one or more mutations into the coding region to alter amino acids so that a non-functional or a less active protein is expressed. In other embodiments, expression of a target gene can be blocked by expression of an antisense RNA or an interfering RNA, and constructs can be introduced that result in cosuppression. In other embodiments, the synthesis or stability of the transcript can be lessened by mutation. In some embodiments, the efficiency by which a protein is translated from mRNA can be modulated by mutation. All of these methods can be readily practiced by one skilled in the art making use of the known or identified sequences encoding target proteins.

In other embodiments, DNA sequences surrounding a target pyruvate decarboxylase coding sequence are also useful in some modification procedures and are available, for example, for yeast such as Saccharomyces cerevisiae in the complete genome sequence coordinated by Genome Project ID9518 of Genome Projects coordinated by NCBI (National Center for Biotechnology Information) with identifying GOPID #13838. An additional non-limiting example of yeast genomic sequences is that of Candida albicans, which is included in GPID #10771, #10701, and #16373. Other yeast genomic sequences can be readily found by one of skill in the art in publicly available databases.

In other embodiments, DNA sequences surrounding a target pyruvate decarboxylase coding sequence can be useful for modification methods using homologous recombination. In a non-limiting example of this method, pyruvate decarboxylase gene flanking sequences can be placed bounding a selectable marker gene to mediate homologous recombination whereby the marker gene replaces the pyruvate decarboxylase gene. In another non-limiting example, partial pyruvate decarboxylase gene sequences and pyruvate decarboxylase gene flanking sequences bounding a selectable marker gene can be used to mediate homologous recombination whereby the marker gene replaces a portion of the target pyruvate decarboxylase gene. In some embodiments, the selectable marker can be bounded by site-specific recombination sites, so that following expression of the corresponding site-specific recombinase, the resistance gene is excised from the pyruvate decarboxylase gene without reactivating the latter. In some embodiments, the site-specific recombination leaves behind a recombination site which disrupts expression of the pyruvate decarboxylase protein. In other embodiments, the homologous recombination vector can be constructed to also leave a deletion in the pyruvate decarboxylase gene following excision of the selectable marker, as is well known to one skilled in the art.

In other embodiments, deletions can be made to a pyruvate decarboxylase target gene using mitotic recombination as described by Wach, et al. (Yeast 10:1793-1808, 1994). Such a method can involve preparing a DNA fragment that contains a selectable marker between genomic regions that can be as short as 20 bp, and which bound a target DNA sequence. In other embodiments, this DNA fragment can be prepared by PCR amplification of the selectable marker gene using as primers oligonucleotides that hybridize to the ends of the marker gene and that include the genomic regions that can recombine with the yeast genome. In some embodiments, the linear DNA fragment can be efficiently transformed into yeast and recombined into the genome resulting in gene replacement including with deletion of the target DNA sequence (as disclosed, for example, in Methods in Enzymology, Volume 194, Guide to Yeast Genetics and Molecular and Cell Biology (Part A, 2004, Christine Guthrie and Gerald R. Fink (Eds.), Elsevier Academic Press, San Diego, Calif.).

Moreover, promoter replacement methods can be used to exchange the endogenous transcriptional control elements allowing another means to modulate expression such as described by Mnaimneh, et al. (Cell 118(1):31-44, 2004).

In other embodiments, the pyruvate decarboxylase target gene encoded activity can be disrupted using random mutagenesis, which can then be followed by screening to identify strains with reduced or substantially eliminated activity. In this type of method, the DNA sequence of the target gene encoding region need not be known.

Methods for creating genetic mutations are common and well known in the art and can be applied to the exercise of creating mutants. Commonly used random genetic modification methods (reviewed in Methods in Yeast Genetics, 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of host cells can involve, but is not limited to, treatment with one of the following DNA mutagens: ethyl methanesulfonate (EMS), nitrous acid, diethyl sulfate, or N-methyl-N'-nitro-N-nitroso-guanidine (MNNG). Such methods of mutagenesis have been reviewed in Spencer, et al. (Mutagenesis in Yeast, 1996, *Yeast Protocols: Methods in Cell and Molecular Biology*. Humana Press, Totowa, N.J.). In some embodiments, chemical mutagenesis with EMS can be performed as disclosed in *Methods in Yeast Genetics*, 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer, et al. (Mutagenesis in Yeast, 1996, *Yeast Protocols: Methods in Cell and Molecular Biology*. Humana Press, Totowa, N.J.). In some embodiments, the introduction of a mutator phenotype can also be used to generate random chromosomal mutations in host cells. In some embodiments, common mutator phenotypes can be obtained through disruption of one or more of the following genes: PMS1, MAGI, RAD18, or RAD51. In other embodiments, restoration of the non-mutator phenotype can be obtained by insertion of the wildtype allele. In other embodiments, collections of modified cells produced from any of these or other known random mutagenesis processes may be screened for reduced or eliminated pyruvate decarboxylase activity.

Genomes have been completely sequenced and annotated and are publicly available for the following yeast strains: *Ashbya gossypii* ATCC 10895, *Candida glabrata* CBS138, *Kluyveromyces lactis* NRRL Y-1140, *Pichia stipitis* CBS 6054, *Saccharomyces cerevisiae* S288c, *Schizosaccharomyces pombe* 972h-, and *Yarrowia lipolytica* CLIB122. Typically BLAST (described above) searching of publicly available databases with known pyruvate decarboxylase polynucleotide or polypeptide sequences, such as those provided herein, is used to identify pyruvate decarboxylase-encoding sequences of other host cells, such as yeast cells.

Accordingly, it is within the scope of the invention to provide pyruvate decarboxylase polynucleotides, genes, and polypeptides having at least about 70% to about 75%, about 75% to about 80%, about 80% to about 85%, about 85% to about 90%, about 90% to about 95%, about 96%, about 97%, about 98%, or about 99% sequence identity to any of the pyruvate decarboxylase polynucleotides or polypeptides disclosed herein (e.g., SEQ ID NOs: 1-20 of Table 5). Identities are based on the Clustal W method of alignment using the default parameters of GAP PENALTY=10, GAP LENGTH PENALTY=0.1, and Gonnet 250 series of protein weight matrix.

The modification of PDC in the host cells disclosed herein to reduce or eliminate PDC activity can be confirmed using methods known in the art. For example, PCR methods well known in the art can be used to confirm deletion of PDC. Other suitable methods will be known to those of skill in the art and include, but are not limited to, lack of growth on yeast extract peptone-dextrose medium (YPD).

Isobutanol and Other Products

In some embodiments of the invention, methods for the production of a product of a biosynthetic pathway are provided which comprise (a) providing a recombinant host cell disclosed herein; and (b) providing media conditions whereby the product of the biosynthetic pathway is produced. In some embodiments, the biosynthetic pathway of the product is derived from pyruvic acid. In other embodiments, the product of the biosynthetic pathway is lactic acid, malic acid, succinic acid, fumaric acid or alanine. In other embodiments, the product is produced as a co-product along with ethanol. In still other embodiments, the product of the biosynthetic pathway is butanol. In still other embodiments, the product of the biosynthetic pathway is isobutanol. In other embodiments, the product is produced at a yield of at least about 50% of that observed when the same recombinant host cell is grown in the presence of yeast extract.

The product of the biosynthetic pathway can be produced at a greater yield or amount compared to the production of the same product in a recombinant host cell that is not provided with media supplemented with thiamine or biosynthetic precursors thereof and/or nicotinic acid, nicotinamid, or biosynthetic precursor of NAD. In some embodiments, this greater yield includes production at a yield of greater than about 10% of theoretical, at a yield of greater than about 20% of theoretical, at a yield of greater than about 25% of theoretical, at a yield of greater than about 30% of theoretical, at a yield of greater than about 40% of theoretical, at a yield of greater than about 50% of theoretical, at a yield of greater than about 60% of theoretical, at a yield of greater than about 70% of theoretical, at a yield of greater than about 75% of theoretical, at a yield of greater than about 80% of theoretical at a yield of greater than about 85% of theoretical, at a yield of greater than about 90% of theoretical, at a yield of greater than about 95% of theoretical, at a yield of greater than about 96% of theoretical, at a yield of greater than about 97% of theoretical, at a yield of greater than about 98% of theoretical, at a yield of greater than about 99% of theoretical, or at a yield of about 100% of theoretical. In other embodiments, the product is produced as a co-product along with ethanol. In still other embodiments, the product of the biosynthetic pathway is isobutanol.

The specific production rate can be at least about 0.10 g/g/h, at least about 0.11 g/g/h, at least about 0.12 g/g/h, at least about 0.13 g/g/h, at least about 0.14 g/g/h, at least about 0.15 g/g/h, at least about 0.16 g/g/h, at least about 0.17 g/g/h, at least about 0.18 g/g/h, at least about 0.19 g/g/h, or at least about 0.20 g/g/h. The specific production rate can also be about 0.05 g/g/h to about 0.50 g/g/h, about 0.05 g/g/h to about 0.40 g/g/h, about 0.05 g/g/h to about 0.30 g/g/h, or about 0.05 to about 0.20 g/g/h. The specific production rate can also be about 0.10 g/g/h to about 0.50 g/g/h, about 0.10 g/g/h to about 0.40 g/g/h, about 0.10 g/g/h to about 0.30 g/g/h, or about 0.10 to about 0.20 g/g/h. The specific production rate can also be about 0.15 g/g/h to about 0.15 g/g/h, about 0.15 g/g/h to about 0.40 g/g/h, about 0.15 g/g/h to about 0.30 g/g/h, or about 0.15 to about 0.20 g/g/h.

The titer (or butanol produced) can be at least about 8 g/L, at least about 10 g/L, at least about 15 g/L, at least about 30 g/L, at least about 35 g/L, at least about 50 g/L, at least about 60 g/L, at least about 70 g/L, at least about 80 g/L, at least about 90 g/L, or at least about 95 g/L. The titer can also be about 8 g/L to about 15 g/L, about 10 g/L to about 30 g/L, about 15 g/L to about 35 g/L, about 15 g/L to about 40 g/L, about 15 g/L to about 50 g/L, about 15 g/L to about 60 g/L, about 15 g/L to about 70 g/L, about 15 g/L to about 80 g/L, about 15 g/L to about 90 g/L, about 15 g/L to about 95 g/L, or about 8 g/L to about 95 g/L.

In some embodiments, the specific rate is at least about 50% of the rate observed when media containing about 20 g/L yeast extract and no additional thiamine or thiamine precursors is used. The rate can be at least about 10%, at least about 20%, at least about 30%, at least about 40%, at least about 50%, at least about 60%, at least about 70%, at least about 80%, or at least about 90% of the rate observed when media containing about 20 g/L yeast extract and no additional thiamine or thiamine precursors is used.

In some embodiments, the titer is at least about 50% of the titer observed when media containing about 20 g/L yeast extract and no additional thiamine or thiamine precursors is used. The titer can be at least about 20%, at least about 30%, at least about 40%, at least about 50%, at least about 60%, at least about 70%, at least about 80%, or at least about 90% of the titer observed when media containing about 20 g/L yeast extract and no additional thiamine or thiamine precursors is used.

In some embodiments, the volumetric rate is increased by at least about 50% as compared to the rate observed when production media containing no thiamine or thiamine precursors is used. The rate can be increased by at least about 20%, at least about 30%, at least about 50%, by at least about 60%, by at least about 70%, by at least about 80%, or by at least about 90% as compared to the rate observed when production media containing no thiamine or thiamine precursors and no multi-component media additives are employed. In some embodiments, the rate can be increased by at least about 200% or at least about 300% as compared to the rate observed when production media containing no thiamine or thiamine precursors and no multi-component media additives are employed.

In some embodiments, the titer is increased by at least about 10% as compared to the titer observed when media containing no thiamine or thiamine precursors and no multi-component media additives are employed. The titer can be increased by at least about 10%, by at least about 20%, by at least about 30%, by at least about 40%, by at least about 50%, by at least about 60%, by at least about 70%, by at least about 80%, or by at least about 90% as compared to the titer observed when media containing no thiamine or thiamine precursors and no multi-component media additives are employed.

In some embodiments, the specific rate is at least about 50% of the rate observed when media containing about 20 g/L yeast extract and no additional nicotinic acid, nicotinamid, or other biosynthetic precursor of NAD is employed. The rate can be at least about 20%, at least about 30%, at least about 40%, at least about 50%, at least about 60%, at least about 70%, at least about 80%, or at least about 90% of the rate observed when media containing about 20 g/L yeast extract and no additional nicotinic acid, nicotinamid, or other biosynthetic precursor of NAD is employed.

In some embodiments, the titer is at least about 50% of the titer observed when media containing about 20 g/L yeast extract and no additional nicotinic acid, nicotinamid, or other biosynthetic precursor of NAD. The titer can be at least about 20%, at least about 30%, at least about 50%, at least about 60%, at least about 70%, at least about 80%, or at least about 90% of the titer observed when media containing about 20 g/L yeast extract and no additional nicotinic acid, nicotinamid, or other biosynthetic precursor of NAD is employed.

In some embodiments, the volumetric rate is increased by at least about 50% as compared to the rate observed when media containing no nicotinic acid, nicotinamid, or other biosynthetic precursor of NAD is used. The rate can be increased by at least about 20%, at least about 30%, at least about 40%, at least about 50%, at least about 60%, at least about 70%, at least about 80%, or at least about 90% as compared to the rate observed when media containing no nicotinic acid, nicotinamid, or other biosynthetic precursor of NAD and no yeast extract is used. In some embodiments, the rate can be increased by at least about 200% or at least about 300% as compared to the rate observed when media containing no nicotinic acid, nicotinamid, or other biosynthetic precursor of NAD and no yeast extract is used.

In some embodiments, the titer is increased by at least about 10% as compared to the titer observed when media containing no nicotinic acid, nicotinamid, or other biosynthetic precursor of NAD and no yeast extract is used. The titer can be increased by at least about 10%, by at least about 20%, by at least about 30%, by at least about 40%, by at least about 50%, by at least about 60%, by at least about 70%, by at least about 80%, or by at least about 90% as compared to the titer observed when media containing no nicotinic acid, nicotinamid, or other biosynthetic precursor of NAD and no yeast extract is used.

Butanol Biosynthetic Pathways

Suitable biosynthetic pathways for production of butanol are known in the art, and certain suitable pathways are described herein. In some embodiments, the butanol biosynthetic pathway comprises at least one gene that is heterologous to the host cell. In some embodiments, the butanol biosynthetic pathway comprises more than one gene that is heterologous to the host cell. In some embodiments, the butanol biosynthetic pathway comprises heterologous genes encoding polypeptides corresponding to every step of a biosynthetic pathway.

Likewise, certain suitable proteins having the ability to catalyze indicated substrate to product conversions are described herein and other suitable proteins are provided in the art. For example, U.S. Patent Application Publication No. 2008/0261230 and U.S. Patent Application Publication No. 2009/0163376, incorporated herein by reference, describe acetohydroxy acid isomeroreductases; U.S. patent application Ser. No. 12/569,636, incorporated by reference, describes dihydroxyacid dehydratases; and an alcohol dehydrogenase is described in U.S. Patent Application Publication No. 2009/0269823, incorporated herein by reference.

1-Butanol Biosynthetic Pathway

A biosynthetic pathway for the production of 1-butanol that may be used is described in U.S. Patent Application Publication No. 2008/0182308A1, incorporated herein by reference. This biosynthetic pathway comprises the following substrate to product conversions:

a) acetyl-CoA to acetoacetyl-CoA, which may be catalyzed, for example, by acetyl-CoA acetyltransferase;

b) acetoacetyl-CoA to 3-hydroxybutyryl-CoA, which may be catalyzed, for example, by 3-hydroxybutyryl-CoA dehydrogenase;

c) 3-hydroxybutyryl-CoA to crotonyl-CoA, which may be catalyzed, for example, by crotonase;

d) crotonyl-CoA to butyryl-CoA, which may be catalyzed, for example, by butyryl-CoA dehydrogenase;

e) butyryl-CoA to butyraldehyde, which may be catalyzed, for example, by butyraldehyde dehydrogenase; and f) butyraldehyde to 1-butanol, which may be catalyzed, for example, by 1-butanol dehydrogenase.

In some embodiments, the 1-butanol biosynthetic pathway comprises at least one gene, at least two genes, at least three genes, at least four genes, or at least five genes that is/are heterologous to the yeast cell.

2-Butanol Biosynthetic Pathway

Biosynthetic pathways for the production of 2-butanol that may be used are described in U.S. Patent Application Publication No. 2007/0259410A1 and U.S. Patent Application Publication No. 2007/0292927A1, and in PCT Publication No. WO 2007/130521, all of which are incorporated herein by reference. One 2-butanol biosynthetic pathway comprises the following substrate to product conversions:

a) pyruvate to alpha-acetolactate, which may be catalyzed, for example, by acetolactate synthase;

b) alpha-acetolactate to acetoin, which may be catalyzed, for example, by acetolactate decarboxylase;
c) acetoin to 2,3-butanediol, which may be catalyzed, for example, by butanediol dehydrogenase;
d) 2,3-butanediol to 2-butanone, which may be catalyzed, for example, by butanediol dehydratase; and
e) 2-butanone to 2-butanol, which may be catalyzed, for example, by 2-butanol dehydrogenase.

In some embodiments, the 2-butanol biosynthetic pathway comprises at least one gene, at least two genes, at least three genes, or at least four genes that is/are heterologous to the yeast cell.

Isobutanol Biosynthetic Pathway

Biosynthetic pathways for the production of isobutanol that may be used are described in U.S. Patent Application Publication No. 2007/0092957 A1 and PCT Publication No. WO 2007/050671, incorporated herein by reference. One isobutanol biosynthetic pathway comprises the following substrate to product conversions:
a) pyruvate to acetolactate, which may be catalyzed, for example, by acetolactate synthase;
b) acetolactate to 2,3-dihydroxyisovalerate, which may be catalyzed, for example, by acetohydroxy acid;
c) 2,3-dihydroxyisovalerate to α-ketoisovalerate, which may be catalyzed, for example, by acetohydroxy acid dehydratase;
d) α-ketoisovalerate to isobutyraldehyde, which may be catalyzed, for example, by a branched-chain keto acid decarboxylase; and
e) isobutyraldehyde to isobutanol, which may be catalyzed, for example, by a branched-chain alcohol dehydrogenase.

In some embodiments, the isobutanol biosynthetic pathway comprises at least one gene, at least two genes, at least three genes, or at least four genes that is/are heterologous to the yeast cell.

Butanol Producing Strains

Microbial hosts for butanol production may be selected from bacteria, cyanobacteria, filamentous fungi, and yeast. The selection of a microbial host for butanol production is described in the art.

As mentioned above, microorganisms may be genetically modified to convert fermentable carbon sources into butanol, specifically 1-butanol, 2-butanol, or isobutanol, using methods known in the art. Suitable strains have been described in the art. Construction of example suitable yeast strains ("NYLA84" and "NYLA93") is provided herein.

Construction of NYLA84 Strain

Construction of expression vectors for isobutanol pathway gene expression in S. cerevisiae Plasmid pLH532 Construction The pLH532 plasmid (SEQ ID NO: 21) was constructed for expression of acetolactate synthase (ALS) and ketol-acid reductoisomerase (KARI) in yeast. pLH532 is a pHR81 vector (ATCC No. 87541) containing the following chimeric genes: 1) the CUP1 promoter (SEQ ID NO: 24), acetolactate synthase coding region from Bacillus subtilis (AlsS; SEQ ID NO: 95; protein SEQ ID NO: 96), and CYC1 terminator2 (SEQ ID NO: 25); 2) an ILV5 promoter (SEQ ID NO: 26), Pf5.IlvC coding region (SEQ ID NO: 23), and ILV5 terminator (SEQ ID NO: 27); and 3) the FBA1 promoter (SEQ ID NO: 28), S. cerevisiae KARI coding region (ILV5; SEQ ID NO: 22), and CYC1 terminator.

The Pf5.IlvC coding region is a sequence encoding KARI derived from Pseudomonas fluorescens that was described in U.S. Patent Application Publication No. 2009/0163376, which is herein incorporated by reference.

The Pf5.IlvC coding region was synthesized by DNA 2.0 (Palo Alto, Calif.) based on codons that were optimized for expression in Saccharomyces cerevisiae.

Expression Vector pLH468

The pLH468 plasmid (SEQ ID NO: 33) was constructed for expression of dihydroxyacid dehydratase (DHAD), KivD, and HADH in yeast. Coding regions for Lactococcus lactis ketoisovalerate decarboxylase (KivD) and horse liver alcohol dehydrogenase (HADH) were synthesized by DNA2.0 based on codons that were optimized for expression in Saccharomyces cerevisiae (SEQ ID NO: 30 and 31, respectively) and provided in plasmids pKivDy-DNA2.0 and pHadhy-DNA2.0. The encoded proteins are SEQ ID NOs: 29 and 32, respectively. Individual expression vectors for KivD and HADH were constructed. To assemble pLH467 (pRS426::$P_{TDH3}$-kivDy-TDH3t), vector pNY8 (SEQ ID NO: 36; also named pRS426.GPD-ald-GPDt, described in U.S. Patent Application Publication No. 2008/0182308, Example 17, which is herein incorporated by reference) was digested with AscI and SfiI enzymes, thus excising the GPD promoter and the ald coding region. A TDH3 promoter fragment (SEQ ID NO: 37) from pNY8 was PCR amplified to add an AscI site at the 5' end and an SpeI site at the 3' end, using 5' primer OT1068 and 3' primer OT1067 (SEQ ID NOs: 38 and 39). The AscI/SfiI digested pNY8 vector fragment was ligated with the TDH3 promoter PCR product digested with AscI and SpeI, and the SpeI-SfiI fragment containing the codon optimized kivD coding region isolated from the vector pKivD-DNA2.0. The triple ligation generated vector pLH467 (pRS426::$P_{TDH3}$-kivDy-TDH3t). pLH467 was verified by restriction mapping and sequencing.

pLH435 (pRS425::$P_{GPM1}$-Hadhy-ADH1t) was derived from vector pRS425::GPM-sadB (SEQ ID NO: 40) which is described in U.S. Provisional Application Ser. No. 61/058,970, Example 3, which is herein incorporated by reference. pRS425::GPM-sadB is the pRS425 vector (ATCC No. 77106) with a chimeric gene containing the GPM1 promoter (SEQ ID NO: 41), coding region from a butanol dehydrogenase of Achromobacter xylosoxidans (sadB; DNA SEQ ID NO: 34; protein SEQ ID NO: 35; disclosed in U.S. Provisional Application Ser. No. 61/048,291), and ADH1 terminator (SEQ ID NO: 42). pRS425::GPMp-sadB contains BbvI and PacI sites at the 5' and 3' ends of the sadB coding region, respectively. A NheI site was added at the 5' end of the sadB coding region by site-directed mutagenesis using primers OT1074 and OT1075 (SEQ ID NO: 45 and 46) to generate vector pRS425-GPMp-sadB-NheI, which was verified by sequencing. pRS425::$P_{GPM1}$-sadB-NheI was digested with NheI and PacI to drop out the sadB coding region, and ligated with the NheI-PacI fragment containing the codon optimized HADH coding region from vector pHadhy-DNA2.0 to create pLH435.

To combine KivD and HADH expression cassettes in a single vector, yeast vector pRS411 (ATCC No. 87474) was digested with SacI and NotI, and ligated with the SacI-SalI fragment from pLH467 that contains the $P_{TDH3}$-kivDy-TDH3t cassette together with the SalI-NotI fragment from pLH435 that contains the $P_{GPM1}$-Hadhy-ADH1t cassette in a triple ligation reaction. This yielded the vector pRS411::$P_{TDH3}$-kivDy-$P_{GPM1}$-Hadhy (pLH441), which was verified by restriction mapping.

In order to generate a co-expression vector for all three genes in the lower isobutanol pathway: ilvD, kivDy and Hadhy, pRS423 FBA ilvD(Strep) (SEQ ID NO: 47) was used, which is described in commonly owned and co-pending U.S. Provisional Application Ser. No. 61/100,792, as the source of the IlvD gene. This shuttle vector contains an F1 origin of replication (nt 1423 to 1879) for maintenance in *E. coli* and a 2 micron origin (nt 8082 to 9426) for replication in yeast. The vector has an FBA1 promoter (nt 2111 to 3108; SEQ ID NO: 49) and FBA terminator (nt 4861 to 5860; SEQ ID NO: 48). In addition, it carries the His marker (nt 504 to 1163) for selection in yeast and ampicillin resistance marker (nt 7092 to 7949) for selection in *E. coli*. The ilvD coding region (nt 3116 to 4828; SEQ ID NO: 43; protein SEQ ID NO: 44) from *Streptococcus mutans* UA159 (ATCC No. 700610) is between the FBA promoter and FBA terminator forming a chimeric gene for expression. In addition there is a lumio tag fused to the ilvD coding region (nt 4829-4849).

The first step was to linearize pRS423 FBA ilvD(Strep) (also called pRS423-FBA(SpeI)-IlvD(*Streptococcus mutans*)-Lumio) with SacI and SacII (with SacII site blunt ended using T4 DNA polymerase), to give a vector with total length of 9,482 bp. The second step was to isolate the kivDy-hADHy cassette from pLH441 with SacI and KpnI (with KpnI site blunt ended using T4 DNA polymerase), which gives a 6,063 bp fragment. This fragment was ligated with the 9,482 bp vector fragment from pRS423-FBA(SpeI)-IlvD (*Streptococcus mutans*)-Lumio. This generated vector pLH468 (pRS423::$P_{FBA1}$-ilvD(Strep)Lumio-FBA it-$P_{TDH3}$-kivDy-TDH3t-$P_{GPM1}$-hadhy-ADH1t), which was confirmed by restriction mapping and sequencing.

Pyruvate Decarboxylase and Hexokinase Gene Inactivation

The following describes insertion-inactivation of endogenous PDC1, PDC5, and PDC6 genes of *S. cerevisiae*. PDC1, PDC5, and PDC6 genes encode the three major isozymes of pyruvate decarboxylase.

Construction of pdc6:: $P_{GPM1}$-sadB Integration Cassette and PDC6 Deletion

A pdc6::$P_{GPM1}$-sadB-ADH1t-URA3r integration cassette was made by joining the GPM-sadB-ADHt segment (SEQ ID NO: 50) from pRS425::GPM-sadB (described above) to the URA3r gene from pUC19-URA3r. pUC19-URA3r (SEQ ID NO: 51) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., Gene 77:61-68, 1989) using as template pRS425::GPM-sadB and pUC19-URA3r plasmid DNAs, with Phusion® DNA polymerase (New England Biolabs Inc., Ipswich, Mass.; Catalog No. F-5405) and primers 114117-11A through 114117-11D (SEQ ID NOs: 52, 53, 54, and 55), and 114117-13A and 114117-13B (SEQ ID NOs: 56 and 57).

The outer primers for the SOE PCR (114117-13A and 114117-13B) contained 5' and 3'~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 112590-34G and 112590-34H (SEQ ID NOs: 58 and 59) and 112590-34F and 112590-49E (SEQ ID NOs: 60 and 61) to verify integration at the PDC6 locus with deletion of the PDC6 coding region. The URA3r marker was recycled by plating on synthetic complete media supplemented with 2% glucose and 5-fluoro-orotic acid (5-FOA) at 30° C. following standard protocols. Marker removal was confirmed by patching colonies from the 5-FOA plates onto SD-URA media to verify the absence of growth. The resulting identified strain has the genotype: BY4700 pdc6::$P_{GPM1}$-sadB-ADH1t.

Construction of pdc1:: $P_{PDC1}$-ilvD Integration Cassette and PDC1 Deletion

A pdc1:: $P_{PDC1}$-ilvD-FBA1t-URA3r integration cassette was made by joining the ilvD-FBA1t segment (SEQ ID NO:62) from pLH468 (described above) to the URA3r gene from pUC19-URA3r by SOE PCR (as described by Horton, et al., supra) using as template pLH468 and pUC19-URA3r plasmid DNAs, with Phusion® DNA polymerase (New England Biolabs Inc., Ipswich, Mass.; Catalog No. F-5405) and primers 114117-27A through 114117-27D (SEQ ID NOs: 63, 64, 65, and 66).

The outer primers for the SOE PCR (114117-27A and 114117-27D) contained 5' and 3'~50 bp regions homologous to regions downstream of the PDC1 promoter and downstream of the PDC1 coding sequence. The completed cassette PCR fragment was transformed into BY4700 pdc6::$P_{GPM1}$-sadB-ADH1t and transformants were maintained on synthetic complete media lacking uracil and supplemented with 2% glucose at 30° C. using standard genetic techniques (*Methods in Yeast Genetics*, 2005, Cold Spring Harbor Laboratory Press, Cold Spring Harbor, N.Y., pp. 201-202). Transformants were screened by PCR using primers 114117-36D and 135 (SEQ ID NOs: 67 and 68), and primers 112590-49E and 112590-30F (SEQ ID NOs: 61 and 69) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6:: $P_{GPM1}$-sadB-ADH1t pdc1:: $P_{PDC1}$-ilvD-FBA1t.

HIS3 Deletion

To delete the endogenous HIS3 coding region, a his3::URA3r2 cassette was PCR-amplified from URA3r2 template DNA (SEQ ID NO: 70). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England Biolabs Inc., Ipswich, Mass.) and primers 114117-45A and 114117-45B (SEQ ID NOs: 71 and 72) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (*Methods in Yeast Genetics*, 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6:: $P_{GPM1}$-sadB-ADH1t pdc1:: $P_{PDC1}$-ilvD-FBA1t Δhis3.

Construction of pdc5::kanMX Integration Cassette and PDC5 Deletion

A pdc5::kanMX4 cassette was PCR-amplified from strain YLR134W chromosomal DNA (ATCC No. 4034091) using Phusion® DNA polymerase (New England Biolabs Inc., Ipswich, Mass.) and primers PDC5::KanMXF and PDC5::KanMXR (SEQ ID NOs:73 and 74) which generated a ~2.2 kb PCR product. The PDC5 portion of each primer was derived from the 5' region upstream of the PDC5 promoter and 3' region downstream of the coding region such that integration of the kanMX4 marker results in replacement of the PDC5 coding region. The PCR product was transformed into NYLA73 using standard genetic techniques (*Methods in Yeast Genetics,* 2005, Cold Spring Harbor Laboratory Press, Cold Spring Harbor, N.Y., pp. 201-202) and transformants were selected on YP media supplemented with 1% ethanol and geneticin (200 μg/ml) at 30° C. Transformants were screened by PCR to verify correct integration at the PDC locus with replacement of the PDC5 coding region using primers PDC5kofor and N175 (SEQ ID NOs: 75 and 76). The identified correct transformants have the genotype: BY4700 pdc6:: $P_{GPM1}$-sadB-ADH1t pdc1:: $P_{PDC1}$-ilvD-FRA1t Δhis3 pdc5::kanMX4. The strain was named NYLA74.

Deletion of HXK2 (hexokinase II)

A hxk2::URA3r cassette was PCR-amplified from URA3r2 template (described above) using Phusion® DNA polymerase (New England Biolabs Inc., Ipswich, Mass.) and primers 384 and 385 (SEQ ID NOs: 77 and 78) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (*Methods in Yeast Genetics,* 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NOs: 79 and 80). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NOs: 81 and 82). The resulting identified strain named NYLA83 has the genotype: BY4700 pdc6:: $P_{GPM1}$-sadB-ADH1t pdc1:: $P_{PDC1}$-ilvD-FBA1t Δhis3 Δhxk2.

Construction of pdc5::kanMX Integration Cassette and PDC5 Deletion

A pdc5::kanMX4 cassette was PCR-amplified as described above. The PCR fragment was transformed into NYLA83, and transformants were selected and screened as described above. The identified correct transformants named NYLA84 have the genotype: BY4700 pdc6:: $P_{GPM1}$-sadB-ADH1t pdc1:: $P_{PDC1}$-ilvD-FBA1t Δhis3 Δhxk2 pdc5::kanMX4.

Plasmid vectors pLH468 and pLH532 were simultaneously transformed into strain NYLA84 (BY4700 pdc6:: $P_{GPM1}$-sadB-ADH1t pdc1::$P_{PDC1}$-ilvD-FBA1t Δhis3 Δhxk2 pdc5::kanMX4) using standard genetic techniques (*Methods in Yeast Genetics,* 2005, Cold Spring Harbor Laboratory Press, Cold Spring Harbor, N.Y.) and the resulting strain ("isobutanol producing NYLA 83 strain") was maintained on synthetic complete media lacking histidine and uracil, and supplemented with 1% ethanol at 30° C.

Construction of NYLA93 (PNY2012)

Described below is insertion-inactivation of endogenous PDC1, PDC5, and PDC6 genes of *S. cerevisiae*. PDC1, PDC5, and PDC6 genes encode the three major isozymes of pyruvate decarboxylase. The resulting PDC inactivation strain was used as a host for expression vectors pYZ067 (SEQ ID NO: 86) and pYZ090 (SEQ ID NO: 85), the construction of which is described in U.S. Provisional Application No. 61/246,844, filed Sep. 29, 2009, herein incorporated by reference.

pYZ090 was constructed to contain a chimeric gene having the coding region of the alsS gene from *Bacillus subtilis* (nt position 457-2172) expressed from the yeast CUP1 promoter (nt 2-449) and followed by the CYC1 terminator (nt 2181-2430) for expression of ALS, and a chimeric gene having the coding region of the ilvC gene from *Lactococcus lactis* (nt 3634-4656) expressed from the yeast ILV5 promoter (2433-3626) and followed by the ILV5 terminator (nt 4670-5292) for expression of KARI.

pYZ067 was constructed to contain the following chimeric genes: 1) the coding region of the ilvD gene from *S. mutans* UA159 (nt position 2260-3971) expressed from the yeast FBA1 promoter (nt 1161-2250) followed by the FBA terminator (nt 4005-4317) for expression of dihydroxy acid dehydratase (DHAD); 2) the coding region for horse liver ADH (nt 4680-5807) expressed from the yeast GPM promoter (nt 5819-6575) followed by the ADH1 terminator (nt 4356-4671) for expression of alcohol dehydrogenase; and 3) the coding region of the KivD gene from *Lacrococcus lactis* (nt 7175-8821) expressed from the yeast TDH3 promoter (nt 8830-9493) followed by the TDH3 terminator (nt 5682-7161) for expression of ketoisovalerate decarboxylase.

Construction of pdc6:: $P_{GPM1}$-sadB Integration Cassette and PDC6 Deletion

A pdc6::$P_{GPM1}$-sadB-ADH1t-URA3r integration cassette was made by joining the GPM-sadB-ADHt segment (SEQ ID NO: 50) from pRS425::GPM-sadB (SEQ ID NO: 40, described above) to the URA3r gene from pUC19-URA3r. pUC19-URA3r (SEQ ID NO: 51) contains the URA3 marker from pRS426 (ATCC No. 77107) flanked by 75 bp homologous repeat sequences to allow homologous recombination in vivo and removal of the URA3 marker. The two DNA segments were joined by SOE PCR (as described by Horton, et al., supra) using as template pRS425::GPM-sadB and pUC19-URA3r plasmid DNAs, with Phusion® DNA polymerase (New England Biolabs Inc., Ipswich, Mass., Catalog No. F-5405) and primers 114117-11A through 114117-11D (SEQ ID NOs: 52-55), and 114117-13A and 114117-13B (SEQ ID NOs: 56 and 57).

The outer primers for the SOE PCR (114117-13A and 114117-13B) contained 5' and 3'~50 bp regions homologous to regions upstream and downstream of the PDC6 promoter and terminator, respectively. The completed cassette PCR fragment was transformed into BY4700 (ATCC No. 200866) and transformants were maintained on synthetic complete media lacking uracil and supplemented with 2% glucose at 30° C. using standard genetic techniques (*Methods in Yeast Genetics,* 2005, Cold Spring Harbor Laboratory Press, Cold Spring Harbor, N.Y., pp. 201-202). Transformants were screened by PCR using primers 112590-34G and 112590-34H (SEQ ID NOs: 58 and 59), and 112590-34F and 112590-49E (SEQ ID NOs: 60 and 61) to verify integration at the PDC6 locus with deletion of the PDC6 coding region. The URA3r marker was recycled by plating on synthetic complete media supplemented with 2% glucose and 5-FOA at 30° C.

following standard protocols. Marker removal was confirmed by patching colonies from the 5-FOA plates onto SD URA-media to verify the absence of growth. The resulting identified strain has the genotype: BY4700pdc6::P$_{GPM1}$-sadB-ADH1t.

Construction of pdc1:: P$_{PDC1}$-ilvD Integration Cassette and PDC1 Deletion

A pdc1:: P$_{PDC1}$-ilvD-FBA1t-URA3r integration cassette was made by joining the ilvD-FBA1t segment (SEQ ID NO: 62) from pLH468 (described above) to the URA3r gene from pUC19-URA3r by SOE PCR (as described by Horton, et al., supra) using as template pLH468 and pUC19-URA3r plasmid DNAs, with Phusion® DNA polymerase (New England Biolabs Inc., Ipswich, Mass., Catalog No. F-5405) and primers 114117-27A through 114117-27D (SEQ ID NOs: 63-66).

The outer primers for the SOE PCR (114117-27A and 114117-27D) contained 5' and 3'~50 bp regions homologous to regions downstream of the PDC1 promoter and downstream of the PDC1 coding sequence. The completed cassette PCR fragment was transformed into BY4700 pdc6::P$_{GPM1}$-sadB-ADH1t and transformants were maintained on synthetic complete media lacking uracil and supplemented with 2% glucose at 30° C. using standard genetic techniques (*Methods in Yeast Genetics,* 2005, Cold Spring Harbor Laboratory Press, Cold Spring Harbor, N.Y., pp. 201-202). Transformants were screened by PCR using primers 114117-36D and 135 (SEQ ID NOs: 67 and 68), and primers 112590-49E and 112590-30F (SEQ ID NOs: 61 and 69) to verify integration at the PDC1 locus with deletion of the PDC1 coding sequence. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain "NYLA67" has the genotype: BY4700 pdc6:: P$_{GPM1}$-sadB-ADH1t pdc1:: P$_{PDC1}$-ilvD-FBA1t.

HIS3 Deletion

To delete the endogenous HIS3 coding region, a his3:: URA3r2 cassette was PCR-amplified from URA3r2 template DNA (SEQ ID NO: 70). URA3r2 contains the URA3 marker from pRS426 (ATCC No. 77107) flanked by 500 bp homologous repeat sequences to allow homologous recombination in vivo and removal of the URA3 marker. PCR was done using Phusion® DNA polymerase (New England Biolabs Inc., Ipswich, Mass.) and primers 114117-45A and 114117-45B (SEQ ID NOs: 71 and 72) which generated a ~2.3 kb PCR product. The HIS3 portion of each primer was derived from the 5' region upstream of the HIS3 promoter and 3' region downstream of the coding region such that integration of the URA3r2 marker results in replacement of the HIS3 coding region. The PCR product was transformed into NYLA67 using standard genetic techniques (*Methods in Yeast Genetics,* 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened to verify correct integration by replica plating of transformants onto synthetic complete media lacking histidine and supplemented with 2% glucose at 30° C. The URA3r marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth. The resulting identified strain, called NYLA73, has the genotype: BY4700 pdc6:: P$_{GPM1}$-sadB-ADH1t pdc1:: P$_{PDC1}$-ilvD-FBA1t Δhis3.

Deletion of Hexokinase 2:

A hxk2::URA3r cassette was PCR-amplified from URA3r2 template (described above) using Phusion® DNA polymerase (New England Biolabs Inc., Ipswich, Mass.) and primers 384 and 385 (SEQ ID NOs: 77 and 78) which generated a ~2.3 kb PCR product. The HXK2 portion of each primer was derived from the 5' region upstream of the HXK2 promoter and 3' region downstream of the coding region such that integration of the URA3r2 marker results in replacement of the HXK2 coding region. The PCR product was transformed into NYLA73 using standard genetic techniques (*Methods in Yeast Genetics,* 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the HXK2 locus with replacement of the HXK2 coding region using primers N869 and N871 (SEQ ID NO: 79 and 80). The URA3r2 marker was recycled by plating on synthetic complete media supplemented with 2% glucose and 5-FOA at 30° C. following standard protocols. Marker removal was confirmed by patching colonies from the 5-FOA plates onto SD-URA media to verify the absence of growth, and by PCR to verify correct marker removal using primers N946 and N947 (SEQ ID NO: 81 and 82). The resulting identified strain named NYLA83 has the genotype: BY4700 pdc6:: P$_{GPM1}$-sadB-ADH1t pdc1:: P$_{PDC1}$-ilvD-FBA1t Δhis3 Δhxk2.

Deletion of NAD-Dependent Glycerol 3-Phosphate Dehydrogenase

A gpd2::loxP-URA3-loxP cassette was PCR-amplified from pUC19::loxP-URA3-loxP plasmid template using Phusion® DNA polymerase (New England Biolabs Inc., Ipswich, Mass.) and primers LA512 and LA513 (SEQ ID NOs: 87 and 88) which generated a ~1.6 kb PCR product. pUC19::loxP-URA3-loxP (SEQ ID NO: 83) contains the URA3 marker from (ATCC No. 77107) flanked by loxP recombinase sites. The GPD2 portion of each primer was derived from the 5' region upstream of the GPD2 promoter and 3' region downstream of the coding region such that integration of the loxP-URA3-loxP marker results in replacement of the GPD2 coding region. The PCR product was transformed into NYLA83 using standard genetic techniques (*Methods in Yeast Genetics,* 2005, Cold Spring Harbor Laboratory Press, Cold Spring Harbor, N.Y., pp. 201-202) and transformants were selected on synthetic complete media lacking uracil and supplemented with 2% glucose at 30° C. Transformants were screened by PCR to verify correct integration at the GPD2 locus with replacement of the HXK2 coding region using primers LA516 and N175 (SEQ ID NO: 89 and 76). The URA3 marker is recycled by transformation with pRS423::P$_{GAL1}$-cre (SEQ ID NO: 84) and plating on synthetic complete media lacking histidine supplemented with 2% glucose at 30° C. Colonies are patched onto YP (1% galactose) plates at 30° C. to induce URA3 marker excision and are transferred onto YPD plates at 30° C. for recovery. Removal of the URA3 marker is confirmed by patching colonies from the YPD plates onto synthetic complete media lacking uracil to verify the absence of growth. The identified correct clones have the genotype: BY4700 pdc6:: P$_{GPM1}$-sadB-ADH1t pdc1:: P$_{PDC1}$-ilvD-FBA1t Δhis3 Δhxk2 Δgpd2::loxP. The strain was named NYLA92.

Construction of pdc5::loxP-kanMX-loxP Integration Cassette and PDC5 Deletion:

A pdc5::loxP-kanMX-loxP cassette was PCR-amplified from plasmid pUC19::loxP-kanMX-loxP (SEQ ID NO: 94) using Phusion® DNA polymerase (New England Biolabs Inc., Ipswich, Mass.) and primers LA249 and LA397 (SEQ ID NOs: 90 and 91) which generated a ~2.2 kb PCR product. pUC19::loxP-kanMX-loxP (SEQ ID NO: 94) contains the kanMX gene from pFA6 (Wach, et al., Yeast 10, 1793-1808, 1994) and *K. lactis* TEF1 promoter and terminator flanked by loxP recombinase sites. The PDC5 portion of each primer was derived from the 5' region upstream of the PDC5 promoter and 3' region downstream of the coding region such that integration of the loxP-kanMX-loxP marker results in replacement of the PDC5 coding region. The PCR product was transformed into NYLA92 using standard genetic techniques (*Methods in Yeast Genetics*, 2005, Cold Spring Harbor Laboratory Press, Cold Spring Harbor, N.Y., pp. 201-202) and transformants were selected on YP media supplemented with 1% ethanol and geneticin (200 µg/ml) at 30° C. Transformants were screened by PCR to verify correct integration at the PDC5 locus with replacement of the PDC5 coding region using primers LA363 and LA364 (SEQ ID NOs: 92 and 93). The identified correct transformants have the genotype: BY4700 pdc6:: $P_{GPM1}$-sadB-ADH1t pdc1:: $P_{PDC1}$-ilvD-FBA1t Δhis3 Δhxk2 Δgpd2::loxP Δpdc5:loxP-kanMX-loxP. The strain was named NYLA93.

Plasmid vectors pYZ067 and pYZ090 were simultaneously transformed into strain NYLA93 (BY4700 pdc6:: $P_{GPM1}$-sadB-ADH1t pdc1:: $P_{PDC1}$-ilvD-FBA1t Δhis3 Δhxk2 Δgpd2::loxP Δpdc5:loxP-kanMX-loxP) using standard genetic techniques (*Methods in Yeast Genetics*, 2005, Cold Spring Harbor Laboratory Press, Cold Spring Harbor, N.Y.) and the resulting strain ("isobutanol producing NYLA93 strain") was maintained on synthetic complete media lacking histidine and uracil, and supplemented with 1% ethanol at 30° C.

Construction of *Saccharomyces cerevisiae* Strain BP1083 ("NGCI-070"; PNY1504)

The strain BP1064 was derived from CEN.PK 113-7D (CBS 8340; Centraalbureau voor Schimmelcultures (CBS) Fungal Biodiversity Centre, Netherlands) and contains deletions of the following genes: URA3, HIS3, PDC1, PDC5, PDC6, and GPD2. BP1064 was transformed with plasmids pYZ090 (SEQ ID NO: 85, described in U.S. Provisional Application Ser. No. 61/246,844) and pLH468 (SEQ ID NO: 33) to create strain NGCI-070 (BP1083, PNY1504).

Deletions, which completely removed the entire coding sequence, were created by homologous recombination with PCR fragments containing regions of homology upstream and downstream of the target gene and either a G418 resistance marker or URA3 gene for selection of transformants. The G418 resistance marker, flanked by loxP sites, was removed using Cre recombinase. The URA3 gene was removed by homologous recombination to create a scarless deletion or if flanked by loxP sites, was removed using Cre recombinase.

The scarless deletion procedure was adapted from Akada, et al., (Yeast 23:399-405, 2006). In general, the PCR cassette for each scarless deletion was made by combining four fragments, A-B-U-C, by overlapping PCR. The PCR cassette contained a selectable/counter-selectable marker, URA3 (Fragment U), consisting of the native CEN.PK 113-7D URA3 gene, along with the promoter (250 bp upstream of the URA3 gene) and terminator (150 bp downstream of the URA3 gene). Fragments A and C, each 500 bp long, corresponded to the 500 bp immediately upstream of the target gene (Fragment A) and the 3' 500 bp of the target gene (Fragment C). Fragments A and C were used for integration of the cassette into the chromosome by homologous recombination. Fragment B (500 bp long) corresponded to the 500 bp immediately downstream of the target gene and was used for excision of the URA3 marker and Fragment C from the chromosome by homologous recombination, as a direct repeat of the sequence corresponding to Fragment B was created upon integration of the cassette into the chromosome. Using the PCR product ABUC cassette, the URA3 marker was first integrated into and then excised from the chromosome by homologous recombination. The initial integration deleted the gene, excluding the 3' 500 bp. Upon excision, the 3' 500 bp region of the gene was also deleted. For integration of genes using this method, the gene to be integrated was included in the PCR cassette between fragments A and B.

URA3 Deletion

To delete the endogenous URA3 coding region, a ura3:: loxP-kanMX-loxP cassette was PCR-amplified from pLA54 template DNA (SEQ ID NO: 103). pLA54 contains the *K. lactis* TEF1 promoter and kanMX marker, and is flanked by loxP sites to allow recombination with Cre recombinase and removal of the marker. PCR was done using Phusion® DNA polymerase (New England BioLabs Inc., Ipswich, Mass.) and primers BK505 and BK506 (SEQ ID NOs: 104 and 105). The URA3 portion of each primer was derived from the 5' region upstream of the URA3 promoter and 3' region downstream of the coding region such that integration of the loxP-kanMX-loxP marker resulted in replacement of the URA3 coding region. The PCR product was transformed into CEN.PK 113-7D using standard genetic techniques (Methods in Yeast Genetics, 2005, Cold Spring Harbor Laboratory Press, Cold Spring Harbor, N.Y., pp. 201-202) and transformants were selected on YPD containing G418 (100 µg/mL) at 30° C. Transformants were screened to verify correct integration by PCR using primers LA468 and LA492 (SEQ ID NOs: 106 and 107) and designated CEN.PK 113-7D Δura3::kanMX.

HIS3 Deletion

The four fragments for the PCR cassette for the scarless HIS3 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact, kit (Qiagen, Valencia, Calif.). HIS3 Fragment A was amplified with primer oBP452 (SEQ ID NO: 112) and primer oBP453 (SEQ ID NO: 113) containing a 5' tail with homology to the 5' end of HIS3 Fragment B. HIS3 Fragment B was amplified with primer oBP454 (SEQ ID NO: 114) containing a 5' tail with homology to the 3' end of HIS3 Fragment A, and primer oBP455 (SEQ ID NO: 115) containing a 5' tail with homology to the 5' end of HIS3 Fragment U. HIS3 Fragment U was amplified with primer oBP456 (SEQ ID NO: 116) containing a 5' tail with homology to the 3' end of HIS3 Fragment B, and primer oBP457 (SEQ ID NO: 117) containing a 5' tail with homology to the 5' end of HIS3 Fragment C. HIS3 Fragment C was amplified with primer oBP458 (SEQ ID NO: 118) containing a 5' tail with homology to the 3' end of HIS3 Fragment U, and primer oBP459 (SEQ ID NO: 119). PCR products were purified with a PCR Purification kit (Qiagen, Valencia, Calif.). HIS3 Fragment AB was created by overlapping PCR by mixing HIS3 Fragment A and HIS3 Fragment B and amplifying with primers oBP452 (SEQ ID NO: 112) and oBP455 (SEQ ID NO: 115). HIS3 Fragment UC was created by overlapping PCR by mixing HIS3 Fragment U and HIS3 Fragment C and amplifying with primers oBP456 (SEQ ID NO: 116) and oBP459 (SEQ ID NO: 119). The resulting PCR products were purified on an agarose gel followed by a Gel Extraction kit (Qiagen, Valencia, Calif.). The HIS3 ABUC cassette was created by overlapping PCR by mixing HIS3 Fragment AB and HIS3 Fragment UC and amplifying with primers oBP452 (SEQ ID NO: 112) and oBP459 (SEQ ID NO: 119). The PCR product was purified with a PCR Purification kit (Qiagen, Valencia, Calif.).

Competent cells of CEN.PK 113-7D Δura3::kanMX were made and transformed with the HIS3 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a his3 knockout were screened for by PCR with primers oBP460 (SEQ ID NO: 120) and oBP461 (SEQ ID NO: 121) using genomic DNA prepared with a Gentra® Puregene® Yeast/Bact. kit (Qiagen, Valencia, Calif.). A correct transformant was selected as strain CEN.PK 113-7D Δura3::kanMX Δhis3::URA3.

KanMX Marker Removal from the Δura3 Site and URA3 Marker Removal from the Δhis3 Site The KanMX marker was removed by transforming CEN.PK 113-7D Δura3::kanMX Δhis3::URA3 with pRS423::PGAL1-cre (SEQ ID NO: 164, described in U.S. Provisional Application No. 61/290,639) using a Frozen-EZ Yeast Transformation II™ kit (Zymo Research Corporation, Irvine, Calif.) and plating on synthetic complete medium lacking histidine and uracil supplemented with 2% glucose at 30° C. Transformants were grown in YP supplemented with 1% galactose at 30° C. for ~6 hours to induce the Cre recombinase and KanMX marker excision and plated onto YPD (2% glucose) plates at 30° C. for recovery. An isolate was grown overnight in YPD and plated on synthetic complete medium containing 5-fluoro-orotic acid (5-FOA, 0.1%) at 30° C. to select for isolates that lost the URA3 marker. 5-FOA resistant isolates were grown in and plated on YPD for removal of the pRS423::PGAL1-cre plasmid. Isolates were checked for loss of the KanMX marker, URA3 marker, and pRS423::PGAL1-cre plasmid by assaying growth on YPD+ G418 plates, synthetic complete medium lacking uracil plates, and synthetic complete medium lacking histidine plates. A correct isolate that was sensitive to G418 and auxotrophic for uracil and histidine was selected as strain CEN.PK 113-7D Δura3::loxP Δhis3 and designated as BP857. The deletions and marker removal were confirmed by PCR and sequencing with primers oBP450 (SEQ ID NO: 122) and oBP451 (SEQ ID NO: 123) for Δura3 and primers oBP460 (SEQ ID NO: 120) and oBP461 (SEQ ID NO: 121) for Δhis3 using genomic DNA prepared with a Gentra® Puregene® Yeast/Bact. kit (Qiagen, Valencia, Calif.).

PDC6 Deletion

The four fragments for the PCR cassette for the scarless PDC6 deletion were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC6 Fragment A was amplified with primer oBP440 (SEQ ID NO: 124) and primer oBP441 (SEQ ID NO: 125) containing a 5' tail with homology to the 5' end of PDC6 Fragment B. PDC6 Fragment B was amplified with primer oBP442 (SEQ ID NO: 126), containing a 5' tail with homology to the 3' end of PDC6 Fragment A, and primer oBP443 (SEQ ID NO: 127) containing a 5' tail with homology to the 5' end of PDC6 Fragment U. PDC6 Fragment U was amplified with primer oBP444 (SEQ ID NO: 128) containing a 5' tail with homology to the 3' end of PDC6 Fragment B, and primer oBP445 (SEQ ID NO: 129) containing a 5' tail with homology to the 5' end of PDC6 Fragment C. PDC6 Fragment C was amplified with primer oBP446 (SEQ ID NO: 130) containing a 5' tail with homology to the 3' end of PDC6 Fragment U, and primer oBP447 (SEQ ID NO: 131). PCR products were purified with a PCR Purification kit (Qiagen, Valencia, Calif.). PDC6 Fragment AB was created by overlapping PCR by mixing PDC6 Fragment A and PDC6 Fragment B and amplifying with primers oBP440 (SEQ ID NO: 124) and oBP443 (SEQ ID NO: 127). PDC6 Fragment UC was created by overlapping PCR by mixing PDC6 Fragment U and PDC6 Fragment C and amplifying with primers oBP444 (SEQ ID NO: 128) and oBP447 (SEQ ID NO: 131). The resulting PCR products were purified on an agarose gel followed by a Gel Extraction kit (Qiagen, Valencia, Calif.). The PDC6 ABUC cassette was created by overlapping PCR by mixing PDC6 Fragment AB and PDC6 Fragment UC and amplifying with primers oBP440 (SEQ ID NO: 124) and oBP447 (SEQ ID NO: 131). The PCR product was purified with a PCR Purification kit (Qiagen, Valencia, Calif.).

Competent cells of CEN.PK 113-7D Δura3::loxP Δhis3 were made and transformed with the PDC6 ABUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc6 knockout were screened for by PCR with primers oBP448 (SEQ ID NO: 132) and oBP449 (SEQ ID NO: 133) using genomic DNA prepared with a Gentra® Puregene® Yeast/Bact. kit (Qiagen, Valencia, Calif.). A correct transformant was selected as strain CEN.PK 113-7D Δura3::loxP Δhis3 Δpdc6::URA3.

CEN.PK 113-7D Δura3::loxP Δhis3 Δpdc6::URA3 was grown overnight in YPD and plated on synthetic complete medium containing 5-fluoro-orotic acid (0.1%) at 30° C. to select for isolates that lost the URA3 marker. The deletion and marker removal were confirmed by PCR and sequencing with primers oBP448 (SEQ ID NO: 132) and oBP449 (SEQ ID NO: 133) using genomic DNA prepared with a Gentra® Puregene® Yeast/Bact. kit (Qiagen, Valencia, Calif.). The absence of the PDC6 gene from the isolate was demonstrated by a negative PCR result using primers specific for the coding sequence of PDC6, oBP554 (SEQ ID NO: 134) and oBP555 (SEQ ID NO: 135). The correct isolate was selected as strain CEN.PK 113-7D Δura3::loxP Δhis3 Δpdc6 and designated as BP891.

PDC1 Deletion ilvDSm Integration

The PDC1 gene was deleted and replaced with the ilvD coding region from *Streptococcus mutans* ATCC No. 700610. The A fragment followed by the ilvD coding region from *Streptococcus mutans* for the PCR cassette for the PDC1 deletion-ilvDSm integration was amplified using Phusion® High Fidelity PCR Master Mix (New England BioLabs Inc., Ipswich, Mass.) and NYLA83 (described herein and in U.S. Provisional Application No. 61/246,709) genomic DNA as template, prepared with a Gentra® Puregene® Yeast/Bact. kit (Qiagen, Valencia, Calif.). PDC1 Fragment A-ilvDSm (SEQ ID NO: 167) was amplified with primer oBP513 (SEQ ID NO: 136) and primer oBP515 (SEQ ID NO: 137) containing a 5' tail with homology to the 5' end of PDC1 Fragment B. The B, U, and C fragments for the PCR cassette for the PDC1 deletion-ilvDSm integration were amplified using Phusion® High Fidelity PCR Master Mix (New England BioLabs Inc., Ipswich, Mass.) and CEN.PK 113-7D genomic DNA as template, prepared with a Gentra® Puregene® Yeast/Bact. kit (Qiagen, Valencia, Calif.). PDC1 Fragment B was amplified with primer oBP516 (SEQ ID NO: 138) containing a 5' tail with homology to the 3' end of PDC1 Fragment A-ilvDSm, and primer oBP517 (SEQ ID NO: 139) containing a 5' tail with homology to the 5' end of PDC1 Fragment U. PDC1 Fragment U was amplified with primer oBP518 (SEQ ID NO: 140) containing a 5' tail with homology to the 3' end of PDC1 Fragment B, and primer oBP519 (SEQ ID NO: 141) containing a 5' tail with homology to the 5' end of PDC1 Fragment C. PDC1 Fragment C was amplified with primer oBP520 (SEQ ID NO: 142), containing a 5' tail with homology to the 3' end of PDC1 Fragment U, and primer oBP521 (SEQ ID NO: 143). PCR products were purified with a PCR Purification kit (Qiagen, Valencia, Calif. PDC1 Fragment A-ilvDSm-B was created by overlapping PCR by mixing PDC1 Fragment A-ilvDSm and PDC1 Fragment B and amplifying with primers oBP513 (SEQ ID NO: 136) and oBP517 (SEQ ID NO: 139). PDC1 Fragment UC was created by overlapping PCR by mixing PDC1 Fragment U and PDC1 Fragment C and amplifying with primers oBP518 (SEQ ID NO: 140) and oBP521 (SEQ ID NO: 143). The resulting PCR products were purified on an agarose gel followed by a Gel Extraction kit (Qiagen, Valencia, Calif.). The PDC1 A-ilvDSm-BUC cassette was created by overlapping PCR by mixing PDC1 Fragment A-ilvDSm-B and PDC1 Fragment UC and amplifying with primers oBP513 (SEQ ID NO: 136) and oBP521 (SEQ ID NO: 143). The PCR product was purified with a PCR Purification kit (Qiagen, Valencia, Calif.).

Competent cells of CEN.PK 113-7D Δura3::loxP Δhis3 Δpdc6 were made and transformed with the PDC1 A-ilvDSm-BUC PCR cassette using a Frozen-EZ Yeast Transformation II™ kit (Zymo Research Corporation, Irvine, Calif.). Transformation mixtures were plated on synthetic complete media lacking uracil supplemented with 2% glucose at 30° C. Transformants with a pdc1 knockout ilvDSm integration were screened for by PCR with primers oBP511 (SEQ ID NO: 144) and oBP512 (SEQ ID NO: 145) using genomic DNA prepared with a Gentra® Puregene® Yeast/Bact. kit (Qiagen, Valencia, Calif.). The absence of the PDC1 gene from the isolate was demonstrated by a negative PCR result using primers specific for the coding sequence of PDC1, oBP550 (SEQ ID NO: 146) and oBP551 (SEQ ID NO: 147). A correct transformant was selected as strain CEN.PK 113-7D Δura3::loxP Δhis3 Δpdc6 Δpdc1::ilvDSm-URA3.

CEN.PK 113-7D Δura3::loxP Δhis3 Δpdc6 Δpdc1::ilvDSm-URA3 was grown overnight in YPD and plated on synthetic complete medium containing 5-fluoro-orotic acid (0.1%) at 30° C. to select for isolates that lost the URA3 marker. The deletion of PDC1, integration of ilvDSm, and marker removal were confirmed by PCR and sequencing with primers oBP511 (SEQ ID NO: 144) and oBP512 (SEQ ID NO: 145) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm and designated as BP907.

PDC5 Deletion sadB Integration

The PDC5 gene was deleted and replaced with the sadB coding region from *Achromobacter xylosoxidans*. A segment of the PCR cassette for the PDC5 deletion-sadB integration was first cloned into plasmid pUC19-URA3MCS.

pUC19-URA3MCS is pUC19 based and contains the sequence of the URA3 gene from *Saccharomyces cerevisiae* situated within a multiple cloning site (MCS). pUC19 contains the pMB1 replicon and a gene coding for beta-lactamase for replication and selection in *Escherichia coli*. In addition to the coding sequence for URA3, the sequences from upstream and downstream of this gene were included for expression of the URA3 gene in yeast. The vector can be used for cloning purposes and can be used as a yeast integration vector.

The DNA encompassing the URA3 coding region along with 250 bp upstream and 150 bp downstream of the URA3 coding region from *Saccharomyces cerevisiae* CEN.PK 113-7D genomic DNA was amplified with primers oBP438 (SEQ ID NO: 110) containing BamHI, AscI, PmeI, and FseI restriction sites, and oBP439 (SEQ ID NO: 111) containing XbaI, PacI, and NotI restriction sites, using Phusion® High Fidelity PCR Master Mix (New England BioLabs Inc., Ipswich, Mass.). Genomic DNA was prepared using a Gentra® Puregene® Yeast/Bact. kit (Qiagen, Valencia, Calif.). The PCR product and pUC19 were ligated with T4 DNA ligase after digestion with BamHI and XbaI to create vector pUC19-URA3MCS. The vector was confirmed by PCR and sequencing with primers oBP264 (SEQ ID NO: 108) and oBP265 (SEQ ID NO: 109).

The coding sequence of sadB and PDC5 Fragment B were cloned into pUC19-URA3MCS to create the sadB-BU portion of the PDC5 A-sadB-BUC PCR cassette. The coding sequence of sadB was amplified using pLH468-sadB (SEQ ID NO: 165) as template with primer oBP530 (SEQ ID NO: 148) containing an AscI restriction site, and primer oBP531 (SEQ ID NO: 149) containing a 5' tail with homology to the 5' end of PDC5 Fragment B. PDC5 Fragment B was amplified with primer oBP532 (SEQ ID NO: 150) containing a 5' tail with homology to the 3' end of sadB, and primer oBP533 (SEQ ID NO: 151) containing a PmeI restriction site. PCR products were purified with a PCR Purification kit (Qiagen, Valencia, Calif.). sadB-PDC5 Fragment B was created by overlapping PCR by mixing the sadB and PDC5 Fragment B PCR products and amplifying with primers oBP530 (SEQ ID NO: 148) and oBP533 (SEQ ID NO: 151). The resulting PCR product was digested with AscI and PmeI and ligated with T4 DNA ligase into the corresponding sites of pUC19-URA3MCS after digestion with the appropriate enzymes. The resulting plasmid was used as a template for amplification of sadB-Fragment B-Fragment U using primers oBP536 (SEQ ID NO: 152) and oBP546 (SEQ ID NO: 153) containing a 5' tail with homology to the 5' end of PDC5 Fragment C. PDC5 Fragment C was amplified with primer oBP547 (SEQ ID NO: 154) containing a 5' tail with homology to the 3' end of PDC5 sadB-Fragment B-Fragment U, and primer oBP539 (SEQ ID NO: 155). PCR products were purified with a PCR Purification kit (Qiagen, Valencia, Calif.). PDC5 sadB-Fragment B-Fragment U-Fragment C was created by overlapping PCR by mixing PDC5 sadB-Fragment B-Fragment U and PDC5 Fragment C and amplifying with primers oBP536 (SEQ ID NO: 152) and oBP539 (SEQ ID NO: 155). The resulting PCR product was purified on an agarose gel followed by a Gel Extraction kit (Qiagen, Valencia, Calif.). The PDC5 A-sadB-BUC cassette was created by amplifying PDC5 sadB-Fragment B-Fragment U-Fragment C with primers oBP542 (SEQ ID NO: 156) containing a 5' tail with homology to the 50 nucleotides immediately upstream of the native PDC5 coding sequence, and oBP539 (SEQ ID NO: 155). The PCR product was purified with a PCR Purification kit (Qiagen, Valencia, Calif.).

Competent cells of CEN.PK 113-7D Δura3::loxP Δhis3 Δpdc6 Δpdc1::ilvDSm were made and transformed with the PDC5 A-sadB-BUC PCR cassette using a Frozen-EZ Yeast Transformation II™ kit (Zymo Research Corporation, Irvine, Calif.). Transformation mixtures were plated on synthetic complete media lacking uracil supplemented with 1% ethanol (no glucose) at 30° C. Transformants with a pdc5 knockout sadB integration were screened for by PCR with primers oBP540 (SEQ ID NO: 157) and oBP541 (SEQ ID NO: 158) using genomic DNA prepared with a Gentra® Puregene® Yeast/Bact. kit (Qiagen, Valencia, Calif.). The absence of the PDC5 gene from the isolate was demonstrated by a negative PCR result using primers specific for the coding sequence of PDC5, oBP552 (SEQ ID NO: 159) and oBP553 (SEQ ID NO: 160). A correct transformant was selected as strain CEN.PK 113-7D Δura3::loxP Δhis3 Δpdc6 Δpdc1::ilvDSm Δpdc5::sadB-URA3.

CEN.PK 113-7D Δura3::loxP Δhis3 Δpdc6 Δpdc1::ilvDSm Δpdc5::sadB-URA3 was grown overnight in YPE (1% ethanol) and plated on synthetic complete medium supplemented with ethanol (no glucose) and containing 5-fluoro-orotic acid (0.1%) at 30° C. to select for isolates that lost the URA3 marker. The deletion of PDC5, integration of sadB, and marker removal were confirmed by PCR with primers oBP540 (SEQ ID NO: 157) and oBP541 (SEQ ID NO: 158) using genomic DNA prepared with a Gentra® Puregene® Yeast/Bact. kit (Qiagen, Valencia, Calif.). The correct isolate was selected as strain CEN.PK 113-7D Δura3::loxP Δhis3 Δpdc6 Δpdc1::ilvDSm Δpdc5::sadB and designated as BP913.

GPD2 Deletion

To delete the endogenous GPD2 coding region, a gpd2::loxP-URA3-loxP cassette was PCR-amplified using loxP-URA3-loxP (SEQ ID NO: 166) as template DNA. loxP-URA3-loxP contains the URA3 marker from (ATCC No. 77107) flanked by loxP recombinase sites. PCR was done using Phusion® DNA polymerase (New England BioLabs Inc., Ipswich, Mass.) and primers LA512 and LA513 (SEQ ID NOs: 87 and 88). The GPD2 portion of each primer was derived from the 5' region upstream of the GPD2 coding region and 3' region downstream of the coding region such that integration of the loxP-URA3-loxP marker resulted in replacement of the GPD2 coding region. The PCR product was transformed into BP913 and transformants were selected on synthetic complete media lacking uracil supplemented with 1% ethanol (no glucose). Transformants were screened to verify correct integration by PCR using primers oBP582 and AA270 (SEQ ID NOs: 161 and 162).

The URA3 marker was recycled by transformation with pRS423::PGAL1-cre (SEQ ID NO: 164) and plating on synthetic complete media lacking histidine supplemented with 1% ethanol at 30° C. Transformants were streaked on synthetic complete medium supplemented with 1% ethanol and containing 5-fluoro-orotic acid (0.1%) and incubated at 30° C. to select for isolates that lost the URA3 marker. 5-FOA resistant isolates were grown in YPE (1% ethanol) for removal of the pRS423::PGAL1-cre plasmid. The deletion and marker removal were confirmed by PCR with primers oBP582 (SEQ ID NO: 161) and oBP591 (SEQ ID NO: 163). The correct isolate was selected as strain CEN.PK 113-7D Δura3::loxP Δhis3 Δpdc6 Δpdc1::ilvDSm Δpdc5::sadB Δgpd2::loxP and designated as PNY1503 (BP1064).

BP1064 was transformed with plasmids pYZ090 (SEQ ID NO: 85) and pLH468 (SEQ ID NO: 33) to create strain NGCI-070 (BP1083; PNY1504).

Growth for Production

Recombinant host cells disclosed herein are grown in production broth which contains suitable carbon substrates. Carbon substrates can include, but are not limited to, monosaccharides such as fructose; oligosaccharides such as lactose, maltose, galactose, or sucrose; polysaccharides such as starch or cellulose; or mixtures thereof and unpurified mixtures from renewable feedstocks such as cheese whey permeate, cornsteep liquor, sugar beet molasses, and barley malt. Other carbon substrates can include ethanol, lactate, succinate, or glycerol.

Additionally the carbon substrate can also be one-carbon substrates such as carbon dioxide or methanol for which metabolic conversion into key biochemical intermediates has been demonstrated. In addition to one and two carbon substrates, methylotrophic organisms are also known to utilize a number of other carbon containing compounds such as methylamine, glucosamine, and a variety of amino acids for metabolic activity. For example, methylotrophic yeasts are known to utilize the carbon from methylamine to form trehalose or glycerol (Bellion, et al., *Microb. Growth C*1-Compd., [Int. Symp.], 7th (1993), 415-32, Editor(s): Murrell, J. Collin; Kelly, Don P. Publisher: Intercept, Andover, UK). Similarly, various species of *Candida* will metabolize alanine or oleic acid (Sulter, et al., Arch. Microbiol. 153:485-489, 1990). Hence it is contemplated that the source of carbon utilized in the present invention can encompass a wide variety of carbon containing substrates and will only be limited by the choice of organism.

Although it is contemplated that all of the above mentioned carbon substrates and mixtures thereof are suitable in the present invention, in some embodiments, the carbon substrates are glucose, fructose, and sucrose, or mixtures of these with C5 sugars such as xylose and/or arabinose for yeasts cells modified to use C5 sugars. Sucrose can be derived from renewable sugar sources such as sugar cane, sugar beets, cassava, sweet sorghum, and mixtures thereof. Glucose and dextrose can be derived from renewable grain sources through saccharification of starch based feedstocks including grains such as corn, wheat, rye, barley, oats, and mixtures thereof. In addition, fermentable sugars can be derived from renewable cellulosic or lignocellulosic biomass through processes of pretreatment and saccharification, as described, for example, in U.S. Patent Application Publication No. 2007/0031918 A1, which is herein incorporated by reference.

Biomass refers to any cellulosic or lignocellulosic material and includes materials comprising cellulose, and optionally further comprising hemicellulose, lignin, starch, oligosaccharides and/or monosaccharides. Biomass can also comprise additional components, such as protein and/or lipid. Biomass can be derived from a single source or biomass can comprise a mixture derived from more than one source; for example, biomass can comprise a mixture of corn cobs and corn stover or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, agave, and mixtures thereof.

Culture Conditions

Typically cells are grown at a temperature in the range of about 20° C. to about 40° C. in an appropriate medium. Suitable pH ranges for the fermentation are between about pH 5.0 to about pH 9.0. In one embodiment, the pH is about pH 6.0 to about pH 8.0. Suitable pH ranges for the fermentation of yeast are typically between about pH 3.0 to about pH 9.0. In one embodiment, the pH is about pH 5.0 to about pH 8.0. Suitable pH ranges for the fermentation of other microorganisms are between about pH 3.0 to about pH 7.5. In one embodiment, the pH is about pH 4.5 to about pH 6.5.

Fermentations can be performed under aerobic or anaerobic conditions. In one embodiment, anaerobic or microaerobic conditions are used for fermentations.

Industrial Batch and Continuous Fermentations

Butanol, or other products, can be produced using a batch method of fermentation. A classical batch fermentation is a closed system where the composition of the production broth is set at the beginning of the fermentation and not subject to artificial alterations during the fermentation. A variation on the standard batch system is the fed-batch system. Fed-batch fermentation processes are also suitable in the present invention and comprise a typical batch system with the exception that the substrate is added in increments as the fermentation progresses. Fed-batch systems are useful when catabolite repression is apt to inhibit the metabolism of the cells and where it is desirable to have limited amounts of substrate in the production broth. Batch and fed-batch fermentations are common and well known in the art and examples can be found in Thomas D. Brock in *Biotechnology: A Textbook of Industrial Microbiology*, Second Edition (1989) Sinauer Associates, Inc., Sunderland, Mass., or Deshpande, Appl. Biochem. Biotechnol. 36:227, 1992, herein incorporated by reference.

Butanol, or other products, can also be produced using continuous fermentation methods. Continuous fermentation is an open system where a defined fermentation medium is added continuously to a bioreactor and an equal amount of conditioned media is removed simultaneously for processing. Continuous fermentation generally maintains the cultures at a constant high density where cells are primarily in log phase growth. Continuous fermentation allows for the modulation of one factor or any number of factors that affect cell growth or end product concentration. Methods of modulating nutrients and growth factors for continuous fermentation processes as well as techniques for maximizing the rate of product formation are well known in the art of industrial microbiology and a variety of methods are detailed by Brock, supra.

It is contemplated that the production of butanol, or other products, can be practiced using batch, fed-batch, or continuous processes and that any known mode of fermentation would be suitable. Additionally, it is contemplated that cells can be immobilized on a substrate as whole cell catalysts and subjected to fermentation conditions for butanol production.

Methods for Isobutanol Isolation from the Fermentation Medium

Bioproduced butanol may be isolated from the fermentation medium using methods known in the art for ABE fermentations (see, e.g., Dune, Appl. Microbiol. Biotechnol. 49:639-648, 1998, Groot, et al., Process. Biochem. 27:61-75, 1992), and references therein). For example, solids may be removed from the fermentation medium by centrifugation, filtration, decantation, or the like. Then, the butanol may be isolated from the fermentation medium using methods such as distillation, azeotropic distillation, liquid-liquid extraction, adsorption, gas stripping, membrane evaporation, or pervaporation.

Because butanol forms a low boiling point, azeotropic mixture with water, distillation may be used to separate the mixture up to its azeotropic composition. Distillation may be used in combination with another separation method to obtain separation around the azeotrope. Methods that may be used in combination with distillation to isolate and purify butanol include, but are not limited to, decantation, liquid-liquid extraction, adsorption, and membrane-based techniques. Additionally, butanol can be isolated using azeotropic distillation using an entrainer (see, e.g., Doherty and Malone, *Conceptual Design of Distillation Systems*, McGraw Hill, New York, 2001).

The butanol-water mixture forms a heterogeneous azeotrope so that distillation may be used in combination with decantation to isolate and purify the butanol. In this method, the butanol containing fermentation broth is distilled to near the azeotropic composition. Then, the azeotropic mixture is condensed, and the butanol is separated from the fermentation medium by decantation. The decanted aqueous phase may be returned to the first distillation column as reflux. The butanol-rich decanted organic phase may be further purified by distillation in a second distillation column.

The butanol may also be isolated from the fermentation medium using liquid-liquid extraction in combination with distillation. In this method, the butanol is extracted from the fermentation broth using liquid-liquid extraction with a suitable solvent. The butanol-containing organic phase is then distilled to separate the butanol from the solvent.

Distillation in combination with adsorption may also be used to isolate butanol from the fermentation medium. In this method, the fermentation broth containing the butanol is distilled to near the azeotropic composition and then the remaining water is removed by use of an adsorbent, such as molecular sieves (Aden, et al., *Lignocellulosic Biomass to Ethanol Process Design and Economics Utilizing Co-Current Dilute Acid Prehydrolysis and Enzymatic Hydrolysis for Corn Stover*, Report NREL/TP-510-32438, National Renewable Energy Laboratory, June 2002).

Additionally, distillation in combination with pervaporation may be used to isolate and purify the butanol from the fermentation medium. In this method, the fermentation broth containing the butanol is distilled to near the azeotropic composition, and then the remaining water is removed by pervaporation through a hydrophilic membrane (Guo, et al., J. Membr. Sci. 245:199-210, 2004).

EXAMPLES

The present invention is further defined in the following Examples. It should be understood that these Examples, while indicating embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, N.Y. (1989) (Maniatis) and by T. J. Silhavy, M. L. Bennan, and L. W. Enquist, *Experiments with Gene Fusions*, Cold Spring Harbor Laboratory Press, Cold Spring Harbor, N.Y. (1984) and by Ausubel, F. M. et al., *Current Protocols in Molecular Biology*, pub. by Greene Publishing Assoc. and Wiley-Interscience (1987), and by *Methods in Yeast Genetics*, 2005, Cold Spring Harbor Laboratory Press, Cold Spring Harbor, N.Y.

Materials and methods suitable for the maintenance and growth of bacterial cultures are well known in the art. Techniques suitable for use in the following Examples can be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of microbial cells were obtained from Aldrich Chemicals (Milwaukee, Wis.), BD Diagnostic Systems (Sparks, Md.), Life Technologies (Rockville, Md.), or Sigma Chemical Company (St. Louis, Mo.) unless otherwise specified. Microbial strains were obtained from The American Type Culture Collection (ATCC), Manassas, Va., unless otherwise noted. Synthetic complete medium is described by Amberg, Burke and Strathern, 2005, Methods in Yeast Genetics, Cold Spring Harbor Laboratory Press, Cold Spring Harbor, N.Y.

Methods for Analyzing Cultivation Experiments

OD at $\lambda=600$ nm can be determined in a spectrophotometer by pipetting a well mixed broth sample into an appropriate cuvette. If biomass concentration of the sample exceeds the linear absorption range of the spectrophotometer (typically OD values from 0.000 to 0.600), sample should be diluted with 0.9% NaCl solution to yield values in the linear range. Dry weight of the cell suspension can be determined by centrifugating 5 mL cell broth in a pre-weighed centrifuge tube, followed by washing with distilled water, drying to constant weight at 80° C. in an oven and determining the weight difference.

Example 1

Thiamine Increases Isobutanol Production

Shake Flask Experimental Procedure

The medium contained the following ingredients per L of water: 6.7 g Yeast Nitrogen Base (YNB) w/o amino acids (Difco 0919-15-3); 2.8 g Yeast Synthetic Drop-out Medium Supplement Without histidine, leucine, tryptophan, and uracil (Sigma Y2001); 20 mL of 1% (w/v) L-leucine; 4 mL of 1% (w/v) L-tryptophan; 5 g ethanol; 3 g glucose; and 1.0 mL of the ergosterol and Tween 80. In order to obtain 10 mL ergosterol and Tween 80 solution, 100 mg of ergosterol were dissolved in 5 mL 100% EtOH and 5 mL Tween 80 and then heated until sterile and dissolved (10 min at 70° C.).

In the shake flask experiments described, the following were added to 125 mL shake flasks: 16 mL of the culture broth; 2 mL of the 1 M MES buffer; and 2 mL of the addition ($H_2O$, YE, TH). The following additions were prepared: yeast extract (YE, final concentration 10 g/L); thiamine (TH, final concentration 6, 60, and 100 mg/L).

In order to provide the culture broth, seed cultures were started in 125 mL shake flasks with air permeable lids (10 mL medium inoculated with 1 mL inoculum from a frozen vial). After 24 hours OD (optical density) in the flask was about 0.7. The OD was measured at $\lambda=600$ nm (Spectrophotometer from Thermo Electron Corporation He$\lambda$ios Alpha, USA). The correlation between OD reading and dry cell weight g/L concentration was experimentally determined as 2.6:1.0. Ergosterol and Tween 80 was added to the medium to a final concentration of 1 mL/L. Seed (10 mL) was inoculated into 2 L shake flask with 135 mL of the medium. Separately, 2 mL of the $H_2O$, YE, TH additions were added to new 125 ml shake flasks. Into the 2 L shake flask, 16 mL of 1 M MES buffer was added and 5.3 mL of 50% (w/w) glucose solution. Eighteen (18) mL of this culture broth was distributed into the 125 mL shake flasks with prepared additions. The aerobic shake flasks with air permeable lid were incubated at 30° C. and 260 rpm. The anaerobic shake flasks were treated in anaerobic hood and incubated at 30° C. and 260 rpm. The anaerobic shake flasks were sampled in the anaerobic hood.

Effect of Thiamine on Isobutanol Production

Figure 1:
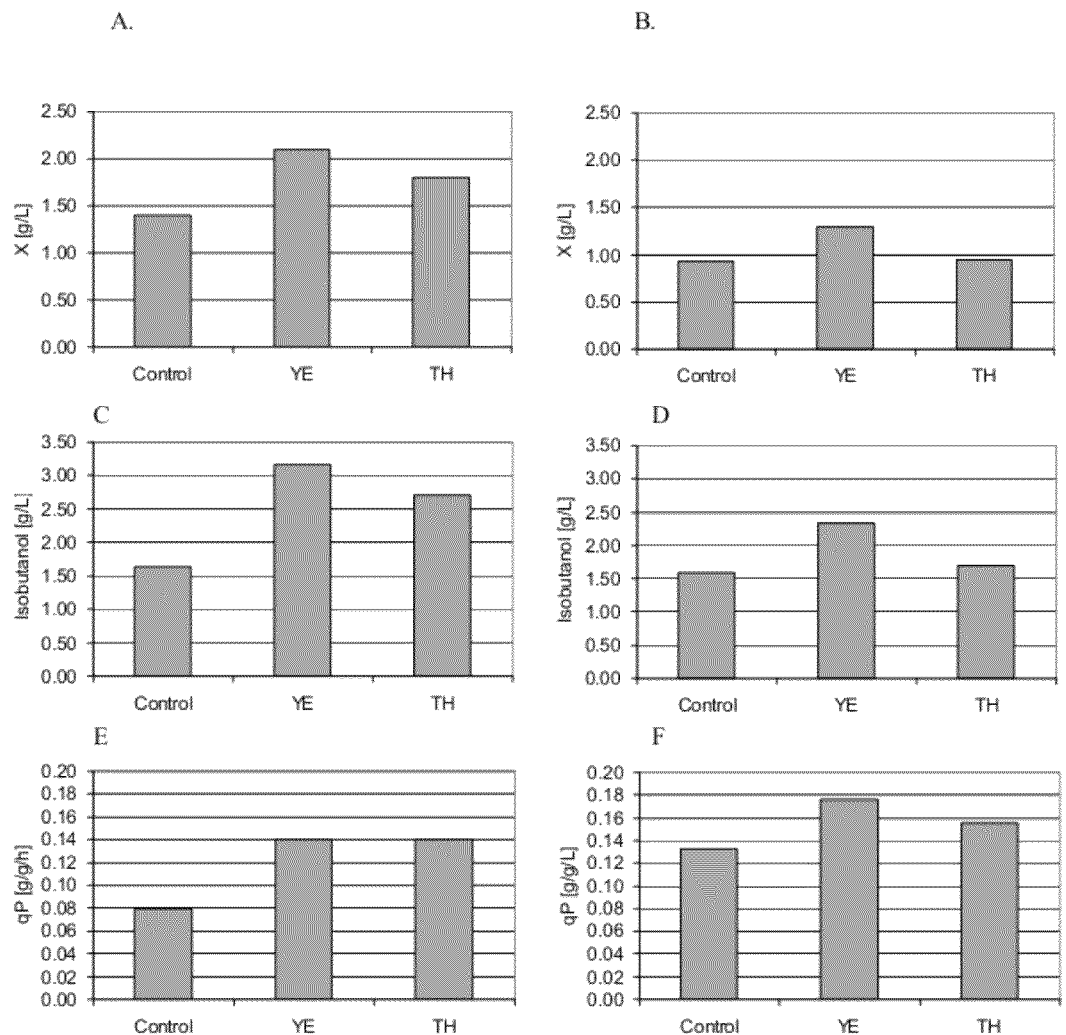
FIG. 1 depicts the final biomass (X; g/L), isobutanol concentration (g/L), and specific isobutanol production rate (qP; g/g/h) in aerobic (left panels) and anaerobic (right panels) shake flask cultivations with the addition of either water (control), yeast extract (YE), or thiamine (TH).

The effect of thiamine on isobutanol production was analyzed using shake flask fermentation. Shake flask fermentations were performed under both aerobic and anaerobic conditions in the presence of water (negative control), yeast extract (YE, positive control, final concentration 10 g/L), or thiamine (TH, final concentration 100 mg/L) with isobutanol producing NYLA84 strain. The final biomass (X), isobutanol concentrations, and specific isobutanol production rates (qP) were measured and are shown in FIG. 1. The isobutanol pathway comprises a KARI enzyme that strongly prefers NADPH, and the resulting redox imbalance cannot be resolved under stringent anaerobic conditions. Therefore, only initial values for qP (during the first 6 fermentation hours) in anaerobic flasks are presented in FIG. 1F. Moreover, because of insufficient oxygen transfer rate at the higher cell densities in aerobic shake flasks, again only initial values for qP (during the first 24 fermentation hours) were considered (FIG. 1E). For this reason, aerobic and anaerobic shake flasks are not directly comparable.

The highest final biomass concentrations and isobutanol titers were achieved with YE addition in both aerobic and anaerobic conditions (FIGS. 1A-D). In aerobic shake flasks, a higher final biomass concentration was achieved with addition of thiamine compared to the control. In aerobic shake flasks, higher titers of isobutanol were achieved with the addition of thiamine compared to the control. In aerobic flasks with thiamine, the initial qP (0.14 g/g/h) was 75% higher than the control and about the same as achieved with yeast extract (FIG. 1E). Similar observations can be made about initial qP in anaerobic flasks (FIG. 1F).

Figure 2:
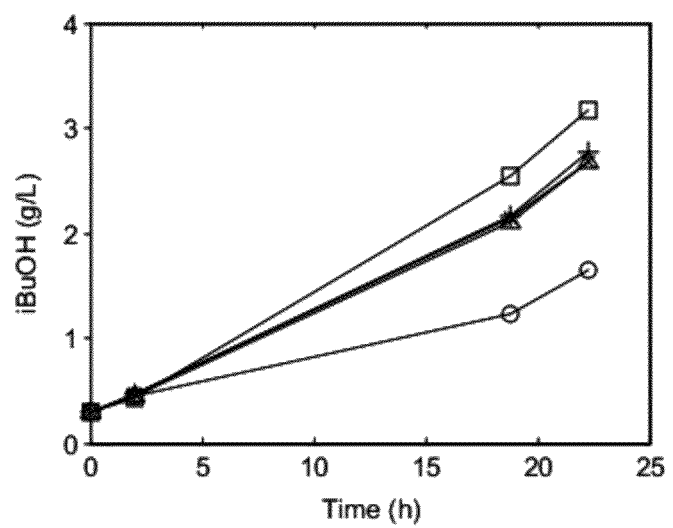
FIG. 2 depicts the isobutanol concentrations in aerobic shake flask cultivations with the addition of 0 (control), 6, 60, or 100 mg/L of thiamine or 10 g/l yeast extract (YE).
Figure 3:
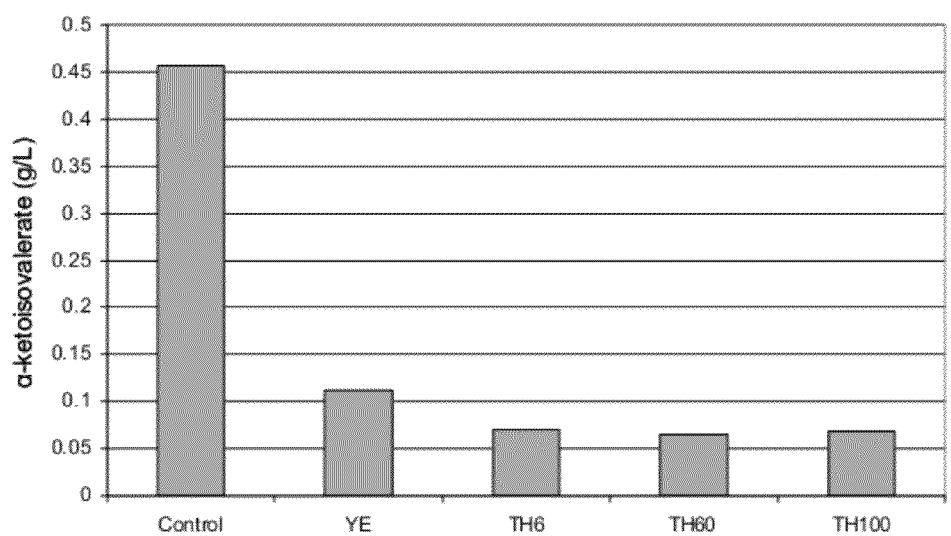
FIG. 3 depicts the α-ketoisovalerate accumulated in aerobic shake flask fermentations with the addition of 0 (control), 6, 60, or 100 mg/L of thiamine (TH) or 10 g/l yeast extract (YE).

In order to investigate influence of the addition of thiamine at different concentrations, aerobic shake flask experiments with final concentrations of 6, 60, and 100 mg/L thiamine were performed. The three concentrations of added vitamins resulted in similar isobutanol titers (FIG. 2). Thus, concentrations as low as 6 mg/L thiamine meet the requirements of the biomass concentrations used in these experiments. It was also observed that the accumulation of keto-isovaleric acid in control shake flasks was several times higher compared to the flasks with yeast extract or thiamine added (FIG. 3).

Examples 2-5

Experiments with Various Thiamine Concentrations in Production Medium

Fermentations with the isobutanol producing NYLA93 strain (construction described herein) were performed in defined medium with various thiamine concentrations in the range of 0 to 100 mg/L.

Example 2: F_140-100 defined medium supplemented with initial thiamine concentrations of 100 mg/L.

Example 3: F_141-20 defined medium supplemented with initial thiamine concentrations of 20 mg/L.

Example 4: F_142-10 defined medium supplemented with initial thiamine concentrations of 10 mg/L.

Example 5: F_143-0 defined medium supplemented with initial thiamine concentrations of 0 mg/L.

Methods:

Inoculum Preparation

1 L of inoculum medium contained: 6.7 g Yeast Nitrogen Base w/o amino acids (Difco 0919-15-3); 2.8 g Yeast Synthetic Drop-out Medium Supplement Without histidine, leucine, tryptophan, and uracil (Sigma Y2001); 20 mL of 1% (w/v) L-leucine; 4 mL of 1% (w/v) L-tryptophan; 0.8 mL of ergosterol and Tween 80; 3 g of ethanol; 3 g of glucose A 125 mL shake flask was inoculated directly from a frozen vial by pipetting the whole vial culture (approx. 1 ml) into 10 mL of the inoculum medium. The flask was incubated at 160 rpm and 30° C. The strain was grown overnight until OD was about 1.0. At this point, four 2 L shake flasks with 160 mL of the inoculum medium were inoculated from the overnight culture. For each fermentor, 160 mL of the inoculum was prepared in 2 L baffled shake flask at 260 rpm and 30° C. When OD at λ=600 nm in the shake flask reached about 1.0, 30 mL of 1M MES buffer and about 160 mL of oleyl alcohol were added to the shake flasks. Twenty-four (24) hours after this point, the oleyl alcohol was removed and fermentors inoculated.

Bioreactor Medium

One (1) L of bioreactor medium contained:
salts: ammonium sulfate 10.0 g, potassium phosphate monobasic 5.33 g, magnesium sulfate heptahydrate 2.0 g, zinc sulfate heptahydrate, 0.47 g.
vitamins: biotin (D−) 0.40 mg, Ca D(+) panthotenate 8.00 mg, myo-inositol 200.00 mg, pyridoxol hydrochloride 8.00 mg, p-aminobenzoic acid 1.60 mg, riboflavin 1.60 mg, folic acid 0.02 mg, niacin 100.0 mg.
amino acids: yeast synthetic drop-out medium supplement without histidine, leucine, tryptophan, and uracil (Sigma Y2001) 2.8 g, 1% (w/v) L-leucine 20 mL, 1% (w/v) L-tryptophan 4 mL.
trace elements: EDTA (Titriplex 1117) 99.38 mg, zinc sulphate heptahydrate 29.81 mg, manganese chloride dehydrate 5.57 mg, cobalt(II)chloride hexahydrate 1.99 mg, copper(II)sulphate pentahydrate 1.99 mg, Di-sodium molybdenum dehydrate 2.65 mg, calcium chloride dehydrate 29.81 mg, iron sulphate heptahydrate 19.88 mg, boric acid, 6.63 mg, potassium iodide 0.66 mg.

Thiamine was added to fermentors according to Table 6.

TABLE 6

| Fermentation | Thiamine start concentration mg/L |
|---|---|
| F_140 - 11162009 | 100 |
| F_141 - 11162009 | 20 |
| F_142 - 11162009 | 10 |
| F_143 - 11162009 | 0 |

Bioreactor Experimental Design

Experiments were executed in 2 L BIOSTAT B-DCU Tween2 L bioreactors from Sartorius (USA). The fermentors are connected to mass spectrometer from Thermo Electron Corporation (USA). Directly after inoculation with 80 mL of inoculum per bioreactor, the volume in bioreactors was about 800 mL, dissolved oxygen tension (DOT) was controlled at 15%, pH was controlled at 5.25, aeration was controlled at 0.5 L/min, 1.4 L of oleyl alcohol was added. Oleyl alcohol was used in order to extract isobutanol from culture broth. In this way, toxicity of isobutanol was lowered in the culture broth.

Analytics

Isobutanol was measured in oleyl alcohol, culture broth, and off-gas samples by GC method, HPLC method, and mass-spectrometry, respectively. The methods are described below.

GC Method

The GC method utilized an ZB-WAXplus column (30 m×0.25 mm ID, 0.25 μm film) from Phenomenex (Torrance, Calif.). The carrier gas was helium at a constant flow rate of 2.3 mL/min; injector split was 1:20 at 250° C.; oven temperature was 70° C. for 1 min, 70° C. to 160° C. at 10° C./min, and 160° C. to 240° C. at 30° C./min. FID detection was used at 260° C. with 40 mL/min helium makeup gas. Culture broth samples were filtered through 0.2 μm spin filters before injection. Depending on analytical sensitivity desired, either 0.1 μL or 0.5 μL injection volumes were used. Calibrated standard curves were generated for the following compounds: ethanol, isobutanol, acetoin, meso-2,3-butanediol, and (2S, 3S)-2,3-butanediol. (2S,3S)-2,3-butanediol retention time is 6.8 minutes. meso-2,3-butanediol retention time is 7.2 minutes. Analytical standards were also utilized to identify retention times for isobutryaldehyde, isobutyric acid, and isoamyl alcohol.

HPLC Method

Analysis for glucose and fermentation by-product composition is well known to those skilled in the art. For example, one high performance liquid chromatography (HPLC) method utilizes a Shodex® SH-1011 column with a Shodex® SH-G guard column (both available from Waters Corporation, Milford, Mass.), with refractive index (RI) detection. Chromatographic separation is achieved using 0.01 M $H_2SO_4$ as the mobile phase with a flow rate of 0.5 mL/min and a column temperature of 50° C. Isobutanol retention time is 47.6 minutes.

HPLC Method for Thiamine Analysis

Samples were prepared by centrifugation of the fermentation or shake flask samples and filtration using 0.2 micron filter.

The method was reversed phase chromatography using Zorbax SB-C8, 4.6×250 mm, 5 micron column. Mobile phase A was 0.05% TFA in $H_2O$ and B was methanol. Flow rate was 1.0 mL/min. Injection volume was 10 pt. Run time was 24 minutes. Column temperature and sample temperature were 30° C. and 10° C., respectively. Detector was PDA (205 nm to 400 nm). Wavelength was 210 nm and 260 nm. Gradient is shown in Table 7.

TABLE 7

| Time (min) | Flow rate | % A | % B |
|---|---|---|---|
| 0 | 1.0 | 97 | 3 |
| 6.5 | 1.0 | 97 | 3 |
| 12 | 1.0 | 50 | 50 |
| 18 | 1.0 | 5 | 95 |
| 19 | 1.0 | 97 | 3 |
| 24 | 1.0 | 97 | 3 |

Figure 4:
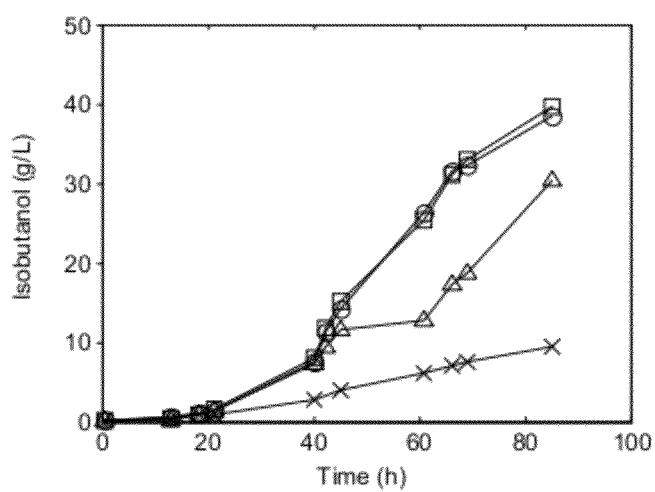
FIG. 4 shows the isobutanol titer during fermentations described in the Examples (F__140-100 (O), F__141-20 (□), F__142-10 (Δ), and F__143-0 (X)).
Figure 5:
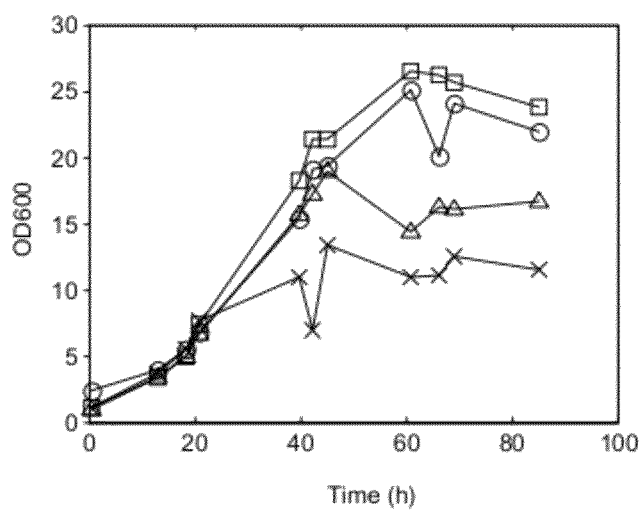
FIG. 5 shows the optical density measured during fermentations described in the Examples (F__140-100 (O), F__141-20 (□), F__142-10 (A), and F__143-0 (X)).
Figure 6:
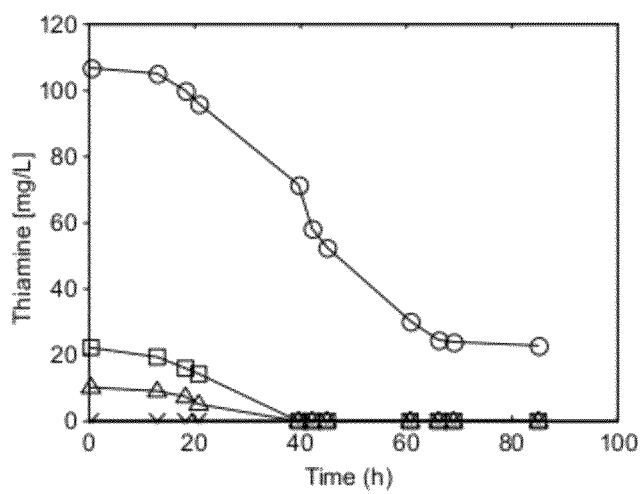
FIG. 6 shows the thiamine concentration in culture medium measured during fermentations described in the Examples (F__140-100 (O), F__141-20 (□), F__142-10 (Δ), and F__143-0 (X)).

The final rate, titer, and yield values (RTY) are shown in Table 8. Isobutanol titers during the fermentation time are shown in FIG. 4 (or Table 9). Volumetric isobutanol production rates and titers were about 4 times higher in fermentations with added thiamine at 100 mg/L (F140) and 20 mg/L (F141) compared to the fermentation without thiamine (F143). Yeast cell concentration, measured as optical density at λ=600 nm in a HEλIOS a (Thermo Electron Corporation, USA) was increased as well (FIG. 5 or Table 10). Thiamine concentration in culture medium is shown in FIG. 6 (or Table 11).

TABLE 8

| Examples | Rate g/L/h | Titer g/L | Yield g/g |
|---|---|---|---|
| F_140-100 | 0.45 | 38.5 | 0.23 |
| F_141-20 | 0.47 | 39.7 | 0.26 |
| F_142-10 | 0.36 | 30.2 | 0.24 |
| F_143-0 | 0.11 | 9.5 | 0.13 |

TABLE 9

Isobutanol titers during the fermentation time

| Time (h) | F_140 | F_141 | F_142 | F_143 |
|---|---|---|---|---|
| 0.39 | 0.0 | 0.0 | 0.0 | 0.0 |
| 12.92 | 0.7 | 0.3 | 0.2 | 0.3 |
| 18.27 | 1.0 | 0.9 | 0.8 | 0.7 |
| 21.05 | 1.4 | 1.5 | 1.3 | 0.8 |
| 39.97 | 7.6 | 8.0 | 7.2 | 2.8 |
| 42.36 | 11.4 | 11.7 | 9.3 | |
| 45.02 | 14.1 | 15.1 | 11.4 | 3.9 |
| 60.92 | 26.2 | 25.4 | 12.8 | 6.0 |
| 66.32 | 31.5 | 31.0 | 17.3 | 7.1 |
| 69.01 | 32.2 | 33.0 | 18.6 | 7.6 |
| 85.15 | 38.5 | 39.7 | 30.2 | 9.5 |

TABLE 10

Yeast cell concentration, measured as optical density

| Time (h) | F_140 | F_141 | F_142 | F_143 |
|---|---|---|---|---|
| 0.39 | 2.42 | 1.1 | 0.9 | 1.1 |
| 12.92 | 3.9 | 3.4 | 3.4 | 3.6 |
| 18.27 | 5.5 | 4.9 | 5.0 | 5.5 |
| 21.05 | 6.84 | 7.4 | 6.6 | 7.6 |
| 39.97 | 15.3 | 18.2 | 15.6 | 10.9 |
| 42.36 | 19.1 | 21.4 | 17.2 | 7.0 |
| 45.02 | 19.4 | 21.3 | 18.9 | 13.4 |
| 60.92 | 25.1 | 26.5 | 14.4 | 10.9 |
| 66.32 | 20.1 | 26.2 | 16.2 | 11.1 |
| 69.01 | 24.1 | 25.6 | 16.1 | 12.5 |
| 85.15 | 22 | 23.8 | 16.7 | 11.5 |

TABLE 11

Thiamine concentration in culture medium

| Time (h) | F_140 | F_141 | F_142 | F_143 |
|---|---|---|---|---|
| 0.39 | 107 | 22 | 10 | 0 |
| 12.92 | 105 | 19 | 9 | 0 |
| 18.27 | 100 | 16 | 7 | 0 |
| 21.05 | 96 | 14 | 5 | 0 |
| 39.97 | 71 | 0 | 0 | 0 |
| 42.36 | 58 | 0 | 0 | 0 |
| 45.02 | 53 | 0 | 0 | 0 |
| 60.92 | 30 | 0 | 0 | 0 |
| 66.32 | 24 | 0 | 0 | 0 |
| 69.01 | 24 | 0 | 0 | 0 |
| 85.15 | 22 | 0 | 0 | 0 |

Example 6

Nicotinic Acid Increases Isobutanol Production

The effect of nicotinic acid on isobutanol production was analyzed in shake flask experiments. Cultivations were performed under both aerobic and anaerobic conditions in the presence of water (negative control), vitamin solution (positive control), yeast extract peptone (YEP, positive control), or nicotinic acid (NA) with strain *Saccharomyces cerevisiae* isobutanol producing NYLA84 strain (construction described elsewhere herein).

Vitamin stock solution contained biotin, 50 mg/L; Ca-panthotenate, 1 g/L; nicotinic acid, 1 g/L; myo-inositol, 25 g/l; thiamine.HCl, 1 g/L; pyridoxine hydrochloride, 1 g/L; p-aminobenzoic acid, 0.2 g/L; riboflavin, 0.2 g/L; and folic acid, 2 mg/L. One liter (1 L) of ergosterol and Tween 80 stock solution contain 10 g of ergosterol dissolved in 500 mL 100% ethanol solution and 500 mL Tween 80.

Experiments were carried out in 125 mL shake flasks with 20 mL shake flask medium. Composition of the base medium was (per L of water): 6.7 g YNB without amino acids (Difco 0919-15-3); 2.8 g Yeast Synthetic Drop-out Medium Supplement without histidine, leucine, tryptophan, and uracil (Sigma Y2001); 20 mL of 1% (w/v) L-leucine; 4 mL of 1% (w/v) L-tryptophan; 0.8 mL of ergosterol and Tween 80 stock solution.

OD at $\lambda$=600 nm was determined in a HE$\lambda$IOS $\alpha$ spectrophotometer (Thermo Electron Corporation, USA). If biomass concentration of the sample exceeded the linear range of the spectrophotometer, sample was diluted with water. Glucose and fermentation by-product analysis were determined by a Waters HPLC utilizing a Bio-Rad Aminex HPX-87H column with diode array (DA) operated at 210 nm and a refractive index (RI) detector at 50° C. Chromatographic separation was achieved using 0.01N $H_2SO_4$ as the mobile phase with a flow rate of 0.6 mL/min and a column temperature of 40° C.

OD at $\lambda$=600 nm was determined in a HE$\lambda$IOS $\alpha$ spectrophotometer (Thermo Electron Corporation, USA). If biomass concentration of the sample exceeded the linear range of the spectrophotometer, sample was diluted with water. Glucose and fermentation by-product analysis were determined by HPLC utilizing a Bio-Rad Aminex HPX-87H column with diode array (DA) at 210 nm and refractive index (RI) detector operated at 50° C. Chromatographic separation was achieved using 0.01 M $H_2SO_4$ as the mobile phase with a flow rate of 0.08 mL/min and a column temperature of 60° C.

Seed cultures were started in 125 mL shake flasks (open cups, 10 mL medium inoculated with 1 mL from a frozen vial). The flasks were incubated at 260 rpm and 30° C. After 24 hours OD in the flask was about 1.0. Ten (10) mL of the seed was inoculated into 2 L shake flask with 135 mL of the medium. Fifty (50) mL of 1M MES buffer was added and 14.3 mL of 50% (w/w) glucose solution.

When OD at $\lambda$=600 nm in the 2 L flask reached about 1.0, 18 mL of this culture broth was distributed in 125 mL shake flasks. Two (2) mL of (a) bidestilled water, (b) nicotinic acid stock solution (with 1 g/L nicotinic acid in water), (c) 2 ml of YEP stock solution (with 10 g/l yeast extract (YE) and 20 g/L peptone), and (d) 20 µL of vitamin stock solution in 1.980 mL of bidest water were added to the cultures. The aerobic shake flasks with air permeable lid were incubated at 30° C. and 260 rpm. The anaerobic shake flasks were started in the anaerobic hood and incubated as well at 30° C. and 260 rpm. Initial OD at $\lambda$=600 nm in the cultures were about 0.700. Aerobic experiments were analyzed after 25.8 h of the process, anaerobic data after 24.2 h. Generated biomass (delta OD), consumed glucose (delta glucose), and produced isobutanol (delta isobutanol) were determined and are shown in FIG. 9.

Negative control cultivations exhibited growth, consumed glucose, and produced isobutanol under aerobic as well as anaerobic conditions. However, experiments supplemented with NA showed increased isobutanol production (FIG. 9A), increased consumption of glucose (FIG. 9B) as well as increased biomass formation (FIG. 9C) as compared to the negative control experiments. Increase was significantly more pronounced under anaerobic than under aerobic conditions. Positive controls containing either a mixture of vitamins or YEP showed improved production of isobutanol, consumption of glucose and production of biomass, indicating additional beneficial effects of other media compounds and/or vitamins.

Example 7

Medium Concentrations of Nicotinic Acid for Isobutanol Production in Aerobic Shake Flask Cultivations The strain used in this Example was the isobutanol producing NYLA 84 strain, described elsewhere herein. Vitamin stock solution contained biotin, 50 mg/L; Ca-panthotenate, 1 g/L; nicotinic acid, 1 g/L; myo-inositol, 25 g/l; thiamine.HCl, 1 g/L; pyridoxine hydrochloride, 1 g/L; p-aminobenzoic acid, 0.2 g/L; riboflavin, 0.2 g/L; and folic acid, 2 mg/L. One liter (1 L) of ergosterol and Tween 80 stock solution contains 10 g of ergosterol dissolved in 500 mL 100% ethanol solution and 500 mL Tween 80. Composition of the base medium was (per L of water): 6.7 g YNB without amino acids (Difco 0919-15-3); 2.8 g Yeast Synthetic Drop-out Medium Supplement without histidine, leucine, tryptophan, and uracil (Sigma Y2001); 20 mL of 1% (w/v) L-leucine; 4 mL of 1% (w/v) L-tryptophan; 5 g ethanol; 3 g glucose; 0.8 mL of Ergosterol & Tween 80 stock solution.

OD at $\lambda=600$ nm was determined in a HEλIOS α spectrophotometer (Thermo Electron Corporation, USA). If biomass concentration of the sample exceeded the linear range of the spectrophotometer, sample was diluted with water. Glucose and fermentation by-product analysis were determined by a Waters HPLC utilizing a Bio-Rad Aminex HPX-87H column with diode array (DA) operated at 210 nm and a refractive index (RI) detector at 50° C. Chromatographic separation was achieved using $0.01N\ H_2SO_4$ as the mobile phase with a flow rate of 0.6 mL/min and a column temperature of 40° C.

Several seed cultures inoculated each with a 1 mL glycerol frozen stock vial were grown in 10 mL base medium for 24 h. At the start of the range finding experiment, seed cultures were pooled and 16 mL each of the pooled seed culture were distributed into 125 mL shake flasks, 2 mL of 1 M MES buffer added, and additionally 2 mL of (a) bidestilled water, (b-d) nicotinic acid (NA) stock solutions with 60 mg/L, 600 mg/L and 1000 mg/L of NA dissolved in bidestilled water, respectively, and (e) YE stock solution with 200 g/l YE. The aerobic shake flasks with air permeable lid were incubated at 30° C. and 260 rpm. Initial OD at $\lambda=600$ nm in the cultures was 0.764. Biomass and isobutanol produced were analyzed at 2.00 h, 18.75 h, and 24.5 h of the process and results are shown in FIG. 11.

Biomass and isobutanol were produced in the control culture without NA. However, NA supplemented cultures with NA concentrations as low as 6 mg/L showed significantly increased biomass and isobutanol titers at all measurement points. Positive control containing YE showed increased titers of biomass and isobutanol, indicating additional beneficial effects of other YE components.

Example 8

Nicotinic Acid Increases Isobutanol Production

The effect of nicotinic acid on isobutanol production was analyzed in shake flask experiments. Cultivations were performed under both aerobic and anaerobic conditions in the presence of water (negative control), vitamin solution (positive control), yeast extract peptone (YEP, positive control), or nicotinic acid (NA) with strain *Saccharomyces cerevisiae* isobutanol producing NYLA84 strain (construction described elsewhere herein).

Vitamin stock solution contained biotin, 50 mg/L; Ca-panthotenate, 1 g/L; nicotinic acid, 1 g/L; myo-inositol, 25 g/l; thiamine.HCl, 1 g/L; pyridoxine hydrochloride, 1 g/L; p-aminobenzoic acid, 0.2 g/L; riboflavin, 0.2 g/L; and folic acid, 2 mg/L. One liter (1 L) of ergosterol and Tween 80 stock solution contain 10 g of ergosterol dissolved in 500 mL 100% ethanol solution and 500 mL Tween 80.

Experiments were carried out in 125 mL shake flasks with 20 mL shake flask medium. Composition of the base medium was (per L of water): 6.7 g YNB without amino acids (Difco 0919-15-3); 2.8 g Yeast Synthetic Drop-out Medium Supplement without histidine, leucine, tryptophan and uracil (Sigma Y2001); 20 mL of 1% (w/v) L-leucine; 4 mL of 1% (w/v) L-tryptophan; 0.8 mL of ergosterol and Tween 80 stock solution.

OD at $\lambda=600$ nm was determined in a HEλIOS α spectrophotometer (Thermo Electron Corporation, USA). If biomass concentration of the sample exceeded the linear range of the spectrophotometer, sample was diluted with water. Glucose and fermentation by-product analysis were determined by a Waters HPLC utilizing a Bio-Rad Aminex HPX-87H column with diode array (DA) operated at 210 nm and a refractive index (RI) detector at 50° C. Chromatographic separation was achieved using $0.01N\ H_2SO_4$ as the mobile phase with a flow rate of 0.6 mL/min and a column temperature of 40° C.

Seed cultures were started in 125 mL shake flasks (open cups, 10 mL medium inoculated with 1 mL from a frozen vial). The flasks were incubated at 260 rpm and 30° C. After 24 hours OD in the flask was about 1.0. Ten (10) mL of the seed was inoculated into 2 L shake flask with 135 mL of the medium. Fifty (50) mL of 1M MES buffer was added and 14.3 mL of 50% (w/w) glucose solution.

When OD at $\lambda=600$ nm in the 2 L flask reached about 1.0, 18 mL of this culture broth was distributed in 125 mL shake flasks. Two (2) mL of (a) bidest. water, (b) nicotinic acid stock solution (with 1 g/L nicotinic acid in water), (c) 2 ml of YEP stock solution (with 10 g/l YE and 20 g/L peptone), and (d) 20 μL of vitamin stock solution in 1.980 mL of bidest water were added to the cultures. The aerobic shake flasks with air permeable lid were incubated at 30° C. and 260 rpm. The anaerobic shake flasks were started in the anaerobic hood and incubated as well at 30° C. and 260 rpm. Initial OD at $\lambda=600$ nm in the cultures were about 0.500. Experiments were sampled after 6.3 and 20.8 h. Generated biomass (delta OD), consumed glucose (delta glucose), and produced isobutanol (delta isobutanol) were determined and are shown in FIG. 10.

Negative control cultivations exhibited growth, consumed glucose, and produced isobutanol under aerobic as well as anaerobic conditions. However, experiments supplemented with NA showed increased isobutanol production and both conditions (FIG. 10A+D), increased consumption of glucose (FIG. 103B+E) as well as increased biomass formation (FIG. 10C+F) as compared to the negative control experiments. The increase was significantly more pronounced under anaerobic than under aerobic conditions. Positive controls containing either a mixture of vitamins or YEP showed improved production of isobutanol, consumption of glucose and production of biomass, indicating additional beneficial effects of other media compounds and/or vitamins.

Example 9

Nicotinic Acid Supplementation Improves Isobutanol Production in Bioreactors

Based on the findings in shake flasks experiments, bioreactor cultivations were performed with the BP1063 isobutanol producing strain (construction described herein) with addition of water (control) and initial nicotinic acid concentrations of 100 mg/L, 20 mg/L and 5 mg/L.

One liter (1 L) of inoculum medium contained: 6.7 g, Yeast Nitrogen Base w/o amino acids (Difco 0919-15-3); 2.8 g, Yeast Synthetic Drop-out Medium Supplement Without histidine, leucine, tryptophan and uracil (Sigma Y2001); 20 mL of 1% (w/v) L-leucine; 4 mL of 1% (w/v) L-tryptophan; 1 mL of ergosterol and Tween 80 solution; 3 g of ethanol; 3 g of glucose. Preparation of ergosterol and Tween 80 solution: for 10 mL of the solution, 100 mg of ergosterol was dissolve in 5 mL 100% EtOH and 5 mL Tween 80. It was heated at 70° C. for 10 minutes.

A 125 mL shake flask was inoculated directly from a frozen vial by pipetting the whole vial culture (approx. 1 ml) into 10 mL of the inoculum medium. The flask was incubated at 260 rpm and 30° C. The strain was grown overnight until OD about 1.0. At this point four 2 L baffled shake flasks with 90 mL of the inoculum medium were inoculated from the overnight culture. The 2 L flasks were incubated at 260 rpm and 30° C. When OD in the flasks reached about 1.0, 10 mL of 1M MES buffer and about 100 mL of oleyl alcohol were added to the shake flasks. Twenty-four (24) hours after this point the oleyl alcohol was removed, the cultures were pooled together and each fermentor was inoculated with 80 mL of the inoculum.

One liter (1 L) of bioreactor medium was prepared with: Salts: ammonium sulfate 10.0 g, potassium phosphate monobasic 5.33 g, magnesium sulfate heptahydrate 2.0 g, zinc sulfate heptahydrate, 0.47 g. Vitamins: biotin (D−) 0.40 mg, Ca D(+) panthotenate 8.00 mg, myo-inositol 200.00 mg, pyridoxol hydrochloride 8.00 mg, p-aminobenzoic acid 1.60 mg, riboflavin 1.60 mg, folic acid 0.02 mg, thiamine 30.0 mg. Amino acids: yeast synthetic drop-out medium supplement without histidine, leucine, tryptophan and uracil (Sigma Y2001) 2.8 g, 1% (w/v) L-leucine 20 mL, 1% (w/v) L-tryptophan 4 mL. Trace elements: EDTA (Titriplex 1117) 99.38 mg, zinc sulphate heptahydrate 29.81 mg, manganese chloride dehydrate 5.57 mg, cobalt(II)chloride hexahydrate 1.99 mg, copper(II)sulphate pentahydrate 1.99 mg, Di-sodium molybdenum dehydrate 2.65 mg, calcium chloride dehydrate 29.81 mg, iron sulphate heptahydrate 19.88 mg, boric acid, 6.63 mg, potassium iodide 0.66 mg. Ergosterol and Tween 80 solution 1 mL. Glucose 20 g.

Experiments were carried out in a 2 L BIOSTAT B-DCU Tween2 L bioreactors from Sartorius (Germany). The fermentors are connected to mass-spec from Thermo Electron Corporation (USA). Directly after inoculation with 80 mL of the inoculum, the volume in fermentors was about 800 mL, dissolved oxygen tension (DOT) was controlled at 10%, pH was controlled at 5.25, aeration was controlled at 0.5 L/min, 0.8 L of oleyl alcohol was added. Oleyl alcohol was used in order to extract isobutanol from culture broth. In this way toxicity of isobutanol was lowered in the culture broth. During the whole fermentation, glucose was kept at about 20 g/L by feeding glucose solution (50% w/w).

OD at λ=600 nm was determined in a HEλIOS a spectrophotometer (Thermo Electron Corporation, USA). If biomass concentration of the sample exceeded the linear range of the spectrophotometer, sample was diluted with water. Glucose and fermentation by-product analysis were determined by HPLC utilizing a Shodex® SH-1011 column with a Shodex® SH-G guard column (both available from Waters Corporation, Milford, Mass.), with diode array (DA) and refractive index (RI) detector. Chromatographic separation was achieved using 0.01 N $H_2SO_4$ as the mobile phase with a flow rate of 0.5 mL/min and a column temperature of 50° C.

Isobutanol was measured in oleyl alcohol, culture broth, and off-gas samples by GC method, HPLC method, and mass-spectrometry, respectively. The methods were described above. Analysis for glucose and fermentation by-product composition is also described above.

For analysis of nicotinamid and nicotinic acid concentrations, samples were prepared by centrifugation of the fermentation and filtered using 0.2 micron filters. An reversed phase HPLC method using a Zorbax SB-C8, 4.6×250 mm, 5 micron column was established. Mobile phase A was 0.05% TFA in $H_2O$ and B was methanol. Eluent gradient is shown above. Flow rate was 1.0 mL/min. Injection volume was 10 pt. Run time was 24 minutes. Column temperature and sample temperature were 30° C. and 10° C., respectively. A PDA detector was used to monitor wavelengths 210 nm and 260 nm. 260 nm is the preferred wavelength to quantify nicotinamid and nicotinic acid in fermentation samples, while the 210 nm signal was used for verification.

Time courses of isobutanol, biomass and NA concentrations in aqueous phase are shown in FIG. 12. It can be seen that supplementation of the bioreactor cultivations with NA concentrations of as low as 5 mg/L lead to improved final isobutanol titers in the aqueous phase. High consumption of NA in excess of 20 mg/L until the end of the process in the 100 mg/L supplemented culture indicates high demand of the isobutanol producing cells for NA.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A commercial method for producing isobutanol comprising:
   a. providing a production culture comprising recombinant cells, wherein the recombinant cells comprise an engineered isobutanol biosynthetic pathway, wherein the engineered isobutanol biosynthetic pathway comprises heterologous polynucleotides encoding polypeptides that catalyze the following substrate to product conversions of the pathway:
      a) pyruvate to acetolactate, catalyzed by an acetolactate synthase;
      b) acetolactate to 2,3-dihydroxyisovalerate, catalyzed by an acetohydroxy acid reductoisomerase;
      c) 2,3-dihydroxyisovalerate to a-ketoisovalerate, catalyzed by a acetohydroxy acid dehydratase;
      d) a-ketoisovalerate to isobutyraldehyde, catalyzed by a branched-chain keto acid decarboxylase; and
      e) isobutyraldehyde to isobutanol, catalyzed by a branched-chain alcohol dehydrogenase,
      wherein the recombinant cells comprise at least one genetic modification that eliminates pyruvate decarboxylase activity,
      and wherein the recombinant cells are capable of producing isobutanol, and production media comprising
         1. thiamine or a biosynthetic precursor thereof;
         2. optionally nicotinic acid, nicotinamid, or a biosynthetic precursor of NAD; and
         3. a production feed derived from biomass comprising a fermentable carbon source;
      wherein the production media contains less than 1 g/L of multi-component media additives; and
   b. contacting the production culture with the production media in a fermentation vessel to form a production broth under conditions whereby isobutanol is produced.

2. The method of claim 1, wherein the production media is substantially free of multi-component media additives.

3. The method of claim 1, wherein the production broth contains at least about 5 mg/L thiamine or a biosynthetic precursor thereof.

4. The method of claim 1, wherein the thiamine or a biosynthetic precursor thereof is present in an amount sufficient to provide at least about 30% of the rate, titer, or specific productivity observed in media that contains about 10 g/L yeast extract.

5. The method of claim 1, wherein the recombinant cells are yeast.

6. The method of claim 5, wherein the yeast is crabtree positive or crabtree negative.

7. The method of claim 1, wherein the recombinant cell comprises a modification of an endogenous gene encoding a thiamine pyrophosphate-dependent (TPP) gene.

8. The method of claim 7, wherein the TPP-dependent gene is a pyruvate decarboxylase gene.

9. The production broth of claim 1, wherein the broth comprises isobutanol.

* * * * *